United States Patent
Stephanopoulos et al.

(10) Patent No.: US 11,142,770 B2
(45) Date of Patent: Oct. 12, 2021

(54) ISOLATED OLEAGINOUS YEAST

(71) Applicant: Massachusetts Institute of Technology, Cambridge, MA (US)

(72) Inventors: Gregory Stephanopoulos, Winchester, MA (US); Kangjian Qiao, Cambridge, MA (US); Peng Xu, Quincy, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/296,148

(22) Filed: Oct. 18, 2016

(65) Prior Publication Data

US 2017/0183670 A1 Jun. 29, 2017

Related U.S. Application Data

(60) Provisional application No. 62/243,824, filed on Oct. 20, 2015.

(51) Int. Cl.
| | | |
|---|---|---|
| *C12N 15/81* | (2006.01) | |
| *C12P 7/64* | (2006.01) | |
| *C12N 15/52* | (2006.01) | |
| *C12N 9/10* | (2006.01) | |
| *C12N 9/00* | (2006.01) | |
| *C12N 1/16* | (2006.01) | |

(52) U.S. Cl.
CPC ............. *C12N 15/81* (2013.01); *C12N 1/16* (2013.01); *C12N 9/1029* (2013.01); *C12N 9/93* (2013.01); *C12N 15/52* (2013.01); *C12P 7/64* (2013.01); *C12Y 203/0102* (2013.01); *C12Y 604/01002* (2013.01); *C12N 2330/51* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 8,916,365 | B2 | 12/2014 | Macool et al. |
| 2010/0305341 | A1 | 12/2010 | Bailey et al. |
| 2012/0149886 | A1 | 6/2012 | Bailey et al. |
| 2013/0143282 | A1 | 6/2013 | Stephanopoulos et al. |
| 2014/0234928 | A1 | 8/2014 | Bailey et al. |
| 2014/0315279 | A1 | 10/2014 | Bailey et al. |

OTHER PUBLICATIONS

Zhang et al. (Biotechnol. Lett., 2013, vol. 35, pp. 2091-2098).*
Lamers et al. (BMC Biotechnology, 2016, 16 (45), pp. 1-10).*
Andre et al., Fusing catalase to an alkane-producing enzyme maintains enzymatic activity by converting the inhibitory byproduct H2O2 to the cosubstrate O2. Proc Natl Acad Sci U S A. Feb. 19, 2013;110(8):3191-6. doi: 10.1073/pnas.1218769110. Epub Feb. 7, 2013.

Beopoulos et al., Control of lipid accumulation in the yeast *Yarrowia lipolytica*. Appl Environ Microbiol. Dec. 2008;74(24):7779-89. doi: 10.1128/AEM.01412-08. Epub Oct. 24, 2008.
Blazeck et al., Harnessing Yarrowia lipolytica lipogenesis to create a platform for lipid and biofuel production. Nat Commun. 2014;5:3131. doi: 10.1038/ncomms4131.
Blazeck et al., Heterologous production of pentane in the oleaginous yeast *Yarrowia lipolytica*. J Biotechnol. Jun. 10, 2013;165(3-4):184-94. doi: 10.1016/j.jbiotec.2013.04.003. Epub Apr. 16, 2013.
Chen et al., One-step transformation of the dimorphic yeast *Yarrowia lipolytica*. Appl Microbiol Biotechnol. Aug. 1997;48(2):232-5.
De Jong et al., Improved production of fatty acid ethyl esters in *Saccharomyces cerevisiae* through up-regulation of the ethanol degradation pathway and expression of the heterologous phosphoketolase pathway. Microb Cell Fact. Mar. 12, 2014;13(1):39. doi: 10.1186/1475-2859-13-39.
Dellomonaco et al., Engineered reversal of the β-oxidation cycle for the synthesis of fuels and chemicals. Nature. Aug. 10, 2011;476(7360):355-9. doi: 10.1038/nature10333.
Drincovich et al., Redox regulation of maize NADP-malic enzyme by thiol-disulfide interchange: effect of reduced thioredoxin on activity. Biochim Biophys Acta. May 18, 1994;1206(1):10-6.
Grimsrud et al., Oxidative stress and covalent modification of protein with bioactive aldehydes. J Biol Chem. Aug. 8, 2008;283(32):21837-41. doi: 10.1074/jbc.R700019200. Epub Apr. 29, 2008.
Guerrero-Castillo et al., In *Yarrowia lipolytica* mitochondria, the alternative NADH dehydrogenase interacts specifically with the cytochrome complexes of the classic respiratory pathway. Biochim Biophys Acta. Feb. 2009;1787(2):75-85. doi: 10.1016/j.bbabio.2008.10.008. Epub Nov. 6, 2008.
Jamieson, Oxidative stress responses of the yeast *Saccharomyces cerevisiae*. Yeast. Dec. 1998;14(16):1511-27.
Kamisaka et al., Overexpression of the active diacylglycerol acyltransferase variant transforms *Saccharomyces cerevisiae* into an oleaginous yeast. Appl Microbiol Biotechnol. Aug. 2013;97(16):7345-55.
Kitamura et al., Mouse aldehyde dehydrogenase ALDH3B2 is localized to lipid droplets via two C-terminal tryptophan residues and lipid modification. Biochem J. Jan. 1, 2015;465(1):79-87. doi: 10.1042/BJ20140624.
Knothe, Biodiesel and renewable diesel: A comparison. Prog. Energy Combust. Sci 2010; 36: 364-373.
Lam et al., Engineering alcohol tolerance in yeast. Science. Oct. 3, 2014;346(6205):71-5. doi: 10.1126/science.1257859. Epub Oct. 2, 2014.

(Continued)

*Primary Examiner* — Hope A Robinson
(74) *Attorney, Agent, or Firm* — Wolf, Greenfield & Sacks, P.C.

(57) ABSTRACT

Some aspects provide engineered microbes for oil production. Methods for microbe engineering and for use of engineered microbes are also provided herein. Such engineered microbes exhibit greatly enhanced conversion yields and TAG synthesis and storage properties.

15 Claims, 34 Drawing Sheets
Specification includes a Sequence Listing.

(56) References Cited

OTHER PUBLICATIONS

Lamonte et al., Acidosis induces reprogramming of cellular metabolism to mitigate oxidative stress. Cancer Metab. Dec. 23, 2013;1(1):23. doi: 10.1186/2049-3002-1-23.

Lazar et al., Hexokinase—A limiting factor in lipid production from fructose in *Yarrowia lipolytica*. Metab Eng. Nov. 2014;26:89-99. doi: 10.1016/j.ymben.2014.09.008. Epub Oct. 13, 2014.

Lennen et al., Microbial production of fatty acid-derived fuels and chemicals. Curr Opin Biotechnol. Dec. 2013;24(6):1044-53. doi: 10.1016/j.copbio.2013.02.028. Epub Mar. 28, 2013.

Li et al., Oxidative stress in fungal fermentation processes: the roles of alternative respiration. Biotechnol Lett. Mar. 2011;33(3):457-67. doi: 10.1007/s10529-010-0471-x. Epub Nov. 19, 2010.

Li-Beisson et al., Acyl-lipid metabolism. *Arabidopsis* Book. 2010;8:e0133. doi: 10.1199/tab.0133. Epub Jun. 11, 2010.

Liu et al., An evolutionary metabolic engineering approach for enhancing lipogenesis in Yarrowia lipolytica. Metab Eng. May 2015;29:36-45. doi: 10.1016/j.ymben.2015.02.003. Epub Feb. 24, 2015.

Lopes et al., Comparison of Yarrowia lipolytica and Pichia pastoris cellular response to different agents of oxidative stress. Appl Biochem Biotechnol. May 2013;170(2):448-58. doi: 10.1007/s12010-013-0205-3. Epub Apr. 2, 2013.

Mano et al., The NADPH:quinone oxidoreductase P1-zeta-crystallin in *Arabidopsis* catalyzes the alpha,beta-hydrogenation of 2-alkenals: detoxication of the lipid peroxide-derived reactive aldehydes. Plant Cell Physiol. Dec. 2002;43(12):1445-55.

McLain et al., α-Ketoglutarate dehydrogenase: a mitochondrial redox sensor. Free Radic Res. Jan. 2011;45(1):29-36. doi: 10.3109/10715762.2010.534163. Epub Nov. 29, 2010.

Medentsev et al., Activation of the alternative oxidase of Yarrowia lipolytica by adenosine 5'-monophosphate. Microbiology. Mar.-Apr. 2004;73(2):117-123.

Medentsev et al., Involvement of the alternative oxidase in respiration of Yarrowia lipolytica mitochondria is controlled by the activity of the cytochrome pathway. FEMS Yeast Res. Dec. 2002;2(4):519-24.

Minard et al., Sources of NADPH and expression of mammalian NADP+-specific isocitrate dehydrogenases in *Saccharomyces cerevisiae*. J Biol Chem. Nov. 20, 1998;273(47):31486-93.

Mlickova et al., Lipid accumulation, lipid body formation, and acyl coenzyme A oxidases of the yeast *Yarrowia lipolytica*. Appl Environ Microbiol. Jul. 2004;70(7):3918-24.

Morano et al., The response to heat shock and oxidative stress in *Saccharomyces cerevisiae*. Genetics. Apr. 2012;190(4):1157-95. doi: 10.1534/genetics.111.128033. Epub Dec. 29, 2011.

Morin et al., Transcriptomic analyses during the transition from biomass production to lipid accumulation in the oleaginous yeast *Yarrowia lipolytica*. PLoS One. 2011;6(11):e27966. doi: 10.1371/journal.pone.0027966. Epub Nov. 22, 2011.

Nicaud, *Yarrowia lipolytica*. Yeast. Oct. 2012;29(10):409-18. doi: 10.1002/yea.2921. Epub Oct. 5, 2012.

Ochoa-Estopier et al., D-stat culture for studying the metabolic shifts from oxidative metabolism to lipid accumulation and citric acid production in Yarrowia lipolytica. J Biotechnol. Jan. 20, 2014;170:35-41. doi: 10.1016/j.jbiotec.2013.11.008. Epub Dec. 4, 2013.

Pfleger et al., Metabolic engineering strategies for microbial synthesis of oleochemicals. Metab Eng. May 2015;29:1-11. doi: 10.1016/j.ymben.2015.01.009. Epub Feb. 7, 2015.

Qiao et al., Engineering lipid overproduction in the oleaginous yeast *Yarrowia lipolytica*. Metab Eng. May 2015;29:56-65. doi: 10.1016/j.ymben.2015.02.005. Epub Feb. 27, 2015.

Rathinasabapathi et al., Metabolic engineering for stress tolerance: Installing osmoprotectant synthesis pathways. Annals of Botany. Oct. 1, 2000; 86(4):709-716.

Reddi et al., SOD1 integrates signals from oxygen and glucose to repress respiration. Cell. Jan. 17, 2013;152(1-2):224-35. doi: 10.1016/j.cell.2012.11.046.

Rosenwasser et al., Mapping the diatom redox-sensitive proteome provides insight into response to nitrogen stress in the marine environment. Proc Natl Acad Sci U S A. Feb. 18, 2014;111(7):2740-5. doi: 10.1073/pnas.1319773111. Epub Feb. 3, 2014.

Ruijter et al., Mannitol is required for stress tolerance in Aspergillus niger conidiospores. Eukaryot Cell. Aug. 2003;2(4):690-8.

Runguphan et al., Metabolic engineering of *Saccharomyces cerevisiae* for production of fatty acid-derived biofuels and chemicals. Metab Eng. Jan. 2014;21:103-13. doi: 10.1016/j.ymben.2013.07.003. Epub Jul. 27, 2013.

Sasaki et al., Link between light and fatty acid synthesis: Thioredoxin-linked reductive activation of plastidic acetyl-CoA carboxylase. Proc Natl Acad Sci U S A. Sep. 30, 1997;94(20):11096-101.

Shen et al., Increased resistance to oxidative stress in transgenic plants by targeting mannitol biosynthesis to chloroplasts. Plant Physiol. Apr. 1997;113(4):1177-83.

Shen et al., Mannitol Protects against Oxidation by Hydroxyl Radicals. Plant Physiol. Oct. 1997;115(2):527-532.

Shi et al., Engineering of chromosomal wax ester synthase integrated *Saccharomyces cerevisiae* mutants for improved biosynthesis of fatty acid ethyl esters. Biotechnol Bioeng. Sep. 2014;111(9):1740-7. doi: 10.1002/bit.25234. Epub Apr. 18, 2014.

Tai et al., Engineered biosynthesis of medium-chain esters in *Escherichia coli*. Metab Eng. Jan. 2015;27:20-28. doi: 10.1016/j.ymben.2014.10.004. Epub Oct. 29, 2014.

Tai et al., Engineering the push and pull of lipid biosynthesis in oleaginous yeast *Yarrowia lipolytica* for biofuel production. Metab Eng. Jan. 2013;15:1-9. doi: 10.1016/j.ymben.2012.08.007. Epub Sep. 28, 2012.

Wallace, Mitochondria and cancer. Nat Rev Cancer. Oct. 2012;12(10):685-98. doi: 10.1038/nrc3365.

Wasylenko et al., The oxidative pentose phosphate pathway is the primary source of NADPH for lipid overproduction from glucose in *Yarrowia lipolytica*. Metab Eng. Jul. 2015;30:27-39. doi: 10.1016/j.ymben.2015.02.007. Epub Mar. 6, 2015.

Wells et al., Redox control of catalysis in ATP-citrate lysate from rat liver. Eur J Biochem. Feb. 15, 1992;204(1):249-55.

Xie et al., Sustainable source of omega-3 eicosapentaenoic acid from metabolically engineered Yarrowia lipolytica: from fundamental research to commercial production. Appl Microbiol Biotechnol. Feb. 2015;99(4):1599-610. doi: 10.1007/s00253-014-6318-y. Epub Jan. 8, 2015.

Xu et al., Assembly of multi-gene pathways and combinatorial pathway libraries through ePathBrick vectors. Methods Mol Biol. 2013;1073:107-29. doi: 10.1007/978-1-62703-625-2_10.

Xu et al., ePathBrick: a synthetic biology platform for engineering metabolic pathways in *E. coli*. ACS Synth Biol. Jul. 20, 2012;1(7):256-66. doi: 10.1021/sb300016b. Epub May 4, 2012.

Xu et al., Improving fatty acids production by engineering dynamic pathway regulation and metabolic control. Proc Natl Acad Sci U S A. Aug. 5, 2014;111(31):11299-304. doi: 10.1073/pnas.1406401111. Epub Jul. 21, 2014.

Xu et al., Modular optimization of multi-gene pathways for fatty acids production in *E. coli*. Nat Commun. 2013;4:1409. doi: 10.1038/ncomms2425.

Xue et al., Production of omega-3 eicosapentaenoic acid by metabolic engineering of Yarrowia lipolytica. Nat Biotechnol. Aug. 2013;31(8):734-40. doi: 10.1038/nbt.2622. Epub Jul. 21, 2013.

Yilancioglu et al., Oxidative stress is a mediator for increased lipid accumulation in a newly isolated *Dunaliella salina* strain. PLoS One. Mar. 20, 2014;9(3):e91957. doi: 10.1371/journal.pone.0091957. eCollection 2014.

Zhou et al., Fatty acid-derived biofuels and chemicals production in *Saccharomyces cerevisiae*. Front Bioeng Biotechnol. Sep. 1, 2014;2:32. doi: 10.3389/fbioe.2014.00032.

Zimniak, Relationship of electrophilic stress to aging. Free Radic Biol Med. Sep. 15, 2011;51(6):1087-105. doi: 10.1016/j.freeradbiomed.2011.05.039. Epub Jun. 12, 2011.

\* cited by examiner

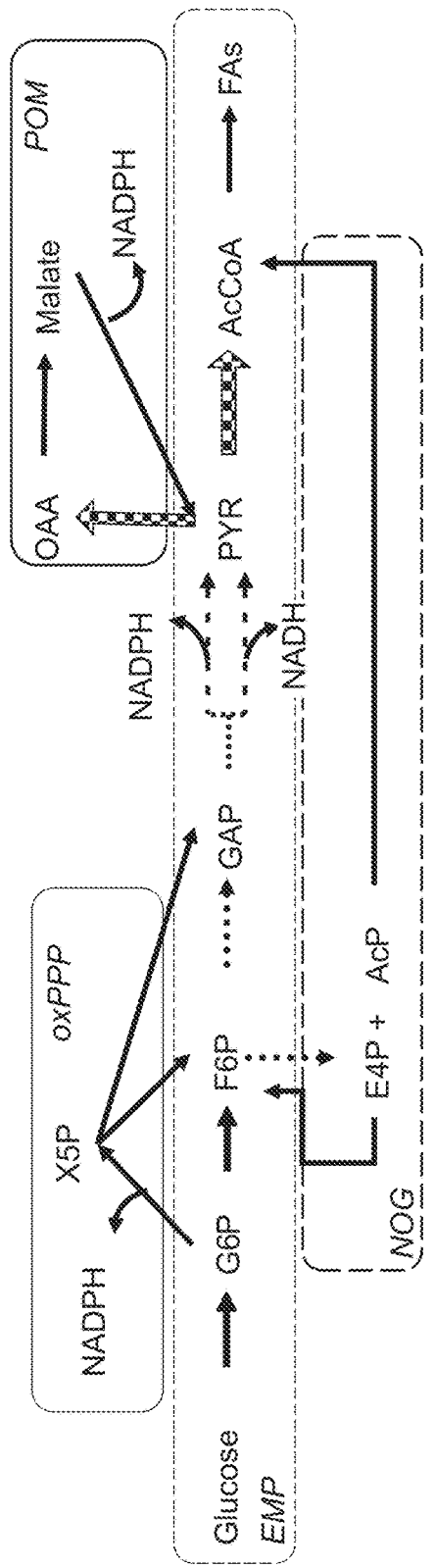
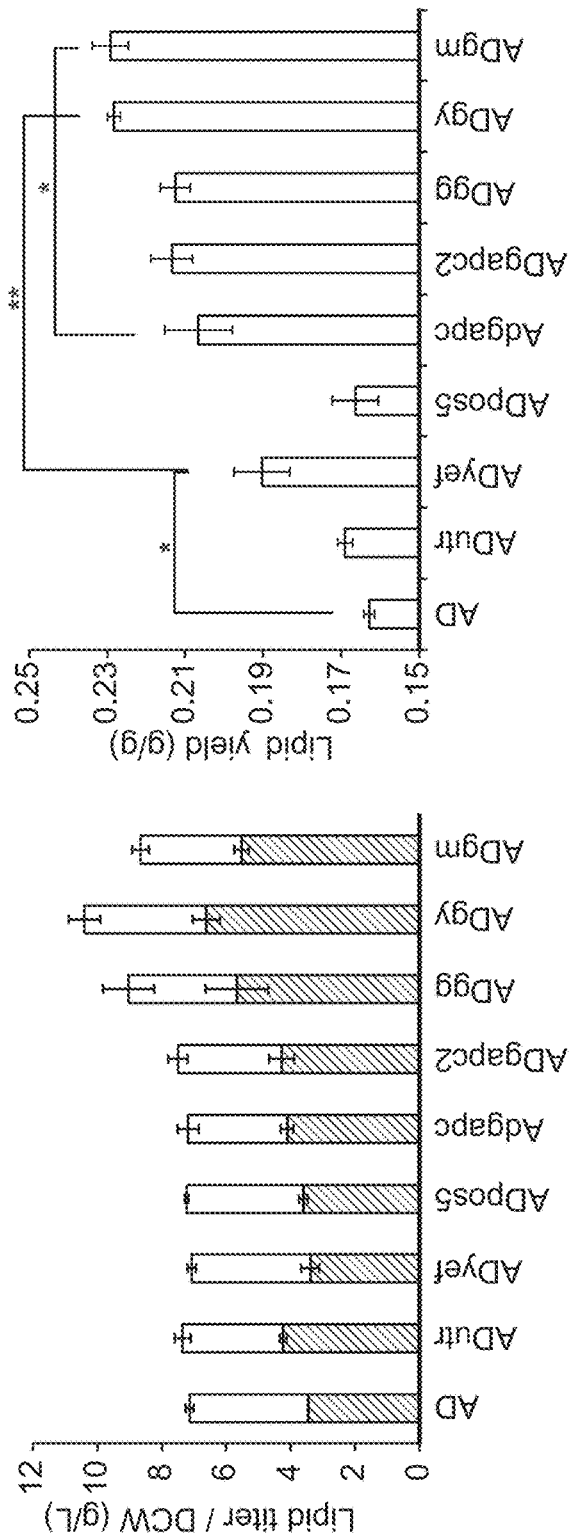
FIG. 4A
FIG. 4B
FIG. 4C

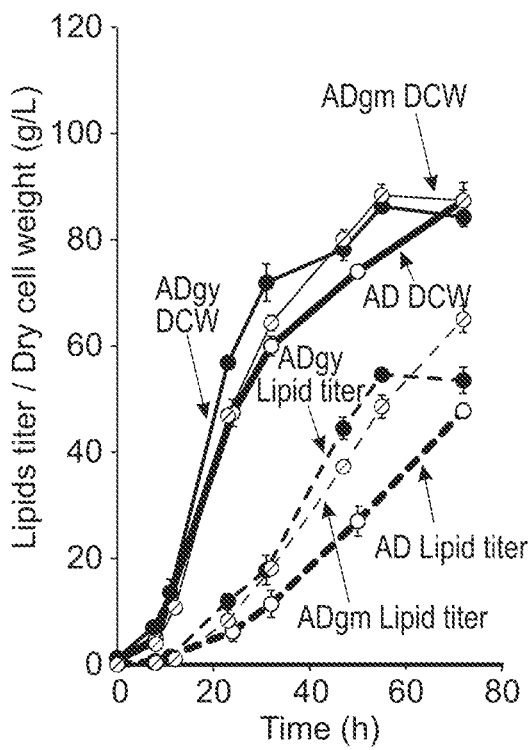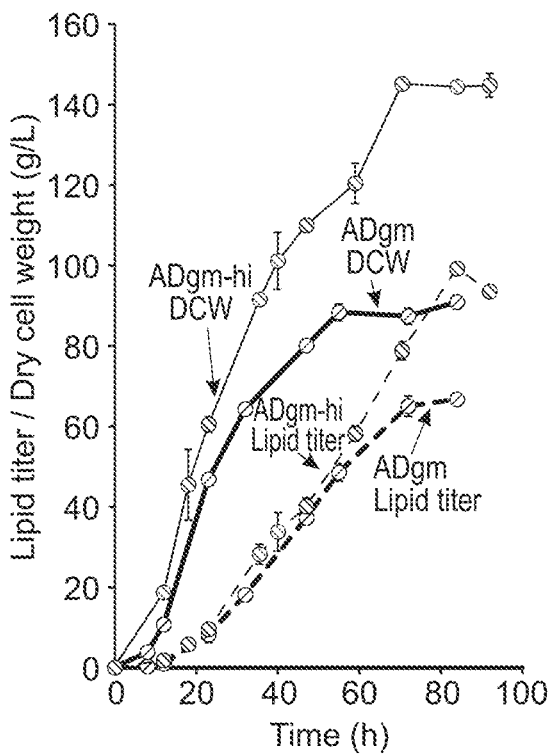
FIG. 5A
FIG. 5B
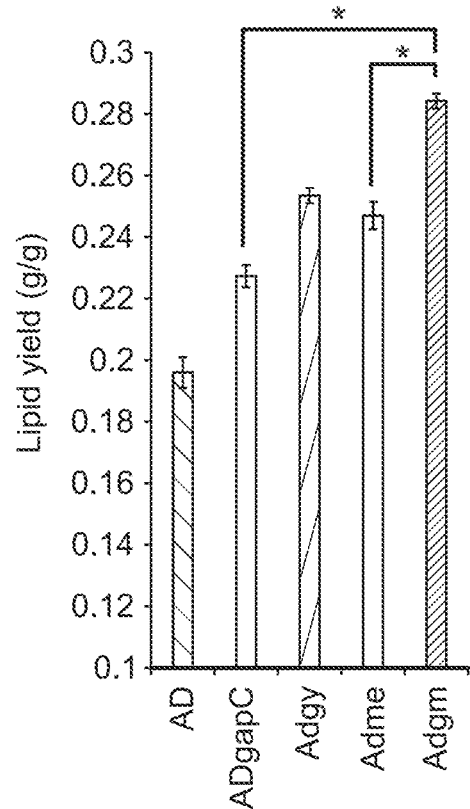
FIG. 5C

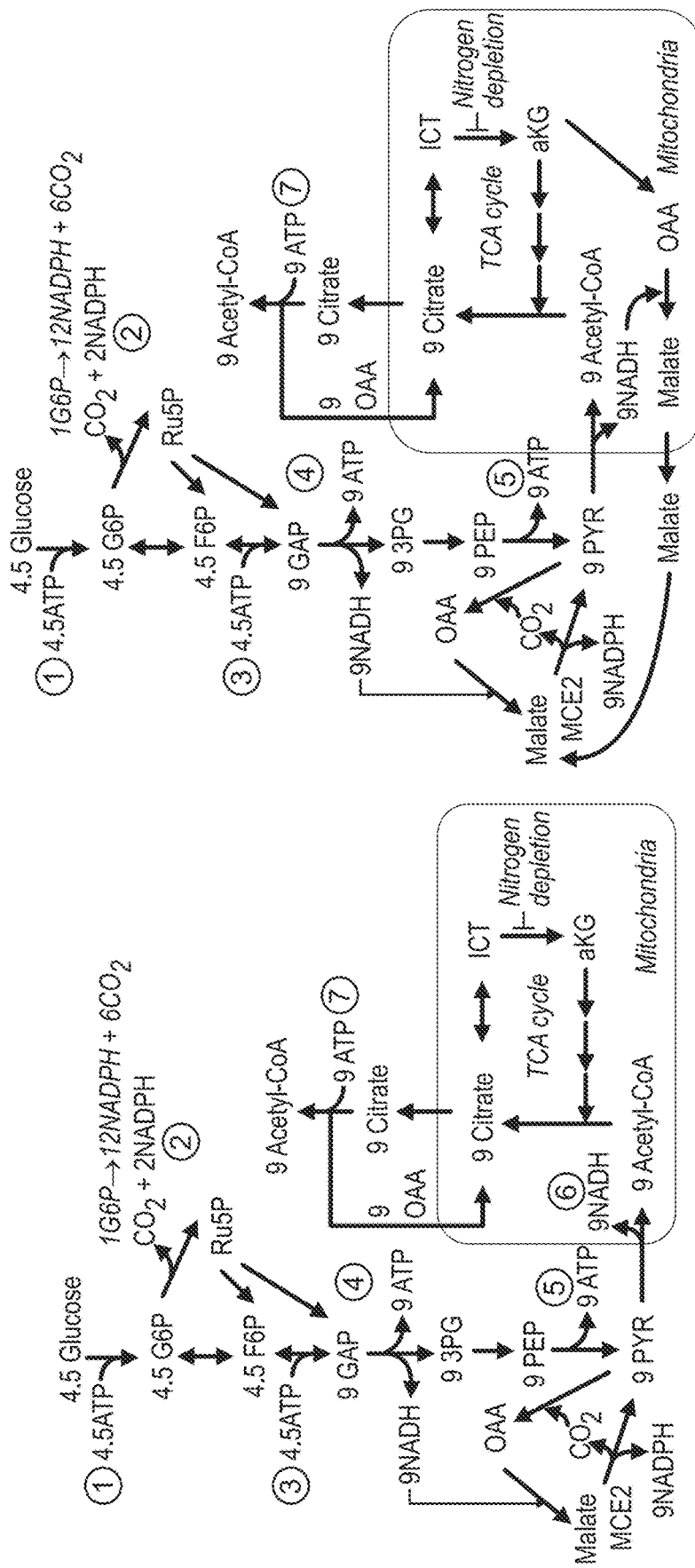

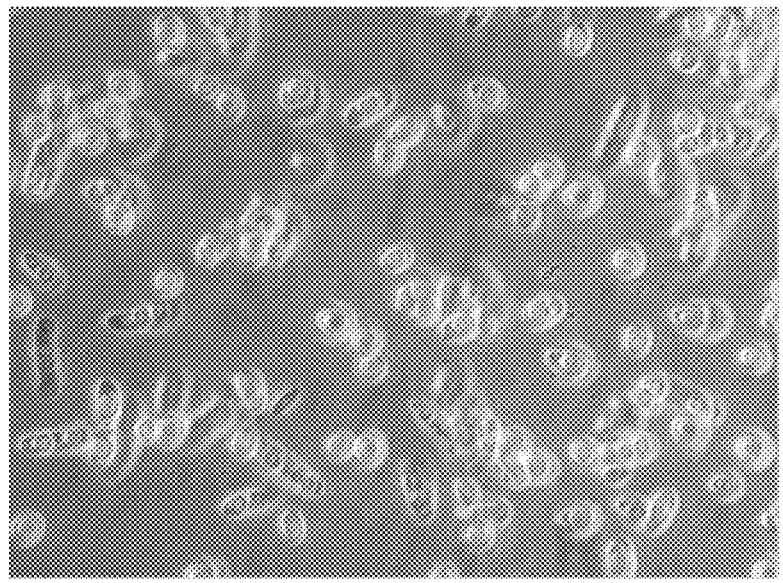
Strain AD, 72 h
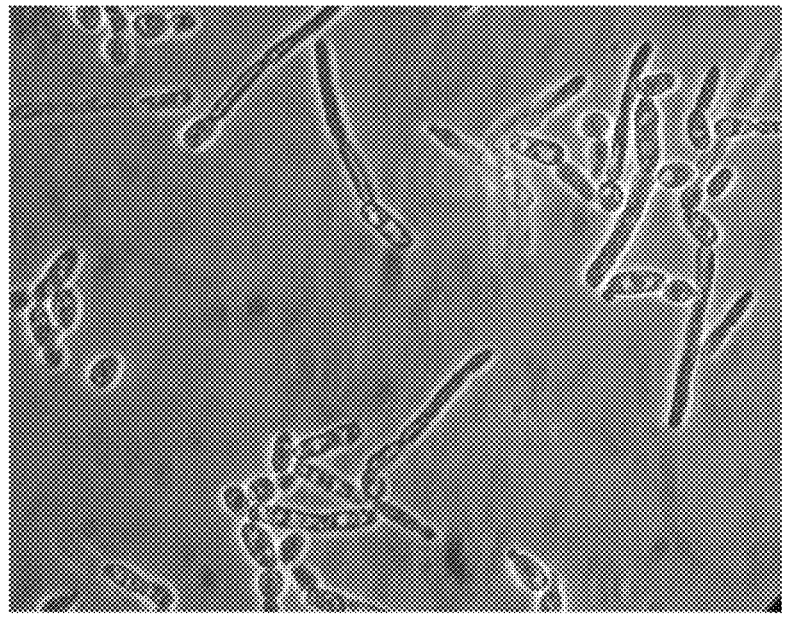
Strain ADpntAB, 72 h
FIG. 9

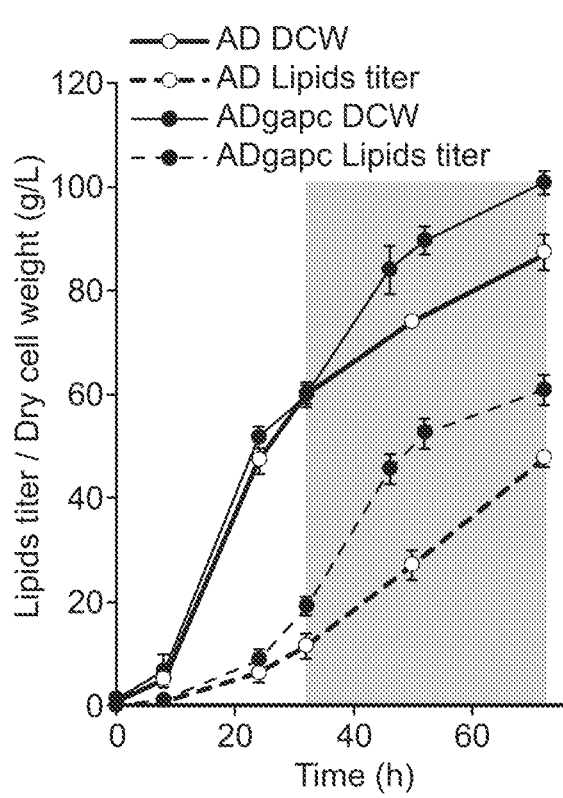
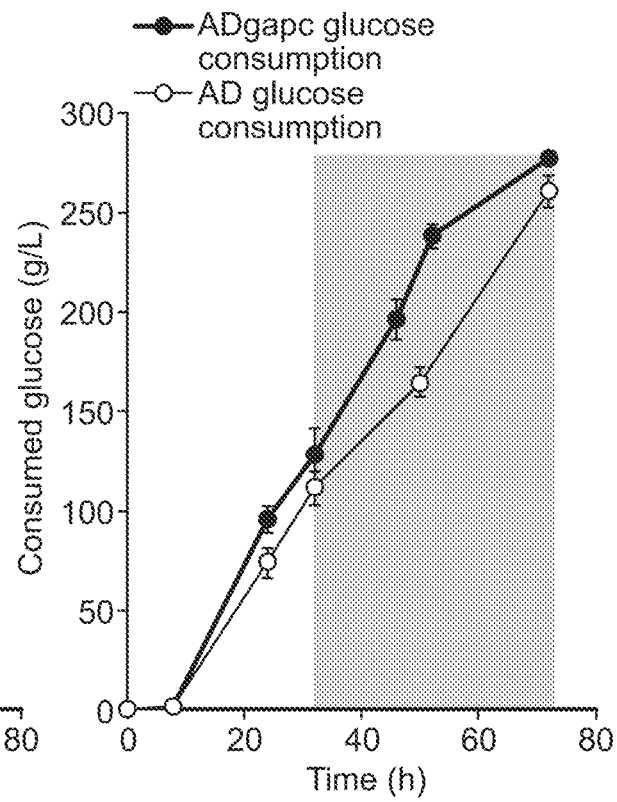
FIG. 11A  FIG. 11B
|  | AD | ADgapc |
|---|---|---|
| Titer (g/L) | 47.8 ± 1.4 | 63.2 ± 2.4 |
| Lipid content | 54.7% ± 1.0% | 62.4% ± 2.0% |
| Process yield (g-FAME/g-Glucose) | 0.184 ± 0.003 | 0.229 ± 0.007 |
| Maximum yield of FAME (g-FAME/g-Glucose) | 0.244 ± 0.009 | 0.291 ± 0.005 |
| Maximum Yield of total fatty acids (g FA/g Glucose) | 0.234 ± 0.009 | 0.279 ± 0.005 |
FIG. 11C

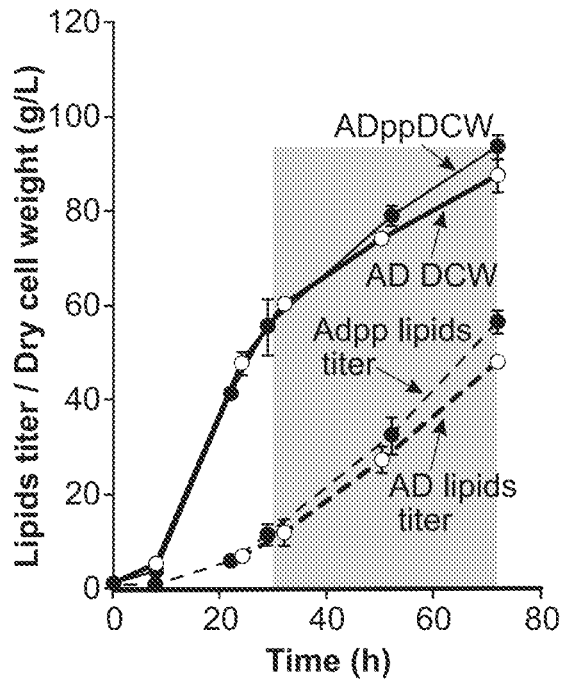
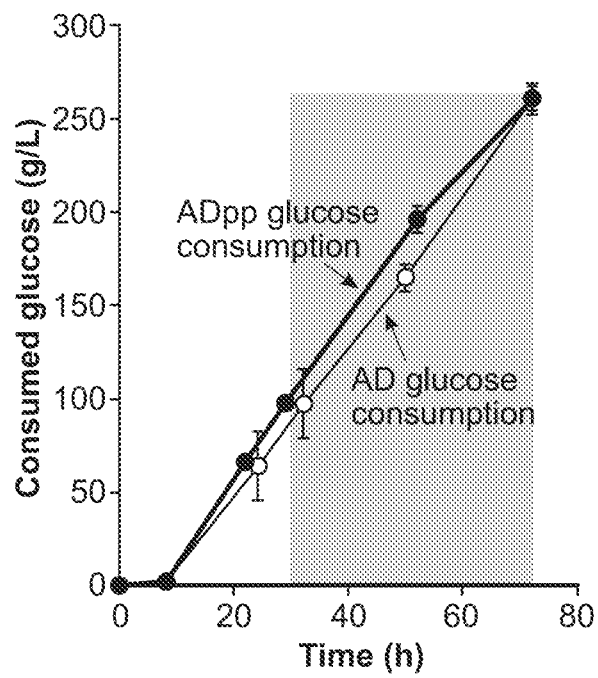
FIG. 13A  FIG. 13B
|  | AD | ADpp |
|---|---|---|
| Titer (g/L) | 47.8 ± 1.4 | 56.2 ± 0.7 |
| Lipid content | 54.7% ± 1.0% | 60.2% ± 2.3% |
| Process yield (g-FAME/g-Glucose) | 0.184 ± 0.003 | 0.216 ± 0.003 |
| Maximum yield of FAME (g-FAME/g-Glucose) | 0.244 ± 0.009 | 0.276 ± 0.007 |
| Maximum Yield of total fatty acids (g FA/g Glucose) | 0.234 ± 0.009 | 0.261 ± 0.007 |
FIG. 13C

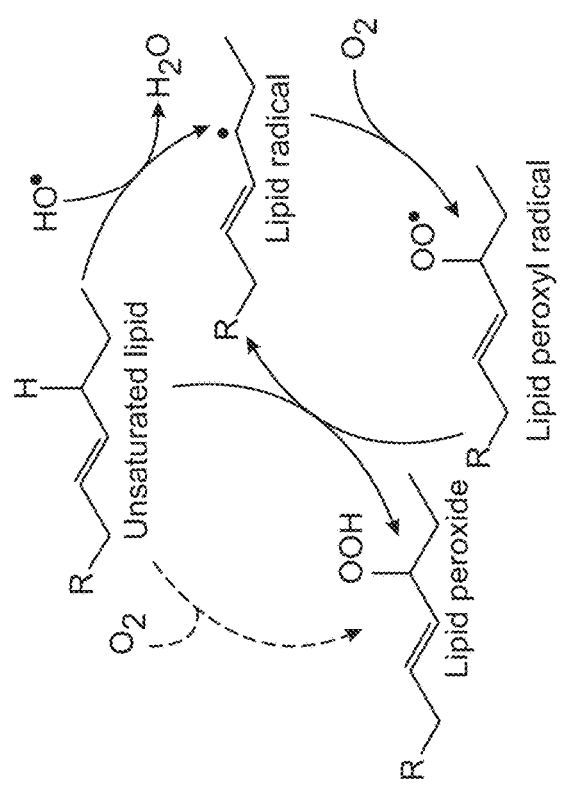
FIG. 18B
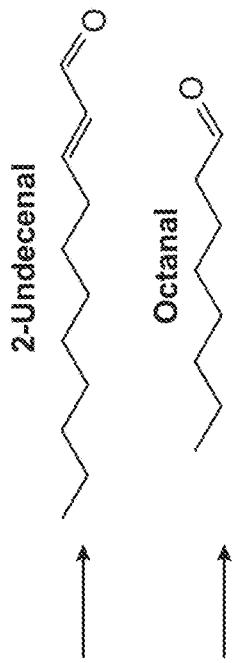
FIG. 18C
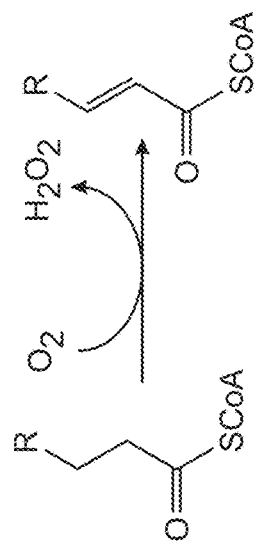
FIG. 18A
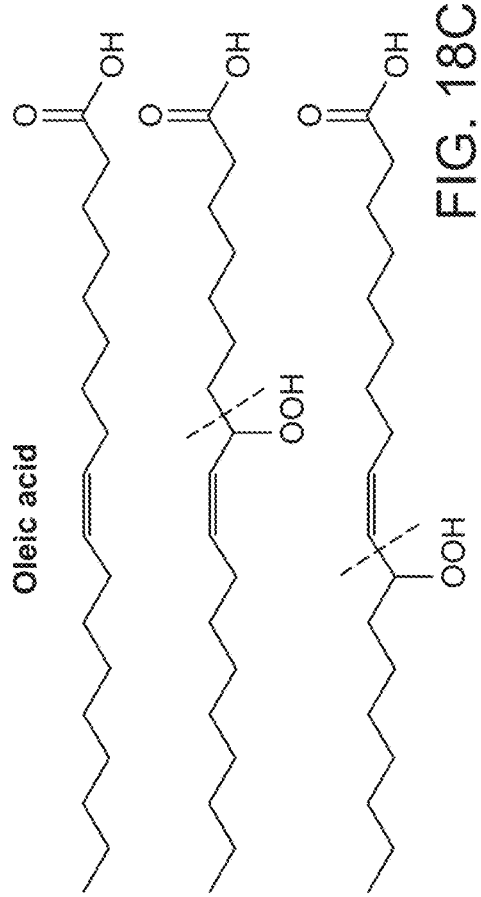

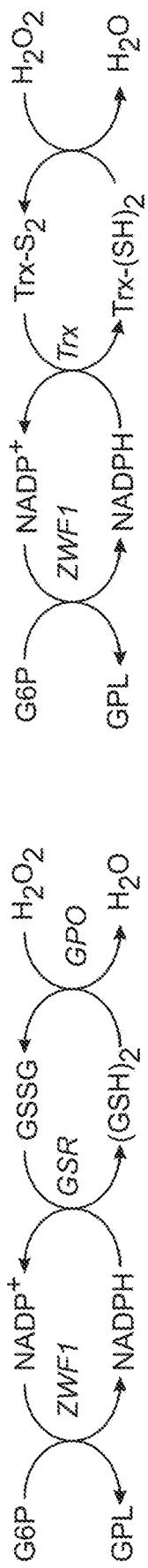
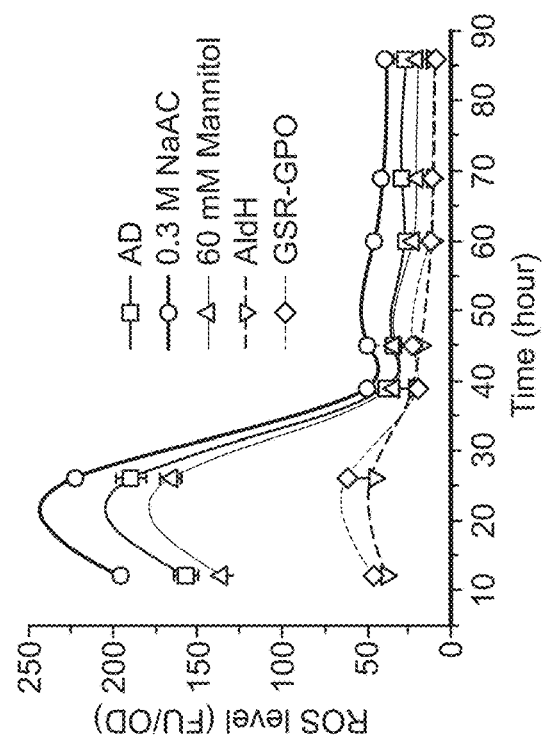
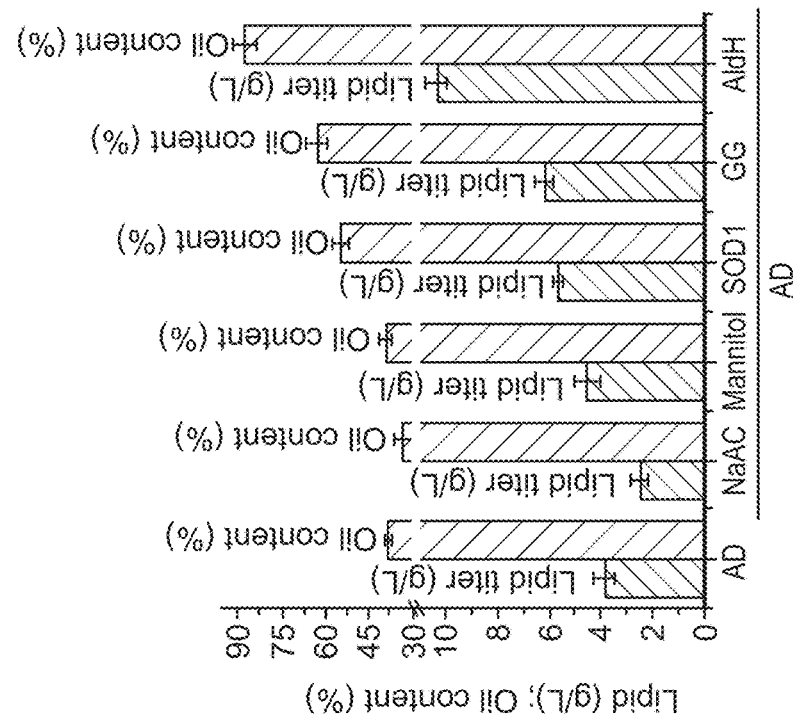
FIG. 19A
FIG. 19B
FIG. 19C
FIG. 19D

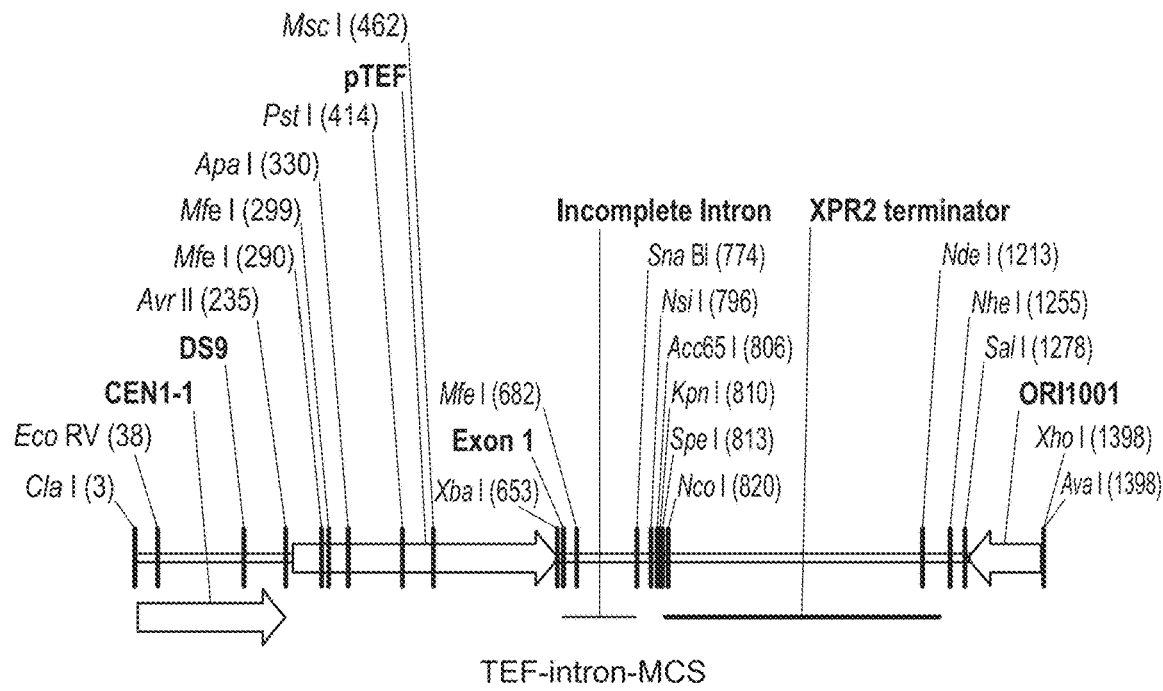

TEF-intron-MCS
1402 bp atcgatgcttttcgtagataatggaatacaaatggatatccagagtatacacatggatagtatacact
gacacgacaattctgtatctctttatgttaactactgtgaggcgttaaatagagcttgatatataaaa
tgttacatttcacagtctgaacttttgcagattacctaatttggtaagatattaattatgaactgaaa
gttgatggcatccctaaatttgatgaaagcctagggacgacagagaccgggttggcggcgcatttgtg
tcccaaaaaacagcccccaattgccccaattgaccccaaattgacccagtagcgggcccaaccccggcg
agagcccccttctccccacatatcaaacctcccccggttcccacacttgccgttaagggcgtagggta
ctgcagtctggaatctacgcttgttcagactttgtacttgtttctttgtctggccatccgggtaaccc
atgccggacgcaaaatagactactgaaaattttttgctttgtggttgggactttagccaagggtata
aaagaccaccgtccccgaattacctttcctcttcttttctctctctccttgtcaactcacacccgaaa
tcgttaagcatttccttctgagtataagaatcattcaaaTCTAGAATGGTGAGTTTCAGAGGCAGCAG
CAATTGCCACGGGCTTTGAGCACACGGCCGGGTGTGGTCCCATTCCCATCGACACAAGACGCCACGTC
ATCCGACCAGCACTTTTTGCAGTACgtatctacacgcgtgctatgcatctgagtgaggtaccgactag
ttccatggcctgtccccacgttgccggtcttgcctcctactacctgtccatcaatgacgaggttctca
cccctgcccaggtcgaggctcttattactgagtccaacaccggtgttcttcccaccaccaacctcaag
ggctctcccaacgctgttgcctacaacggtgttggcatttaggcaattaacagatagtttgccggtga
taattctcttaacctcccacactcctttgacataacgatttatgtaacgaaactgaaatttgaccaga
tattgttgtaaatagaaaatctggcttgtaggtggcaaaatgcggcgtctttgttcatcaattccctc
tgtgactactcgtcatccctttatgttcgactgtcgtatttcttattttccatacatatgcaagtgag
atgcccgtgtccgttatcaaatctagttagctagcgagacaataacggaggagtcgactatgtctgat
aaaaggatgtaacataggcaagctgctcgtgagtgttgagtacgaaccttagatccaaatcacccgca
cccacggatatacttgcttgaatatacagtagtatgctcgag

FIG. 29

ISOLATED OLEAGINOUS YEAST

RELATED APPLICATION

This application claims the benefit under 35 U.S.C. § 119(e) of U.S. Provisional Application Ser. No. 62/243,824, entitled "STRAIN AND BIOPROCESS ENGINEERING FOR HIGH LIPID PRODUCTION," filed on Oct. 20, 2015, the entire content of which is herein incorporated by reference.

GOVERNMENT SUPPORT

This invention was made with Government support under Grant No. DE-SC0008744 awarded by the U.S. Department of Energy. The Government has certain rights in the invention.

BACKGROUND

Sustainably produced biofuels are an alternative to fossil fuels and may help to alleviate the depletion of easily accessible fossil fuel stocks while avoiding fossil fuel-associated pollution and greenhouse gas emission, thus satisfying a rising demand for affordable energy in a sustainable way. The development of methods and oil-producing organisms suitable for the efficient conversion of carbon sources to lipids is important for widespread implementation of microbial biofuel production.

SUMMARY

Microbial oil production by heterotrophic organisms is a most promising path for the cost-effective production of biofuels from renewable resources provided high conversion yields can be achieved. The key to cost-effective microbial oil production from renewable feedstocks is a high carbohydrate to oil conversion yield. Metabolic engineering has emerged as the enabling technology applied to this end and numerous examples exist of successful pathway engineering that markedly improved the performance of microbial biocatalysts in the synthesis of chemical, pharmaceutical and fuel products.

According to one aspect, isolated oleaginous yeast cells are provided. The isolated oleaginous yeast cells include (1) one or more synthetic metabolic pathway(s) that recycle(s) cytosolic NADH to cytosolic NADPH via genetic modifications including (a) increasing expression of a $NADP^+$-dependent malic enzyme gene product; and/or (b) increases expression of a $NADP^+$-dependent glyceraldehyde-3-phosphate dehydrogenase gene product;

(2) one or more synthetic metabolic pathway(s) that recycle(s) cytosolic NADH to cytosolic acetyl-CoA via genetic modification that increases expression of a phosphoketolase gene product and a phosphotransacetylase gene product;

(3) one or more synthetic metabolic pathway(s) that recycle(s) mitochondrial NADH to cytosolic NADPH via genetic modifications including (a) increases expression of a pyruvate formate lyase gene product, pyruvate formate lyase activating enzyme product and a $NADP^+$-dependent formate dehydrogenase gene product; and/or (b) increases expression of a $NADP^+$-dependent malic enzyme gene product and a cytosolic pyruvate dehydrogenase gene products; (c) increases expression of a $NAD^+$-dependent pyruvate dehydrogenase gene product;

(4) one or more synthetic metabolic pathway(s) that enrich(es) the cofactor NADP via genetic modification that increases expression of a $NAD^+/NADH$ kinase gene product; or (5) a combination of any of the one or more synthetic metabolic pathway(s) of (1), (2), (3) and (4).

In some embodiments, the cell includes genetic modifications that increase expression of an acetyl-CoA carboxylase gene product, and/or a diacylglyceride acyltransferase gene product.

According to another aspect, isolated oleaginous yeast cells are provided. The isolated oleaginous yeast cells include (1) one or more synthetic metabolic pathway(s) that remove(s) toxic aldehyde species via genetic modifications including increasing the expression of an aldehyde dehydrogenase gene product (AldH);

(2) one or more synthetic metabolic pathway(s) that remove(s) reactive oxygen species via genetic modifications including increased expression of ROS-scavenging pathways including (a) a glutathione disulfide reductase (GSR) and (b) a glutathione peroxidase (GPO) gene product, or (c) a thioredoxin reductase (Trx) gene product, or (d) a superoxide dismutase gene product (SOD1);

(3) one or more synthetic metabolic pathway(s) that provide(s) additional NADPH to complete the activity of glutathione disulfide reductase (GSR), glutathione peroxidase (GPO) and thioredoxin reductase (Trx) via genetic modifications including increased expression of a glucose-6-phosphate dehydrogenase (ZWF1) gene product; or (4) a combination of any of the one or more synthetic metabolic pathway(s) of (1), (2), and (3).

In some embodiments, the cell includes genetic modifications that increase expression of an acetyl-CoA carboxylase gene product and/or a diacylglyceride acyltransferase gene product.

In some embodiments, the acetyl-CoA carboxylase gene product is an ACC1 gene product of *Yarrowia lipolytica*; optionally the acetyl-CoA carboxylase gene product is encoded by SEQ ID NO: 55.

In some embodiments, the diacylglyceride acyltransferase gene product is a DGA1 gene product of *Yarrowia lipolytica*; optionally the diacylglyceride acyltransferase gene product is encoded by SEQ ID NO: 53.

In some embodiments, the $NADP^+$-dependent malic enzyme gene product is a MCE2 gene product of *Mucor circinelloides*; optionally the $NADP^+$-dependent malic enzyme gene product is encoded by SEQ ID NO: 1.

In some embodiments, the $NADP^+$- dependent glyceraldehyde-3-phosphate dehydrogenase gene product is a GapC gene product of *Clostridium acetobutylicum* or a GPD1 gene product of *Kluyveromyces lactis*; optionally the glyceraldehyde-3-phosphate dehydrogenase gene product is encoded by SEQ ID NO: 3 or SEQ ID NO: 5.

In some embodiments, the aldehyde dehydrogenase gene product is an AldH gene product of *E. coli*; optionally the aldehyde dehydrogenase gene product is encoded by SEQ ID NO: 29.

In some embodiments, the aldehyde dehydrogenase gene product is an YALI0C03025p gene product of *Y. lipolytica*; optionally the aldehyde dehydrogenase gene product is encoded by SEQ ID NO: 31.

In some embodiments, the aldehyde dehydrogenase gene product is an YALI0F04444p gene product of *Y. lipolytica*; optionally the aldehyde dehydrogenase gene product is encoded by SEQ ID NO: 33.

In some embodiments, the aldehyde dehydrogenase gene product is an YALI0E00264p gene product of *Y. lipolytica*; optionally the aldehyde dehydrogenase gene product is encoded by SEQ ID NO: 35.

In some embodiments, the aldehyde dehydrogenase gene product is an YALI0D07942p gene product of *Y. lipolytica*; optionally the aldehyde dehydrogenase gene product is encoded by SEQ ID NO: 37.

In some embodiments, the glutathione disulfide reductase gene product is a GSR gene product of *Yarrowia lipolytica*; optionally the glutathione disulfide reductase gene product is encoded by SEQ ID NO: 39.

In some embodiments, the glutathione peroxidase gene product is a GPO gene product of *Yarrowia lipolytica*; optionally the glutathione peroxidase gene product is encoded by SEQ ID NO: 41.

In some embodiments, the superoxide dismutase gene product is an SOD1 gene product of *Yarrowia lipolytica*; optionally the superoxide dismutase gene product is encoded by SEQ ID NO: 45.

In some embodiments, the thioredoxin reductase gene product is a TRX gene product of *Yarrowia lipolytica*; optionally the thioredoxin reductase gene product is encoded by SEQ ID NO: 43.

In some embodiments, the glucose-6-phosphate dehydrogenase gene product is a ZWF1 gene product of *Saccharomyces cerevisiae*; optionally the glucose-6-phosphate dehydrogenase gene product is encoded by SEQ ID NO: 47.

In some embodiments, the glucose-6-phosphate dehydrogenase gene product is a ZWF1 gene product (YALI0E22649g) of *Yarrowia lipolytica*; optionally the glucose-6-phosphate dehydrogenase gene product is encoded by SEQ ID NO: 49.

In some embodiments, the NADP specific isocitrate dehydrogenase gene product is an IDP2 gene product (YALI0F04095g) of *Yarrowia lipolytica*; optionally the NADP specific isocitrate dehydrogenase gene product is encoded by SEQ ID NO: 51.

In some embodiments, the phosphoketolase gene product is a PK gene product of *Leuconostoc mesenteroides*; optionally the phosphoketolase gene product is encoded by SEQ ID NO: 7.

In some embodiments, the phosphotransacetylase gene product is a PTA gene product of *Clostridium kluyveri*; optionally the Phosphotransacetylase gene product is encoded by SEQ ID NO: 9.

In some embodiments, the pyruvate formate lyase gene product is a PflB gene product of *Escherichia coli*; optionally the pyruvate formate lyase gene product is encoded by SEQ ID NO: 11.

In some embodiments, the pyruvate formate lyase activating enzyme gene product is a PflA gene product of *Escherichia coli*; optionally the pyruvate formate lyase activating enzyme gene product is encoded by SEQ ID NO: 13.

In some embodiments, the NADP$^+$-dependent formate dehydrogenase gene product is a FDH gene product of *Burkholderia stabilis*; optionally the NADP$^+$-dependent formate dehydrogenase gene product is encoded by SEQ ID NO: 15.

In some embodiments, the NAD$^+$-dependent pyruvate dehydrogenase comprises an E1 pyruvate dehydrogenase (AceE) gene product of *Escherichia coli*, an E2 dihydrolipoyl transacetylase (AceF) gene product of *Escherichia coli* and an E3 dihydrolipoyl dehydrogenase (Lpd) gene product of *Escherichia coli*; optionally the E1 pyruvate dehydrogenase gene product, the E2 dihydrolipoyl transacetylase gene product and the E3 dihydrolipoyl dehydrogenase gene product are encoded by SEQ ID NO: 17, SEQ ID NO: 19 and SEQ ID NO: 21, respectively.

In some embodiments, the NADP$^+$-dependent pyruvate dehydrogenase including three subunits: an E1 pyruvate dehydrogenase gene product of *Escherichia coli*, an E2 dihydrolipoyl transacetylase gene product of *Escherichia coli*, and a mutant of an E3 dihydrolipoyl transacetylase gene product of *Escherichia coli*; optionally the mutant of E3 dihydrolipoyl dehydrogenase gene product is encoded by SEQ ID NO: 23.

In some embodiments, the NAD$^+$/NADH kinase gene product is a YEF1 or POS5 gene product from *Yarrowia lipolytica*; optionally the NAD$^+$/NADH kinase gene product is encoded by SEQ ID NO: 27 or SEQ ID NO: 25.

In some embodiments, the genetic modification includes a nucleic acid construct that increases the expression of the gene products, the nucleic acid construct. The nucleic acid construct includes (a) an expression cassette comprising a nucleic acid sequence encoding the gene products under the control of a suitable homologous or heterologous promoter, and/or (b) a nucleic acid sequence that modulates the level of expression of the gene products when inserted into the genome of the cell. In some embodiments, the promoter is an inducible or a constitutive promoter. In some embodiments, the promoter is a TEF promoter or a *Yarrowia lipolytica* glyceraldehyde-3-phosphate dehydrogenase promoter. In some embodiments, the nucleic acid construct further comprises an intron. In some embodiments, the intron is downstream of the transcription initiation site, optionally wherein the intron is within the nucleic acid sequence encoding the gene product.

In some embodiments, the nucleic acid construct inhibits or disrupts the natural regulation of a native gene encoding the gene product resulting in overexpression of the native gene. In some embodiments, inhibition or disruption of the natural regulation of the native gene is mediated by deletion, disruption, mutation and/or substitution of a regulatory region, or a part of a regulatory region regulating expression of the gene.

In some embodiments, the gene product is a transcript or a protein.

In some embodiments, the nucleic acid construct is inserted into the genome of the cell.

In some embodiments, the increased expression of the gene product confers a phenotype of increased lipid titer, increased lipid productivity and/or increased lipid yield. In some embodiments, the lipid titer is at least 25 g/L. In some embodiments, the lipid titer is 25-150 g/L. In some embodiments, the lipid productivity is at least 0.25 g/L/h. In some embodiments, the lipid productivity is 0.25 g/L/h to 1.5 g/L/h. In some embodiments, the lipid yield is at least 0.220 g-fatty acid methyl esters/g-glucose. In some embodiments, the lipid yield is 0.220 g-fatty acid methyl esters/g-glucose to 0.280 g-fatty acid methyl esters/g-glucose.

In some embodiments, the cell is a *Y. lipolytica* cell.

According to another aspect, cultures comprising the foregoing oleaginous yeast cells are provided. In some embodiments, the cultures further include a carbon source. In some embodiments, the carbon source comprises a fermentable sugar. In some embodiments, the fermentable sugar is a C6 sugar. In some embodiments, the carbon source comprises glucose. In some embodiments, the carbon source comprises glycerol.

In some embodiments, the cultures exhibit a lipid titer of 25 g/L to 150 g/L. In some embodiments, the cultures exhibit a lipid productivity of 0.25 g/L/h to 1.5 g/L/h. In some embodiments, the cultures exhibit a lipid yield of 0.220 g-fatty acid methyl esters/g-glucose to 0.280 g-fatty acid methyl esters/g-glucose.

According to another aspect, methods are provided that include culturing any of the foregoing isolated oleaginous yeast cells with a carbon source. In some embodiments, the carbon source comprises a fermentable sugar. In some embodiments, the carbon source comprises glucose. In some embodiments, the carbon source comprises glycerol.

In some embodiments, the culturing includes incubating the isolated oleaginous yeast cell in a bioreactor. In some embodiments, the culturing is performed in a fed batch process or a continuous process. In some embodiments, the methods further include adding an additional amount of the carbon source or an amount of an additional carbon source one or more times during the culturing. In some embodiments, the carbon source or the additional carbon source is added by step-wise exponential addition. In some embodiments, the culture has less than 30 g/L citrate.

In some embodiments, the methods further include titrating the concentration of nitrogen source, for example ammonium sulfate in the starting medium.

The subject matter of this application may involve, in some cases, interrelated products, alternative solutions to a particular problem, and/or a plurality of different uses of a single system or article.

Other advantages, features, and uses will be apparent from the detailed description of certain non-limiting embodiments, the drawings, and the claims.

BRIEF DESCRIPTION OF THE DRAWINGS

FIG. 1A represents central carbon metabolic pathways involved in supplying cytosolic acetyl-CoA (EMP, part of TCA cycle) and NADPH (pentose phosphate pathway) from glucose in support of lipogenesis. Different from *S. cerevisiae*, with sugar carbon sources cytosolic acetyl-CoA is exclusively synthesized from citrate in a reaction catalyzed by ACL. Under nitrogen starvation conditions, metabolic flux is channeled into the citrate node due to the shut-down of the TCA cycle by inactivation of isocitrate dehydrogenase. FIG. 1B depicts biosynthesis of fatty acids in *Y. lipolytica*, as exemplified using stearic acid. Formation of SA is an energy intensive process, requiring 1 acetyl-CoA, 8 malonyl-CoA and 16 NADPH to afford 1 SA.

FIG. 2A depicts the three synthetic pathways allowing direct conversion of NADH.c to NADPH by (i) expression of *E. coli* transhydrogenases; (ii) replacing endogenous ylGPD with NADPH-dependent GAP dehydrogenases; (iii) the installment of the POM cycle via expression of NADPH-dependent malic enzyme. Effects of the individually introduced synthetic pathways on (FIG. 2B) lipid titer and dry cell weight, and on (FIG. 2C) lipid yield of engineered *Y. lipolytica* were measured in shake flask cultures. The best producers ADgapc and ADme were further characterized in 1.5 liter bioreactor experiments. FIG. 2D depicts the time-course profile of lipid accumulation (lipid titer) and cell growth (dry cell weight) of ADgapc and ADme compared to those of control strain AD in fed-batch fermentations. Error bars represent standard deviations in all graphs (some error bars are smaller than the plot symbols). For FIGS. 2B and 2C, n=3; For FIG. 2D, n=2. Error bars, mean±s. d. Statistically significant differences between each engineered *Y. lipolytica* strain and the baseline strain AD were denoted *(P<0.05), **(P<0.01).

FIG. 3A depicts the effects of NOG pathway on lipid titer and cell mass accumulation in shake flask culture. FIG. 3B depicts that in comparison to that of AD, lipid yield of ADpp is elevated significantly in both shake flask culture (S) and fed-batch fermentation (B). FIG. 3C shows the time course performance of AD and ADpp in fed-batch fermentations. For FIGS. 3A and 3B, n=3; For FIG. 3C, n=2. Error bars, mean±s. d., *(P<0.05), **(P<0.01).

FIGS. 4A-4C. Further improvement of lipids yields via increasing competitiveness of the synthetic pathways. FIG. 4A illustrates the three synthetic pathways, including NADPH-dependent GAPD (dashed arrows), POM cycle (checker filled arrows), and NOG pathway (dotted arrows), that successfully contributed to yield improvement. FIG. 4B depicts lipid titer and dry cell weight, and FIG. 4C depicts lipid yield of engineered *Y. lipolytica* strains ADutr, ADyef and ADpos5 that respectively expressed NADH/NAD+ kinases—ylUTR, ylYEF and ylPOS5, ADgapc2 and ADgg constructed via overexpression of NADP+-dependent GAPDs-GapC and GPD1, ADgy collectively expressing GapC and ylYEF1 and ADgm with both GapC and activated POM cycle. While strengthening the synthetic pathways via overexpression of the committed enzymes (ADgapc2 and ADgg) were demonstrated to be ineffective, enrichment of the intracellular pool of cofactor NADP+(ADyef and ADgy), and combination of two parallel synthetic pathways (ADgm) led to significant lipid yield improvement. For FIGS. 4B and 4C, n=3. Error bars, mean±s. d. *(P<0.05), **(P<0.01).

FIGS. 5A-5C. Fed-batch cultivation of engineered *Y. lipolytica* ADgy and ADme. FIG. 5A shows time course profiles of cell growth and lipid production of ADgy and ADgm in comparison to those of AD under the same fermentation conditions. FIG. 5B depicts optimization of the fed-batch fermentation by increasing nitrogen in the form of ammonium two-fold. FIG. 5C shows the lipid yields obtained in ADgy and ADgm compared to those obtained using baseline strain AD and intermediate strains ADgapc and ADme. For FIGS. 5A, 5B and 5C, n=2. Error bars, mean±s. d., *(P<0.05).

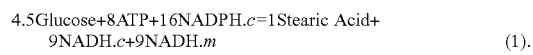

Figure 1A:
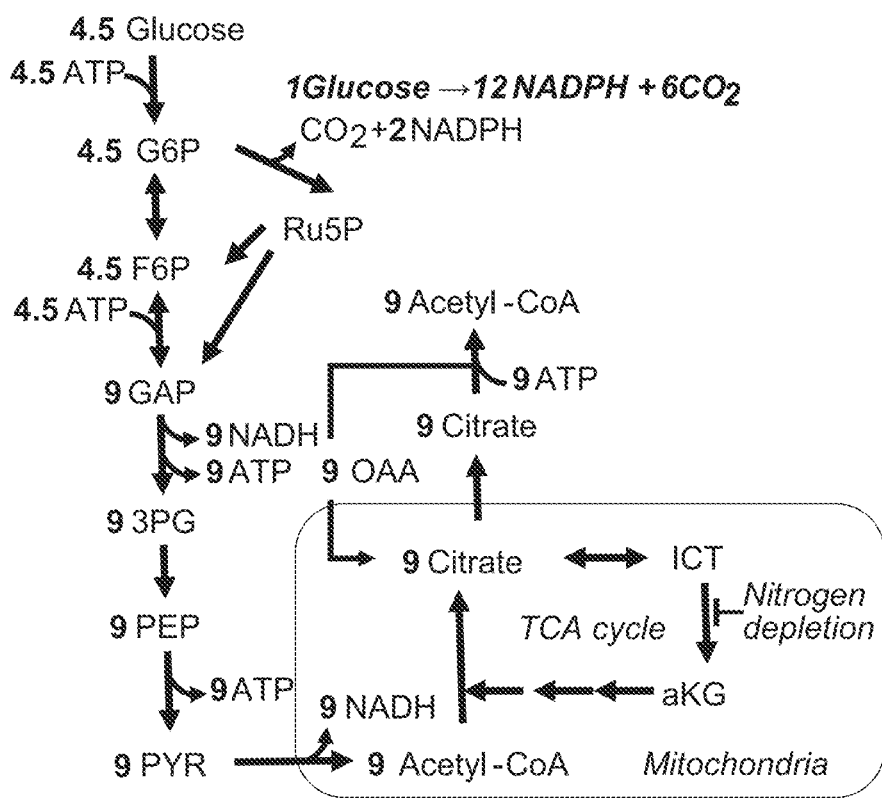
FIGS. 1A and 1B. Overall stoichiometry of de novo fatty acid biosynthesis from glucose in *Y. lipolytica* under nitrogen starvation conditions.

$$4.5 \text{Glucose} + 8\text{ATP} + 16\text{NADPH}.c = 1 \text{Stearic Acid} + 9\text{NADH}.c + 9\text{NADH}.m \quad (1).$$

Due to the higher energy density of SA in comparison to that of glucose, additional glucose has to be anabolized to generate energy cofactors, in particular, ATP and NADPH to support the fatty acid synthesis. ATPs are generated through complete oxidation of glucose to carbon dioxide with theoretical maximal depicted in equation S2 assuming maximum efficiency of ATP production shown in equation S3 and S4:

$$1 \text{Glucose} \rightarrow 32 \text{ATP} \quad (S2).$$

$$1\text{NADH}.m \sim 2.5\text{ATP}(S3); 1\text{NADH}.c \sim 1.5\text{ATP} \quad (S4).$$

Moreover, pentose phosphate pathway has been demonstrated to be sufficient to supply the NADPH for fatty acid biosynthesis in *Y. lipolytica*[48] with the stoichiometry shown in equation S5:

$$1 \text{Glucose} + 1 \text{ATP} \rightarrow 12 \text{NADPH} + 6 CO_2 \tag{S5}$$

Combining equations S1-S5 allows simplification of S1 to equation S6, which is the basis for the theoretical lipid yield (YL) of wild type *Y. lipolytica* of 0.271 g-SA/g-Glucose:

$$5.83 \text{Glucose} \rightarrow 1 \text{Stearic Acid} + 28 \text{ATP} \tag{S6}$$

When one assumes that NADH can be directly converted to NADPH without any energy penalty, sufficient NADPH for lipid synthesis is provided by the EMP and TCA Cycle, PPP flux is unnecessary, and equation (1) becomes equation S7. Combination of equations S7 with S2 and S3 affords equation S8, and therefore the YL is elevated to 0.344 g-SA/g-glucose:

$$4.5 \text{Glucose} + 8 \text{ATP} = 1 \text{Stearic Acid} + 2 NADH.m \tag{S7}$$

$$4.59 \text{Glucose} = 1 \text{Stearic Acid} \tag{S8}$$

Figure 7A:
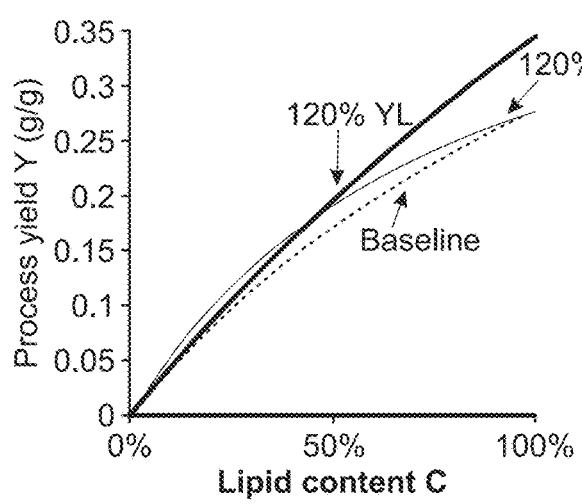
Figure 7B:
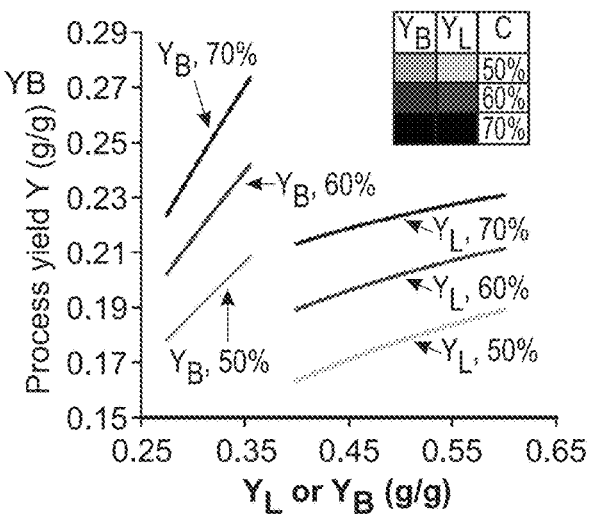

FIGS. 7A-7D. In silico mathematical optimization of Y by varying the three parameters-YB, YL and C. FIG. 7A depicts process yield Y as functions of lipid content C for three sets of YL and YB: baseline (YL, 0.271 g/g, YB, 0.55 g/g; 120% YL (YL, 0.325 g/g, YB, 0.55 g/g; 120% YB (YL, 0.271 g/g, YB, 0.66 g/g). FIG. 7B shows process yield as a function of the lipid yield YL and non-lipid biomass yield YB for three different lipid content C=50%, 60% and 70% (as indicated by the color intensity of the heat map). Single-point sensitivity tornado charts for (FIG. 7C) process yield Y with C at the baseline of 50% and (FIG. 7D) process yield Y with C at its baseline of 70%.

Figures 8A, 8B:
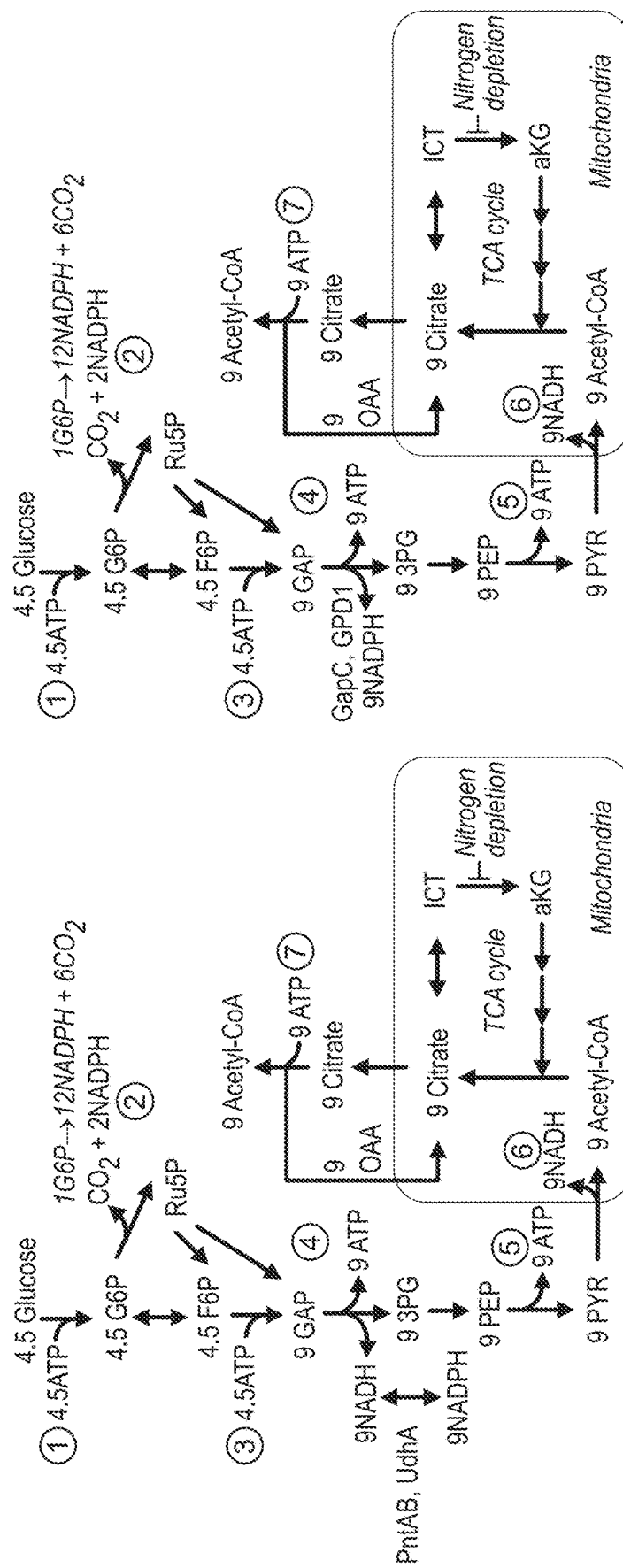

FIGS. 8A-8C. Central carbon and engineered synthetic networks used to convert cytosolic NADH equivalents to NADPH. Three strategies presented would allow, in the cytosol of a yeast cell, FIG. 8A depicts formation of NADPH from NADH directly through heterologous expression of *E. coli* transhydrogenases PntAB and/or UdhA, FIG. 8B depicts generation of NADPH via introduction of NADP+-dependent glyceraldehyde-3-phosphate dehydrogenases, FIG. 8C shows regeneration of NADPH by the activation of pyruvate-oxaloacetate-malate (POM) cycle. Ideally, if each synthetic pathway operates at its own maximum efficiency, all 9 cytosolic NADH can be replaced with NADPH:

$$4.5 \text{Glucose} + 8 \text{ATP} + 7 NADPH.c \rightarrow 1 \text{Stearic Acid} + 9 NADH.m \tag{S12}$$

Combining equations S12 with S2-S5 gives equation S13, which is the basis for the theoretical lipid yield (YL) of engineered *Y. lipolytica* (0.311 g-SA/g-Glucose):

$$5.08 \text{Glucose} = 1 \text{Stearic Acid} + 13.9 \text{ATP} \tag{S13}$$

FIG. 8D depicts installation of engineered POM cycle that regenerates NADPH from both cytosolic and mitochondrial NADHs, leading to elevation of YL to 0.329 g-SA/g-glucose (Equation S14).

$$4.81 \text{Glucose} = 1 \text{Stearic Acid} \tag{S14}$$

FIG. 9. Microscopic images of engineered *Y. lipolytica* strain AD and strain ADpntAB expressing the two *E. coli* membrane-bound proteins PntA and PntB. Both strains were cultured in shake flask containing fermentation medium for 72 h before sampling for imaging. Clearly, ADpntAB cells exhibited elongated or filamentous morphology, while most AD cells remained spherical with identifiable lipid bodies (bright) at the centers of individual cells.

Figure 10:
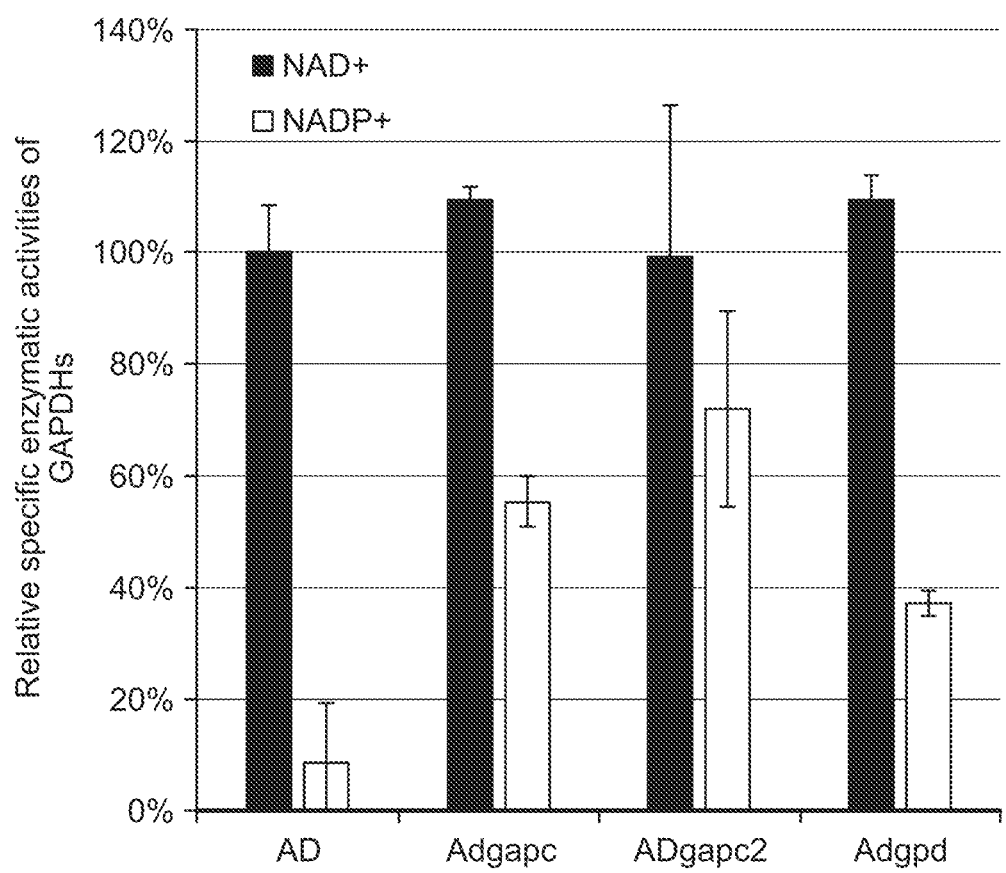

FIG. 10. Specific enzymatic activities of GAPDHs in the presence of NADP+ and NAD+. Whole cell lysates of a series of engineered *Y. lipolytica* strains were prepared from cells harvested at 48 h of shake flask cultures and assayed in vitro with glyceraldehyde-3-phophate in the presence of either NADP+ or NAD+. The total protein concentration of each lysate was determined and the specific activity of GAPDHs are normalized by specific activity of lysate from strain AD in presence of NAD+. Native *Y. lipolytica* GADPH showed cofactor specificity toward NAD+, while almost no activity was detected using NADP+. Introduction of heterologous GAPDHs including GapC from *Clostridium acetobutylicum* and GPD1 from *Kluyveromyces lactis* enables the generation of NADPH from NADP+. Error bars mean±s. d., n=3, biological replicates.

FIGS. 11A-11C. Time course profiles of (FIG. 11A) cell growth and lipid production and (FIG. 11B) glucose consumption of AD and ADgapc in fed-batch fermentations. The fermentation characteristics including lipids titer, lipid content, process yield and maximum FAME and FA yield are shown in FIG. 11C. The maximum yield is the yield calculated by dividing the lipids made during lipid production phase (highlighted in gray in FIG. 11A) by the glucose consumed in the same phase (highlighted in gray in FIG. 11B). The maximum FA yield of ADgapc is higher than the stoichiometric theoretical maximum yield obtained in wild type *Y. lipolytica*. Error bars mean±s. d., n=2, biological replicates.

Figure 12:
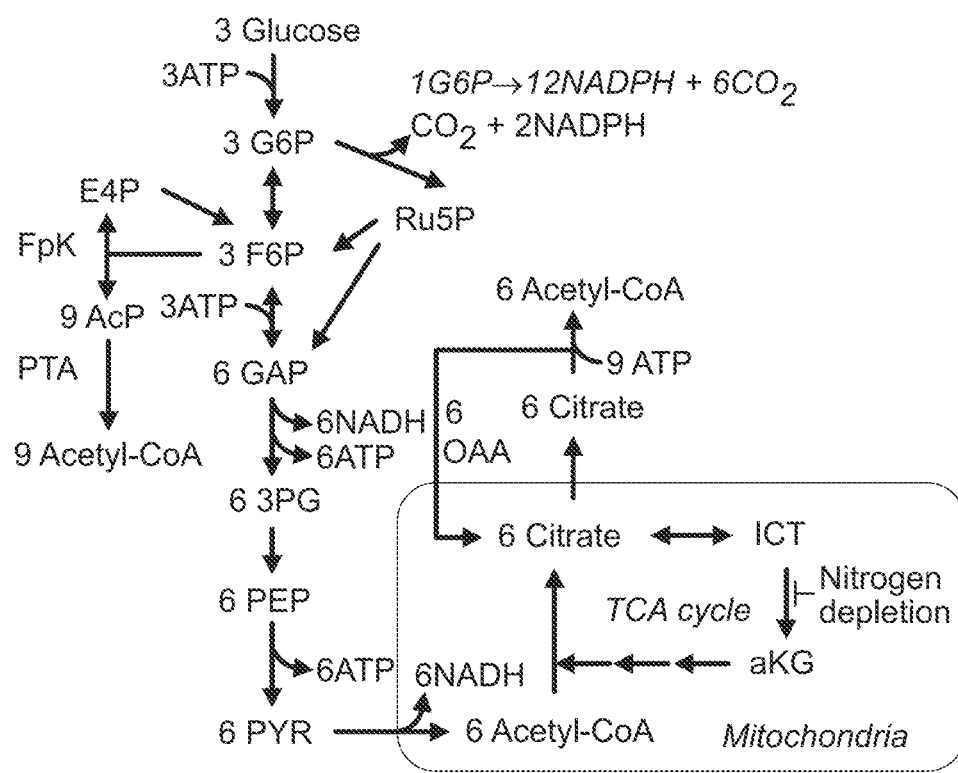

FIG. 12. Illustration of NOG pathway that branches out from the EMP from F6P. Functional reconstitution of NOG pathway would allow complete carbon conversion, leading to the formation of 3 mol acetyl-CoA from 1 mol glucose:

$$1 \text{Glucose} + 1 \text{ATP} \rightarrow 3 \text{Acetyl-CoA} \tag{S14}$$

If one assumes acetyl-CoA in Eq. S1 is exclusively supplied by NOG pathway, while ATP and NADPH are derived from oxidative respiration and pentose phosphate pathway, Eq. S1 can be simplified to Eq. S15:

$$4.72 \text{Glucose} \rightarrow 1 \text{Stearic Acid} \tag{S15}$$

Therefore, the theoretical lipid yield reaches 0.335 g-SA/g-glucose when NOG pathway is working at 100% capacity.

FIGS. 13A-13C. Time course profiles of (FIG. 13A) cell growth and lipid production and (FIG. 13B) glucose consumption of AD and ADpp in fed-batch fermentations. The fermentation characteristics including lipid titer, lipid content, process yield and maximum FAME and FA yield are shown in FIG. 13C. The maximum yields are calculated by dividing the lipids synthesized during lipid production phase (highlighted in gray in FIG. 13A) by the glucose consumed in the same phase (highlighted in gray in FIG. 13B). Error bars mean±s. d., n=2, biological replicates.

Figure 14A:
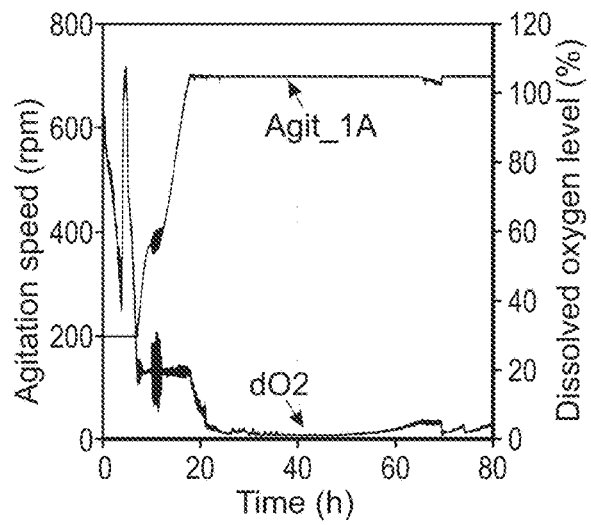
Figure 14B:
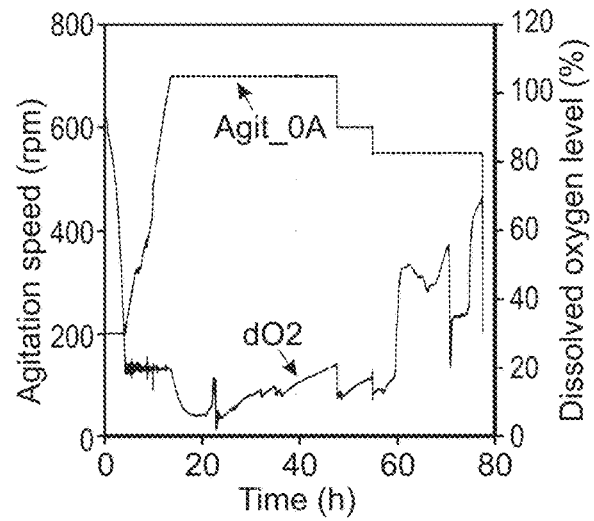
Figure 14C:
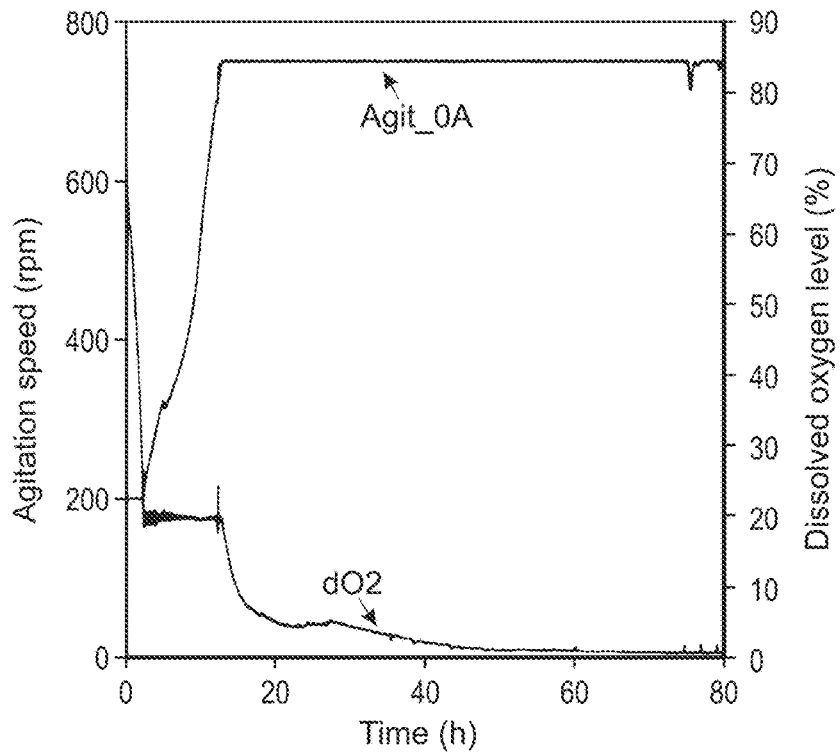

FIGS. 14A-14C. Time course of agitation (Agit_0A) and dissolved oxygen (d02) of fed-batch fermentations of (FIG. 14A) AD, (FIG. 14B) ADgm and (FIG. 14C) ADgm-hi. The maximum agitation speed is 750 rpm and the aeration rate is fixed to 5 vlm. As illustrated in FIG. 14B, the d02 level is gradually increased after 20 h. The spikes in d02 level led to accumulation of byproduct citrate. In comparison, the fermentation of AD features no increase of d02 level throughout the first 60 hours as shown in FIG. 14A. Doubling the initial concentration of ammonium in the starting fermentation medium increased the cell number and recreated the micro-aerobic conditions that prohibit citrate production without significantly compromising the lipid biosynthesis as shown in FIG. 14C.

Figure 15:
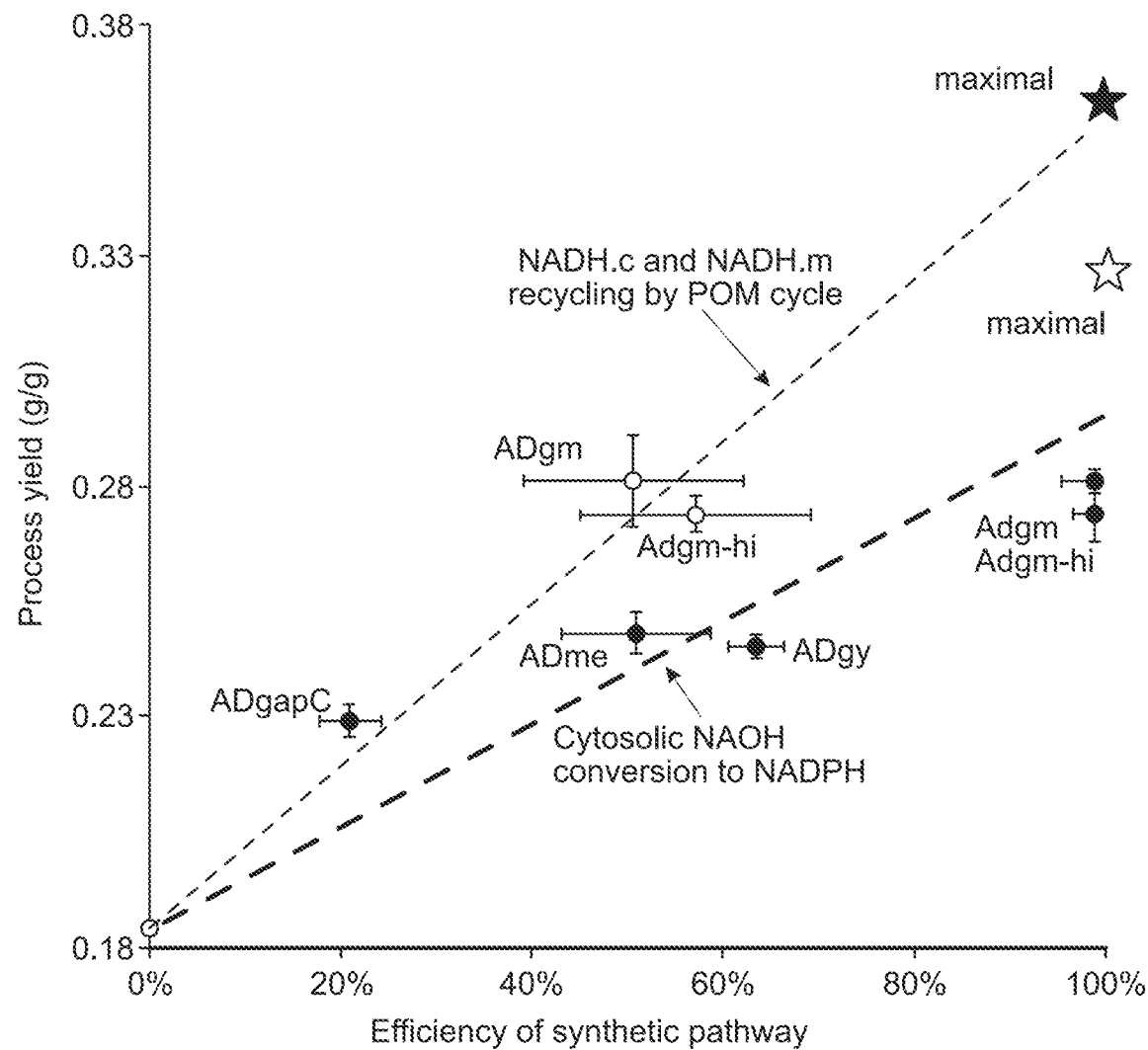

FIG. 15. The process yields of lipids from different engineered *Y. lipolytica* strains are positively correlated with the efficiencies of the introduced synthetic pathways. The measured lipid process yields are plotted against their individual pathway efficiencies when YL=0.311 g/g, representing only cytosolic NADH conversion to NADPH. The trend-line (dash line) was added and the maximum yield represented by a white star. When both NADH.c and NADH.m are recycled by POM cycle, the plot and its trend-line are shown with maximum yield represented by a black star. Error bars mean±s. d., n=2.

Figure 16:
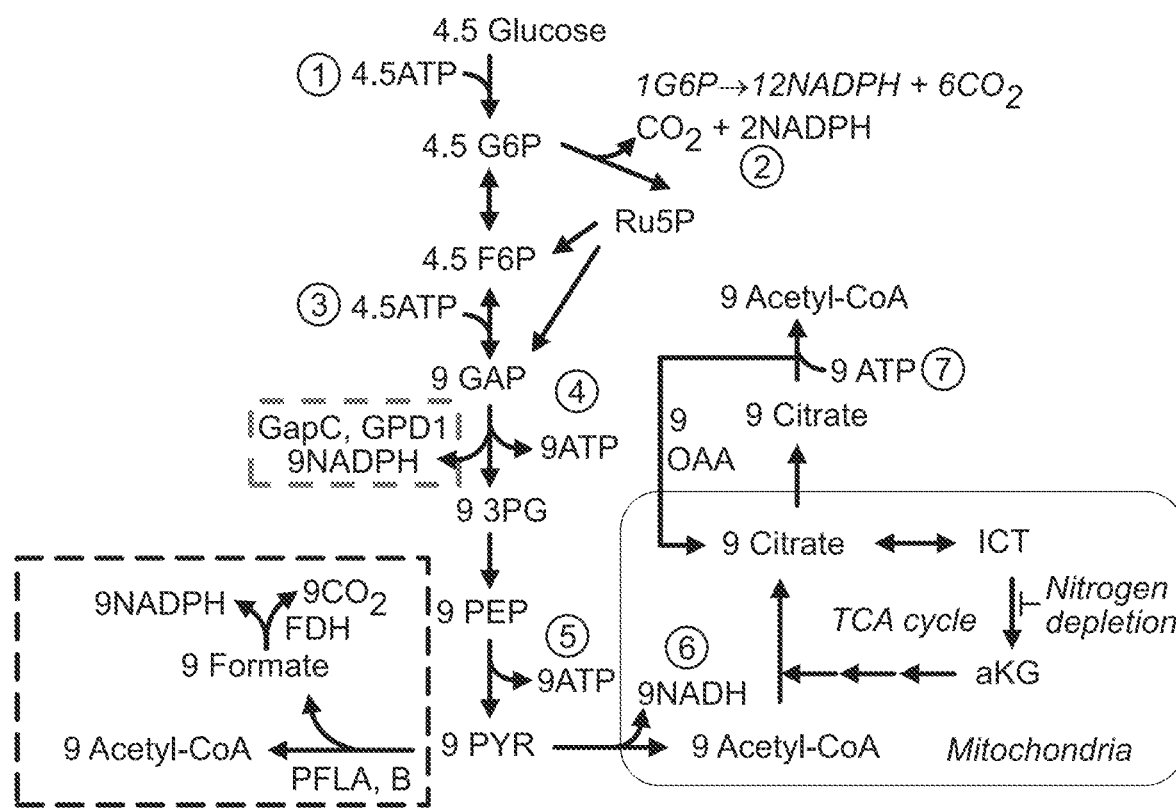

FIG. 16. Intercepting pyruvate from entering into mitochondrion by introduction of the competitive synthetic pathway that converts 1 pyruvate to 1 acetyl-CoA, 1 CO2 and 1 NADPH. The synthetic pathway was proposed to be enabled by expressing *E. coli* pyruvate-formate lyase PFLB, its cognate activating enzyme PFLA and the NADP+-dependent formate dehydrogenase. Combination of the synthetic pathway (enclosed by a black dashed line) with NADP+-dependent GPDs (enclosed by a gray dashed line) allows substitution of glycolytic NADH with NADPH:

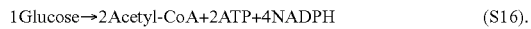

1Glucose→2Acetyl-CoA+2ATP+4NADPH     (S16).

Since the acetyl-CoA is generated from pyruvate directly instead of through activity of ACL, the ATP needed for fatty acid synthesis is less, leading to Eq. S17:

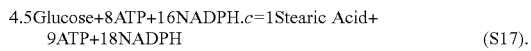

4.5Glucose+8ATP+16NADPH.c=1Stearic Acid+
9ATP+18NADPH     (S17).

Therefore, the theoretical maximum yield is 0.351 g-SA/g-glucose. Furthermore, per mol SA synthesized using this stoichiometry there would be 2 mol NADPH and 1 mol ATP in excess. The net ATP gain would make this synthetic pathway very favorable under anaerobic condition if the excess NADPHs could be oxidized in a futile pathway or by production of a reduced molecule, such as mannitol.

Figure 17:
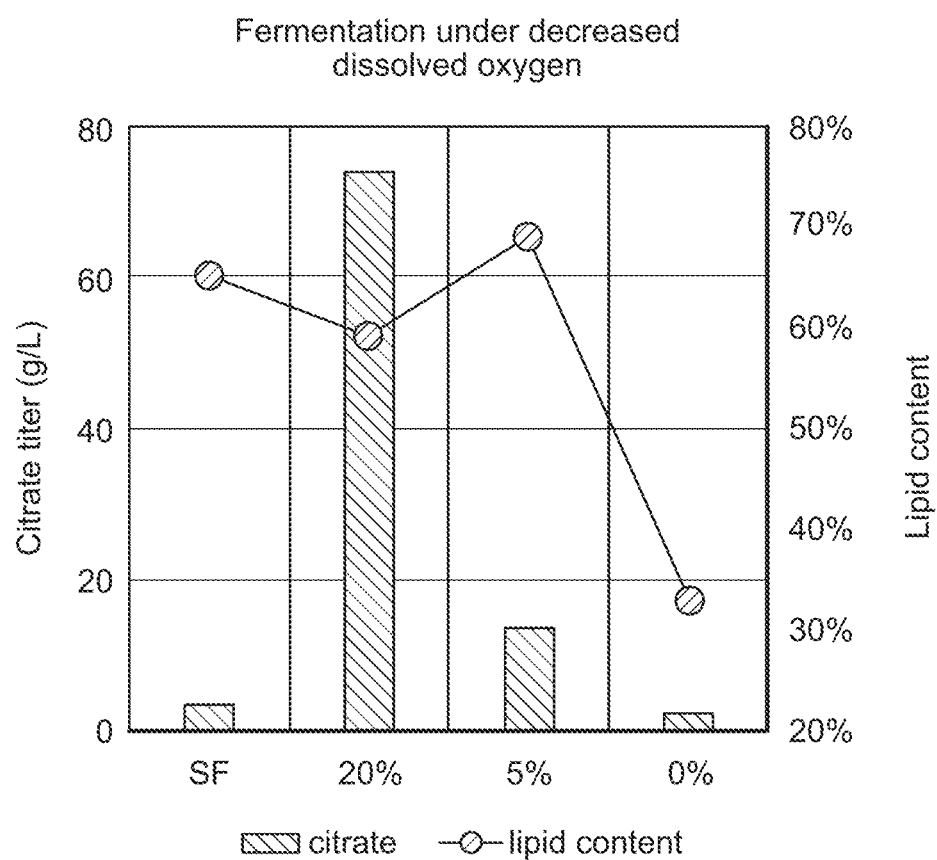

FIG. 17. The accumulation of lipids and citrate of strain ADgm in the presence of different dissolved oxygen levels during lipid production phase. The cells are harvested at the end of the fermentation in shake flask (SF) culture (144 h) and 1.5 liter bioreactor (72 h). Under low dissolved oxygen levels, including SF and 5% in bioreactor operation, optimum production of lipids is observed as indicated by the high lipid contents (above 60%). However, the high oxygen level (20% or above) completely induces citrate production while to some extent compromising lipid accumulation. Lipid production ceased entirely when cells were incubated in anaerobic conditions (0% or below). Morphological changes (elongated cell shapes or hyphae formation) of *Y. lipolytica* were observed at 0% oxygen level.

Figure 18D:
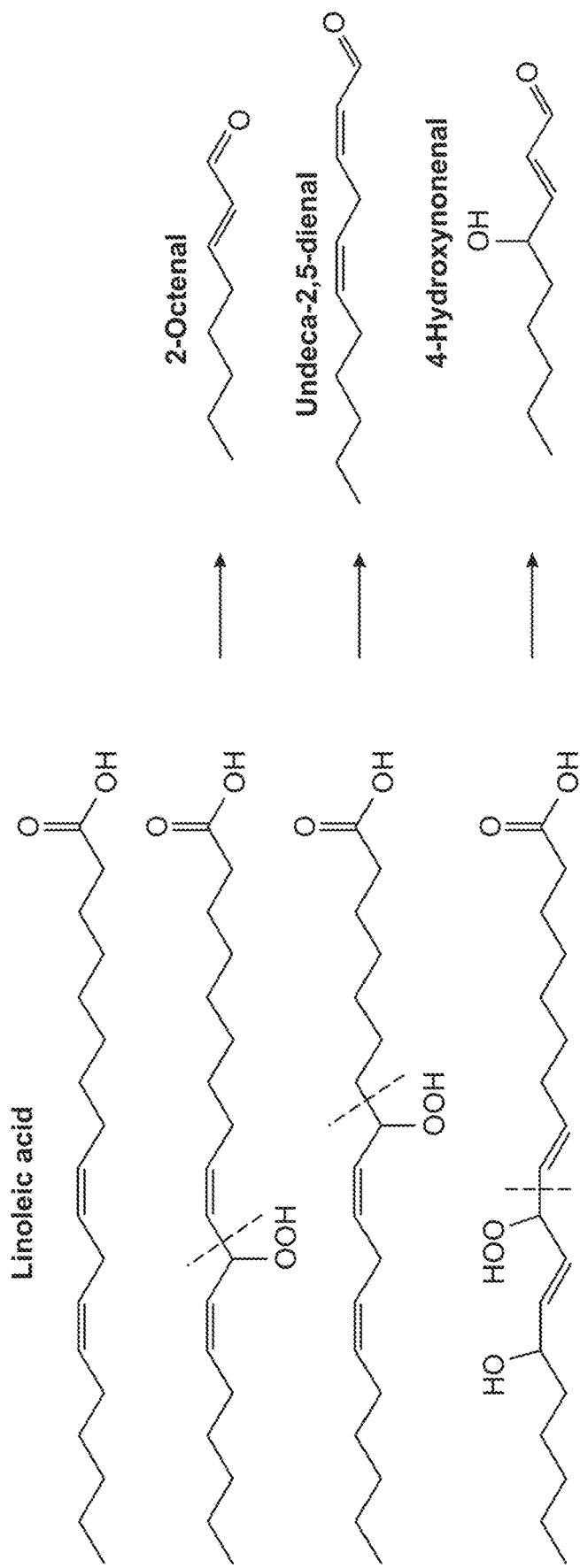

FIGS. 18A-18D. Lipid oxidation and peroxidation generate reactive oxygen and aldehyde species. (FIG. 18A depicts enzyme (acyl-CoA oxidase) catalyzed oxidation of fatty acyl-CoA generates hydrogen peroxide ($H_2O_2$). FIG. 18B shows hydroxyl radical (OH) and oxygen ($O_2$) induced oxidation of unsaturated fatty acids generate lipid peroxide. The black dashed line indicates enzyme (lipoxygenase) catalyzed oxidation of unsaturated fatty acids. FIG. 18C depicts autolysis ((3-scission) of oleic acid peroxide generates reactive aldehydes. FIG. 18D shows autolysis ((3-scission) of linoleic acid peroxide generates reactive aldehydes.

Figure 19E:
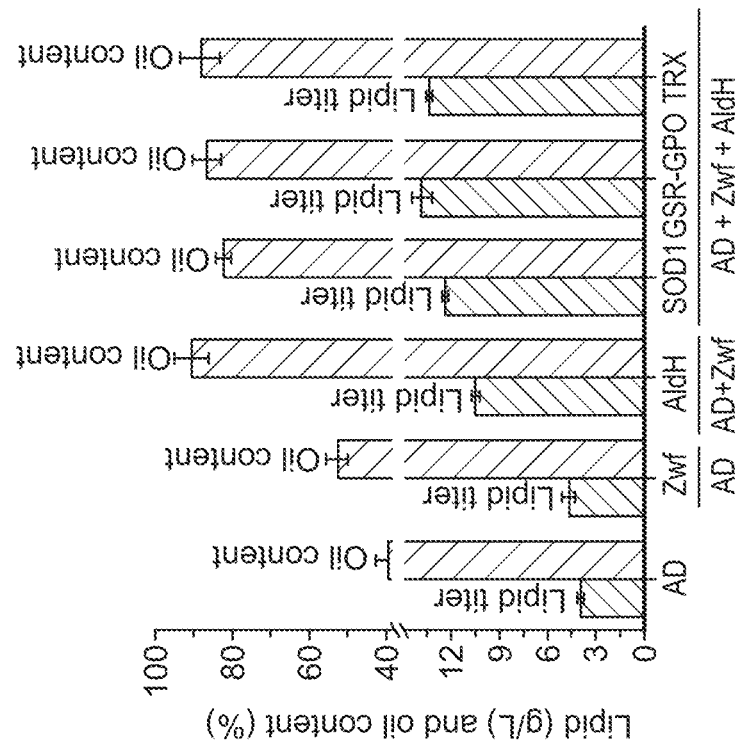
Figure 19F:
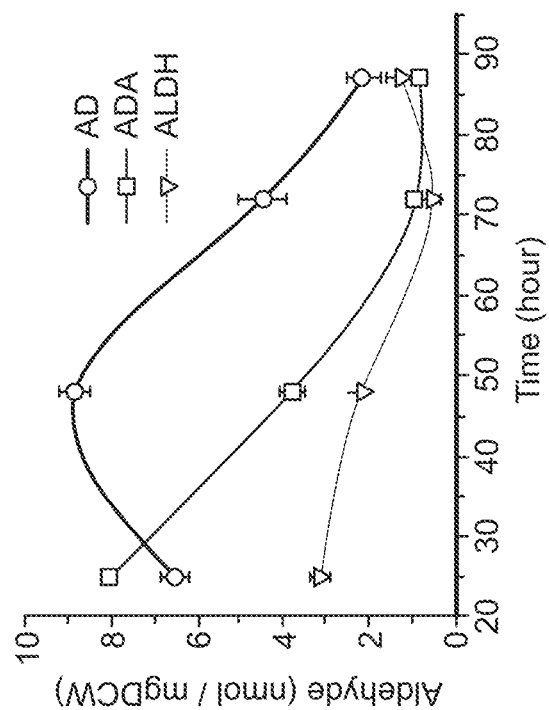

FIGS. 19A-19F. Reactive oxygen and aldehyde—scavenging mechanism in *Y. lipolytica*. FIG. 19A shows glutathione mediated hydrogen peroxide scavenging process depends on glutathione disulfide reductase (GSR) and glutathione peroxidase (GPO). FIG. 19B shows thioredoxin reductase mediated hydrogen peroxide scavenging process. FIG. 19C depicts lipid level and oil content in *Yarrowia* expressing putative hydrogen peroxide and aldehyde scavenging enzymes. GG denotes the coexpression of GSR and GPO. FIG. 19D shows expression of GSR-GPO and aldehyde dehydrogenase (AldH) lowers the level of reactive oxygen species in *Yarrowia*. FIG. 19E depicts lipid level and oil content in *Yarrowia* with combined expression of AldH and hydrogen peroxide-scavenging enzymes. FIG. 19F shows intracellualar aldehyde level in AD, ADA and ALDH strains.

Figure 20B:
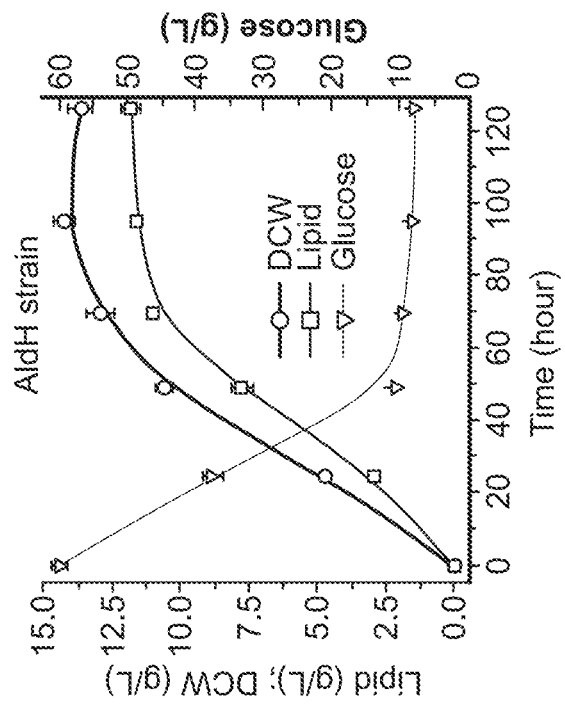
Figure 20A:
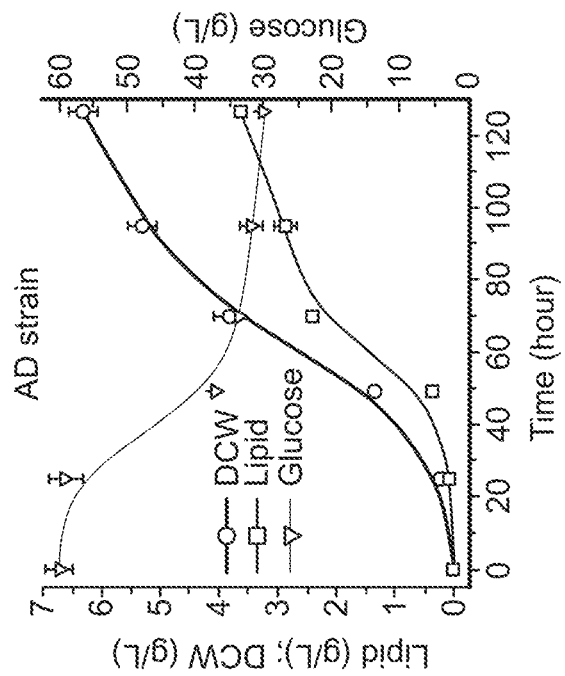
Figure 20D:
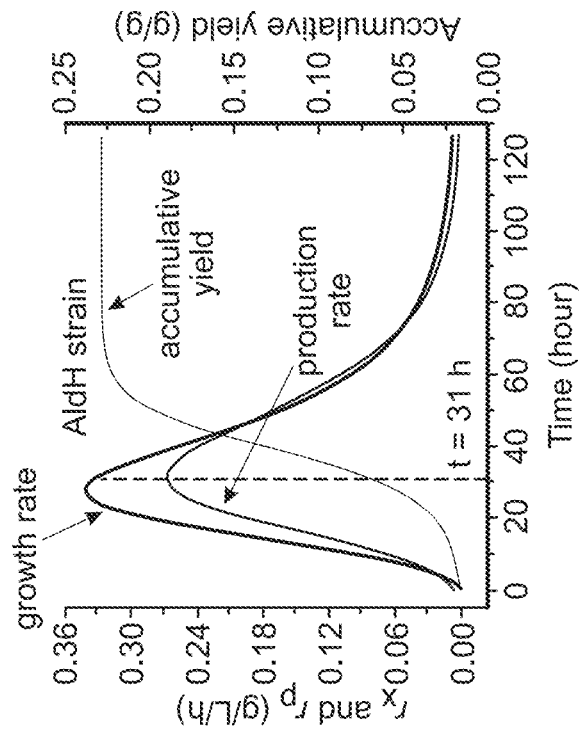

FIGS. 20A-20D. Comparison of metabolic performance of AD strain and AldH strain. FIG. 20A depicts cell growth, lipid production and glucose consumption of AD strain in shaker flask. FIG. 20B shows cell growth, lipid production and glucose consumption of AldH strain in shaker flask (FIG. 20C) Cell growth rate ($r_x$), lipid production rate ($r_p$) and accumulative lipid yield of AD strain. FIG. 20D depicts cell growth rate ($r_x$), lipid production rate ($r_p$) and accumulative lipid yield of AldH strain.

Figure 21A:
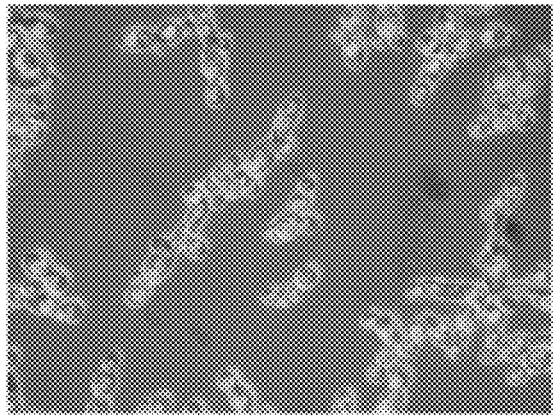
Figure 21B:
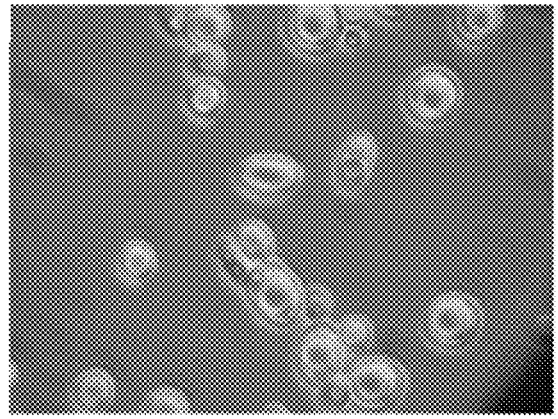
Figure 21C:
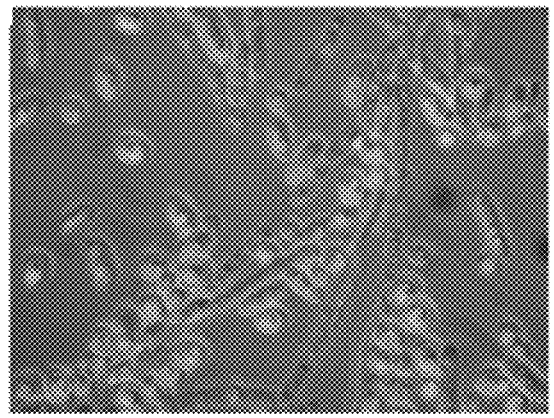
Figure 21D:
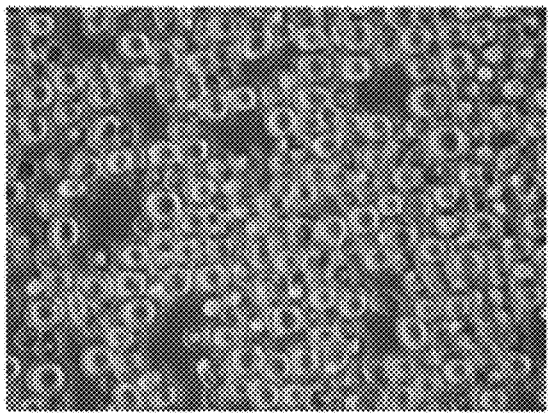

FIGS. 21A-21D. Cell morphology change in AD strain and AldH strain. FIG. 21A shows AD strain in flask culture. FIG. 21B depicts AldH strain in flask culture. FIG. 21C shows AldH strain treated with 5 mM $H_2O_2$ for 30 min in flask. FIG. 21D depicts AldH strain in fed-batch bioreactor.

Figure 22A:
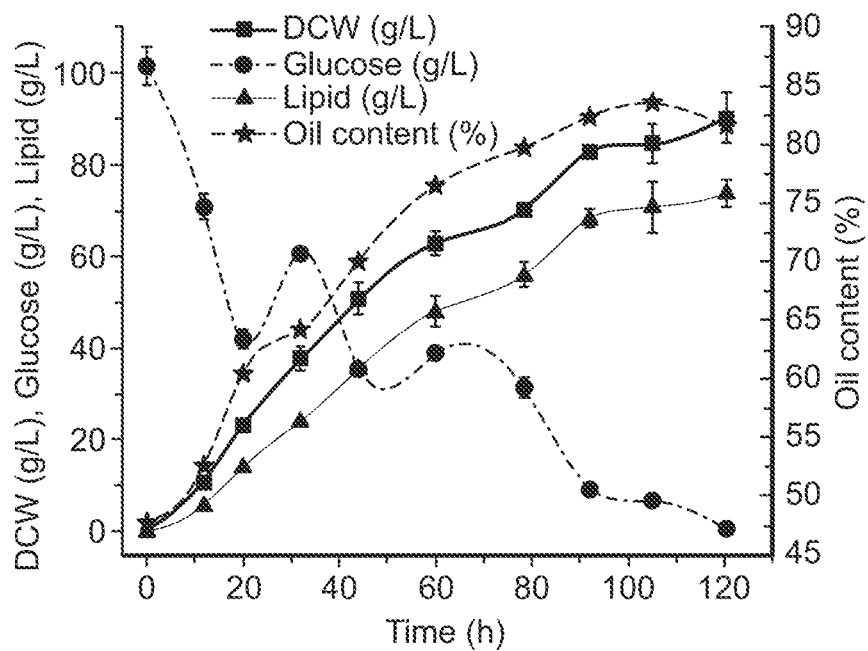
Figure 22B:
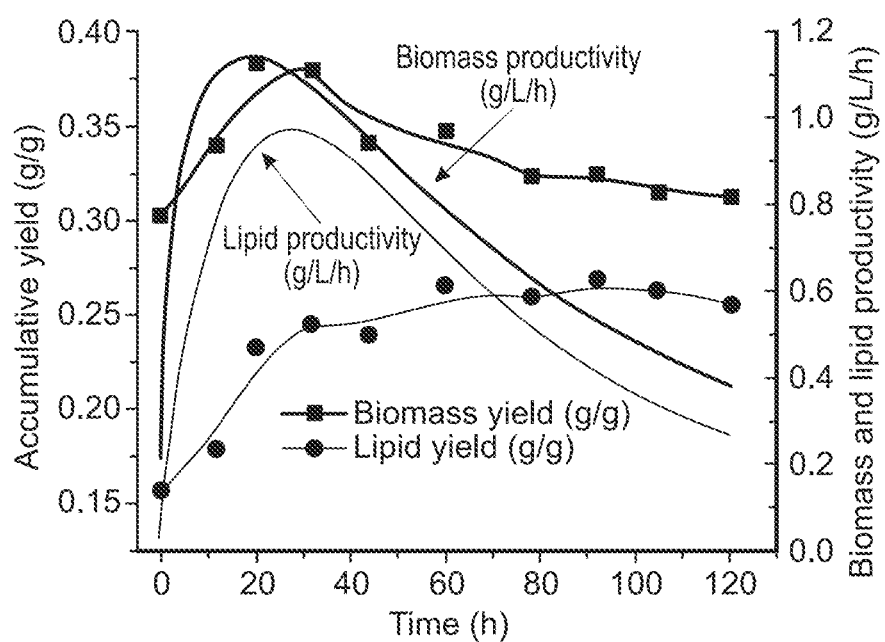

FIGS. 22A and 22B. Feb-batch fermentation performance of AldH strain. FIG. 22A shows cell growth (g/L), residual glucose (g/L), lipid production (g/L) and oil content (g/gDCW) in fed-batch bioreactor. FIG. 22B depicts accumulative biomass yield (g/gGlucose), lipid yield (g/gGlucose) and instantaneous biomass productivity (g/L/h) and lipid productivity (g/L/h) in fed-batch bioreactor.

Figure 23:
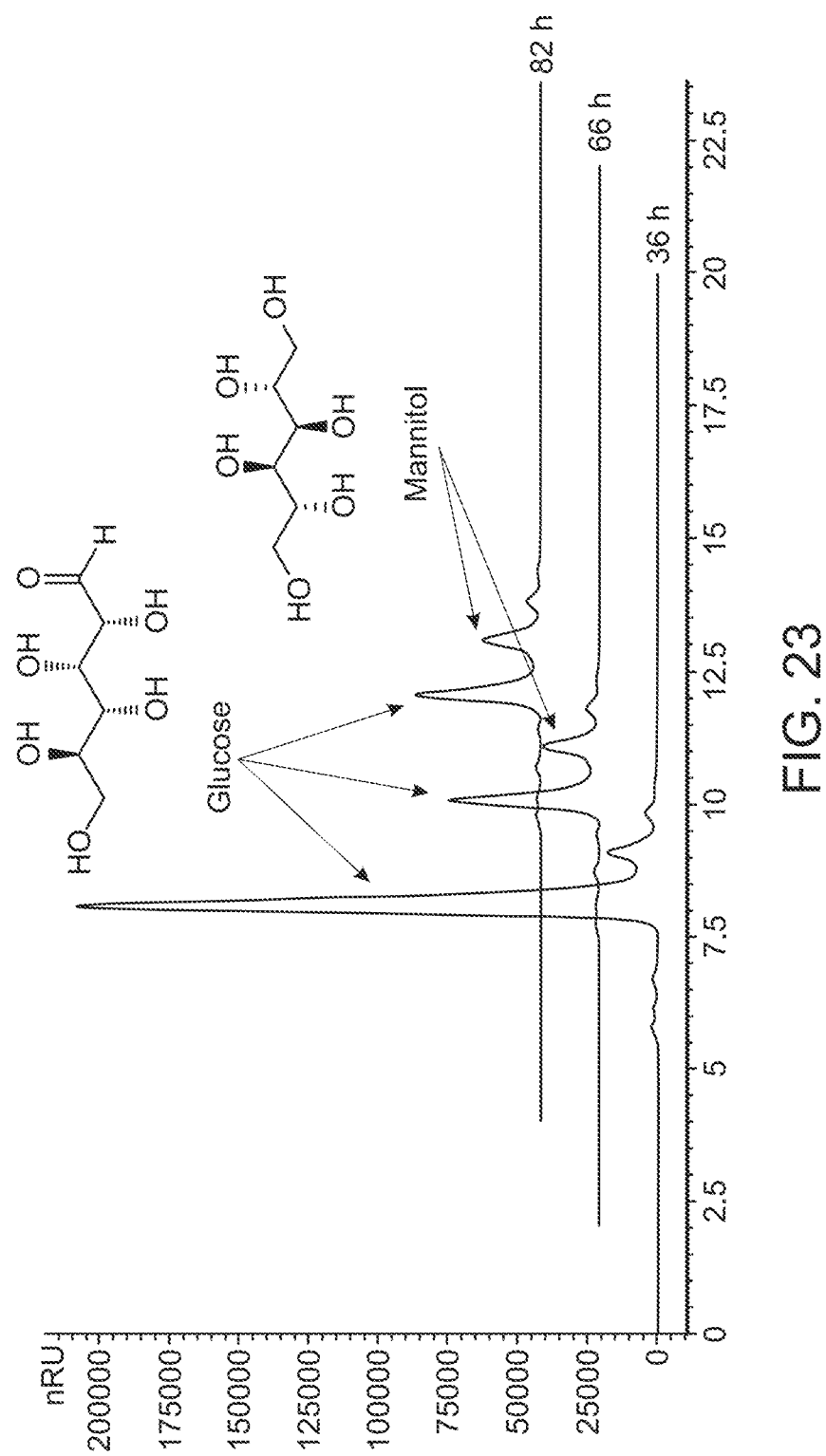

FIG. 23. Extracellular metabolites analysis at different time points shows secretion of mannitol accompanying with lipid accumulation and glucose consumption.

Figure 24:
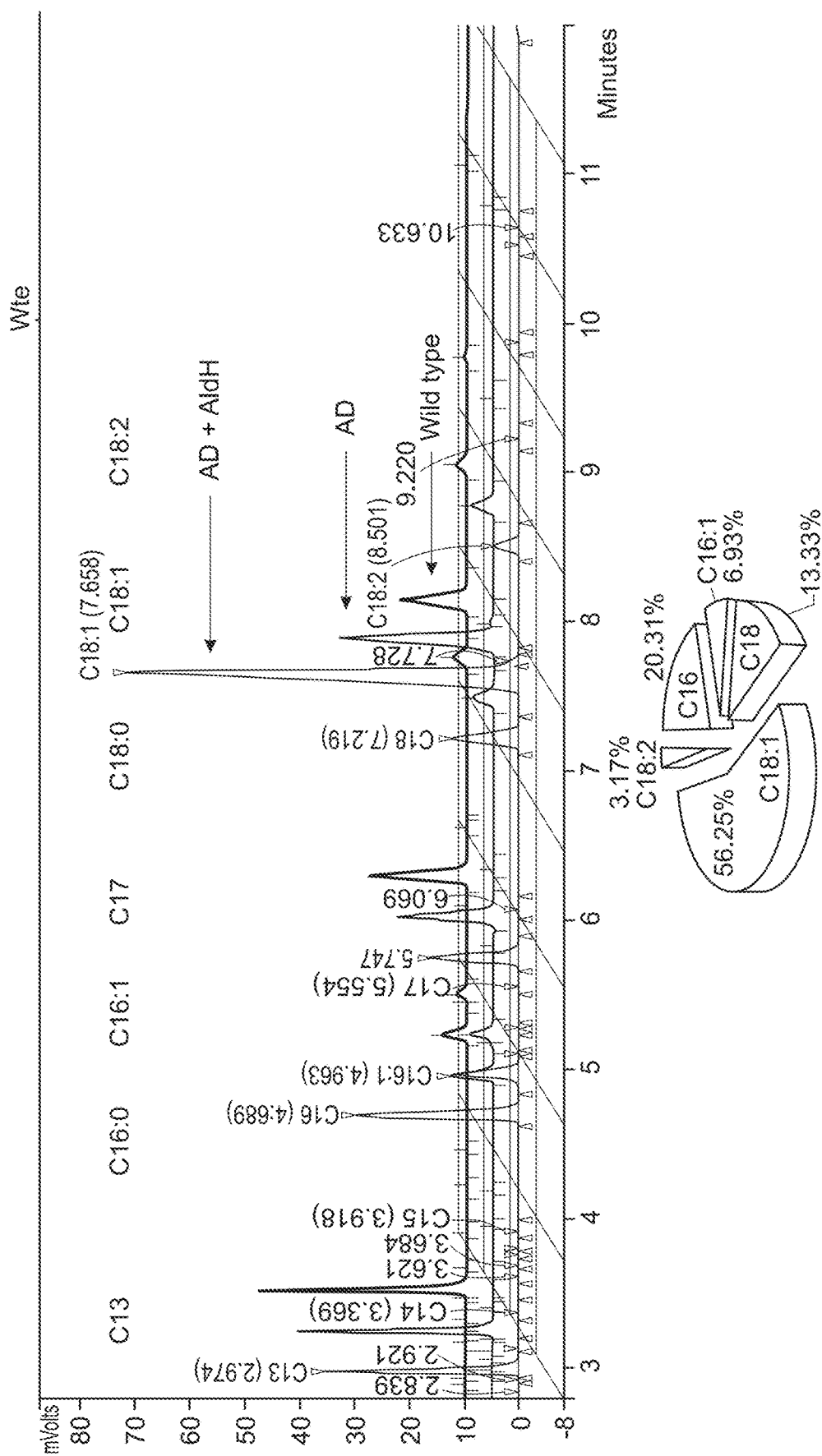

FIG. 24. Overlay of GC-FID profiles indicate almost similar fatty acids composition in the wild type, AD and AldH strain. AldH exhibits significant increased lipid titer as seen the increase peak area for individual fatty acids. C13 and C17 peak are internal standards.

Figure 25:
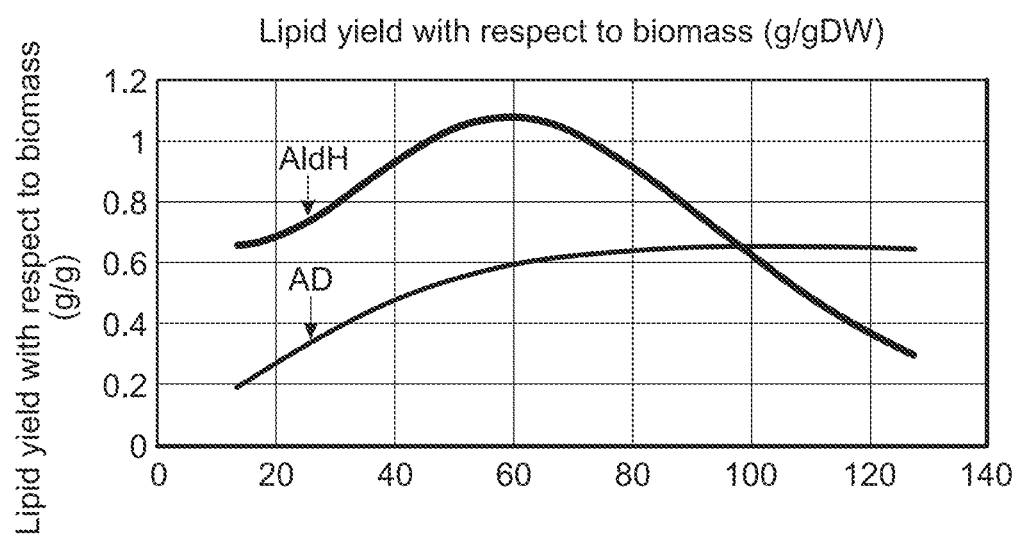

FIG. 25. Instantaneous specific lipid yield (g/g, lipid production rate divided by cell growth rate) in AD and AldH strain.

Figure 26:
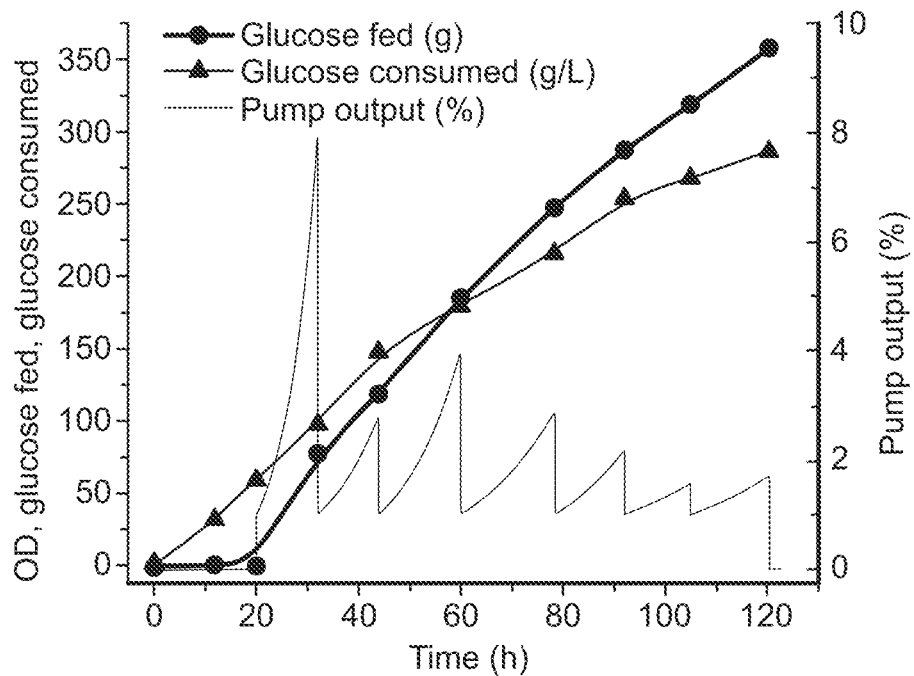

FIG. 26. Step-wise exponential feeding of glucose to minimize the secretion of citrate and elicit lipid accumulation in engineered AldH strain.

Figure 27:
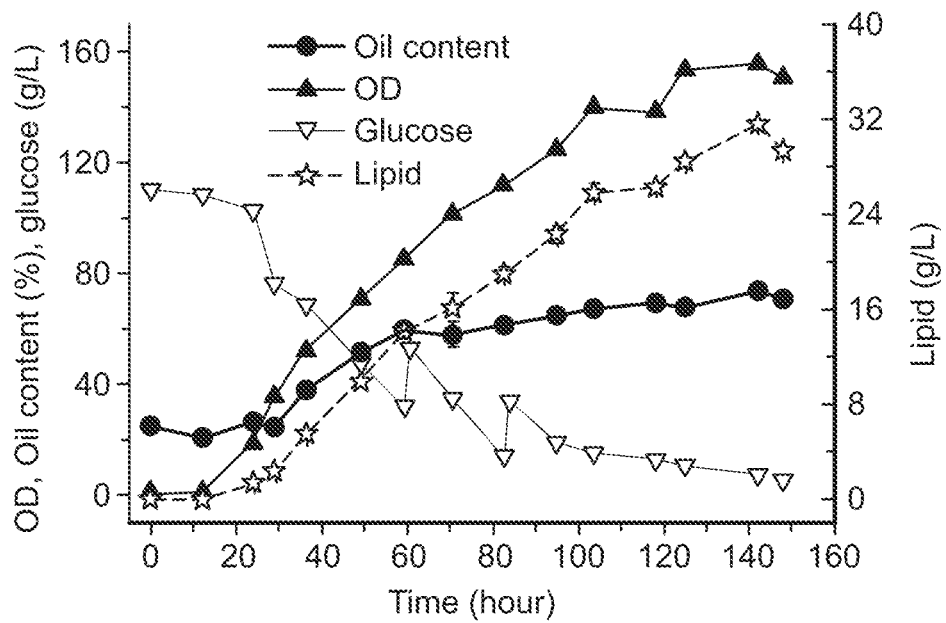

FIG. 27. Batch bioreactor performance of engineered AldH strain with glucose pulse-feeding.

Figure 28:
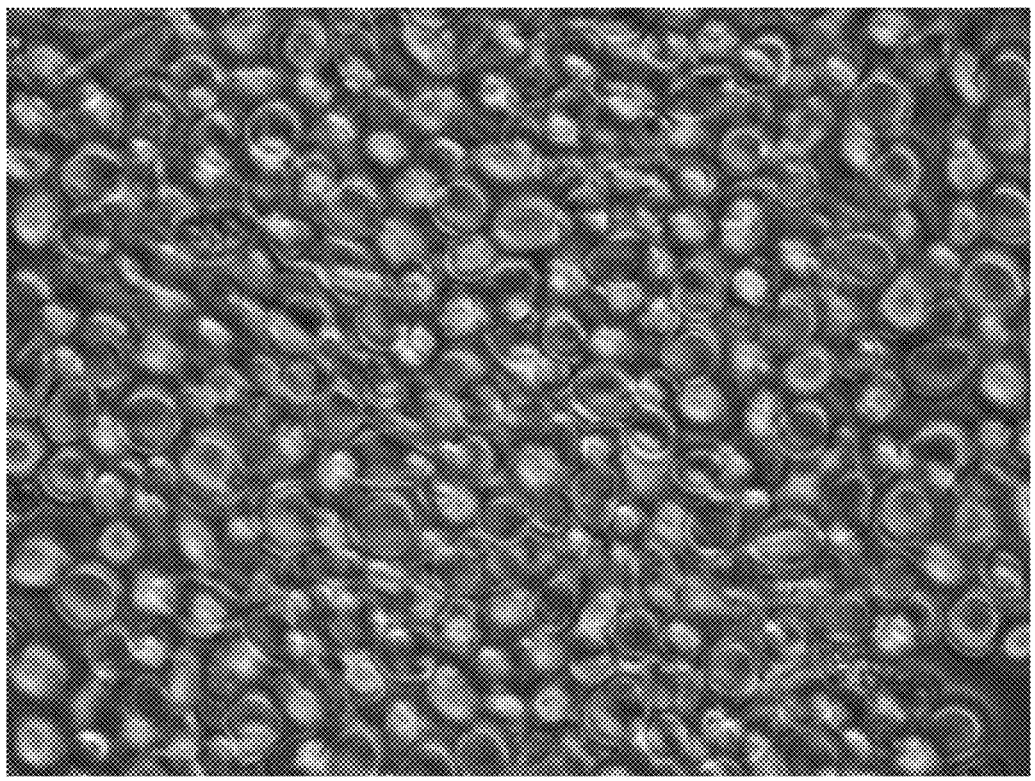

FIG. 28. Cell with enhancement of oxidative stress defense pathways and aldehyde detoxification pathways maintains singular and round shape in the optimized bioreactor with glucose step-wise exponential feeding.

FIG. 29. Synthetic gene fragment TEF-intron-MCS with ePathBrick features. The bold uppercase sequence indicates XbaI site, the bold underlined sequence indicates exon and the gray highlighted uppercase sequence indicates incomplete intron. This figure depicts SEQ ID NO: 135.

Figure 30:
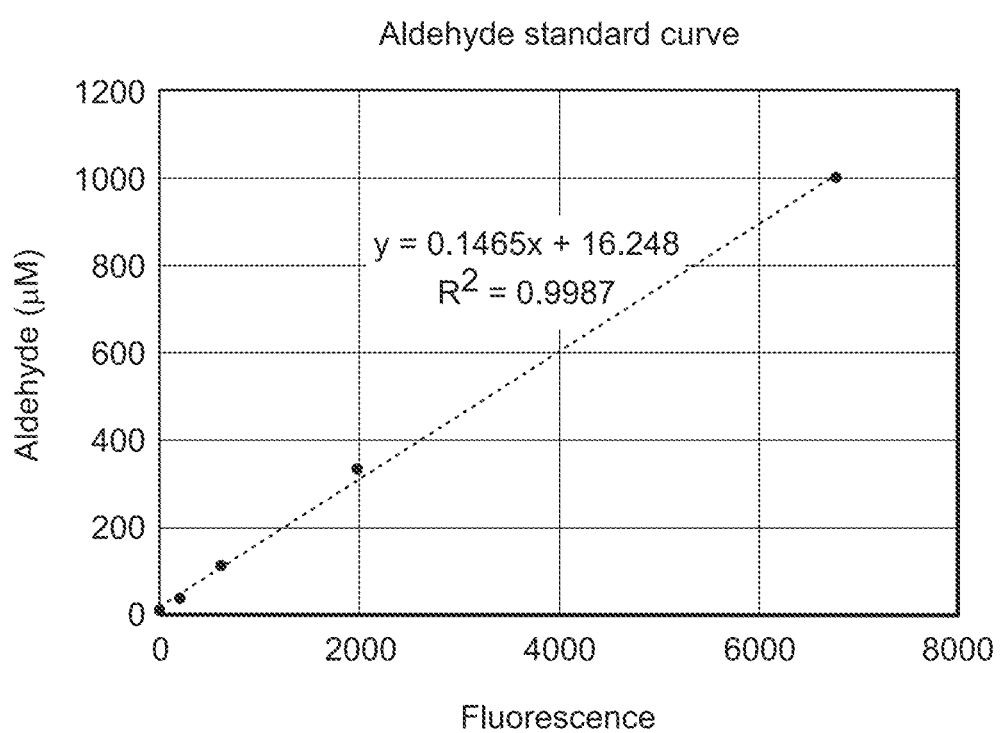

FIG. 30. Aldehyde quantification standard curve. Aldehyde concentration is linearly correlated with fluorescence unit.

DETAILED DESCRIPTION OF CERTAIN EMBODIMENTS

Production of lipids by microbial fermentation of carbohydrate feedstocks outcompetes oil crops in terms of productivity. However, presently achievable carbohydrates-tolipids process yields are not yet at a point that can support cost-effective production of lipids and biodiesel. To maximize process yields, one needs to maximize lipid content as well as capture as many of the electrons generated from the catabolism of the available substrate as possible. As shown herein, overall lipid process yield, Y, is significantly improved via introduction of synthetic pathways that effectively recycle glycolytic NADHs into cytosolic NADPH and acetyl-CoA to be used for lipid synthesis. Strain construction was guided by a quantitative model that predicted Y from the non-lipids biomass yield, lipid content, and yield of lipid synthesis pathway, $Y_L$, with $Y_L$ becoming the key driver of process yield maximization at high lipid content. In total, thirteen rationally designed strain constructs were evaluated in shake flask and bioreactor experiments to identify the best strain of oleaginous yeast that achieved a lipid titer of 99 g/L with a productivity of 1.3 g/L/h and an overall process yield 0.274 g FAME/g glucose. This strain harbored overexpression of Acetyl-CoA carboxylase 1 (ACC1) and Diacylglyceride Acyltransferase 1 (DGA1) along with NADPH-dependent Malic Enzyme McMCE2 from *Mucor circinelloides* and glyceraldehyde-3-phosphate dehydrogenase GapC from *Clostridium acetobutylicum*.

Harnessing metabolic engineering to produce fuels and green chemicals is made more difficult as microbes are constantly facing environmental stress in industrial fermentation settings. Phenotypic engineering that targets stress response pathways is an important step to deliver efficient microbial biocatalysts and achieve high titer, yield and productivity. Lipids, particularly unsaturated fatty acids, are highly susceptible to oxygen-centered radical attack and the reactive oxygen and aldehyde species arising from lipid peroxidation toxify critical pathway enzymes and limit productivity and yield. To solve this challenge, oxidative stress defense pathways were engineered to control and improve lipid biosynthesis in oleaginous yeast, specifically *Yarrowia lipolytica*. By mitigating reactive oxygen and aldehyde species, cell growth and lipid production were synchronized, cell physiology and morphology were optimized, and industrially-relevant levels of lipid titer (72.7 g/L), oil content (82.5%) and productivity (0.97 g/L/h) were achieved.

Further improvements are achieved by combining these two approaches (engineering pathways that recycle glycolytic NADHs into cytosolic NADPH and acetyl-CoA, and engineering oxidative stress defense pathways). Additional improvements are achieved by bioprocess optimization, such as controlling the rate of feeding of carbon source to provide stepwise exponential feeding and/or controlling $dO_2$ levels and/or increasing nitrogen and/or increasing cell numbers in cultures.

Some aspects of this disclosure provide engineered microbes for the production of biofuel or biofuel precursor. The term "biofuel" refers to a fuel that is derived from a biological source, such as a living cell, microbe, fungus, or plant. The term includes, for example, fuel directly obtained from a biological source, for example, by conventional extraction, distillation, or refining methods, and fuel produced by processing a biofuel precursor obtained from a biological source, for example by chemical modification, such as transesterification procedures. Examples of biofuels that are directly obtainable are alcohols such as ethanol, propanol, and butanol, fat, and oil. Examples of biofuels that are obtained by processing of a biofuel precursor (e.g., a lipid), are biodiesel (e.g., produced by transesterification of a lipid), and green diesel/modified oil fuels (e.g., produced by hydrogenation of an oil). Biodiesel, also referred to as fatty acid methyl (or ethyl) ester, is one of the economically most important biofuels today and can be produced on an industrial scale by transesterification of lipids, in which sodium hydroxide and methanol (or ethanol) reacts with a lipid, for example, a triacylglycerol, to produce biodiesel and glycerol.

Feedstocks for industrial-scale production of biodiesel include animal fats, vegetable oils, palm oil, hemp, soy, rapeseed, flax, sunflower, and oleaginous algae. In other approaches, biomass is converted by a microbe into a biofuel precursor, for example, a lipid, that is subsequently extracted and further processed to yield a biofuel. The term "biomass" refers to material produced by growth and/or propagation of a living cell or organism, for example, a microbe. Biomass may contain cells, microbes and/or intracellular contents, for example cellular fatty acids and TAGs, as well as extracellular material. Extracellular material includes, but is not limited to, compounds secreted by a cell, for example, secreted fatty acids or TAGs. Important types of biomass for biofuel production are algal biomass and plant-derived biomass, for example, corn stover and wood fiber. In some embodiments, biomass for biofuel or biofuel precursor production may comprise plant derived sugars, for example, sugarcane or corn derived sugars.

Some aspects of this disclosure relate to the engineering and development of a microbial source of lipids, useful, for example, for economically viable, industrial-scale biodiesel production. The term "lipid" refers to fatty acids and their derivatives. Accordingly, examples of lipids include fatty acids (FA, both saturated and unsaturated); glycerides or glycerolipids, also referred to as acylglycerols (such as monoglycerides (monoacylglycerols), diglycerides (diacylglycerols), triglycerides (triacylglycerols, TAGs, or neutral fats); phosphoglycerides (glycerophospholipids); non-glycerides (sphingolipids, sterol lipids, including cholesterol and steroid hormones, prenol lipids including terpenoids, fatty alcohols, waxes, and polyketides); and complex lipid derivatives (sugar-linked lipids or glycolipids, and protein-linked lipids). Lipids are an essential part of the plasma membrane of living cells and microbes. Some cells and microbes also produce lipids to store energy, for example in the form of triacylglycerols in lipid bodies, lipid droplets, or vacuoles.

Some aspects relate to engineered microbes for biofuel or biofuel precursor production. In some embodiments, the microbes provided herein are engineered to optimize their lipid metabolism for lipid production. The term "lipid metabolism" refers to the molecular processes that involve the creation or degradation of lipids. Fatty acid synthesis, fatty acid oxidation, fatty acid desaturation, TAG synthesis, TAG storage and TAG degradation are examples of processes that are part of the lipid metabolism of a cell. Accordingly, the term "fatty acid metabolism" refers to all cellular or organismic processes that involve the synthesis, creation, transformation or degradation of fatty acids. Fatty acid synthesis, fatty acid oxidation, TAG synthesis, and TAG degradation are examples of processes are part of the fatty acid metabolism of a cell.

The term "triacylglycerol" (TAG, sometimes also referred to as triglyceride) refers to a molecule comprising a single molecule of glycerol covalently bound to three fatty acid molecules, aliphatic monocarboxylic acids, via ester bonds, one on each of the glycerol molecule's three hydroxyl (OH) groups. Triacylglycerols are highly concentrated stores of metabolic energy because of their reduced, anhydrous nature, and are a suitable feedstock for biodiesel production.

Many cells and organisms store metabolic energy in the form of fatty acids and fatty acid derivatives, such as TAGs. Fatty acids and their derivatives, such as TAGs, provide an ideal form to store metabolic energy. The energy contained in the C—C bonds can be efficiently released by β-oxidation, a reaction formally equivalent to the reverse of fatty acid biosynthesis, but mediated and regulated by different enzymes constituting a different molecular pathway. Microbes can derive fatty acids from external supply, endogenous turnover, and de novo synthesis. Some aspects relate to the identification of a microbe for biofuel or biofuel precursor production based on the microbe's ability to synthesize and store fatty acids or fatty acid derivatives, such as TAGs, efficiently from an externally supplied carbon source.

Natural fatty acid molecules commonly have an unbranched, aliphatic chain, or tail, of 4 to 28 carbon atoms. Fatty acids are referred to as "saturated", if all carbon atoms of the aliphatic chain are connected via a C—C single bond, or as "unsaturated", if two or more carbon atoms are connected via a C=C double bond. Unsaturated fatty acids play important roles in the regulation of membrane fluidity, cellular activity, metabolism and nuclear events governing gene transcription.

The spectrum of fatty acids in yeast consists mostly of C16 and C18 fatty acids, for example palmitic acid (C16), palmitoleic acid (C16), stearic acid (C18) and oleic acid (C18). Palmitic acid is an unbranched, saturated fatty acid, with an aliphatic chain of 16 carbon atoms (carbon atoms/unsaturated bonds: 16.0). Stearic acid is an unbranched, saturated fatty acid with an aliphatic chain of 18 carbon atoms (18.0). Palmitoleic acid is a monounsaturated fatty acid with an aliphatic chain of 16 carbon atoms (16.1). Oleic acid is a monounsaturated fatty acid with an aliphatic chain of 18 carbon atoms (18.1). Minor fatty acid species in yeast include C14 and C26 fatty acids, which play essential functions in protein modification or as components of sphingolipids and GPI anchors, respectively.

De novo synthesis of fatty acids utilizes substantial amounts of metabolites, acetyl-CoA, ATP and NADPH, and thus competes with other cellular processes that are dependent on these compounds. NADPH is required for two reduction steps in the fatty acid elongation cycle, linking fatty acid synthesis to the metabolic state of the cell and results in fatty acid synthesis being restricted to conditions of high energy load of the cells, indicated by increased ATP/AMP ratio, elevated reduction equivalents and elevated acetyl-CoA pool. Almost all subcellular organelles are involved in fatty acid metabolism, indicating that maintenance of fatty acid homeostasis requires regulation at multiple levels.

Most organisms, including yeast, are able to synthesize fatty acids de novo from a variety of carbon sources. In an initial step, acetyl-CoA is carboxylated by the addition of $CO_2$ to malonyl-CoA, by the enzyme acetyl-CoA carboxylase (ACC; encoded by ACC1 and HFA1 in yeast). Biotin is an essential cofactor in this reaction, and is covalently attached to the ACC apoprotein, by the enzyme biotin:apoprotein ligase (encoded by BPL1/ACC2 in yeast). ACC is a trifunctional enzyme, harboring a biotin carboxyl carrier protein (BCCP) domain, a biotin-carboxylase (BC) domain, and a carboxyl-transferase (CT) domain. In most bacteria, these domains are expressed as individual polypeptides and assembled into a heteromeric complex. In contrast, eukaryotic ACC, including mitochondrial ACC variants (Hfa1 in yeast) harbor these functions on a single polypeptide. Malonyl-CoA produced by ACC serves as a two carbon donor in a cyclic series of reactions catalyzed by fatty acid synthase, FAS, and elongases.

The immediate product of de novo fatty acid synthesis are saturated fatty acids. Saturated fatty acids are known to be the precursors of unsaturated fatty acids in eukaryotes, including yeast. Unsaturated fatty acids are generally produced by desaturation of C—C single bonds in saturated fatty acids by specialized enzymes, called desaturases. In eukaryotes, unsaturated fatty acids play important roles in the regulation of membrane fluidity, cellular activity, metabolism and nuclear events that govern gene transcription. Typically, about 80% of yeast fatty acids are monounsaturated, meaning that they contain one unsaturated bond in their aliphatic chain.

Some aspects of this disclosure provide strategies for engineering microbes for oil production. For example, the oleaginous yeast cells described herein may have one or more genetic modifications that increase lipid titer, lipid productivity, overall process yield, and oil content. The genetic modifications include (1) one or more synthetic metabolic pathway(s) that recycle(s) cytosolic NADH to cytosolic NADPH via genetic modifications including (a) increasing expression of a NADP+-dependent malic enzyme gene product; and/or (b) increases expression of a NADP+-dependent glyceraldehyde-3-phosphate dehydrogenase gene product;

(2) one or more synthetic metabolic pathway(s) that recycle(s) cytosolic NADH to cytosolic acetyl-CoA via genetic modification that increases expression of a phosphoketolase gene product and a Phosphotransacetylase gene product;

(3) one or more synthetic metabolic pathway(s) that recycle(s) mitochondrial NADH to cytosolic NADPH via genetic modifications including (a) increases expression of a pyruvate formate lyase gene product, pyruvate formate lyase activating enzyme product and a NADP+-dependent formate dehydrogenase gene product; and/or (b) increases expression of a NADP+-dependent malic enzyme gene product and a cytosolic pyruvate dehydrogenase gene products; (c) increases expression of a NAD+-dependent pyruvate dehydrogenase gene product;

(4) one or more synthetic metabolic pathway(s) that enrich(es) the cofactor NADP+ via genetic modification that increases expression of a NAD+/NADH kinase gene product; or (5) a combination of any of the one or more synthetic metabolic pathway(s) of (1), (2), (3) and (4);

and/or (1) one or more synthetic metabolic pathway(s) that remove(s) toxic aldehyde species via genetic modifications including increasing the expression of an aldehyde dehydrogenase gene product (AldH);

(2) one or more synthetic metabolic pathway(s) that remove(s) reactive oxygen species via genetic modifications including increased expression of ROS-scavenging pathways including (a) a glutathione disulfide reductase (GSR) and a glutathione peroxidase (GPO) gene product, or (b) a thioredoxin reductase (Trx) gene product, or (c) a superoxide dismutase gene product (SOD1);

(3) one or more synthetic metabolic pathway(s) that provide(s) additional NADPH to complete the activity of glutathione disulfide reductase (GSR), glutathione peroxidase (GPO) and thioredoxin reductase (Trx) via genetic modifications including increased expression of a glucose-6-phosphate dehydrogenase (ZWF1) gene product; or (4) a combination of any of the one or more synthetic metabolic pathway(s) of (1), (2), and (3).

NADP+-dependent malic enzyme gene and gene product sequences are well known to those of skill in the art. Exemplary, representative gene and gene product sequences include:

MCE2 from *Mucor circinelloides*, NCBI Accession ID: ABM45933 Nucleotide sequence (SEQ ID NO: 1):
ATGTCGCCTATTATTGATTTTGTTCGTCGCCAATTGTCCTCTACAAAGTT

GCATGAAGAGCAGCAAACAGCAACTACAAATGATTTGGTCTCTAGATCAG

GCTATCTAAATGAAGGCAAGTATGAGGTCCGCTTGAATTGTATCAATGCT

GGCTGCTTACAAAAAAAACTAAACTATATAGGTACTGCCATGGATCCTGC

TAAACGTCAAAGACTTGGATTGAACGGTCTTTTACCTGCTGGTGTAGAGA

CATTGGAAATTCAAAAAGCTCGCGCCCTCAGAGTGCTTCGTTCAAAACAC

AATTTATTAGAAAAATACATTTTAATGGCTCAACTTCGTACCACCAACGT

CCGCTTATTTTACAAGATTGTCATTGATGAATTAGAGACCGTTCAATTGG

CTCCTGTTATCTATACCCCGACTGTTGGTACCGCATGCTTGGAATACTCT

ACCATCTATCCCTTCTTGGCTGCCCCTGGTGTGCCGGATGGTCTTTACCT

CACCAAAGCCGAATTACCGGAACTGTGTCAAACCATTCGTAACTATCGTC

CTACGGATACTGAGGGTTTTGAGCCAGAGATTGCTGTGATTTCTGATGGG

TCTCGAATTTTGGGTCTGGGTGATTTGGGAACAAATGGCATGGGTATTCC

AATGGGTAAACTTCAGCTCTATGTTGCTGGTGCTGGTATTGATCCTCGTC

GTACGTTACCCATCATTTTGGATTTGGGTACAAACAATGAAAAGTTGCTC

AATGATGAGTTTTATATTGGTCTTCGTCAAAAGCGACCCAATGATGAGGA

GTTTTATCAAACAGTTGATACAGTCTTGACAGCATTACATACCGTGTACC

CCAACCTACTCATCCAGTTTGAAGATTGGTCTTCTGAACACGCATTTGGC

CTCTTGGAAAAGTACCAAAATCAAATGCTTTGTTTTAACGACGACATACA

GGGCACAGGTGCTGTCATATTATCTGGTGTCATTAATGCTATTCGCAAGG

TTGAGAAAGAGAATCAAGTGTCTCCTCGTGATCATCGTATCGTGTTCTAC

GGTGCTGGTTCTGCTGCTATCGGTGTTGCTCGTCAAATTCAAAGCTACTT

CCAAATTGAACACAACATGACTGAGGAAGAAGCTAAGCATGTGTTCTGGA

TTGTTGATTCCAAGGGTCTTGTTACTACTACACGAGGCGATAAATTAGCT

CAACACAAGGTGTATTACGCACGAGGCGATAATGAAGGCCAACAGTACAA

GGAATTGATTGATATTGTCAACTATAATCTCTACAGTTTGATTGGTTTAT

CATCTACTACAGGTGCCTTTAATACTCAAGTCCTTGAGCGTCTTGCCTCA

CTCAATGAGCAACCTATTGTTTTCCCTCTTTCCAATCCAGCCACACAAGC

AGAATGTACATTTGAGCAAGCCATGGAAGCTACCAACAACAAGGTTATTT

TTGCATCTGGTACTGCTTTCCCTGCATATACCATCAAATCCACTGGCGAA

GTAAATACCCCTGGTCAAGGCAACAACATGTACATCTTCCCTGGTTTGGG

TCTGGGTGCTTGTCTGGCTAACCCAGCACATTTCGATCGCATGATCTACG

AAGCATCCAAAGCACTTGCTGACTCACTTACGAGGGAAGAAATCAGTAAG

GCCTGGTTATATCCATCTTTAAACTATCGTAGCGTATCAGCCATCGTTGC

AGCAGCTGTATGTCAAGAGACTTTGAATGAAAACCTAGCAACGTCTCAAG

CTATGATGACGCAGTGTAAATCACATGAAGATATTCTAGATTATGTTAGT

GCTCATATGTGGTCTCCCGACTATGGAAACAACAACAGCAATCAGCAAGC

TGGTAAATTGTAG

Amino acid sequence (SEQ ID NO: 2):
MSPIIDFVRRQLSSTKLHEEQQTATTNDLVSRSGYLNEGKYEVRLNCINA

GCLQKKLNYIGTAMDPAKRQRLGLNGLLPAGVETLEIQKARALRVLRSKH

NLLEKYILMAQLRTTNVRLFYKIVIDELETVQLAPVIYTPTVGTACLEYS

TIYPFLAAPGVPDGLYLTKAELPELCQTIRNYRPTDTEGFEPEIAVISDG

SRILGLGDLGTNGMGIPMGKLQLYVAGAGIDPRRTLPIILDLGTNNEKLL

NDEFYIGLRQKRPNDEEFYQTVDTVLTALHTVYPNLLIQFEDWSSEHAFG

LLEKYQNQMLCFNDDIQGTGAVILSGVINAIRKVEKENQVSPRDHRIVFY

GAGSAAIGVARQIQSYFQIEHNMTEEEAKHVFWIVDSKGLVTTTRGDKLA

QHKVYYARGDNEGQQYKELIDIVNYNLYSLIGLSSTTGAFNTQVLERLAS

LNEQPIVFPLSNPATQAECTFEQAMEATNNKVIFASGTAFPAYTIKSTGE

VNTPGQGNNMYIFPGLGLGACLANPAHFDRMIYEASKALADSLTEEEISK

AWLYPSLNYRSVSAIVAAAVCQETLNENLATSQAMMTQCKSHEDILDYVS

AHMWSPDYGNNNSNQQAGKL

NADP+-dependent glyceraldehyde-3-phosphate dehydrogenase gene and gene product sequences are well known to those of skill in the art. Exemplary, representative gene and gene product sequences include:

GapC from *Clostridium acetobutylicum*
Nucleotide sequence (SEQ ID NO: 3):
ATGGCAAAGATAGCTATTAATGGTTTTGGAAGAATAGGAAGATTAGCTTT

AAGAAGAATTCTTGAAGTACCTGGATTGGAAGTTGTTGCAATAAACGACT

TAACTGATGCAAAAATGTTAGCACACTTATTTAAATATGATTCATCACAA

GGAAGATTCAATGGAGAAATTGAAGTTAAAGAAGGAGCTTTCGTAGTAAA

CGGAAAAGAAGTTAAAGTTTTCGCTGAAGCAGATCCTGAAAAATTACCTT

GGGGAGATCTTGGAATAGACGTTGTTCTTGAGTGCACAGGTTTCTTCACA

AAGAAAGAAAAGCAGAAGCTCACGTAAGAGCAGGCGCTAAAAAAGTTGT

TATATCAGCTCCAGCTGGAAACGACTTAAAGACAATAGTTTTCAACGTTA

ATAATGAAGATCTTGATGGAACAGAAACAGTTATATCAGGTGCATCATGC

ACAACTAACTGCTTAGCTCCAATGGCTAAAGTATTAAATGATAAATTTGG

AATAGAAAAGGATTCATGACTACAATTCATGCGTTCACTAATGACCAAA

ACACATTAGATGGTCCACACAGAAAAGGAGATTTAAGAAGAGCTAGAGCT

GCTGCTGTAAGTATCATCCCTAACTCAACTGGTGCTGCTAAAGCTATAAG

CCAAGTTATTCCTGACTTAGCTGGAAAATTAGACGGAAACGCTCAAAGAG

TTCCAGTTCCAACTGGTTCAATAACTGAATTAGTTTTCAGTTCTTAAGAAA

AAAGTTACAGTTGAAGAAATCAACGCTGCTATGAAAGAAGCTGCTGATGA

ATCATTTGGATACACTGAAGATCCAATCGTTTCAGCTGACGTAGTAGGAA

TCAACTACGGATCATTATTTGATGCAACTTTAACTAAAATTGTTGATGTT

AACGGATCACAATTAGTTAAAACAGCTGCTTGGTATGATAATGAAATGTC

-continued

ATACACTTCACAATTAGTTAGAACTTTAGCTTACTTTGCAAAAATAGCAA

AATAG

Amino acid sequence (SEQ ID NO: 4):
AKIAINGFGRIGRLALRRILEVPGLEVVAINDLTDAKMLAHLFKYDSSQG

RFNGEIEVKEGAFVVNGKEVKVFAEADPEKLPWGDLGIDVVLECTGFFTK

KEKAEAHVRAGAKKVVISAPAGNDLKTIVFNVNNEDLDGTETVISGASCT

TNCLAPMAKVLNDKFGIEKGFMTTIHAFTNDQNTLDGPHRKGDLRRARAA

AVSIIPNSTGAAKAISQVIPDLAGKLDGNAQRVPVPTGSITELVSVLKKK

VTVEEINAAMKEAADESFGYTEDPIVSADVVGINYGSLFDATLTKIVDVN

GSQLVKTAAWYDNEMSYTSQLVRTLAYFAKIAK

GPD1 from *Kluyveromyces lactis*
Nucleotide sequence (SEQ ID NO: 5):
ATGCCCGATATGACCAACGAGTCCTCTTCGAAGCCCGCCCAGATCAACAT

CGGCATCAACGGCTTCGGCCGAATCGGACGACTGGTGCTGCGAGCCGCCC

TGACCCACCCCGAGGTGAAGGTGCGACTGATCAACAACCCCTCTACCACC

CCCGAGTACGCCGCCTACCTGTTCAAGTACGACTCTACCCACGGCAAGTA

CCGAGGCGAGGTCGAGTTCGACGACGAGCGAATCATCATCCAGAACGACC

ACGTGTCTGCCCACATCCCCCTGTCTCACTTCCGAGAGCCCGAGCGAATC

CCCTGGGCCTCTTACAACGTGGACTACGTGATCGACTCTACCGGCGTGTT

CAAGGAAGTGGACACCGCCTCTCGACACAAGGGCGTGAAGAAGGTGATCA

TCACCGCCCCCTCTAAGACCGCCCCCATGTACGTGTACGGCGTGAACCAC

GTGAAGTACAACCCCCTGACCGACCACGTGGTGTCTAACGCCTCTTGCAC

CACCAACTGCCTGGCCCCCCTGGTGAAGGCCCTGGACGACGAGTTCGGCA

TCGAAGAGGCCCTGATGACCACCATCCACGCCACCACCGCCTCTCAGAAG

ACTGTCGACGGCACCTCTTCTGGCGGCAAGGACTGGCGAGGCGGCCGATC

TTGCCAGGGCAACATCATCCCCTCTTCTACCGGCGCTGCCAAGGCCGTGG

GCAAGATCCTGCCCGAGCTGAACGGCAAGATCACCGGCATGTCTATCCGA

GTGCCCACCATCAACATCTCCCTGGTGGACCTGACCTTCCGAACCGCCAA

GAAGACCTCTTACGACGACATCATGAAGGCCCTCGAGCAGCGATCTCGAT

CTGACATGAAGGGCGTCCTGGGCGTGACCAAGGACGCCGTGGTGTCCTCT

GACTTCACCTCTGACTCTCGATCTTCTATCGTGGACGCCAAGGCCGGCAT

CGAGCTGAACGACCACTTCTTCAAGGTGCTGTCTTGGTACGACAACGAGT

ACGGCTACTCTTCTCGAGTGGTCGACCTGTCTATCTTCATGGCCCAGAAG

GACTTCGAGGCCGGCGTGTAA

Amino acid sequence (SEQ ID NO: 6):
MPDMTNESSSKPAQINIGINGFGRIGRLVLRAALTHPEVKVRLINNPSTT

PEYAAYLFKYDSTHGKYRGEVEFDDERIIIQNDHVSAHIPLSHFREPERI

PWASYNVDYVIDSTGVFKEVDTASRHKGVKKVIITAPSKTAPMYVYGVNH

VKYNPLTDHVVSNASCTTNCLAPLVKALDDEFGIEEALMTTIHATTASQK

TVDGTSSGGKDWRGGRSCQGNIIPSSTGAAKAVGKILPELNGKITGMSIR

VPTINISLVDLTFRTAKKTSYDDIMKALEQRSRSDMKGVLGVTKDAVVSS

DFTSDSRSSIVDAKAGIELNDHFFKVLSWYDNEYGYSSRVVDLSIFMAQK

DFEAGV

Phosphoketolase gene and gene product sequences are well known to those of skill in the art. Exemplary, representative gene and gene product sequences include:

PK from *Leuconostoc mesenteroides*
Nucleotide sequence (codon optimized for *Y. lipolytica*) (SEQ ID NO: 7):
ATGGCCGATTTCGACTCTAAAGAATACTTGGAATTGGTTGACAAATGGTG

GAGAGCTACCAATTATTTGTCTGCCGGTATGATCTTCTTGAAGTCTAATC

CTTTGTTCTCCGTTACCAACACTCCAATCAAAGCTGAAGATGTTAAGGTT

AAGCCAATTGGTCATTGGGGTACTATTTCTGGTCAAACTTTCTTGTACGC

TCATGCCAACAGATTGATTAACAAGTACGGTTTGAATATGTTCTACGTTG

GTGGTCCAGGTCATGGTGGTCAAGTTATGGTTACTAATGCTTATTTGGAT

GGTGCCTACACTGAAGATTACCCAGAAATTACCCAAGACATCGAAGGTAT

GTCTCACTTGTTTAAGAGATTCTCATTCCCAGGTGGTATCGGTTCTCATA

TGACTGCTCAAACTCCAGGTTCTTTACATGAAGGTGGTGAATTGGGTTAC

TCTTTGTCTCATGCTTTTGGTGCTGTTTTGGATAACCCAGATCAAGTTGC

TTTTGCTGTTGTTGGTGATGGTGAAGCTGAAACTGGTCCATCTATGGCTT

CATGGCATTCTATTAAGTTCTTGAACGCTAAGAATGATGGTGCCGTTTTG

CCAGTTTTGGATTTGAATGGTTTCAAGATCTCCAACCCAACCATCTTCTC

TAGAATGTCCGATGAAGAAATCACCAAGTTCTTTGAAGGTTTGGGTTACA

GTCCAAGATTCATCGAAAACGATGATATCCATGATTACGCCACCTATCAT

CAATTGGCTGCTAACATTTTGGATCAAGCCATCGAAGATATCCAAGCCAT

TCAAAATGATGCCAGAGAAAACGGTAAATACCAAGATGGTGAAATTCCAG

CTTGGCCAGTTATTATTGCTAGATTGCCAAAAGGTTGGGGTGGTCCAACT

CATGATGCTTCTAACAATCCAATCGAAAACTCTTTCAGAGCCCATCAAGT

TCCATTGCCATTGGAACAACATGATTTGGCTACTTTGCCAGAATTCGAAG

ATTGGATGAATTCCTACAAGCCTGAAGAATTATTCAACGCCGATGGTTCC

TTGAAGGATGAATTGAAAGCTATTGCTCCAAAGGGTGACAAAAGAATGTC

TGCTAATCCAATTACTAATGGTGGTGCCGATAGATCCGATTTGAAATTGC

CAAATTGGAGAGAATTCGCCAACGATATTAACGATGACACCAGAGGTAAA

GAATTCGCTGATTCTAAGAGAAACATGGATATGGCTACCTTGTCTAATTA

CTTGGGTGCAGTTTCTCAATTGAACCCTACTAGATTCAGATTTTTCGGTC

CAGACGAAACCATGTCTAATAGATTGTGGGGTTTGTTCAACGTTACTCCA

AGACAATGGATGGAAGAAATCAAAGAACCACAAGATCAATTATTGTCCCC

AACCGGTAGAATCATTGACTCTCAATTGTCTGAACATCAAGCTGAAGGTT

GGTTGGAAGGTTATACTTTGACTGGTAGAGTTGGTATTTTCGCCTCTTAC

GAATCTTTCTTGAGAGTTGTTGATACCATGGTTACCCAACATTTCAAGTG

GTTGAGACATGCTTCAGAACAAGCTTGGAGAAATGATTACCCATCCTTGA

ACTTGATTGCTACTTCTACTGCTTTCCAACAAGATCATAACGGTTACACT

CATCAAGATCCAGGTATGTTGACTCATTTGGCTGAAAAGAAGTCCAACTT

-continued

```
CATCAGAGAATATTTGCCAGCTGATGGTAACTCTTTGTTGGCTGTCCAAG

AAAGAGCTTTTTCCGAAAGACATAAGGTCAACTTGTTGATCGCTTCTAAG

CAACCTAGACAACAATGGTTCACTGTTGAAGAAGCTGAAGTTTTGGCTAA

CGAAGGTTTGAAGATTATTGATTGGGCTTCTACAGCTCCATCCTCCGATG

TTGATATTACTTTTGCTTCTGCTGGTACTGAACCTACCATTGAAACTTTG

GCTGCTTTGTGGTTGATCAATCAAGCTTTTCCAGATGTCAAGTTCAGATA

CGTTAATGTCGTCGAATTATTGAGATTGCAAAAAAAGTCCGAACCTAACA

TGAACGACGAAAGAGAATTGTCTGCAGAAGAATTCAACAAGTACTTCCAA

GCTGATACCCCAGTTATTTTTGGTTTCCATGCTTACGAAAACTTGATCGA

ATCATTCTTCTTCGAACGTAAATTCACTGGTGATGTTTACGTTCACGGTT

ACAGAGAAGATGGTGATATTACCACTACCTACGATATGAGAGTTTACTCC

CATTTGGATAGATTCCACCAAGCTAAAGAAGCTGCCGAAATTTTGTCTGC

AAACGGTAAGATAGATCAAGCTGCTGCTGATACTTTCATTGCCAAGATGG

ATGATACCTTGGCTAAGCACTTTCAAGTTACTAGAAACGAAGGTAGAGAT

ATCGAAGAATTCACAGATTGGACTTGGTCCCCATTGAAATAA
```

Amino acid sequence (SEQ ID NO: 8):
MADFDSKEYLELVDKWWRATNYLSAGMIFLKSNPLFSVTNTPIKAEDVKV
KPIGHWGTISGQTFLYAHANRLINKYGLNMFYVGGPGHGGQVMVTNAYLD
GAYTEDYPEITQDIEGMSHLFKRFSFPGGIGSHMTAQTPGSLHEGGELGY
SLSHAFGAVLDNPDQVAFAVVGDGEAETGPSMASWHSIKFLNAKNDGAVL
PVLDLNGFKISNPTIFSRMSDEEITKFFEGLGYSPRFIENDDIHDYATYH
QLAANILDQAIEDIQAIQNDARENGKYQDGEIPAWPVIIARLPKGWGGPT
HDASNNPIENSFRAHQVPLPLEQHDLATLPEFEDWMNSYKPEELFNADGS
LKDELKAIAPKGDKRMSANPITNGGADRSDLKLPNWREFANDINDDTRGK
EFADSKRNMDMATLSNYLGAVSQLNPTRFRFFGPDETMSNRLWGLFNVTP
RQWMEEIKEPQDQLLSPTGRIIDSQLSEHQAEGWLEGYTLTGRVGIFASY
ESFLRVVDTMVTQHFKWLRHASEQAWRNDYPSLNLIATSTAFQQDHNGYT
HQDPGMLTHLAEKKSNFIREYLPADGNSLLAVQERAFSERHKVNLLIASK
QPRQQWFTVEEAEVLANEGLKIIDWASTAPSSDVDITFASAGTEPTIETL
AALWLINQAFPDVKFRYVNVVELLRLQKKSEPNMNDERELSAEEFNKYFQ
ADTPVIFGFHAYENLIESFFFERKFTGDVYVHGYREDGDITTTYDMRVYS
HLDRFHQAKEAAEILSANGKIDQAAADTFIAKMDDTLAKHFQVTRNEGRD
IEEFTDWTWSPLK Phosphotransacetylase gene and gene product sequences are well known to those of skill in the art. Exemplary, representative gene and gene product sequences include:

```
PTA from Clostridium kluyveri
Nucleotide sequence (codon optimized for Y.
lipolytica) (SEQ ID NO: 9):
ATGAAGTTGATGGAAAACATCTTCGGTTTGGCTAAGGCTGATAAGAAGAA

AATCGTTTTGGCTGAAGGTGAAGAAGAAAGAAACATTAGAGCCTCCGAAG

AAATCATCAGAGATGGTATTGCTGATATCATCTTGGTCGGTTCTGAATCC

GTTATCAAAGAAAATGCTGCTAAGTTCGGTGTTAACTTGGCTGGTGTTGA

AATAGTTGATCCAGAAACTTCTTCTAAGACTGCTGGTTACGCTAATGCCT

TCTACGAAATTAGAAAGAACAAGGGTGTTACCTTGGAAAAGGCAGATAAG

ATAGTTAGAGATCCAATCTACTTCGCTACCATGATGGTTAAGTTGGGTGA

TGCTGATGGTTTGGTTTCTGGTGCTATTCATACAACCGGTGATTTGTTAA

GACCAGGTTTACAAATCGTTAAGACTGTTCCAGGTGCTTCCGTTGTTTCT

TCTGTTTTTTTGATGTCTGTTCCAGACTGCGAATATGGTGAAGATGGTTT

TTTGTTGTTCGCTGATTGTGCTGTTAACGTTTGTCCAACTGCTGAAGAAT

TGTCCTCTATTGCTATTACTACTGCTGAAACCGCTAAGAACTTGTGCAAA

ATTGAACCTAGAGTTGCCATGTTGTCTTTCTCTACTATGGGTTCTGCTTC

CCATGAATTGGTTGATAAGGTTACTAAGGCTACCAAGTTGGCTAAAGAAG

CTAGACCAGATTTGGATATCGATGGTGAATTACAATTGGATGCCTCCTTG

GTTAAGAAGGTTGCTGATTTGAAAGCTCCAGGTTCTAAAGTTGCTGGTAA

GGCTAATGTTTTGATCTTCCCAGATATTCAAGCCGGTAACATTGGTTACA

AGTTGGTTCAAAGATTTGCTAAGGCAGAAGCCATTGGTCCAATTTGTCAA

GGTTTTGCTAAGCCAATCAACGACTTGTCTAGAGGTTGTTCTGTTGATGA

TATCGTTAAGGTTGTTGCCGTTACTGCTGTTCAAGCTCAAGCACAAGGTT

AA
```

Amino acid sequence (SEQ ID NO: 10):
KLMENIFGLAKADKKKIVLAEGEEERNIRASEEIIRDGIADIILVGSESV
IKENAAKFGVNLAGVEIVDPETSSKTAGYANAFYEIRKNKGVTLEKADKI
VRDPIYFATMMVKLGDADGLVSGAIHTTGDLLRPGLQIVKTVPGASVVSS
VFLMSVPDCEYGEDGFLLFADCAVNVCPTAEELSSIAITTAETAKNLCKI
EPRVAMLSFSTMGSASHELVDKVTKATKLAKEARPDLDIDGELQLDASLV
KKVADLKAPGSKVAGKANVLIFPDIQAGNIGYKLVQRFAKAEAIGPICQG
FAKPINDLSRGCSVDDIVKVVAVTAVQAQAQG Pyruvate formate lyase gene and gene product sequences are well known to those of skill in the art. Exemplary, representative gene and gene product sequences include:

```
PflB from Escherichia coli
Nucleotide sequence (SEQ ID NO: 11):
ATGTCCGAGCTTAATGAAAAGTTAGCCACAGCCTGGGAAGGTTTTACCAA

AGGTGACTGGCAGAATGAAGTAAACGTCCGTGACTTCATTCAGAAAAACT

ACACTCCGTACGAGGGTGACGAGTCCTTCCTGGCTGGCGCTACTGAAGCG

ACCACCACCCTGTGGGACAAAGTAATGGAAGGCGTTAAACTGGAAAACCG

CACTCACGCGCCAGTTGACTTTGACACCGCTGTTGCTTCCACCATCACCT

CTCACGACGCTGGCTACATCAACAAGCAGCTTGAGAAAATCGTTGGTCTG

CAGACTGAAGCTCCGCTGAAACGTGCTCTTATCCCGTTCGGTGGTATCAA

AATGATCGAAGGTTCCTGCAAAGCGTACAACCGCGAACTGGATCCGATGA

TCAAAAAAATCTTCACTGAATACCGTAAAACTCACAACCAGGGCGTGTTC

GACGTTTACACTCCGGACATCCTGCGTTGCCGTAAATCTGGTGTTCTGAC

CGGTCTGCCAGATGCATATGGCCGTGGCCGTATCATCGGTGACTACCGTC
```

-continued
```
GCGTTGCGCTGTACGGTATCGACTACCTGATGAAAGACAAACTGGCACAG
TTCACTTCTCTGCAGGCTGATCTGGAAAACGGCGTAAACCTGGAACAGAC
TATCCGTCTGCGCGAAGAAATCGCTGAACAGCACCGCGCTCTGGGTCAGA
TGAAAGAAATGGCTGCGAAATACGGCTACGACATCTCTGGTCCGGCTACC
AACGCTCAGGAAGCTATCCAGTGGACTTACTTCGGCTACCTGGCTGCTGT
TAAGTCTCAGAACGGTGCTGCAATGTCCTTCGGTCGTACCTCCACCTTCC
TGGATGTGTACATCGAACGTGACCTGAAAGCTGGCAAGATCACCGAACAA
GAAGCGCAGGAAATGGTTGACCACCTGGTCATGAAACTGCGTATGGTTCG
CTTCCTGCGTACTCCGGAATACGATGAACTGTTCTCTGGCGACCCGATCT
GGGCAACCGAATCTATCGGTGGTATGGGCCTCGACGGTCGTACCCTGGTT
ACCAAAAACAGCTTCCGTTTCCTGAACACCCTGTACACCATGGGTCCGTC
TCCGGAACCGAACATGACCATTCTGTGGTCTGAAAAACTGCCGCTGAACT
TCAAGAAATTCGCCGCTAAAGTGTCCATCGACACCTCTTCTCTGCAGTAT
GAGAACGATGACCTGATGCGTCCGGACTTCAACAACGATGACTACGCTAT
TGCTTGCTGCGTAAGCCCGATGATCGTTGGTAAACAAATGCAGTTCTTCG
GTGCGCGTGCAAACCTGGCGAAAACCATGCTGTACGCAATCAACGGCGGC
GTTGACGAAAAACTGAAAATGCAGGTTGGTCCGAAGTCTGAACCGATCAA
AGGCGATGTCCTGAACTATGATGAAGTGATGGAGCGCATGGATCACTTCA
TGGACTGGCTGGCTAAACAGTACATCACTGCACTGAACATCATCCACTAC
ATGCACGACAAGTACAGCTACGAAGCCTCTCTGATGGCGCTGCACGACCG
TGACGTTATCCGCACCATGGCGTGTGGTATCGCTGGTCTGTCCGTTGCTG
CTGACTCCCTGTCTGCAATCAAATATGCGAAAGTTAAACCGATTCGTGAC
GAAGACGGTCTGGCTATCGACTTCGAAATCGAAGGCGAATACCCGCAGTT
TGGTAACAATGATCCGCGTGTAGATGACCTGGCTGTTGACCTGGTAGAAC
GTTTCATGAAGAAAATTCAGAAACTGCACACCTACCGTGACGCTATCCCG
ACTCAGTCTGTTCTGACCATCACTTCTAACGTTGTGTATGGTAAGAAAAC
GGGTAACACCCCAGACGGTCGTCGTGCTGGCGCGCCGTTCGGACCGGGTG
CTAACCCGATGCACGGTCGTGACCAGAAAGGTGCAGTAGCCTCTCTGACT
TCCGTTGCTAAACTGCCGTTTGCTTACGCTAAAGATGGTATCTCCTACAC
CTTCTCTATCGTTCCGAACGCACTGGGTAAAGACGACGAAGTTCGTAAGA
CCAACCTGGCTGGTCTGATGGATGGTTACTTCCACCACGAAGCATCCATC
GAAGGTGGTCAGCACCTGAACGTTAACGTGATGAACCGTGAAATGCTGCT
CGACGCGATGGAAAACCCGGAAAAATATCCGCAGCTGACCATCCGTGTAT
CTGGCTACGCAGTACGTTTCAACTCGCTGACTAAAGAACAGCAGCAGGAC
GTTATTACTCGTACCTTCACTCAATCTATGTAA
```
Amino acid sequence (SEQ ID NO: 12):
SELNEKLATAWEGFTKGDWQNEVNVRDFIQKNYTPYEGDESFLAGATEAT

TTLWDKVMEGVKLENRTHAPVDFDTAVASTITSHDAGYINKQLEKIVGLQ

TEAPLKRALIPFGGIKMIEGSCKAYNRELDPMIKKIFTEYRKTHNQGVFD

VYTPDILRCRKSGVLTGLPDAYGRGRIIGDYRRVALYGIDYLMKDKLAQF

TSLQADLENGVNLEQTIRLREEIAEQHRALGQMKEMAAKYGYDISGPATN

AQEAIQWTYFGYLAAVKSQNGAAMSFGRTSTFLDVYIERDLKAGKITEQE

AQEMVDHLVMKLRMVRFLRTPEYDELFSGDPIWATESIGGMGLDGRTLVT

KNSFRFLNTLYTMGPSPEPNMTILWSEKLPLNFKKFAAKVSIDTSSLQYE

NDDLMRPDFNNDDYAIACCVSPMIVGKQMQFFGARANLAKTMLYAINGGV

DEKLKMQVGPKSEPIKGDVLNYDEVMERMDHFMDWLAKQYITALNIIHYM

HDKYSYEASLMALHDRDVIRTMACGIAGLSVAADSLSAIKYAKVKPIRDE

DGLAIDFEIEGEYPQFGNNDPRVDDLAVDLVERFMKKIQKLHTYRDAIPT

QSVLTITSNVVYGKKTGNTPDGRRAGAPFGPGANPMHGRDQKGAVASLTS

VAKLPFAYAKDGISYTFSIVPNALGKDDEVRKTNLAGLMDGYFHHEASIE

GGQHLNVNVMNREMLLDAMENPEKYPQLTIRVSGYAVRFNSLTKEQQQDV

ITRTFTQSM

Pyruvate formate lyase activating enzyme gene and gene product sequences are well known to those of skill in the art. Exemplary, representative gene and gene product sequences include:

PflA from *Escherichia coli*
Nucleotide sequence (SEQ ID NO: 13):
```
ATGTCAGTTATTGGTCGCATTCACTCCTTTGAATCCTGTGGAACCGTAG
ACGGCCCAGGTATTCGCTTTATCACCTTTTTCCAGGGCTGCCTGATGCG
CTGCCTGTATTGTCATAACCGCGACACCTGGGACACGCATGGCGGTAAA
GAAGTTACCGTTGAAGATTTGATGAAGGAAGTGGTGACCTATCGCCACT
TTATGAACGCTTCCGGCGGCGGCGTTACCGCATCCGGCGGTGAAGCAAT
CCTGCAAGCTGAGTTTGTTCGTGACTGGTTCCGCGCCTGCAAAAAGAA
GGCATTCATACCTGTCTGGACACCAACGGTTTTGTTCGTCGTTACGATC
CGGTGATTGATGAACTGCTGGAAGTAACCGACCTGGTAATGCTCGATCT
CAAACAGATGAACGACGAGATCCACCAAAATCTGGTTGGAGTTTCCAAC
CACCGCACGCTGGAGTTCGCTAAATATCTGGCGAACAAAAATGTGAAGG
TGTGGATCCGCTACGTTGTTGTCCCAGGCTGGTCTGACGATGACGATTC
AGCGCATCGCCTCGGTGAATTTACCCGTGATATGGGCACGTTGAGAAAA
TCGAGCTTCTCCCCTACCACGAGCTGGGCAAACACAAATGGGTGGCAAT
GGGTGAAGAGTACAAACTCGACGGTGTTAAACCACCGAAGAAAGAGACC
ATGGAACGCGTGAAAGGCATTCTTGAGCAGTACGGTCATAAGGTAATGT
TCTAA
```
Amino acid sequence (SEQ ID NO: 14):
MSVIGRIHSFESCGTVDGPGIRFITFFQGCLMRCLYCHNRDTWDTHGGK

EVTVEDLMKEVVTYRHFMNASGGGVTASGGEAILQAEFVRDWFRACKKE

GIHTCLDTNGFVRRYDPVIDELLEVTDLVMLDLKQMNDEIHQNLVGVSN

HRTLEFAKYLANKNVKVWIRYVVVPGWSDDDSAHRLGEFTRDMGNVEK

IELLPYHELGKHKWVAMGEEYKLDGVKPPKKETMERVKGILEQYGHKVM

F

NADP+-dependent formate dehydrogenase gene and gene product sequences are well known to those of skill in the art. Exemplary, representative gene and gene product sequences include:

FDH from *Burkholderia stabilis*
Nucleotide sequence (codon optimized for *Y. lipolytica*) (SEQ ID NO: 15):
ATGGCTACTGTTTTGTGTGTCTTGTATCCAGATCCAGTTGATGGTTATCC

ACCACATTATGTTAGAGATACCATTCCAGTTATTACCAGATACGCTGATG

GTCAAACTGCTCCAACTCCAGCTGGTCCACCAGGTTTTAGACCAGGTGAA

TTGGTTGGTTCTGTTTCTGGTGCTTTGGGTTTGAGAGGTTATTTGGAAGC

TCATGGTCATACTTTGATCGTTACCTCTGATAAGGATGGTCCAGATTCTG

AATTCGAAAGAAGATTGCCAGACGCCGATGTTGTTATTTCTCAACCATTT

TGGCCAGCTTACTTGACCGCTGAAAGAATTGCTAGAGCACCAAAATTGAG

ATTGGCTTTGACTGCTGGTATTGGTTCTGATCATGTTGATTTGGATGCTG

CTGCTAGAGCCCATATTACTGTTGCTGAAGTTACTGGTTCCAACTCTATT

TCAGTTGCCGAACACGTTGTTATGACTACTTTGGCTTTGGTCAGAAACTA

CTTGCCATCTCATGCTATTGCTCAACAAGGTGGTTGGAATATTGCTGATT

GTGTCTCTAGATCCTACGATGTTGAAGGTATGCATTTTGGTACTGTTGGT

GCTGGTAGAATTGGTTTGGCTGTTTTGAGAAGATTGAAGCCATTTGGTTT

ACACTTGCACTACACCCAAAGACATAGATTGGATGCAGCTATCGAACAAG

AATTGGGTTTAACTTATCATGCTGATCCAGCTTCATTGGCTGCTGCTGTT

GATATAGTTAACTTGCAAATCCCATTATACCCATCCACCGAACATTTGTT

TGATGCTGCTATGATTGCTAGAATGAAGAGAGGTGCATACTTGATTAACA

CCGCTAGAGCTAAATTGGTTGATAGAGATGCTGTTGTTAGAGCTGTTACT

TCTGGTCATTTGGCTGGTTATGGTGGTGATGTTTGGTTTCCACAACCAGC

TCCAGCTGATCATCCTTGGAGAGCTATGCCTTTTAATGGTATGACTCCAC

ATATCTCCGGTACATCTTTGTCTGCTCAAGCTAGATATGCTGCTGGTACT

TTGGAAATATTGCAATGTTGGTTTGACGGTAGACCAATCAGAAACGAATA

TTTGATTGTCGACGGTGGTACTTTAGCTGGTACTGGTGCTCAATCTTACA

GATTAACTTAA

Amino acid sequence (SEQ ID NO: 16):
MATVLCVLYPDPVDGYPPHYVRDTIPVITRYADGQTAPTPAGPPGFRPGE

LVGSVSGALGLRGYLEAHGHTLIVTSDKDGPDSEFERRLPDADVVISQPF

WPAYLTAERIARAPKLRLALTAGIGSDHVDLDAAARAHITVAEVTGSNSI

SVAEHVVMTTLALVRNYLPSHAIAQQGGWNIADCVSRSYDVEGMHFGTVG

AGRIGLAVLRRLKPFGLHLHYTQRHRLDAAIEQELGLTYHADPASLAAAV

DIVNLQIPLYPSTEHLFDAAMIARMKRGAYLINTARAKLVDRDAVVRAVT

SGHLAGYGGDVWFPQPAPADHPWRAMPFNGMTPHISGTSLSAQARYAAGT

LEILQCWFDGRPIRNEYLIVDGGTLAGTGAQSYRLT

NAD+-dependent pyruvate dehydrogenase gene and gene product sequences are well known to those of skill in the art. NAD+-dependent pyruvate dehydrogenase comprises an E1 pyruvate dehydrogenase (AceE) gene product of *Escherichia coli*, an E2 dihydrolipoyl transacetylase (AceF) gene product of *Escherichia coli* and an E3 dihydrolipoyl dehydrogenase (Lpd) gene product of *Escherichia coli*. Listed the three subunits independently. Exemplary, representative gene and gene product sequences include:

E1 pyruvate dehydrogenase gene and gene product sequences are well known to those of skill in the art. Exemplary, representative gene and gene product sequences include:
E1 Pyruvate Dehydrogenase AceE from *Escherichia coli*

Nucleotide sequence (SEQ ID NO: 17):
ATGTCAGAACGTTTCCCAAATGACGTGGATCCGATCGAAACTCGCGACTG

GCTCCAGGCGATCGAATCGGTCATCCGTGAAGAAGGTGTTGAGCGTGCTC

AGTATCTGATCGACCAACTGCTTGCTGAAGCCCGCAAAGGCGGTGTAAAC

GTAGCCGCAGGCACAGGTATCAGCAACTACATCAACACCATCCCCGTTGA

AGAACAACCGGAGTATCCGGGTAATCTGGAACTGGAACGCCGTATTCGTT

CAGCTATCCGCTGGAACGCCATCATGACGGTGCTGCGTGCGTCGAAAAAA

GACCTCGAACTGGGCGGCCATATGGCGTCCTTCCAGTCTTCCGCAACCAT

TTATGATGTGTGCTTTAACCACTTCTTCCGTGCACGCAACGAGCAGGATG

GCGGCGACCTGGTTTACTTCCAGGGCCACATCTCCCCGGGCGTGTACGCT

CGTGCTTTCCTGGAAGGTCGTCTGACTCAGGAGCAGCTGGATAACTTCCG

TCAGGAAGTTCACGGCAATGGCCTCTCTTCCTATCCGCACCCGAAACTGA

TGCCGGAATTCTGGCAGTTCCCGACCGTATCTATGGGTCTGGGTCCGATT

GGTGCTATTTACCAGGCTAAATTCCTGAAATATCTGGAACACCGTGGCCT

GAAAGATACCTCTAAACAAACCGTTTACGCGTTCCTCGGTGACGGTGAAA

TGGACGAACCGGAATCCAAAGGTGCGATCACCATCGCTACCCGTGAAAAA

CTGGATAACCTGGTCTTCGTTATCAACTGTAACCTGCAGCGTCTTGACGG

CCCGGTCACCGGTAACGGCAAGATCATCAACGAACTGGAAGGCATCTTCG

AAGGTGCTGGCTGGAACGTGATCAAAGTGATGTGGGGTAGCCGTTGGGAT

GAACTGCTGCGTAAGGATACCAGCGGTAAACTGATCCAGCTGATGAACGA

AACCGTTGACGGCGACTACCAGACCTTCAAATCGAAAGATGGTGCGTACG

TTCGTGAACACTTCTTCGGTAAATATCCTGAAACCGCAGCACTGGTTGCA

GACTGGACTGACGAGCAGATCTGGGCACTGAACCGTGGTGGTCACGATCC

GAAGAAAATCTACGCTGCATTCAAGAAAGCGCAGGAAACCAAAGGCAAAG

CGACAGTAATCCTTGCTCATACCATTAAAGGTTACGGCATGGGCGACGCG

GCTGAAGGTAAAAACATCGCGCACCAGGTTAAGAAAATGAACATGGACGG

TGTGCGTCATATCCGCGACCGTTTCAATGTGCCGGTGTCTGATGCAGATA

TCGAAAAACTGCCGTACATCACCTTCCCGGAAGGTTCTGAAGAGCATACC

TATCTGCACGCTCAGCGTCAGAAACTGCACGGTTATCTGCCAAGCCGTCA

GCCGAACTTCACCGAGAAGCTTGAGCTGCCGAGCCTGCAAGACTTCGGCG

CGCTGTTGGAAGAGCAGAGCAAAGAGATCTCTACCACTATCGCTTTCGTT

CGTGCTCTGAACGTGATGCTGAAGAACAAGTCGATCAAAGATCGTCTGGT

ACCGATCATCGCCGACGAAGCGCGTACTTTCGGTATGGAAGGTCTGTTCC

GTCAGATTGGTATTTACAGCCCGAACGGTCAGCAGTACACCCCGCAGGAC

CGCGAGCAGGTTGCTTACTATAAAGAAGACGAGAAAGGTCAGATTCTGCA

GGAAGGGATCAACGAGCTGGGCGCAGGTTGTTCCTGGCTGGCAGCGGCGA

CCTCTTACAGCACCAACAATCTGCCGATGATCCCGTTCTACATCTATTAC

TCGATGTTCGGCTTCCAGCGTATTGGCGATCTGTGCTGGGCGGCTGGCGA

```
CCAGCAAGCGCGTGGCTTCCTGATCGGCGGTACTTCCGGTCGTACCACCC
TGAACGGCGAAGGTCTGCAGCACGAAGATGGTCACAGCCACATTCAGTCG
CTGACTATCCCGAACTGTATCTCTTACGACCCGGCTTACGCTTACGAAGT
TGCTGTCATCATGCATGACGGTCTGGAGCGTATGTACGGTGAAAAACAAG
AGAACGTTTACTACTACATCACTACGCTGAACGAAAACTACCACATGCCG
GCAATGCCGGAAGGTGCTGAGGAAGGTATCCGTAAAGGTATCTACAAACT
CGAAACTATTGAAGGTAGCAAAGGTAAAGTTCAGCTGCTCGGCTCCGGTT
CTATCCTGCGTCACGTCCGTGAAGCAGCTGAGATCCTGGCGAAAGATTAC
GGCGTAGGTTCTGACGTTTATAGCGTGACCTCCTTCACCGAGCTGGCGCG
TGATGGTCAGGATTGTGAACGCTGGAACATGCTGCACCCGCTGGAAACTC
CGCGCGTTCCGTATATCGCTCAGGTGATGAACGACGCTCCGGCAGTGGCA
TCTACCGACTATATGAAACTGTTCGCTGAGCAGGTCCGTACTTACGTACC
GGCTGACGACTACCGCGTACTGGGTACTGATGGCTTCGGTCGTTCCGACA
GCCGTGAGAACCTGCGTCACCACTTCGAAGTTGATGCTTCTTATGTCGTG
GTTGCGGCGCTGGGCGAACTGGCTAAACGTGGCGAAATCGATAAGAAAGT
GGTTGCTGACGCAATCGCCAAATTCAACATCGATGCAGATAAAGTTAACC
CGCGTCTGGCGTAA
```

Amino acid sequence (SEQ ID NO: 18):
MADFDSKEYLELVDKWWRATNYLSAGMIFLKSNPLFSVTNTPIKAEDVKV
KPIGHWGTISGQTFLYAHANRLINKYGLNMFYVGGPGHGGQVMVTNAYLD
GAYTEDYPEITQDIEGMSHLFKRFSFPGGIGSHMTAQTPGSLHEGGELGY
SLSHAFGAVLDNPDQVAFAVVGDGEAETGPSMASWHSIKFLNAKNDGAVL
PVLDLNGFKISNPTIFSRMSDEEITKFFEGLGYSPRFIENDDIHDYATYH
QLAANILDQAIEDIQAIQNDARENGKYQDGEIPAWPVIIARLPKGWGGPT
HDASNNPIENSFRAHQVPLPLEQHDLATLPEFEDWMNSYKPEELFNADGS
LKDELKAIAPKGDKRMSANPITNGGADRSDLKLPNWREFANDINDDTRGK
EFADSKRNMDMATLSNYLGAVSQLNPTRFRFFGPDETMSNRLWGLFNVTP
RQWMEEIKEPQDQLLSPTGRIIDSQLSEHQAEGWLEGYTLTGRVGIFASY
ESFLRVVDTMVTQHFKWLRHASEQAWRNDYPSLNLIATSTAFQQDHNGYT
HQDPGMLTHLAEKKSNFIREYLPADGNSLLAVQERAFSERHKVNLLIASK
QPRQQWFTVEEAEVLANEGLKIIDWASTAPSSDVDITFASAGTEPTIETL
AALWLINQAFPDVKFRYVNVVELLRLQKKSEPNMNDERELSAEEFNKYFQ
ADTPVIFGFHAYENLIESFFFERKFTGDVYVHGYREDGDITTTYDMRVYS
HLDRFHQAKEAAEILSANGKIDQAAADTFIAKMDDTLAKHFQVTRNEGRD
IEEFTDWTWSPLK E2 dihydrolipoyl transacetylase gene and gene product sequences are well known to those of skill in the art. Exemplary, representative gene and gene product sequences include:

E2 dihydrolipoyl transacetylase AceF from *Escherichia coli* Nucleotide sequence (SEQ ID NO: 19):
```
ATGGCTATCGAAATCAAAGTACCGGACATCGGGGCTGATGAAGTTGAAAT
CACCGAGATCCTGGTCAAAGTGGGCGACAAAGTTGAAGCCGAACAGTCGC
TGATCACCGTAGAAGGCGACAAAGCCTCTATGGAAGTTCCGTCTCCGCAG
GCGGGTATCGTTAAAGAGATCAAAGTCTCTGTTGGCGATAAAACCCAGAC
CGGCGCACTGATTATGATTTTCGATTCCGCCGACGGTGCAGCAGACGCTG
CACCTGCTCAGGCAGAAGAGAAGAAAGAAGCAGCTCCGGCAGCAGCACCA
GCGGCTGCGGCGGCAAAAGACGTTAACGTTCCGGATATCGGCAGCGACGA
AGTTGAAGTGACCGAAATCCTGGTGAAAGTTGGCGATAAAGTTGAAGCTG
AACAGTCGCTGATCACCGTAGAAGGCGACAAGGCTTCTATGGAAGTTCCG
GCTCCGTTTGCTGGCACCGTGAAAGAGATCAAAGTGAACGTGGGTGACAA
AGTGTCTACCGGCTCGCTGATTATGGTCTTCGAAGTCGCGGGTGAAGCAG
GCGCGGCAGCTCCGGCCGCTAAACAGGAAGCAGCTCCGGCAGCGGCCCT
GCACCAGCGGCTGGCGTGAAAGAAGTTAACGTTCCGGATATCGGCGGTGA
CGAAGTTGAAGTGACTGAAGTGATGGTGAAAGTGGGCGACAAAGTTGCCG
CTGAACAGTCACTGATCACCGTAGAAGGCGACAAAGCTTCTATGGAAGTT
CCGGCGCCGTTTGCAGGCGTCGTGAAGGAACTGAAAGTCAACGTTGGCGA
TAAAGTGAAAACTGGCTCGCTGATTATGATCTTCGAAGTTGAAGGCGCAG
CGCCTGCGGCAGCTCCTGCGAAACAGGAAGCGGCAGCGCCGGCACCGGCA
GCAAAAGCTGAAGCCCCGGCAGCAGCACCAGCTGCGAAAGCGGAAGGCAA
ATCTGAATTTGCTGAAAACGACGCTTATGTTCACGCGACTCCGCTGATCC
GCCGTCTGGCACGCGAGTTTGGTGTTAACCTTGCGAAAGTGAAGGGCACT
GGCCGTAAAGGTCGTATCCTGCGCGAAGACGTTCAGGCTTACGTGAAAGA
AGCTATCAAACGTGCAGAAGCAGCTCCGGCAGCGACTGGCGGTGGTATCC
CTGGCATGCTGCCGTGGCCGAAGGTGGACTTCAGCAAGTTTGGTGAAATC
GAAGAAGTGGAACTGGGCCGCATCCAGAAAATCTCTGGTGCGAACCTGAG
CCGTAACTGGGTAATGATCCCGCATGTTACTCACTTCGACAAAACCGATA
TCACCGAGTTGGAAGCGTTCCGTAAACAGCAGAACGAAGAAGCGGCGAAA
CGTAAGCTGGATGTGAAGATCACCCCGGTTGTCTTCATCATGAAAGCCGT
TGCTGCAGCTCTTGAGCAGATGCCTCGCTTCAATAGTTCGCTGTCGGAAG
ACGGTCAGCGTCTGACCCTGAAGAAATACATCAACATCGGTGTGGCGGTG
GATACCCCGAACGGTCTGGTTGTTCCGGTATTCAAAGACGTCAACAAGAA
AGGCATCATCGAGCTGTCTCGCGAGCTGATGACTATTTCTAAGAAAGCGC
GTGACGGTAAGCTGACTGCGGGCGAAATGCAGGGCGGTTGCTTCACCATC
TCCAGCATCGGCGGCCTGGGTACTACCCACTTCGCGCCGATTGTGAACGC
GCCGGAAGTGGCTATCCTCGGCGTTTCCAAGTCCGCGATGGAGCCGGTGT
GGAATGGTAAAGAGTTCGTGCCGCGTCTGATGCTGCCGATTTCTCTCTCC
TTCGACCACCGCGTGATCGACGGTGCTGATGGTGCCCGTTTCATTACCAT
CATTAACAACACGCTGTCTGACATTCGCCGTCTGGTGATGTAA
```

Amino acid sequence (SEQ ID NO: 20):
MAIEIKVPDIGADEVEITEILVKVGDKVEAEQSLITVEGDKASMEVPSPQ
AGIVKEIKVSVGDKTQTGALIMIFDSADGAADAAPAQAEEKKEAAPAAAP
AAAAAKDVNVPDIGSDEVEVTEILVKVGDKVEAEQSLITVEGDKASMEVP

APFAGTVKEIKVNVGDKVSTGSLIMVFEVAGEAGAAAPAAKQEAAPAAAP

APAAGVKEVNVPDIGGDEVEVTEVMVKVGDKVAAEQSLITVEGDKASMEV

PAPFAGVVKELKVNVGDKVKTGSLIMIFEVEGAAPAAAPAKQEAAAPAPA

AKAEAPAAAPAAKAEGKSEFAENDAYVHATPLIRRLAREFGVNLAKVKGT

GRKGRILREDVQAYVKEAIKRAEAAPAATGGGIPGMLPWPKVDFSKFGEI

EEVELGRIQKISGANLSRNWVMIPHVTHFDKTDITELEAFRKQQNEEAAK

RKLDVKITPVVFIMKAVAAALEQMPRFNSSLSEDGQRLTLKKYINIGVAV

DTPNGLVVPVFKDVNKKGIIELSRELMTISKKARDGKLTAGEMQGGCFTI

SSIGGLGTTHFAPIVNAPEVAILGVSKSAMEPVWNGKEFVPRLMLPISLS

FDHRVIDGADGARFITIINNTLSDIRRLVM

E3 dihydrolipoyl dehydrogenase gene and gene product sequences are well known to those of skill in the art. Exemplary, representative gene and gene product sequences include:

```
E3 dihydrolipoyl dehydrogenase Lpd from
Escherichia coli Nucleotide sequence (SEQ ID
NO: 21):
```
ATGAGTACTGAAATCAAAACTCAGGTCGTGGTACTTGGGGCAGGCCCCGC

AGGTTACTCCGCTGCCTTCCGTTGCGCTGATTTAGGTCTGGAAACCGTAA

TCGTAGAACGTTACAACACCCTTGGCGGTGTTTGCCTGAACGTCGGCTGT

ATCCCTTCTAAAGCACTGCTGCACGTAGCAAAAGTTATCGAAGAAGCCAA

AGCGCTGGCTGAACACGGTATCGTCTTCGGCGAACCGAAAACCGATATCG

ACAAGATTCGTACCTGGAAAGAGAAAGTGATCAATCAGCTGACCGGTGGT

CTGGCTGGTATGGCGAAAGGCCGCAAAGTCAAAGTGGTCAACGGTCTGGG

TAAATTCACCGGGGCTAACACCCTGGAAGTTGAAGGTGAGAACGGCAAAA

CCGTGATCAACTTCGACAACGCGATCATTGCAGCGGGTTCTCGCCCGATC

CAACTGCCGTTTATTCCGCATGAAGATCCGCGTATCTGGGACTCCACTGA

CGCGCTGGAACTGAAAGAAGTACCAGAACGCCTGCTGGTAATGGGTGGCG

GTATCATCGGTCTGGAAATGGGCACCGTTTACCACGCGCTGGGTTCACAG

ATTGACGTGGTTGAAATGTTCGACCAGGTTATCCCGGCAGCTGACAAAGA

CATCGTTAAAGTCTTCACCAAGCGTATCAGCAAGAAATTCAACCTGATGC

TGGAAACCAAAGTTACCGCCGTTGAAGCGAAAGAAGACGGCATTTATGTG

ACGATGGAAGGCAAAAAAGCACCCGCTGAACCGCAGCGTTACGACGCCGT

GCTGGTAGCGATTGGTCGTGTGCCGAACGGTAAAAACCTCGACGCAGGCA

AAGCAGGCGTGGAAGTTGACGACCGTGGTTTCATCCGCGTTGACAAACAG

CTGCGTACCAACGTACCGCACATCTTTGCTATCGGCGATATCGTCGGTCA

ACCGATGCTGGCACACAAAGGTGTTCACGAAGGTCACGTTGCCGCTGAAG

TTATCGCCGGTAAGAAACACTACTTCGATCCGAAAGTTATCCCGTCCATC

GCCTATACCGAACCAGAAGTTGCATGGGTGGGTCTGACTGAGAAAGAAGC

GAAAGAGAAAGGCATCAGCTATGAAACCGCCACCTTCCCGTGGGCTGCTT

CTGGTCGTGCTATCGCTTCCGACTGCGCAGACGGTATGACCAAGCTGATT

TTCGACAAGAATCTCACCGTGTGATCGGTGGTGCGATTGTCGGTACTAA

CGGCGGCGAGCTGCTGGGTGAAATCGGCCTGGCAATCGAAATGGGTTGTG

ATGCTGAAGACATCGCACTGACCATCCACGCGCACCCGACTCTGCACGAG

TCTGTGGGCCTGGCGGCAGAAGTGTTCGAAGGTAGCATTACCGACCTGCC

GAACCCGAAAGCGAAGAAGAAGTAA

```
Amino acid sequence (SEQ ID NO: 22):
```
MSTEIKTQVVVLGAGPAGYSAAFRCADLGLETVIVERYNTLGGVCLNVGC

IPSKALLHVAKVIEEAKALAEHGIVFGEPKTDIDKIRTWKEKVINQLTGG

LAGMAKGRKVKVVNGLGKFTGANTLEVEGENGKTVINFDNAIIAAGSRPI

QLPFIPHEDPRIWDSTDALELKEVPERLLVMGGGIIGLEMGTVYHALGSQ

IDVVEMFDQVIPAADKDIVKVFTKRISKKFNLMLETKVTAVEAKEDGIYV

TMEGKKAPAEPQRYDAVLVAIGRVPNGKNLDAGKAGVEVDDRGFIRVDKQ

LRTNVPHIFAIGDIVGQPNILAHKGVHEGHVAAEVIAGKKHYFDPKVIPS

IAYTEPEVAWVGLTEKEAKEKGISYETATFPWAASGRAIASDCADGMTKL

IFDKESHRVIGGAIVGTNGGELLGEIGLAIEMGCDAEDIALTIHAHPTLH

ESVGLAAEVFEGSITDLPNPKAKKK

Mutant of E3 dihydrolipoyl dehydrogenase gene and gene product sequences are well known to those of skill in the art. Exemplary, representative gene and gene product sequences include:

```
Mutant of E3 dihydrolipoyl dehydrogenase Lpdm
from Escherichia coli Nucleotide sequence (SEQ
ID NO: 23):
```
ATGAGTACTGAAATCAAAACTCAGGTCGTGGTACTTGGGGCAGGCCCCGC

AGGTTACTCCGCTGCCTTCCGTTGCGCTGATTTAGGTCTGGAAACCGTAA

TCGTAGAACGTTACAACACCCTTGGCGGTGTTTGCCTGAACGTCGGCTGT

ATCCCTTCTAAAGCACTGCTGCACGTAGCAAAAGTTATCGAAGAAGCCAA

AGCGCTGGCTGAACACGGTATCGTCTTCGGCGAACCGAAAACCGATATCG

ACAAGATTCGTACCTGGAAAGAGAAAGTGATCAATCAGCTGACCGGTGGT

CTGGCTGGTATGGCGAAAGGCCGCAAAGTCAAAGTGGTCAACGGTCTGGG

TAAATTCACCGGGGCTAACACCCTGGAAGTTGAAGGTGAGAACGGCAAAA

CCGTGATCAACTTCGACAACGCGATCATTGCAGCGGGTTCTCGCCCGATC

CAACTGCCGTTTATTCCGCATGAAGATCCGCGTATCTGGGACTCCACTGA

CGCGCTGGAACTGAAAGAAGTACCAGAACGCCTGCTGGTAATGGGTGGCG

GTATCATCGCTCTGGAAATGGCTACCGTTTACCACGCGCTGGGTTCACAG

ATTGACGTGGTTGTTCGTAAACATCAGGTTATCCGTGCAGCTGACAAAGA

CATCGTTAAAGTCTTCACCAAGCGTATCAGCAAGAAATTCAACCTGATGC

TGGAAACCAAAGTTACCGCCGTTGAAGCGAAAGAAGACGGCATTTATGTG

ACGATGGAAGGCAAAAAAGCACCCGCTGAACCGCAGCGTTACGACGCCGT

GCTGGTAGCGATTGGTCGTGTGCCGAACGGTAAAAACCTCGACGCAGGCA

AAGCAGGCGTGGAAGTTGACGACCGTGGTTTCATCCGCGTTGACAAACAG

CTGCGTACCAACGTACCGCACATCTTTGCTATCGGCGATATCGTCGGTCA

ACCGATGCTGGCACACAAAGGTGTTCACGAAGGTCACGTTGCCGCTGAAG

TTATCGCCGGTAAGAAACACTACTTCGATCCGAAAGTTATCCCGTCCATC

-continued
GCCTATACCGAACCAGAAGTTGCATGGGTGGGTCTGACTGAGAAAGAAGC

GAAAGAGAAAGGCATCAGCTATGAAACCGCCACCTTCCCGTGGGCTGCTT

CTGGTCGTGCTATCGCTTCCGACTGCGCAGACGGTATGACCAAGCTGATT

TTCGACAAAGAATCTCACCGTGTGATCGGTGGTGCGATTGTCGGTACTAA

CGGCGGCGAGCTGCTGGGTGAAATCGGCCTGGCAATCGAAATGGGTTGTG

ATGCTGAAGACATCGCACTGACCATCCACGCGCACCCGACTCTGCACGAG

TCTGTGGGCCTGGCGGCAGAAGTGTTCGAAGGTAGCATTACCGACCTGCC

GAACCCGAAAGCGAAGAAGAAGTAA

Amino acid sequence (SEQ ID NO: 24):
MSTEIKTQVVVLGAGPAGYSAAFRCADLGLETVIVERYNTLGGVCLNVGC

IPSKALLHVAKVIEEAKALAEHGIVFGEPKTDIDKIRTWKEKVINQLTGG

LAGMAKGRKVKVVNGLGKFTGANTLEVEGENGKTVINFDNAIIAAGSRPI

QLPFIPHEDPRIWDSTDALELKEVPERLLVMGGGIIALEMATVYHALGSQ

IDVVVRKHQVIRAADKDIVKVFTKRISKKFNLMLETKVTAVEAKEDGIYV

TMEGKKAPAEPQRYDAVLVAIGRVPNGKNLDAGKAGVEVDDRGFIRVDKQ

LRTNVPHIFAIGDIVGQPNILAHKGVHEGHVAAEVIAGKKHYFDPKVIPS

IAYTEPEVAWVGLTEKEAKEKGISYETATFPWAASGRAIASDCADGMTKL

IFDKESHRVIGGAIVGTNGGELLGEIGLAIEMGCDAEDIALTIHAHPTLH

ESVGLAAEVFEGSITDLPNPKAKKK

NAD+/NADH kinase gene and gene product sequences are well known to those of skill in the art. Proteins in *Y. lipolytica* catalyzing the phosphorylation of NADH to form NADPH include: POS5, UTR1, and YEF1. Exemplary, representative gene and gene product sequences include:

PerOxide Sensitive gene and gene product sequences are well known to those of skill in the art. Exemplary, representative gene and gene product sequences include:

POS5 from *Yarrowia lipolytica*, NCBI Accession
No. YALI0E17963p Nucleotide sequence (SEQ ID
NO: 25):
ATGCGACTACTCATCCGCCGAACCGGTATAACACGGCCCCACAGCGTGCA

AGCGCGCCGATCCACATGGATTCGGCTTCTCTCGACCGAGATATTGCATG

CAGAACTGCTTCCCGACCGCCAGTCGCCCCACTACGTCCAGGAGTCGACC

TCTCTGTCATCTCTGGTGTGGGACAAGCCTCTGGAAAACGTTCTGATCGT

CAAAAAACCCTGGGACCACAATGTGCGCGAGTCGCTCATCCAGATGGCAT

CTCACATCCAGCGCCGGTACCCCCGAGTCAACATTCTGGTGGAGGAACAT

GTGGCCGACGAGGTCCAGAAGCAGATTGGAGCCGCAGGCGTGACCGCCAT

CCACACGGGCCAGGAGAGGTGCTGAGAAACAAGACGGATCTGCTCGTGA

CTCTGGGAGGCGACGGAACTATTCTACATGCCACCTCCATGTTTGCTTCC

GGAGAAGTGCCGCCGGTGCTGTCCTTTTCGCTGGGGACTCTGGGTTTCCT

GCTGCCGTTTGATTTCAAGGACTTCAAAACTGCATTCGACATGGTGTACT

CGTCGCAGGCCTCGGTGGTCAACCGCGCCCGCCTAGCATGTCAGAAAATG

TCCATTCGCAAGGAAATCACCCACTTGCCCTCCCAATCGCACATTGAACA

CAACTCAACCCATGTCTACGGCAATCCCGACGACTACAATCTTAGCCCAC

TAACCTACGCCATGAACGACATCAACATCCACCGTGGGAGCTGAGCCGCAT

CTCACCAAGCTCGACATCCACGTTGACGGCGAGTTCATCACCCGAGCCAT

TGCTGACGGTGTCACCATCGCCACACCCACGGGCTCCACGGCCTACTCGC

TGTCGTCTGGCGGCTCCATTGTGCATCCCCGAGTCGCCTGCATTCTGCTG

ACCCCCATCTGTCCGCGATCGCTGTCATTCCGGCCTCTCATTTTCCCAGC

CACCTCCAAAATATGCATCACCGCCTCGTCCGAATCTCGAGGTAGAGGCG

CCGAGCTGTCTGTCGACGGAATCGCCAAGGGTCTGGTTCGACCCAGCGAC

AAGATTCTGGTCGAAAGCGAAACCGGCCACAACTCGGGCATCTGGTGCGT

GGCCAAGACAGACAGAGACTGGGTCAGTGGCCTCAACGGGTTACTGGGCT

TCAATAGCAGTTTTGGCAAGGGCGGGGAGGCGTCAGGCGATGTTGCTTAG

Amino acid sequence (SEQ ID NO: 26):
RLLIRRTGITRPHSVQARRSTWIRLLSTEILHAELLPDRQSPHYVQESTS

LSSLVWDKPLENVLIVKKPWOHNVRESLIQMASHIQRRYPRVNILVEEHV

ADEVQKQIGAAGVTAIHTGPGEVLRNKTDLLVTLGGDGTILHATSMFASG

EVPPVLSFSLGTLGFLLPFDFKDFKTAFDMVYSSQASVVNRARLACQKMS

IRKEITHLPSQSHIEHNSTHVYGNPDDYNLSPLTYANINDINIHRGAEPH

LTKLDIHVDGEFITRAIADGVTIATPTGSTAYSLSSGGSIVHPRVACILL

TPICPRSLSFRPLIFPATSKICITASSESRGRGAELSVDGIAKGLVRPSD

KILVESETGHNSGIWCVAKTDRDWVSGLNGLLGFNSSFGKGGEASGDVA

YEF1 gene and gene product sequences are well known to those of skill in the art. Exemplary, representative gene and gene product sequences include:

YEF1 from *Yarrowia lipolytica*, NCBI Accession No.
YALI0E23991p Nucleotide sequence (SEQ ID NO: 27):
ATGGCCCGCAACACAACGGACCGCCATCTCACCGTGCTTGTCCATGATCT

GCTAAACATTGCCGACGAGCATACCGGCAGCTCGCTGCTGAGCACCAACC

AGGCTCGCGCGGAGGCGACAGGCCACATTCTGTGCGAAAAGTCGCGCCAC

TCTCGAGAGGAGCTCAACGAGTTTGTCATGAACGTCCGGGGTCTGTCCAA

CCGGCTGAGCAACCTCAAGTTGAAGCCGCAGCTGCGACAAGTGATGATTG

TAGCGAAACTGCAGGATAAAGACATCATTGCCAAGACGCGCGACTTTGCG

TCGCTGCTGATGAAACGTGGAATCTCCGTCTACGTGCAGAAAGAGCTGGC

GGCCCATCCTCTGTTCAACCTCAATGGACTTGAGGGAGACGCCAAAAACG

CCGACACAAAGTTCCACACTTGGTCCGAGGTGGCTCTGCCGGACCCCAAC

AAACTGGACCTGGTCGTGACCCTTGGGGGCGACGGAACGGTGCTATTTGT

GTCCTGGCTGTTCCAGCAGATTGTGCCACCGGTGGTCTCCTTTGGCCTGG

GCTCTCTGGGATTCCTCACCGAGTACGAGTGGGACAGACGTGAGGAGACG

ATCGATTCGATCGACAAAAACGGCATCTATCTGTCGTTGAGAATGCGGTT

CGAGTGCCGCGTCATCCGAGCTGTCAAGGACGACGGAGAGGACTGGATGA

CCCGAGACTTGGACGACGAAATTCGTTCCATGGTTACCTCCCACAACTCG

ACCGACAACCTGGACGAGTACTCGTACGACAAGCATTACGTGGACGCCAC

GCACTCGATTCTCAACGACTTGGTGGTTGACCGAGGCACAAACTCCACCA

TGACCACCACAGAGCTGTACACGGACTTTGATCACCCTGACCACCGTACAG

GCCGATGGACTGGTGATTGCCACTCCTTCTGGATCCACGGCGTACTCCCT

-continued

```
GTCCGCAGGAGGATCTCTTGTTCACCCCGATATCCCCGGCATTCTCATTT

CCCCCATTTGTCCCCATACTCTGAGTTTCCGGCCGGTTGTTGTGCCCGAT

AATACTACGATTCGAATCGGAGTGCCATACGATGCTCGGGCGTCGGCGTA

CTGCTCGTTCGACGGCCGATCGAGGGTGGAACTGACGCCTGGAGACTTTA

TCACCGTCACCGCGTCGCGATTCCCATTCCCCAAGGTGCAGTCGGAGGCT

GGGTCCGAGTGGTATTCTGGTTTGTCCAATACGTTGAACTGGAACCAGCG

AAAGCGACAGAAGCGGTTCACCAACATTTAA
```

Amino acid sequence (SEQ ID NO: 28):
```
MARNTTDRHLTVLVHDLLNIADEHTGSSLLSTNQARAEATGHILCEKSRH

SREELNEFVMNVRGLSNRLSNLKLKPQLRQVMIVAKLQDKDIIAKTRDFA

SLLMKRGISVYVQKELAAHPLFNLNGLEGDAKNADTKFHTWSEVALPDPN

KLDLVVTLGGDGTVLFVSWLFQQIVPPVVSFGLGSLGFLTEYEWDRREET

IDSIDKNGIYLSLRMRFECRVIRAVKDDGEDWMTRDLDOEIRSMVTSHNS

TDNLDEYSYDKHYVDATHSILNDLVVDRGTNSTMTTTELYTDFDHLTTVQ

ADGLVIATPSGSTAYSLSAGGSLVHPDIPGILISPICPHTLSFRPVVVPD

NTTIRIGVPYDARASAYCSFDGRSRVELTPGDFITVTASRFPFPKVQSEA

GSEWYSGLSNTLNWNQRKRQKRFTNI
```

Aldehyde dehydrogenase gene and gene product sequences are well known to those of skill in the art. Exemplary, representative gene and gene product sequences include the following aldehyde dehydrogenase genes:

AldH from *Escherichia coli*, ECOCYC Accession ID: EG10036 Nucleotide sequence (SEQ ID NO: 29):
```
ATGAATTTTCATCATCTGGCTTACTGGCAGGATAAAGCGTTAAGTCTCG

CCATTGAAAACCGCTTATTTATTAACGGTGAATATACTGCTGCGGCGGA

AAATGAAACCTTTGAAACCGTTGATCCGGTCACCCAGGCACCGCTGGCG

AAAATTGCCCGCGGCAAGAGCGTCGATATCGACCGTGCGATGAGCGCAG

CACGCGGCGTATTTGAACGCGGCGACTGGTCACTCTCTTCTCCGGCTAA

ACGTAAAGCGGTACTGAATAAACTCGCCGATTTAATGGAAGCCCACGCC

GAAGAGCTGGCACTGCTGGAAACTCTCGACACCGGCAAACCGATTCGTC

ACAGTCTGCGTGATGATATTCCCGGCGCGGCGCGCCATTCGCTGGTA

CGCCGAAGCGATCGACAAAGTGTATGGCGAAGTGGCGACCACCAGTAGC

CATGAGCTGGCGATGATCGTGCGTGAACCGGTCGGCGTGATTGCCGCCA

TCGTGCCGTGGAACTTCCCGCTGTTGCTGACTTGCTGGAAACTCGGCCC

GGCGCTGGCGGCGGGAAACAGCGTGATTCTAAAACCGTCTGAAAAATCA

CCGCTCAGTGCGATTCGTCTCGCGGGGCTGGCGAAAGAAGCAGGCTTGC

CGGATGGTGTGTTGAACGTGGTGACGGGTTTTGGTCATGAAGCCGGGCA

GGCGCTGTCGCGTCATAACGATATCGACGCCATTGCCTTTACCGGTTCA

ACCCGTACCGGGAAACAGCTGCTGAAAGATGCGGGCGACAGCAACATGA

AACGCGTCTGGCTGGAAGCGGGCGGCAAAAGCGCCAACATCGTTTTCGC

TGACTGCCCGGATTTGCAACAGGCGGCAAGCGCCACCGCAGCAGGCATT

TTCTACAACCAGGGACAGGTGTGCATCGCCGGAACGCGCCTGTTGCTGG
```

-continued

```
AAGAGAGCATCGCCGATGAATTCTTAGCCCTGTTAAAACAGCAGGCGCA

AAACTGGCAGCCGGGCCATCCACTTGATCCCGCAACCACCATGGGCACC

TTAATCGACTGCGCCCACGCCGACTCGGTCCATAGCTTTATTCGGGAAG

GCGAAAGCAAAGGGCAACTGTTGTTGGATGGCCGTAACGCCGGGCTGGC

TGCCGCCATCGGCCCGACCATCTTTGTGGATGTGGACCCGAATGCGTCC

TTAAGTCGCGAAGAGATTTTCGGTCCGGTGCTGGTGGTCACGCGTTTCA

CATCAGAAGAACAGGCGCTACAGCTTGCCAACGACAGCCAGTACGGCCT

TGGCGCGGCGGTATGGACGCGCGACCTCTCCCGCGCGCACCGCATGAGC

CGACGCCTGAAAGCCGGTTCCGTCTTCGTCAATAACTACAACGACGGCG

ATATGACCGTGCCGTTTGGCGGCTATAAGCAGAGCGGCAACGGTCGCGA

CAAATCCCTGCATGCCCTTGAAAAATTCACTGAACTGAAAACCATCTGG

ATAAGCCTGGAGGCCTGA
```

Amino acid sequence (SEQ ID NO: 30):
```
MNFHHLAYWQDKALSLAIENRLFINGEYTAAAENETFETVDPVTQAPLA

KIARGKSVDIDRAMSAARGVFERGDWSLSSPAKRKAVLNKLADLMEAHA

EELALLETLDTGKPIRHSLRDDIPGAARAIRWYAEAIDKVYGEVATTSS

HELAMIVREPVGVIAAIVPWNFPLLLTCWKLGPALAAGNSVILKPSEKS

PLSAIRLAGLAKEAGLPDGVLNVVTGFGHEAGQALSRHNDIDAIAFTGS

TRTGKQLLKDAGDSNMKRVWLEAGGKSANIVFADCPDLQQAASATAAGI

FYNQGQVCIAGTRLLLEESIADEFLALLKQQAQNWQPGHPLDPATTMGT

LIDCAHADSVHSFIREGESKGQLLLDGRNAGLAAAIGPTIFVDVDPNAS

LSREEIFGPVLVVTRFTSEEQALQLANDSQYGLGAAVWTRDLSRAHRMS

RRLKAGSVFVNNYNDGDMTVPFGGYKQSGNGRDKSLHALEKFTELKTIW

ISLEA
```

YALI0C03025p from *Yarrowia lipolytica*, NCBI Accession ID: YALI0C03025p Nucleotide sequence (SEQ ID NO: 31):
```
ATGTCTCTTTTCAGCAAACTTACCCTAGCCAACGGCCTTGAGGTCGATC

AGCCCACTGGCCTTTTCATTAACGGCGAATTCGTTGCCGCGAAGTCTGG

CAAAACGTTTGAAACCATCAACCCTACCACCGAGGAAGTGATTTGTTCC

GTTTCTGAGGCAGATGAGGAAGATGTGAATGCTGCTGTTGACGCTGCTG

CTGCTGCTTTCAAGACCTGGGGTTTCAAGACTGCTCCCAGTGCTCGAGG

TGCGGCTCTATTCAAGCTGGCGGACCTCATTGAGCGAGACCTCGATATC

ATCGCTGCGATTGAAACGACTGACAACGGTAAGGTGTACGCCCATGCCA

AGGGTGATGTTGCTCTGGTTGTCAAGGTCATTCGATTTTATGCAGGATA

TGCTGACAAGATCTACGGAGACGTTATCCATGGTAACGATGGACACTTT

TCCTACACTCGAAAGGAGCCCATTGGAGTTTGTGGACAAATCATTCCCT

GGAACTTCCCCTTGGTCATGTGGTCCTGGAAGATTGCTCCTGCTCTGGC

TACCGGTAACACTGTGGTTCTCAAGAGTGCCGAGTCTACTCCTCTGTCT

GCTCTGTACGCGGCCAAGCTCGCCCAGGAAGCAGGTATTCCCGCAGGCG

TGCTCAACATTGTTTCAGGTTACGGAAAGGTCGGCGCTTTGATGACTAA

CCACCCCAAGATCCGAAAGGTGGCTTTCACAGGCTCGACTGCTACCGGC

AAGCAGGTTCTCAAGGGTGCAGCTCTGTCCAACCTGAAGAAGATCTCCC
```

-continued

TTGAGCTTGGAGGAAAGTCTCCCAACATCATCTTTGATGATGCCAACCT

GCCCAACGCCATCTCCTGGGCTGCTCTTGGTATCTTCTTCAACTCTGGA

GAAGTCTGTGCTGCTGCCTCTCGTCTCTATGTTCAGGAGGGAGTCTACC

ACGAAGTCGTTGCTGCTCTCAAACAGCGAGCTGAGGCATTGGTTGTGGG

CGATCCCTTTGACCAGCAGACCTTCCAGGGGGCCCAGACCTCCAAGATT

CAGTTCGACCGAGTCATGAGCTTCATTGAGGCGGAAAGGCCGAGGGAG

CTACTCTGCTGACCGGAGGCTGCCGAGCAAAGGACAAGGGCTATTTCAT

CCGGCCCACTGTCTTCACCGACGTTAAAAAGGACATGAAGATTGTGCAG

GAAGAGATCTTTGGCCCCGTTGTCGTTGTGACCAAGTTCAAGACTCTTG

AGGAGGTCATTGAGCTTGCCAACGACTCTGAGTACGGCCTGGCTGCGGG

TGTGCACACCCAGGACATTTCTCGAGCCCACTATTTGGCAGAGAACCTC

CATGCCGGAACTGTGTGGGTTAATACCTACAACTCGTTTCACATCTCGC

TTCCTTTTGGAGGTTTCAACCAGAGTGGTTTCGGTAAGGAGATGGGCAA

GGACGGACTGGACAGTTATATTCAGACCAAGGCTGTTCGAATCATGTTT

GACCAGGCCAAGCTGCAGTAA

Amino acid sequence (SEQ ID NO: 32):
MSLFSKLTLANGLEVDQPTGLFINGEFVAAKSGKTFETINPTTEEVICS
VSEADEEDVNAAVDAAAAAFKTWGFKTAPSARGAALFKLADLIERDLDI
IAAIETTDNGKVYAHAKGDVALVVKVIRFYAGYADKIYGDVIHGNDGHF
SYTRKEPIGVCGQIIPWNFPLVMWSWKIAPALATGNTVVLKSAESTPLS
ALYAAKLAQEAGIPAGVLNIVSGYGKVGALMTNHPKIRKVAFTGSTATG
KQVLKGAALSNLKKISLELGGKSPNIIFDDANLPNAISWAALGIFFNSG
EVCAAASRLYVQEGVYHEVVAALKQRAEALVVGDPFDQQTFQGAQTSKI
QFDRVMSFIEAGKAEGATLLTGGCRAKDKGYFIRPTVFTDVKKDMKIVQ
EEIFGPVVVVTKFKTLEEVIELANDSEYGLAAGVHTQDISRAHYLAENL
HAGTVWVNTYNSFHISLPFGGFNQSGFGKEMGKDGLDSYIQTKAVRIMF
DQAKLQ YALI0F04444p from Yarrowia lipolytica, NCBI
Accession ID: YALI0F04444p Nucleotide sequence
(SEQ ID NO: 33):
ATGCCATATATACGGTGTCTGGGGACTGTATCGGTCCCATCAACCAAT

TGCTCAACATGTCCATCTCCATTTCGCTGCCCAACGGAAACAAGTACGA

ACAGCCCACGGGCATTTTCATCAACAACGAGTGGTCCGAGGCCTCCGAC

AAGGGTACCATTCCCGTCTACAACCCGTCGACCGGCGACGAGGTGGTGC

AGGTGGCGGCTGCTACTGCTGAGGACGTGGATCGGGCAGTAGTTGCTGC

TCGAAAGGCGTTCCAGAGCTGGCGAGATGTCCCCGGTGAGGAGCGTGCC

AAGTTGCTGGACAACTTCATCAATCTGGTGTCCAAGAACCTCGACACGG

TGGCTGCCATCGAGGCTCTCGATTCCGGCAAGCCTCTTCAGCTCAATGC

TCGGGGTGACATCGCCGGCGGCCTGGCCGTCTACAAGTACTACGCAGGG

TGGGCGGACAAGGTGTTTGGTAAGACCATTGTCAACACCACCAAGAAGC

TGGCGTACACTCTTCACGAGCCCCATGGAGTGTGTGGTCAGATCATTCC

CTGGAACTATCCGTTTCTGATGGCCGCGTGGAAGATTGCGCCTGCAATT

GCGGCTGGCAACGTGGTGGTGATGAAGCTCGCGGAAAACACCCCTCTGT

CGATGCTGTATCTGTGCAATCTGTTCAAGGAGGCCGGGTTCCCTCCCGG

AGTGATCAACATCTTCACTGGCCACGGCGCCAAGGCTGGCTCGCGACTG

GCTGAGCACCCGGATGTCGACAAGATTGCCTTCACCGGCTCCACCGCCA

CCGGCCGAATCATCATGAAGCTGGCCGCTACCAACCTCAAGGCCATCAC

TCTGGAATGTGGAGGCAAGTCGCCCATGATTGTTCTGGGAGATGCCGAT

CTCGACCAGGCCACCAAATGGGCCCATGCCGGTATTATGACCAACCAGG

GCCAGATCTGCTGCGGTGTGTCGCGAGTGCTGGTTCACGAGTCCATCTA

CGACCAGTTTGTCGACAAGTACGTCGAGGTGGTCAAGCAGCGGTCTCGA

GTCGGAGACATGTTCCAGGACAAGATTCTCCAAGGCCCCCAGGTCTCCA

AGGTCCAGCAGGAGAAGGTGCTTGGCTACATTGAGAAGGGCAAGGAGGA

GGGCGCCAAGCTGGTCTACTCTGGCGCTGTGGCTGCCGAGGCGCTCGAA

AAGGGCTACTTTGTGCCCCCCACTGTGTTTGCTGACGTCAGAGACGACA

TGGTGATTTCTCGAGAGGAGATTTTCGGACCTGTGGTTGCCATCGCCAA

GTTCTCCGACGTGGAAGACGCCATCAACCGAGCCAACGACTCCGAGTAC

GGTTTGGCCGCGTCCGTCTACACCAAGGACCTGACCGAGGCCCACCGAA

TCTCCCGACGGCTCGAAAGTGGCCAGGTGTTCATCAACATGGCCCATAT

GGGCGACTACCGAATGCCTTTTGGAGGATACAAACAGAGTGGAATTGGA

CGAGAGTTGGGCGAGTATGGTCTCGATACTTATACTCAGTGCAAGGCGG

TGCATATTAACATGGGTATGAAGTTGTAG

Amino acid sequence (SEQ ID NO: 34):
MPYIRCLGDCIGPINQLLNMSISISLPNGNKYEQPTGIFINNEWSEASD
KGTIPVYNPSTGDEVVQVAAATAEDVDRAVVAARKAFQSWRDVPGEERA
KLLDNFINLVSKNLDTVAAIEALDSGKPLQLNARGDIAGGLAVYKYYAG
WADKVFGKTIVNTTKKLAYTLHEPHGVCGQIIPWNYPFLMAAWKIAPAI
AAGNVVVMKLAENTPLSMLYLCNLFKEAGFPPPGVINIFTGHGAKAGSRL
AEHPDVDKIAFTGSTATGRIIMKLAATNLKAITLECGGKSPMIVLGDAD
LDQATKWAHAGIMTNQGQICCGVSRVLVHESIYDQFVDKYVEVVKQRSR
VGDMFQDKILQGPQVSKVQQEKVLGYIEKGKEEGAKLVYSGAVAAEALE
KGYFVPPTVFADVRDDMVISREEIFGPVVAIAKFSDVEDAINRANDSEY
GLAASVYTKDLTEAHRISRRLESGQVFINMAHMGDYRMPFGGYKQSGIG
RELGEYGLDTYTQCKAVHINMGMKL YALI0E00264p from Yarrowia lipolytica, NCBI
Accession ID: YALI0E00264p Nucleotide sequence
(SEQ ID NO: 35):
ATGCTCCGACGAATCACTCTCAACCAGTTTAAGGGCGGCCTGCGACGGC

TGTCCACCCTTACCCCCGTCAAGAACGAACCTCTGACCCTGCCCAACGG

CGCCAAGTACGAGCAGCCCGTCGGTCTCTTCATCAACGGCGAGTTCGTC

AAGTCTCAGTCCGAAAGCGATTCGAGACCGAGAACCCCACCACCGAGA

CCCCCATCATCTCCGTTTACGAGGCTGGTGAGGCTGATGCCAACGCAGC

TGTCGAGGCTGCCAAGAATGCCTTCAAGAACTGGGGCTTCAAGACCGCT

CCTTCCGAGCGAGGAGTCCTGCTCAACAAGCTCGCTGATCTCATTGAGC

GAGATCTCGACCTCATTTCTGCCATTGAGACCACCGACAACGGTAAGGT

-continued

CTTTGCCCAGGCCCAGGGTGACGTCGCCCTCGTCGTCAAGGTGCTCCGA

TACTACGCTGGATTTGCCGACAAGATTGGCGGCGACCTCGTCCAGACCA

ACGACGGCTTCTTCAACTACACCCGAAAGGAGCCTCTCGGAGTGTGTGG

CCAGATCATCCCCTGGAACTTCCCTCTGCTCATGTGGGCCTGGAAGATT

GCCCCCGCTCTGACCACTGGTAACACCGTGGTTCTTAAGACCGCCGAGT

CCACCCCTCTGTCCGCCCTGTACGCCTGTAAGCTCTCCCAGGAGGCTGG

CTTCCCCAAGGGTGTTCTCAACGTTGTGTCCGGTTATGGCCCCGTTGGA

GGCGTTCTGTCCGCCCACCCCGACATCAAGAAGATTGCTTTCACCGGCT

CCACCGCCACTGGTAAGCAGGTTGCTAAGACCGCCCTGACCTCCAACCT

CAAGAAGACCACCATGGAGCTCGGTGGTAAGTCCCCCAACATTATCTTC

GACGACGCCAACCTCGAGGACGCTCTTTCTGCCGCCGCTCTCGGTATCT

TCTTCAACTCCGGAGAGGTCTGCTGCGCCGGCTCTCGACTCTTTGTCCA

AGCCGGTGTCTACGACCAGGTTGTCGAGGCCTTCAAGAAGAAGGCTGAG

TCCGTCAAGGTCGGTGATCCCTTCGACCCCAACTCTCTCCAGGGTCCCC

AGCAGAACAAGAACCAGTTCAAGAAGATTCTGGGATACATTGAGCAGGG

CCAGAAGGAGGGCGCCCATCTCCTGTGTGGAGGATCTGCCCAGGCCGGT

CCTAACAAGGGATACTTCATCCAGCCCACCGTTTTCACCGACGTGAACA

ACGATATGTCCATTGTGCGAGAGGAGATTTTCGGCCCCGTCCTGACCAT

CACCAAGTTCAACACCGTTGACGAAGTGATTGACATGGCCAACGACTCC

GAGTACGGTCTTGCCGCTGGTATCCACACCACTGATATCAACAAGGCCC

ACTATGTTGCTGAGAACATTGCCTCCGGTACCATCTGGGTCAACTGCTA

CAACGCCTTCCACGAGGCCGTTCCCTTTGGAGGATACAAGCAGTCTGGT

TTCGGTAAGGAGATGGGTCGAGATGGTCTTGAGAACTACCTCCAGACCA

AGGCAGTTCGAGTCAAGCTTGATGAGCGAAAGTGGGCTGACAAGCAGTG

A

Amino acid sequence (SEQ ID NO: 36):
MLRRITLNQFKGGLRRLSTLTPVKNEPLTLPNGAKYEQPVGLFINGEFV

KSQSGKRFETENPTTETPIISVYEAGEADANAAVEAAKNAFKNWGFKTA

PSERGVLLNKLADLIERDLDLISAIETTDNGKVFAQAQGDVALVVKVLR

YYAGFADKIGGDLVQTNDGFFNYTRKEPLGVCGQIIPWNFPLLMWAWKI

APALTTGNTVVLKTAESTPLSALYACKLSQEAGFPKGVLNVVSGYGPVG

GVLSAHPDIKKIAFTGSTATGKQVAKTALTSNLKKTTMELGGKSPNIIF

DDANLEDALSAAALGIFFNSGEVCCAGSRLFVQAGVYDQVVEAFKKKAE

SVKVGDPFDPNSLQGPQQNKNQFKKILGYIEQGQKEGAHLLCGGSAQAG

PNKGYFIQPTVFTDVNNDMSIVREEIFGPVLTITKFNTVDEVIDMANDS

EYGLAAGIHTTDINKAHYVAENIASGTIWVNCYNAFHEAVPFGGYKQSG

FGKEMGRDGLENYLQTKAVRVKLDERKWADKQ

YALI0D07942p from Yarrowia lipolytica, NCBI
Accession ID: YALI0D07942p Nucleotide sequence
(SEQ ID NO: 37):
AGTGAGTATTAATATGGAGGACACCAGTTGCACAGATTCAGATACAGCT

CTTACATTCTGTTGTCTCAGACTCGATTCGATCACTGTCGTCTACACTC

CTCGATAACCGATAACCGACACGTACTGATAACGATCTCAACCCCATAG

CATAGATCGTCCAACAACGCCACCCAAAATATTCCCACAACATGTACCG

ACTATCACAACTCCACGGCCACATTGCGCCCAATACGTCGTTTGCCATC

TATAAGGCGCCCAAGAAGGCCGCTCCTGCCGTCGCTGCTAACCTAGTGC

AAGTTACTCTTCCCGACGGAAAGTCCTACGACCAGCCCACCAAGCTCTT

CATCAACAACGAGTGGGTCGATGGTCACGGCGGCTCAATTGAGTCTGTC

AACCCCGCCACCGAGCAGGTCATCTGCTCCGTTGAGGCCGCTGACGAGA

GTGATGTCGACAAGGCTGTTCAGGCCGCTCGAAACTGCTACGAGAACGT

CTGGCGAAAGGTCACCGGTGCCGAGCGAGCACAGCTCATGCGCAAGCTT

GCCGACCTTGTCGAGAAGAACAAGGACCTGCTCACCTCCATTGAGGCTG

CCGACTCTGGAAAGCCCAAGTACGGCAACTGTGACGGAGACGTGGACGA

GCTCATCTACGTCCTGCGATACTACTCCGGCCTGGCTGAGAAGGCTGGC

AATGGAGTCACCATTTCTACCTCCAACGAAAAGTTTGCCTACACCATCC

ACGAGCCTTACGGAGTCTGTGGCCAGATCATCCCCTGGAACTACCCCAT

TGCTATGGCTGCCTGGAAGCTAGGTCCCTGTCTCGCTGCCGGTAACGTG

CTGGTCATGAAGCTTTCCGAATACACCCCTCTGTCCATGCTGGTCATCT

GCAACCTGGTCAAGGAGGCTGGTTTCCCCCCTGGCGTGGTGAACGTGGT

TAACGGCTACGGCGCCAAGGCCGGCAACCGACTGGCTGAGCACCCCGAC

GTTGACAAGATTGCCTTCACCGGTTCTACCGCTACCGGTCGATCTGTCA

TGAAGGCTGCTACCGAAACATGAAGGCCGTGACCATGGAGCTTGGAGG

AAAGTCCTCTGCTCATTTTCGACGACTGCGATCTCGCCAAGGCCATC

GAGTGGGCCCACATTGGCATCATGTACAACATGGGCCAGGTGTGTTCCG

CCACCTCTCGAATCCTGGTGCAAGAAGGCATTGCCGACAAGTTCGTCGA

GGGTTTCATCAAGCAGTGTAATGAGGCCTCCATTCTGGGTTGTCCTTTG

GACCAGAAGACCTCTCACGGTCCTCAGGTCAACAAGATCCAGTATGAGA

AGGTGCTCGGATACATTGAGAAGGGTAAGGCTGAGGGAGCCAAGTGCAT

TCTGGGAGGTGAGGCTGCCCCCAAAACGGCAAGGGCTATTTCATTAAG

CCCACCGCCTTCACCAACGTCAACAAGGACATGACCATCTGGAAGGAGG

AGATTTTCGGCCCTGTCGTGGTAATTGACACCTTCAAGACCGAGGAGGA

GGCCATTGCCAAGGCCAACGATACTCCGTACGGTCTGGCTGCCGCTCTG

TTTACCGAGAACATTCGGCGAGCCCACCGGGTTGTCAAGGAGCTGCGAG

CTGGTCAGGTCTGGGTCAACTCTGATAACGACTCCGATCCTCGAGTTCC

CTTTGGTGGTGTCAAGCAGAGTGGTATTGGTCGAGAGCTTGGTGAGTAT

GGTCTTTCTATTTACACCCAGGCCAAGGCCGTCCACATTAACCTGGATT

AG

Amino acid sequence (SEQ ID NO: 38):
MQVTLPDGKSYDQPTKLFINNEWVDGHGGSIESVNPATEQVICSVEAAD

ESDVDKAVQAARNCYENVWRKVTGAERAQLMRKLADLVEKNKDLLTSIE

AADSGKPKYGNCDGDVDELIYVLRYYSGLAEKAGNGVTISTSNEKFAYT

IHEPYGVCGQIIPWNYPIAMAAWKLGPCLAAGNVLVMKLSEYTPLSMLV

ICNLVKEAGFPPGVVNVVNGYGAKAGNRLAEHPDVDKIAFTGSTATGRS

```
VMKAATGNMKAVTMELGGKSPLLIFDDCDLAKAIEWAHIGIMYNMGQVC

SATSRILVQEGIADKFVEGFIKQCNEASILGCPLDQKTSHGPQVNKIQY

EKVLGYIEKGKAEGAKCILGGEAAPQNGKGYFIKPTAFTNVNKDMTIWK

EEIFGPVVVIDTFKTEEEAIAKANDTPYGLAAALFTENIRRAHRVVKEL

RAGQVWVNSDNDSDPRVPFGGVKQSGIGRELGEYGLSIYTQAKAVHINL

D
```

Glutathione disulfide reductase gene and gene product sequences are well known to those of skill in the art. Exemplary, representative gene and gene product sequences include:

```
GSR from Yarrowia lipolytica, NCBI Accession ID:
YALI0E18029p Nucleotide sequence (SEQ ID NO: 39):
ATGGCTTCTATCCCCCATTATGACTATCTGGTTATCGGCGGAGGCTCTGG

AGGTGTTGCTTCTGCTCGTCGAGCCGCCTCGTACGGCGCCAAAACACTGC

TGATCGAGGGCAAGGCGCTGGGAGGCACCTGCGTCAACGTGGGCTGTGTG

CCCAAAAAGGTCATGTGGAACGCGTCCGATCTGGCGGGCCGAATCCGACA

GGCCAAGGAGTACGGCTTCCCCGACGTGGACCCCAAGTACGCCGACAAC

TTTGACTGGTCCGGATTCAAGGCCAAGCGAGACGCTTACGTCAAGCGACT

CAATGGAATCTACGAACGAAACCTCCAGAAGGAGGGCGTCGAGTACGTGT

TTGGCTGGGCCACCCTCTACAAGCAGGAGGGCCAGGAGTTCCCCCTGGTA

CATGTCAAGAGCGACGACGGCAATACCAAGCTGTATTCTGCCAAGAAGAT

TATGATTGCCACCGGCGGAAAGCCCCGTCTGCCCGACGTGCCTGGAGCCG

AGTACGGCATTGACTCCGACGGCTTCTTTGCTCTCGAGACCCAGCCCAAG

CGAGTGGCGGTGGTTGGAGGAGGCTACATTGGCGTGGAGCTGGCTGGTGT

CTTCCACGGACTCAACTCCGAGACCACCCTCTTCTGCCGAGGCCAGACGG

TGCTCCGAGCGTTCGACATCATGATCCAGGACACCATCACCGACTACTAC

GTCAAGGAGGGCATCAACGTGCTCAAGGGCTCCGGCGTCAAGAAGATTGT

CAAGAAGGACAATGGCGAGCTGCTCGTCACCTACGAGCAGGATGGCGCCG

AGAAGGATATCACTCTTGACTCACTTATTTGGACCATTGGACGAGAGCCT

CTCAAGGACACCCTCAACCTCGGCGAGTTTGGCATCAAGACCAACAAGCG

GGGCTACATTGAGGTCGACGAGTACCAGCGATCGTCCGTTGACAACATTT

ACTCGCTTGGAGACGTTTGCGGCAAGGTCGAGCTAACCCCCATGGCTATT

GCTGCCGGACGAAAGCTGTCCAACCGGCTGTTTGGTCCCACAGAGTTCAA

GAACCAGAAGCAGGACTACACCGATGTTCCTTCTGCCGTCTTTTCCCACC

CCGAGGTTGGCTCCATCGGTATCACCGAGGCTGCCGCCAAGGAGCAGTAT

GGCGAGGAGAACGTCAAGGTCTACACCTCCAAGTTTGTCGCCATGTACTA

CGCCATGCTCGAGGAGAAGGCTCCCACCGCCTACAAGCTGGTGTGTGCCG

GCAAGGACGAGAAGGTTGTTGGTCTGCACATTGTTGGCGCTGACTCTGCC

GAGATTCTGCAGGGTTTCGGCGTGGCCATTCGAATGGGAGCCACCAAGGC

CGATTTCGACAATGTTGTGGCTATCCATCCCACTTCTGCCGAGGAGCTGG

TGACCATGAGATAG

Amino acid sequence (SEQ ID NO: 40):
MASIPHYDYLVIGGGSGGVASARRAASYGAKTLLIEGKALGGTCVNVGCV

PKKVMWNASDLAGRIRQAKEYGFPDVDPKYADNFDWSGFKAKRDAYVKRL

NGIYERNLQKEGVEYVFGWATLYKQEGQEFPLVHVKSDDGNTKLYSAKKI

MIATGGKPRLPDVPGAEYGIDSDGFFALETQPKRVAVVGGGYIGVELAGV

FHGLNSETTLFCRGQTVLRAFDIMIQDTITDYYVKEGINVLKGSGVKKIV

KKDNGELLVTYEQDGAEKDITLDSLIWTIGREPLKDTLNLGEFGIKTNKR

GYIEVDEYQRSSVDNIYSLGDVCGKVELTPMAIAAGRKLSNRLFGPTEFK

NQKQDYTDVPSAVFSHPEVGSIGITEAAAKEQYGEENVKVYTSKFVAMYY

AMLEEKAPTAYKLVCAGKDEKVVGLHIVGADSAEILQGFGVAIRMGATKA

DFDNVVAIHPTSAEELVTMR
```

Glutathione peroxidase gene and gene product sequences are well known to those of skill in the art. Exemplary, representative gene and gene product sequences include:

```
GPO from Yarrowia lipolytica, NCBI Accession ID:
YALI0E02310p Nucleotide sequence (SEQ ID NO: 41):
ATGTCCGCCGAGAAAACCAATACCGCTTTCTACAACCTCGCTCCACTCGA

CAAGAACGGAGAGCCTTTCCCCTTCAAGCAGCTTGAGGGCAAGGTCGTGC

TCATCGTGAACGTCGCCTCCAAGTGTGGCTTTACTCCCCAATACAAGGGC

CTTGAGGAGGTCTACCAGAAGTACAAGGATCAGGGATTCACCATCATCGG

CTTCCCCTGCAACCAGTTTGGTGGCCAAGAGCCTGGTTCCGCTGACGAGA

TCTCCTCCTTCTGTCAGCTGAACTACGGCGTCACTTTCCCCGTTCTTCAG

AAGATCAACGTCAACGGCAACGACGCCGACCCCGTCTACGTCTACCTGAA

GGAGCAGAAGGCTGGTCTGCTGGGCTTCCGAGGAATCAAGTGGAACTTTG

AGAAGTTCCTGGTTGATAAGCACGGTAACGTCGTCGACCGATATGCTTCC

CTCAAGACCCCCGCCGGCCTCGAATCCACCATCGAGACCCTCCTCAAAAA

GCCCTAA

Amino acid sequence (SEQ ID NO: 42):
MSAEKTNTAFYNLAPLDKNGEPFPFKQLEGKVVLIVNVASKCGFTPQYKG

LEEVYQKYKDQGFTIIGFPCNQFGGQEPGSADEISSFCQLNYGVTFPVLQ

KINVNGNDADPVYVYLKEQKAGLLGFRGIKWNFEKFLVDKHGNVVDRYAS

LKTPAGLESTIETLLKKP
```

Thioredoxin reductase gene and gene product sequences are well known to those of skill in the art. Exemplary, representative gene and gene product sequences include:

```
TRX from Yarrowia lipolytica, NCBI Accession ID:
YALI0D27126p Nucleotide sequence (SEQ ID NO: 43):
ATGACCCACAGCCCAGTTGTTATCATCGGTTCCGGCCCCGCCGCCCACAC

CGCTGCCATCTACCTTTCTCGAGCCGAGATCAAGCCCACTCTCTACGAGG

GAATGATGGCCAACGGCATTGCTGCCGGCGGTCAGCTCACCACTACCACT

GAGATTGAGAACTTCCCCGGCTTCCCCGACGGAATCATGGGCTCCCAGCT

CATGGAGGACATGCGAAAGCAGTCCATCCGATTCGGCACCGAGATCATCA

CCGAGACCGTCTCCAAGGTCGATCTGTCCCAGCGACCCTTCAAGTACTGG

ACCGAGTTCAATGAGGACGAGGAGCCCCACACTGCCGACGCCATTATTCT

TGCCACCGGTGCCTCTGCCAAGCGACTCTCTCTGCCCGGTGAGGACCAGT
```

```
ACTGGCAGCAGGGTATCTCTGCCTGCGCTGTCTGTGACGGTGCTGTCCCC

ATTTTCCGAAACAAGCCTCTCGCCGTTGTCGGAGGAGGAGACTCTGCCGC

TGAGGAGGCCCTCTTCCTCACCAAGTACGGCTCCAAGGTCTACGTCATTG

TCCGAAAGGACAAGCTGCGAGCTTCCGCCGTTATGGCCAAGCGACTGGCC

TCCCACCCCAAGGTCGAGATTCTCTTCAACCACGTGTCCATCGAGGCCAA

GGGAGACGGCAAGCTGCTGAACGCCCTGGAGATCGAGAACACCCTGACCG

GCGAGAAGCGAGACCTCGAGGTCAACGGTCTGTTCTACGCCATTGGTCAC

ATCCCCGCCACCTCCATCGTCAAGGGCCAGGTCGAGACCGACGAGGAGG

CTACGTTGTTACCGTCCCCGGTACCGCCAACACCTCCGTCAAGGGTGTCT

TTGCCGCTGGTGATGTCCAGGACAAGCGATACCGACAGGCCATTACCTCT

GCTGGTACCGGCTGCATGGCTGCTCTCGACTGTGAGAAGCTGCTTGCTGA

GGAGGAATAG

Amino acid sequence (SEQ ID NO: 44):
MTHSPVVIIGSGPAAHTAAIYLSRAEIKPTLYEGMMANGIAAGGQLTTTT

EIENFPGFPDGINGSQLMEDMRKQSIRFGTEIITETVSKVDLSQRPFKYW

TEFNEDEEPHTADAIILATGASAKRLSLPGEDQYWQQGISACAVCDGAVP

IFRNKPLAVVGGGDSAAEEEALFLTKYGSKVYVIVRKDKLRASAVMAKRLA

SHPKVEILFNHVSIEAKGDGKLLNALEIENTLTGEKRDLEVNGLFYAIGH

IPATSIVKGQVETDEEGYVVTVPGTANTSVKGVFAAGDVQDKRYRQAITS

AGTGCMAALDCEKLLAEEE
```

Superoxide dismutase gene and gene product sequences are well known to those of skill in the art. Exemplary, representative gene and gene product sequences include:

```
SOD1 from Yarrowia lipolytica, NCBI Accession ID:
YALI0E12133p Nucleotide sequence (SEQ ID NO: 45):
ATGGTCAAGGCTGGTGAGTACGAGAGCAAGGCCCGGAATCGGGCACATTG

AGCGGCCAGCGGGTCAATTGAAGGCCGCTCGACCGGTCCACACCCACAGG

TTGGCCGCTACGTTGACTTCGACAACCGTCTGGAAGGTGGCGGAACGTTG

CGCCGTGTGAGGTGGCAGGTGACTCAGAAGTTGCTCATTGTTTGTTGAGA

TCAGACCCCACAAGCACAATTGCATTTTAGGAGGGAATTGAGAGCCCTAC

CTCACGGAATAGTCCATGTCGTTGTTCGCCACTTGCCCACACTGCACATT

CTAACCCAGTCGCTGTTCTTCGAGGAGATTCCAAGGTCTCCGGTACTGTC

ACTTTCGAGCAGGACTCTGAGTCCGGCCCCGTCACTGTCACCTACGACAT

CAAGGGCAACGATCCCAACGCTGAGCGAGGATTCCACGTCCACGAGTTTG

GTGACAACACCAACGGCTGCACTTCTGCCGGCCCCCACTTCAACCCCTTC

AAGAAGAACCACGGTGGTCCCACCGACTCTGAGCGACACGTTGGTGACCT

CGGAAACGTCAAGACTGACTCTGAGGGTGTTGCCAAGGGTGTTCTCAAGG

ACTCTCTTCTCAAGCTGACTGGTGACAACTCCATTGTTGGCCGAACCGTC

GTTATCCACGGTGGTGAGGACGATCTTGGAAAGGGTGGCCATGCCGACTC

TCTCAAGACCGGAAACGCTGGCCCTCGACCCGCCTGCGGTGTCATTGGTC

TTACCGCCTAA
```

```
Amino acid sequence (SEQ ID NO: 46):
MVKAVAVLRGDSKVSGTVTFEQDSESGPVTVTYDIKGNDPNAERGFHVHE

FGDNTNGCTSAGPHFNPFKKNHGGPTDSERHVGDLGNVKTDSEGVAKGVL

KDSLLKLTGDNSIVGRTVVIHGGEDDLGKGGHADSLKTGNAGPRPACGVI

GLTA
```

Glucose-6-phosphate dehydrogenase gene and gene product sequences are well known to those of skill in the art. Exemplary, representative gene and gene product sequences include the following ZWF1 sequences:

```
ZWF1 from Saccharomyces cerevisiae, NCBI Accession
ID: YNL241C Nucleotide sequence (SEQ ID NO: 47):
ATGAGTGAAGGCCCCGTCAAATTCGAAAAAAATACCGTCATATCTGTCTT

TGGTGCGTCAGGTGATCTGGCAAAGAAGAAGACTTTTCCCGCCTTATTTG

GGCTTTTCAGAGAAGGTTACCTTGATCCATCTACCAAGATCTTCGGTTAT

GCCCGGTCCAAATTGTCCATGGAGGAGGACCTGAAGTCCCGTGTCCTACC

CCACTTGAAAAAACCTCACGGTGAAGCCGATGACTCTAAGGTCGAACAGT

TCTTCAAGATGGTCAGCTACATTTCGGGAAATTACGACACAGATGAAGGC

TTCGACGAATTAAGAACGCAGATCGAGAAATTCGAGAAAAGTGCCAACGT

CGATGTCCCACACCGTCTCTTCTATCTGGCCTTGCCGCCAAGCGTTTTTT

TGACGGTGGCCAAGCAGATCAAGAGTCGTGTGTACGCAGAGAATGGCATC

ACCCGTGTAATCGTAGAGAAACCTTTCGGCCACGACCTGGCCTCTGCCAG

GGAGCTGCAAAAAAACCTGGGGCCCCTCTTTAAAGAAGAAGAGTTGTACA

GAATTGACCATTACTTGGGTAAAGAGTTGGTCAAGAATCTTTTAGTCTTG

AGGTTCGGTAACCAGTTTTTGAATGCCTCGTGGAATAGAGACAACATTCA

AAGCGTTCAGATTTCGTTTAAAGAGAGGTTCGGCACCGAAGGCCGTGGCG

GCTATTTCGACTCTATAGGCATAATCAGAGACGTGATGCAGAACCATCTG

TTACAAATCATGACTCTCTTGACTATGGAAAGACCGGTGTCTTTTGACCC

GGAATCTATTCGTGACGAAAAGGTTAAGGTTCTAAAGGCCGTGGCCCCCA

TCGACACGGACGACGTCCTCTTGGGCCAGTACGGTAAATCTGAGGACGGG

TCTAAGCCCGCCTACGTGGATGATGACACTGTAGACAAGGACTCTAAATG

TGTCACTTTTGCAGCAATGACTTTCAACATCGAAAACGAGCGTTGGGAGG

GCGTCCCCATCATGATGCGTGCCGGTAAGGCTTTGAATGAGTCCAAGGTG

GAGATCAGACTGCAGTACAAAGCGGTCGCATCGGGTGTCTTCAAAGACAT

TCCAAATAACGAACTGGTCATCAGAGTGCAGCCCGATGCCGCTGTGTACC

TAAAGTTTAATGCTAAGACCCCTGGTCTGTCAAATGCTACCCAAGTCACA

GATCTGAATCTAACTTACGCAAGCAGGTACCAAGACTTTTGGATTCCAGA

GGCTTACGAGGTGTTGATAAGAGACGCCCTACTGGGTGACCATTCCAACT

TTGTCAGAGATGACGAATTGGATATCAGTTGGGGCATATTCACCCCATTA

CTGAAGCACATAGAGCGTCCGGACGGTCCAACACCGGAAATTTACCCCTA

CGGATCAAGAGGTCCAAAGGGATTGAAGGAATATATGCAAAAACACAAGT

ATGTTATGCCCGAAAAGCACCCTTACGCTTGGCCCGTGACTAAGCCAGAA

GATACGAAGGATAATTAG
```

Amino acid sequence (SEQ ID NO: 48):
MSEGPVKFEKNTVISVFGASGDLAKKKTFPALFGLFREGYLDPSTKIFGY
ARSKLSMEEDLKSRVLPHLKKPHGEADDSKVEQFFKMVSYISGNYDTDEG
FDELRTQIEKFEKSANVDVPHRLFYLALPPSVFLTVAKQIKSRVYAENGI
TRVIVEKPFGHDLASARELQKNLGPLFKEEELYRIDHYLGKELVKNLLVL
RFGNQFLNASWNRDNIQSVQISFKERFGTEGRGGYFDSIGIIRDVMQNHL
LQINITLLTMERPVSFDPESIRDEKVKVLKAVAPIDTDDVLLGQYGKSED
GSKPAYVDDDTVDKDSKCVTFAAMTFNIENERWEGVPIMMRAGKALNESK
VEIRLQYKAVASGVFKDIPNNELVIRVQPDAAVYLKFNAKTPGLSNATQV
TDLNLTYASRYQDFWIPEAYEVLIRDALLGDHSNFVRDDELDISWGIFTP
LLKHIERPDGPTPEIYPYGSRGPKGLKEYMQKHKYVMPEKHPYAWPVTKP
EDTKDN ZWF1 from *Yarrowia lipolytica*, NCBI Accession ID: YALI0E22649p Nucleotide sequence (SEQ ID NO: 49):
ATGACTGGCACCTTACCCAAGTTCGGCGACGGAACCACCATTGTGGTTCT
TGGAGCCTCCGGCGACCTCGCTAAGAAGAAGACCGTGAGTATTGAACCAG
ACTGAGGTCAATTGAAGAGTAGGAGAGTCTGAGAACATTCGACGGACCTG
ATTGTGCTCTGGACCACTCAATTGACTCGTTGAGAGCCCCAATGGGTCTT
GGCTAGCCGAGTCGTTGACTTGTTGACTTGTTGAGCCCAGAACCCCCAAC
TTTTGCCACCATACACCGCCATCACCATGACACCCAGATGTGCGTGCGTA
TGTGAGAGTCAATTGTTCCGTGGCAAGGCACAGCTTATTCCACCGTGTTC
CTTGCACAGGTGGTCTTTACGCTCTCCCACTCTATCCGAGCAATAAAAGC
GGAAAAACAGCAGCAAGTCCCAACAGACTTCTGCTCCGAATAAGGCGTCT
AGCAAGTGTGCCCAAAACTCAATTCAAAAATGTCAGAAACCTGATATCAA
CCCGTCTTCAAAAGCTAACCCCAGTTCCCCGCCCTCTTCGGCCTTTACCG
AAACGGCCTGCTGCCCAAAAATGTTGAAATCATCGGCTACGCACGGTCGA
AAATGACTCAGGAGGAGTACCACGAGCGAATCAGCCACTACTTCAAGACC
CCCGACGACCAGTCCAAGGAGCAGGCCAAGAAGTTCCTTGAGAACACCTG
CTACGTCCAGGGCCCTTACGACGGTGCCGAGGGCTACCAGCGACTGAATG
AAAAGATTGAGGAGTTTGAGAAGAAGAAGCCCGAGCCCCACTACCGTCTT
TTCTACCTGGCTCTGCCCCCCAGCGTCTTCCTTGAGGCTGCCAACGGTCT
GAAGAAGTATGTCTACCCCGGCGAGGGCAAGGCCCGAATCATCATCGAGA
AGCCCTTTGGCCACGACCTGGCCTCGTCACGAGAGCTCCAGGACGGCCTT
GCTCCTCTCTGGAAGGAGTCTGAGATCTTCCGAATCGACCACTACCTCGG
AAAGGAGATGGTCAAGAACCTCAACATTCTGCGATTTGGCAACCAGTTCC
TGTCCGCCGTGTGGGACAAGAACACCATTTCCAACGTCCAGATCTCCTTC
AAGGAGCCCTTTGGCACTGAGGGCCGAGGTGGATACTTCAACGACATTGG
AATCATCCGAGACGTTATTCAGAACCATCTGTTGCAGGTTCTGTCCATTC
TAGCCATGGAGCGACCCGTCACTTTCGGCGCCGAGGACATTCGAGATGAG
AAGGTCAAGGTGCTCCGATGTGTCGACATTCTCAACATTGACGACGTCAT
TCTCGGCCAGTACGGCCCCTCTGAAGACGGAAAGAAGCCCGGATACACCG
ATGACGATGGCGTTCCCGATGACTCCCGAGCTGTGACCTTTGCTGCTCTC
CATCTCCAGATCCACAACGACAGATGGGAGGGTGTTCCTTTCATCCTCCG
AGCCGGTAAGGCTCTGGACGAGGGCAAGGTCGAGATCCGAGTGCAGTTCC
GAGACGTGACCAAGGGCGTTGTGGACCATCTGCCTCGAAATGAGCTCGTC
ATCCGAATCCAGCCCTCCGAGTCCATCTACATGAAGATGAACTCCAAGCT
GCCTGGCCTTACTGCCAAGAACATTGTCACCGACCTGGATCTGACCTACA
ACCGACGATACTCGGACGTGCGAATCCCTGAGGCTTACGAGTCTCTCATT
CTGGACTGCCTCAAGGGTGACCACACCAACTTTGTGCGAAACGACGAGCT
GGACATTTCCTGGAAGATTTTCACCGATCTGCTGCACAAGATTGACGAGG
ACAAGAGCATTGTGCCCGAGAAGTACGCCTACGGCTCTCGTGGCCCCGAG
CGACTCAAGCAGTGGCTCCGAGACCGAGGCTACGTGCGAAACGGCACCGA
GCTGTACCAATGGCCTGTCACCAAGGGCTCCTCGTGA Amino acid sequence (SEQ ID NO: 50):
MTGTLPKFGDGTTIVVLGASGDLAKKKTFPALFGLYRNGLLPKNVEIIGY
ARSKMTQEEYHERISHYFKTPDDQSKEQAKKFLENTCYVQGPYDGAEGYQ
RLNEKIEEFEKKKPEPHYRLFYLALPPSVFLEAANGLKKYVYPGEGKARI
IIEKPFGHDLASSRELQDGLAPLWKESEIFRIDHYLGKEMVKNLNILRFG
NQFLSAVWDKNTISNVQISFKEPFGTEGRGGYFNDIGIIRDVIQNHLLQV
LSILAMERPVTFGAEDIRDEKVKVLRCVDILNIDDVILGQYGPSEDGKKP
GYTDDDGVPDDSRAVTFAALHLQIHNDRWEGVPFILRAGKALDEGKVEIR
VQFRDVTKGVVDHLPRNELVIRIQPSESIYMKMNSKLPGLTAKNIVTDLD
LTYNRRYSDVRIPEAYESLILDCLKGDHTNFVRNDELDISWKIFTDLLHK
IDEDKSIVPEKYAYGSRGPERLKQWLRDRGYVRNGTELYQWPVTKGSS Isocitrate dehydrogenase NADP-dependent gene and gene product sequences are well known to those of skill in the art. Exemplary, representative gene and gene product sequences include:

IDP2 from *Yarrowia lipolytica*, NCBI Accession ID: YALI0F04095p Nucleotide sequence (SEQ ID NO: 51):
ATGTCCACCACCGCTACTCGAGGCCTGTCCACCAAGATCAAGGTCAAGAA
CCCCATTGTCGAGCTCGATGGTGATGAGATGACCCGAATCATCTGGAAGT
CCATCAAGGACAAGCTCATTCTGCCCTATCTCGACATTGATCTTAAGTAC
TACGATCTGGGCATCGAGTACCGAGACCAGACTAACGACCAGGTGACCAT
TGACGCCGCCGAGGCCATCAAGAAGTACCAGGTCGGTGTCAAGTGCGCCA
CCATCACCCCCGACGAGGCCCGAGTCAAGGAGTTTGGCCTCAAGAAGATG
TGGCTGTCGCCCAACGGTACCATCCGAAACATTCTCGGCGGTACTGTTTT
CCGAGAGCCCATTGTCATTCCCGCCGTCCCCCGGCTTGTGCCCGGATGGA
AGGAGCCTATCATCATTGGTCGACACGCCCACGGCGACCAGTACAAGGCC
CAGGATGCCGTCATCCCCGGCGCCGGTGAGCTGACTCTTAACTTCAAGCC
CGCTAACGGAGGCGACGAGCAGGTCATCAAGGTGTACACCTACGACGCCC
CTGGTGTCGCCATGGCCATGTACAACACTGACGAGTCCATCACCGGCTTT
GCCTACTCTTCATTCAACCTGGCTCTGCAGAAGAAGCTGCCCCTGTACAT
GTCTACCAAGAACACCATCCTTAAGAAGTACGACGGCCGATTCAAGGACA
TTTTCCAGGAGATTTACGACAAGGAGTACAAGGATAAGTTTGATGCTGCC -continued

```
GGCATTTGGTACGAGCACCGACTCATTGATGACATGGTCGCCCAGATGAT

CAAGTCTAAGGGAGGCTTCATCATGGCCCTCAAGAACTACGACGGAGACG

TGCAGTCCGACATTGTTGCCCAGGGCTTTGGCTCTCTCGGTCTCATGACC

TCTGTTCTCGTCACCCCCGACGGAAAGACCTTTGAGTCCGAGGCCGCCCA

CGGCACCGTGACTCGACACTACCGACAGCACCAGCAGGGCAAGGAGACCT

CTACCAACTCCATTGCCTCCATCTTCGCCTGGACCCGAGGCCTCATCCAG

CGAGGCATTCTCGACGAGACCCCTGAGGTGACCAAGTTTGCCGAGGCTCT

CGAGAAGGCCACCGTCGACACTGTTGACAAGGACGGCATTATGACCAAGG

ATCTGGCTCTGGCCGGTGGCAAGACCGACCGATCCTCGTATGTGCTGACC

GAGGAGTTTATCGACGCTGTGGCCAACAGACTGAAGAAGGACCTGGCTTA

G

Amino acid sequence (SEQ ID NO: 52):
MSTTATRGLSTKIKVKNPIVELDGDEMTRIIWKSIKDKLILPYLDIDLKY

YDLGIEYRDQTNDQVTIDAAEAIKKYQVGVKCATITPDEARVKEFGLKKM

WLSPNGTIRNILGGTVFREPIVIPAVPRLVPGWKEPIIGRHAHGDQYKA

QDAVIPGAGELTLNFKPANGGDEQVIKVYTYDAPGVAMAMYNTDESITGF

AYSSFNLALQKKLPLYMSTKNTILKKYDGRFKDIFQEIYDKEYKDKFDAA

GIWYEHRLIDDMVAQMIKSKGGFIMALKNYDGDVQSDIVAQGFGSLGLMT

SVLVTPDGKTFESEAAHGTVTRHYRQHQQGKETSTNSIASIFAWTRGLIQ

RGILDETPEVTKFAEALEKATVDTVDKDGIMTKDLALAGGKTDRSSYVLT

EEFIDAVANRLKKDLA
```

In some embodiments, such strategies further include genetic engineering of oleaginous microbes, for example, *Y. lipolytica*, to simultaneously amplify a push-step (e.g., ACC1 overexpression) and a pull-step (e.g., DGA1 overexpression) of lipid synthesis. The genetic modifications include a genetic modification that increases expression of an acetyl-CoA carboxylase gene product and a genetic modification that increases expression of a diacylglyceride acyltransferase gene product. As disclosed herein, significant increases of lipid production in oleaginous yeast host cells were achieved using these strategies.

According to some aspects of this invention, modifying the lipid metabolism in a microbe in accordance with methods provided herein allows for the generation of a microbe optimized for use in biofuel or biofuel precursor production processes. Some aspects provide strategies and methods for engineering the fatty acid metabolism in a microbe resulting in increased synthesis rate and accumulation of fatty acids and fatty acid derivatives in the microbe.

Some aspects provide methods that include genetic modifications resulting in the modulation of the expression and/or activity of gene products regulating the lipid metabolism of microbes for biofuel or biofuel precursor production. Such genetic modifications according to some aspects are targeted to increase carbohydrate to fatty acid and/or TAG conversion in order to optimize the modified microbe for large-scale production of lipids from a carbon source, for example, a carbohydrate source. Some modifications provided according to some aspects, for example, overexpression, knockout, knock-down, activation and/or inhibition of specific gene products, may be effected alone or in combination, and/or in combination with other modifications known to those of skill in the art. The term "modification" refers to both genetic manipulation, for example, overexpression, knock-out, knock-down, activation and/or inhibition of specific gene products, and non-genetic manipulation, for example, manipulation of the cell number, dissolved oxygen, growth media (including nitrogen concentration), substrate (e.g., carbon source), substrate feeding rate, pH, temperature, conversion process, etc.

A modification of gene expression, also referred to herein as a modulation of gene expression, can be a disruption or inhibition of the natural regulation of expression, an overexpression, an inhibition of expression, or a complete abolishment of expression of a given gene. The insertion of a heterologous promoter upstream of a native gene sequence, for example the native DGA1 or ACC1 gene sequence, or the deletion of regulatory sequences within a promoter, for example regulatory sequences that mediate the feedback inhibition of the DGA1 or ACC1 gene by saturated fatty acids, are examples of a disruption or inhibition of the natural regulation of expression. Strategies for the modulation of gene expression may include genetic alterations, for example by recombinant technologies, such as gene targeting or viral transductions, or non-genetic alterations, for example environmental alterations known to result in the up- or down-regulation of gene expression, or transient delivery of modulators, for example drugs or small RNA molecules to the target cells. Methods for genetic and non-genetic alterations of microbes are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology*, Part A, Volume 194 (Methods in Enzymology Series, 194), Academic Press (Mar. 11, 2004); Christine Guthrie and Gerald R. Fink, *Guide to Yeast Genetics and Molecular and Cell Biology, Part B*, Volume 350 (Methods in Enzymology, Vol 350), Academic Press; 1st edition (Jul. 2, 2002); Christine Guthrie and Gerald R. Fink, *Guide to Yeast Genetics and Molecular and Cell Biology*, Part C, Volume 351, Academic Press; 1st edition (Jul. 9, 2002); Gregory N. Stephanopoulos, Aristos A. Aristidou and Jens Nielsen, *Metabolic Engineering: Principles and Methodologies*, Academic Press; 1 edition (Oct. 16, 1998); and Christina Smolke, *The Metabolic Pathway Engineering Handbook: Fundamentals*, CRC Press; 1 edition (Jul. 28, 2009), all of which are incorporated by reference herein.

The terms "overexpression" or "increased expression", as used herein, refers to an increased level of expression of a given gene product in a given cell, cell type or cell state, as compared to a reference cell, for example, a wild type cell of the same cell type or a cell of the same cell type but lacking a specific modification, for example, a genetic modification. Forced, continuous expression of the DGA1 and/or ACC1 gene in *Y. lipolytica* cells exhibiting concentrations of saturated fatty acids that would inhibit DGA1 or ACC1 gene expression in wild-type cells is an example of gene overexpression.

Some aspects provide a method for the manipulation of the activity of a diacylglycerol acyltransferase 1 (DGA1) gene product in a microbe for biofuel or biofuel precursor production. The DGA1 gene encodes an acyltransferase that catalyzes the terminal step of triacylglycerol (TAG) formation, acylating diacylglycerol using acyl-CoA as an acyl donor. The result of this acyltransferase reaction are triacylglycerols, which do not exhibit the same inhibitory feedback effect on fatty acid synthesis as fatty acids themselves. TAGs are typically stored in lipid bodies or vacuoles in lipid producing cells. In some embodiments, the manipulation is an overexpression. In some embodiments, the manipulation is effected by contacting a microbe for biofuel or biofuel precursor production with an expression construct comprising a nucleic acid coding for a DGA1 gene product, for example, a DGAT2 protein, operably linked to a heterologous promoter, for example, a constitutive or an inducible promoter. In some embodiments, the nucleic acid coding for a DGA1 gene product comprises the coding sequence of SEQ ID NO: 53. In some embodiments, the DGA1 is *Y. lipolytica* DGA1, for example, *Y. lipolytica* DGA1 comprising the amino acid sequence of SEQ ID NO: 54. In some embodiments, the microbe is *Y. lipolytica*. In some embodiments, manipulation of the activity of a DGA1 gene product in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. DGA1 gene and gene product sequences are well known to those of skill in the art. Exemplary, representative gene and gene product sequences can be found under entry XM_504700 in the NCBI database (www.ncbi.nlm.nih.gov).

Non-limiting examples of suitable sequences of DGA1 nucleic acid and protein sequences are provided below. Additional suitable DGA1 sequences, including sequences from other species, will be apparent to those of skill in the art, and the invention is not limited in this respect.

```
>gi|50554582|ref|XM_504700.1| Yarrowia lipolytica
YALI0E32769p (YALI0E32769g) mRNA, complete cds
Nucleotide sequence (SEQ ID NO: 53):
ATGACTATCGACTCACAATACTACAAGTCGCGAGACAAAAACGACACGGC
ACCCAAAATCGCGGGAATCCGATATGCCCCGCTATCGACACCATTACTCA
ACCGATGTGAGACCTTCTCTCTGGTCTGGCACATTTTCAGCATTCCCACT
TTCCTCACAATTTTCATGCTATGCTGCGCAATTCCACTGCTCTGGCCATT
TGTGATTGCGTATGTAGTGTACGCTGTTAAAGACGACTCCCCGTCCAACG
GAGGAGTGGTCAAGCGATACTCGCCTATTTCAAGAAACTTCTTCATCTGG
AAGCTCTTTGGCCGCTACTTCCCCATAACTCTGCACAAGACGGTGGATCT
GGAGCCCACGCACACATACTACCCTCTGGACGTCCAGGAGTATCACCTGA
TTGCTGAGAGATACTGGCCGCAGAACAAGTACCTCCGAGCAATCATCTCC
ACCATCGAGTACTTTCTGCCCGCCTTCATGAAACGGTCTCTTTCTATCAA
CGAGCAGGAGCAGCCTGCCGAGCGAGATCCTCTCCTGTCTCCCGTTTCTC
CCAGCTCTCCGGGTTCTCAACCTGACAAGTGGATTAACCACGACAGCAGA
TATAGCCGTGGAGAATCATCTGGCTCCAACGGCCACGCCTCGGGCTCCGA
ACTTAACGGCAACGGCAACAATGGCACCACTAACCGACGACCTTTGTCGT
CCGCCTCTGCTGGCTCCACTGCATCTGATTCCACGCTTCTTAACGGGTCC
CTCAACTCCTACGCCAACCAGATCATTGGCGAAAACGACCCACAGCTGTC
GCCCACAAAACTCAAGCCCACTGGCAGAAAATACATCTTCGGCTACCACC
CCCACGGCATTATCGGCATGGGAGCCTTTGGTGGAATTGCCACCGAGGGA
GCTGGATGGTCCAAGCTCTTTCCGGGCATCCCTGTTTCTCTTATGACTCT
CACCAACAACTTCCGAGTGCCTCTCTACAGAGAGTACCTCATGAGTCTGG
GAGTCGCTTCTGTCTCCAAGAAGTCCTGCAAGGCCCTCCTCAAGCGAAAC
CAGTCTATCTGCATTGTCGTTGGTGGAGCACAGGAAAGTCTTCTGGCCAG
ACCCGGTGTCATGGACCTGGTGCTACTCAAGCGAAAGGGTTTTGTTCGAC
TTGGTATGGAGGTCGGAAATGTCGCCCTTGTTCCCATCATGGCCTTTGGT
GAGAACGACCTCTATGACCAGGTTAGCAACGACAAGTCGTCCAAGCTGTA
CCGATTCCAGCAGTTTGTCAAGAACTTCCTTGGATTCACCCTTCCTTTGA
TGCATGCCCGAGGCGTCTTCAACTACGATGTCGGTCTTGTCCCCTACAGG
CGACCCGTCAACATTGTGGTTGGTTCCCCCATTGACTTGCCTTATCTCCC
ACACCCCACCGACGAAGAAGTGTCCGAATACCACGACCGATACATCGCCG
AGCTGCAGCGAATCTACAACGAGCACAAGGATGAATATTTCATCGATTGG
ACCGAGGAGGGCAAAGGAGCCCCAGAGTTCCGAATGATTGAGTAA >gi|50554583|ref|XP_504700.1| YALI0E32769p
[Yarrowia lipolytica] Amino acid sequence
(SEQ ID NO: 54):
MTIDSQYYKSRDKNDTAPKIAGIRYAPLSTPLLNRCETFSLVWHIFSIPT
FLTIFMLCCAIPLLWPFVIAYVVYAVKDDSPSNGGVVKRYSPISRNFFIW
KLFGRYFPITLHKTVDLEPTHTYYPLDVQEYHLIAERYWPQNKYLRAIIS
TIEYFLPAFMKRSLSINEQEQPAERDPLLSPVSPSSPGSQPDKWINHDSR
YSRGESSGSNGHASGSELNGNGNNGTTNRRPLSSASAGSTASDSTLLNGS
LNSYANQIIGENDPQLSPTKLKPTGRKYIFGYHPHGIIGMGAFGGIATEG
AGWSKLFPGIPVSLMTLTNNFRVPLYREYLMSLGVASVSKKSCKALLKRN
QSICIVVGGAQESLLARPGVMDLVLLKRKGFVRLGMEVGNVALVPIMAFG
ENDLYDQVSNDKSSKLYRFQQFVKNFLGFTLPLMHARGVFNYDVGLVPYR
RPVNIVVGSPIDLPYLPHPTDEEVSEYHDRYIAELQRIYNEHKDEYFIDW
TEEGKGAPEFRMIE
```

Some aspects provide a method for the manipulation of an acetyl-CoA carboxylase (ACC) gene product in a microbe for biofuel or biofuel precursor production, for example, in *Y. lipolytica*. ACC gene products mediate the conversion of acetyl-CoA, the main C2-precursor in fatty acid synthesis, to malonyl-CoA, which is considered the first committed step in fatty acid synthesis and has been suggested to also be the rate-limiting step in fatty acid synthesis (see Cao Y, Yang J, Xian M, Xu X, Liu W. Increasing unsaturated fatty acid contents in *Escherichia coli* by coexpression of three different genes. Appl Microbiol Biotechnol. 2010). In some embodiments, ACC activity manipulation is ACC overexpression. In some embodiments, the manipulation is effected by contacting a microbe for biofuel or biofuel precursor production with an expression construct comprising a nucleic acid coding for an ACC gene product, for example, an ACC1 protein, operably linked to a heterologous promoter, for example, a constitutive or an inducible promoter. In some embodiments, the nucleic acid coding for an ACC gene product comprises the coding sequence of SEQ ID NO: 55. In some embodiments, the ACC gene product is an ACC1 protein comprising the amino acid sequence of SEQ ID NO: 56. In some embodiments, ACC overexpression in a microbe increases fatty acid synthesis rate and/or confers a beneficial phenotype for large-scale carbohydrate to biofuel or biofuel precursor conversion, for example increased lipid synthesis rate, increased carbohydrate to lipid conversion efficiency, increased lipid storage and, increased growth rate, increased tolerance to concentrations of a substance, e.g. a carbon source, a biofuel or biofuel precursor, or a toxic substance. ACC gene and gene product sequences are well known to those of skill in the art. Exemplary, representative gene and gene product sequences can be found under the entry for GeneIDs: 855750 and 2909424, or under the entry NC_006069 in the NCBI database (www.ncbi.nlm.nih.gov).

Non-limiting examples of suitable sequences of ACC nucleic acid and protein sequences are provided below. Additional suitable ACC sequences, including sequences from other species, will be apparent to those of skill in the art, and the invention is not limited in this respect.

ACC Encoding Nucleic Acid Sequence:

```
Nucleotide sequence (SEQ ID NO: 55):
ATGCGACTGCAATTGAGGACACTAACACGTCGGTT

TTTCAGGTGAGTAAACGACGGTGGCCGTGGCCAC

GACAGCCGAGGCGTCACGATGGGCCAGACGAGCACATT

CTCGCCGCCACAACCTCGCCAGCACAAGAAACTAACC

CAGTATGGCTTCAGGATCTTCAACGCCAGATGTGGCTC

CCTTGGTGGACCCCAACATTCACAAAGGTCTCGCCTC

TCATTTCTTTGGACTCAATTCTGTCCACACAGCCAAGC

CCTCAAAAGTCAAGGAGTTTGTGGCTTCTCACGGAGG

TCATACAGTTATCAACAAGGTGAGTATTTGACGTTTAG

ACTGTATAACAGGCGGCCGCAGTGCAACAACGACCAA

AAAGGGTCGAAAAAGGGTCGAAAACGGACACAAAAGCT

GGAAAACAAGAGTGTAATACATTCTTACACGTCCAAT

TGTTAGACAAACACGGCTGTTCGGTCCCAAAACCACCA

GTATCACCTATTTTCCACTTGTGTCTCGGATCTGATC

ATAATCTGATCTCAAGATGAAATTTACGCCACCGACAT

GATATTGTGATTTTCGGATTCTCCAGACCGAGCAGAT

TCCAGCAATACCACCACTTGCCCACCTTCAGCGGCCTC

TCGGCGCGATTCGCCACTTTCCCCAACGAGTGTTACT

AACCCAGGTCCTCATCGCTAACAACGGTATTGCCGCAG

TAAAGGAGATCCGTTCAGTACGAAAATGGGCCTACGA

GACCTTTGGCGACGAGCGAGCAATCTCGTTCACCGTCA

TGGCCACCCCCGAAGATCTCGCTGCCAACGCCGACTA

CATTAGAATGGCCGATCAGTACGTCGAGGTGCCCGGAG

GAACCAACAACAACAACTACGCCAACGTCGAGCTGAT

TGTCGACGTGGCTGAGCGATTCGGCGTCGATGCCGTGT

GGGCCGGATGGGGCCATGCCAGTGAAAATCCCCTGCT

CCCCGAGTCGCTAGCGGCCTCTCCCCGCAAGATTGTCT

TCATCGGCCCTCCCGGAGCTGCCATGAGATCTCTGGG

AGACAAAATTTCTTCTACCATTGTGGCCCAGCACGCAA
```

```
AGGTCCCGTGTATCCCGTGGTCTGGAACCGGAGTGGA

CGAGGTTGTGGTTGACAAGAGCACCAACCTCGTGTCCG

TGTCCGAGGAGGTGTACACCAAGGGCTGCACCACCGG

TCCCAAGCAGGGTCTGGAGAAGGCTAAGCAGATTGGAT

TCCCCGTGATGATCAAGGCTTCCGAGGGAGGAGGAGG

AAAGGGTATTCGAAAGGTTGAGCGAGAGGAGGACTTCG

AGGCTGCTTACCACCAGGTCGAGGGAGAGATCCCCGG

CTCGCCCATCTTCATTATGCAGCTTGCAGGCAATGCCC

GGCATTTGGAGGTGCAGCTTCTGGCTGATCAGTACGG

CAACAATATTTCACTGTTTGGTCGAGATTGTTCGGTTC

AGCGACGGCATCAAAAGATTATTGAGGAGGCTCCTGT

GACTGTGGCTGGCCAGCAGACCTTCACTGCCATGGAGA

AGGCTGCCGTGCGACTCGGTAAGCTTGTCGGATATGT

CTCTGCAGGTACCGTTGAATATCTGTATTCCCATGAGG

ACGACAAGTTCTACTTCTTGGAGCTGAATCCTCGTCT

TCAGGTCGAACATCCTACCACCGAGATGGTCACCGGTG

TCAACCTGCCCGCTGCCCAGCTTCAGATCGCCATGGG

TATCCCCCTCGATCGAATCAAGGACATTCGTCTCTTTT

ACGGTGTTAACCCTCACACCACCACTCCAATTGATTT

CGACTTCTCGGGCGAGGATGCTGATAAGACACAGCGAC

GTCCCGTCCCCCGAGGTCACACCACTGCTTGCCGAAT

CACATCCGAGGACCCTGGAGAGGGTTTCAAGCCCTCCG

GAGGTACTATGCACGAGCTCAACTTCCGATCCTCGTC

CAACGTGTGGGGTTACTTCTCCGTTGGTAACCAGGGAG

GTATCCATTCGTTCTCGGATTCGCAGTTTGGTCACAT

CTTCGCCTTCGGTGAGAACCGAAGTGCGTCTCGAAAGC

ACATGGTTGTTGCTTTGAAGGAACTATCTATTCGAGG

TGACTTCCGAACCACCGTCGAGTACCTCATCAAGCTGC

TGGAGACACCGGACTTCGAGGACAACACCATCACCAC

CGGCTGGCTGGATGAGCTTATCTCCAACAAGCTGACTG

CCGAGCGACCCGACTCGTTCCTCGCTGTTGTTTGTGG

TGCTGCTACCAAGGCCCATCGAGCTTCCGAGGACTCTA

TTGCCACCTACATGGCTTCGCTAGAGAAGGGCCAGGT

CCCTGCTCGAGACATTCTCAAGACCCTTTTCCCCGTTG

ACTTCATCTACGAGGGCCAGCGGTACAAGTTCACCGC

CACCCGGTCGTCTGAGGACTCTTACACGCTGTTCATCA

ACGGTTCTCGATGCGACATTGGAGTTAGACCTCTTTC

TGACGGTGGTATTCTGTGTCTTGTAGGTGGGAGATCCC

ACAATGTCTACTGGAAGGAGGAGGTTGGAGCCACGCG

ACTGTCTGTTGACTCCAAGACCTGCCTTCTCGAGGTGG
```

```
AGAACGACCCCACTCAGCTTCGATCTCCCTCTCCCGG
TAAGCTGGTTAAGTTCCTGGTCGAGAACGGCGACCACG
TGCGAGCCAACCAGCCCTATGCCGAGATTGAGGTCAT
GAAGATGTACATGACTCTCACTGCTCAGGAGGACGGTA
TTGTCCAGCTGATGAAGCAGCCCGGTTCCACCATCGA
GGCTGGCGACATCCTCGGTATCTTGGCCCTTGATGATC
CTTCCAAGGTCAAGCATGCCAAGCCCTTTGAGGGCCA
GCTTCCCGAGCTTGGACCCCCACTCTCAGCGGTAACA
AGCCTCATCAGCGATACGAGCACTGCCAGAACGTGCT
CCATAACATTCTGCTTGGTTTCGATAACCAGGTGGTGA
TGAAGTCCACTCTTCAGGAGATGGTTGGTCTGCTCCG
AAACCCTGAGCTTCCTTATCTCCAGTGGGCTCATCAGG
TGTCTTCTCTGCACACCCGAATGAGCGCCAAGCTGGA
TGCTACTCTTGCTGGTCTCATTGACAAGGCCAAGCAGC
GAGGTGGCGAGTTTCCTGCCAAGCAGCTTCTGCGAGC
CCTTGAGAAGGAGGCGAGCTCTGGCGAGGTCGATGCGC
TCTTCCAGCAAACTCTTGCTCCTCTGTTTGACCTTGC
TCGAGAGTACCAGGACGGTCTTGCTATCCACGAGCTTC
AGGTTGCTGCAGGCCTTCTGCAGGCCTACTACGACTC
TGAGGCCCGGTTCTGCGGACCCAACGTACGTGACGAGG
ATGTCATTCTCAAGCTTCGAGAGGAGAACCGAGATTC
TCTTCGAAAGGTTGTGATGGCCCAGCTGTCTCATTCTC
GAGTCGGAGCCAAGAACAACCTTGTGCTGGCCCTTCT
CGATGAATACAAGGTGGCCGACCAGGCTGGCACCGACT
CTCCTGCCTCCAACGTGCACGTTGCAAAGTACTTGCG
ACCTGTGCTGCGAAAGATTGTGGAGCTGGAATCTCGAG
CTTCTGCCAAGGTATCTCTGAAAGCCCGAGAGATTCT
CATCCAGTGCGCTCTGCCCTCTCTAAAGGAGCGAACTG
ACCAGCTTGAGCACATTCTGCGATCTTCTGTCGTCGA
GTCTCGATACGGAGAGGTTGGTCTGGAGCACCGAACTC
CCCGAGCCGATATTCTCAAGGAGGTTGTCGACTCCAA
GTACATTGTCTTTGATGTGCTTGCCCAGTTCTTTGCCC
ACGATGATCCCTGGATCGTCCTTGCTGCCCTGGAGCT
GTACATCCGACGAGCTTGCAAGGCCTACTCCATCCTGG
ACATCAACTACCACCAGGACTCGGACCTGCCTCCCGT
CATCTCGTGGCGATTTAGACTGCCTACCATGTCGTCTG
CTTTGTACAACTCAGTAGTGTCTTCTGGCTCCAAAAC
CCCCACTTCCCCCTCGGTGTCTCGAGCTGATTCGTCT
CCGACTTTTCGTACACCGTTGAGCGAGACTCTGCTCC
CGCTCGAACCGGAGCGATTGTTGCCGTGCCTCATCTGG
ATGATCTGGAGGATGCTCTGACTCGTGTTCTGGAGAA
CCTGCCCAAACGGGGCGCTGGTCTTGCCATCTCTGTTG
GTGCTAGCAACAAGAGTGCCGCTGCTTCTGCTCGTGA
CGCTGCTGCTGCTGCCGCTTCATCCGTTGACACTGGCC
TGTCCAACATTTGCAACGTTATGATTGGTCGGGTTGA
TGAGTCTGATGACGACGACACTCTGATTGCCCGAATCT
CCCCAGGTCATTGAGGACTTTAAGGAGGACTTTGAGGC
CTGTTCTCTGCGACGAATCACCTTCTCCTTCGGCAACT
CCCGAGGTACTTATCCCAAGTATTTCACGTTCCGAGG
CCCCGCATACGAGGAGGACCCCACTATCCGACACATTG
AGCCTGCTCTGGCCTTCCAGCTGGAGCTCGCCCGTCT
GTCCAACTTCGACATCAAGCCTGTCCACACCGACAACC
GAAACATCCACGTGTACGAGGCTACTGGCAAGAACGC
TGCTTCCGACAAGCGGTTCTTCACCCGAGGTATCGTAC
GACCTGGTCGTCTTCGAGAGAACATCCCCACCTCGGA
GTATCTCATTTCCGAGGCTGACCGGCTCATGAGCGATA
TTTTGGACGCTCTAGAGGTGATTGGAACCACCAACTC
GGATCTCAACCACATTTTCATCAACTTCTCAGCCGTCT
TTGCTCTGAAGCCCGAGGAGGTTGAAGCTGCCTTTGG
CGGTTTCCTGGAGCGATTTGGCCGACGTCTGTGGCGAC
TTCGAGTCACCGGTGCCGAGATCCGAATGATGGTATC
CGACCCCGAAACTGGCTCTGCTTTCCCTCTGCGAGCAA
TGATCAACAACGTCTCTGGTTACGTTGTGCAGTCTGA
GCTGTACGCTGAGGCCAAGAACGACAAGGGCCAGTGGA
TTTTCAAGTCTCTGGGCAAGCCCGGCTCCATGCACAT
GCGGTCTATCAACACTCCCTACCCCACCAAGGAGTGGC
TGCAGCCCAAGCGGTACAAGGCCCATCTGATGGGTAC
CACCTACTGCTATGACTTCCCCGAGCTGTTCCGACAGT
CCATTGAGTCGGACTGGAAGAAGTATGACGGCAAGGC
TCCCGACGATCTCATGACTTGCAACGAGCTGATTCTCG
ATGAGGACTCTGGCGAGCTGCAGGAGGTGAACCGAGA
GCCCGGCGCCAACAACGTCGGTATGGTTGCGTGGAAGT
TTGAGGCCAAGACCCCCGAGTACCCTCGAGGCCGATC
TTTTCATCGTGGTGGCCAACGATATCACCTTCCAGATTG
GTTCGTTTGGCCCTGCTGAGGACCAGTTCTTCTTCAA
GGTGACGGAGCTGGCTCGAAAGCTCGGTATTCCTCGAA
TCTATCTGTCTGCCAACTCTGGTGCTCGAATCGGCAT
TGCTGACGAGCTCGTTGGCAAGTACAAGGTTGCGTGGA
ACGACGAGACTGACCCCTCCAAGGGCTTCAAGTACCT
TTACTTCACCCCTGAGTCTCTTGCCACCCTCAAGCCCG
ACACTGTTGTCACCACTGAGATTGAGGAGGAGGGTCC
```

-continued

```
CAACGGCGTGGAGAAGCGTCATGTGATCGACTACATTG
TCGGAGAGAAGGACGGTCTCGGAGTCGAGTGTCTGCG
GGGCTCTGGTCTCATTGCAGGCGCCACTTCTCGAGCCT
ACAAGGATATCTTCACTCTCACTCTTGTCACCTGTCG
ATCCGTTGGTATCGGTGCTTACCTTGTTCGTCTTGGTC
AACGAGCCATCCAGATTGAGGGCCAGCCCATCATTCT
CACTGGTGCCCCCGCCATCAACAAGCTGCTTGGTCGAG
AGGTCTACTCTTCCAACTTGCAGCTTGGTGGTACTCA
GATCATGTACAACAACGGTGTGTCTCATCTGACTGCCC
GAGATGATCTCAACGGTGTCCACAAGATCATGCAGTG
GCTGTCATACATCCCTGCTTCTCGAGGTCTTCCAGTGC
CTGTTCTCCCTCACAAGACCGATGTGTGGGATCGAGA
CGTGACGTTCCAGCCTGTCCGAGGCGAGCAGTACGATG
TTAGATGGCTTATTTCTGGCCGAACTCTCGAGGATGG
TGCTTTCGAGTCTGGTCTCTTTGACAAGGACTCTTTCC
AGGAGACTCTGTCTGGCTGGGCCAAGGGTGTTGTTGT
TGGTCGAGCTCGTCTTGGCGGCATTCCCTTCGGTGTCA
TTGGTGTCGAGACTGCGACCGTCGACAATACTACCCC
TGCCGATCCCGCCAACCCGGACTCTATTGAGATGAGCA
CCTCTGAAGCCGGCCAGGTTTGGTACCCCAACTCGGC
CTTCAAGACCTCTCAGGCCATCAACGACTTCAACCATG
GTGAGGCGCTTCCTCTCATGATTCTTGCTAACTGGCG
AGGCTTTTCTGGTGGTCAGCGAGACATGTACAATGAGG
TTCTCAAGTACGGATCTTTCATTGTTGATGCTCTGGT
TGACTACAAGCAGCCCATCATGGTGTACATCCCTCCCA
CCGGTGAGCTGCGAGGTGGTTCTTGGGTTGTGGTTGA
CCCCACCATCAACTCGGACATGATGGAGATGTACGCTG
ACGTCGAGTCTCGAGGTGGTGTGCTGGAGCCCGAGGG
AATGGTCGGTATCAAGTACCGACGAGACAAGCTACTGG
ACACCATGGCTCGTCTGGATCCCGAGTACTCCTCTCT
CAAGAAGCAGCTTGAGGAGTCTCCCGATTCTGAGGAGC
TCAAGGTCAAGCTCAGCGTGCGAGAGAAGTCTCTCAT
GCCCATCTACCAGCAGATCTCCGTGCAGTTTGCCGACT
TGCATGACCGAGCTGGCCGAATGGAGGCCAAGGGTGT
CATTCGTGAGGCTCTTGTGTGGAAGGATGCTCGTCGAT
TCTTCTTCTGGCGAATCCGACGACGATTAGTCGAGGA
GTACCTCATTACCAAGATCAATAGCATTCTGCCCTCTT
GCACTCGGCTTGAGTGTCTGGCTCGAATCAAGTCGTG
GAAGCCTGCCACTCTTGATCAGGGCTCTGACCGGGGTG
TTGCCGAGTGGTTTGACGAGAACTCTGATGCCGTCTC
TGCTCGACTCAGCGAGCTCAAGAAGGACGCTTCTGCCC
AGTCGTTTGCTTCTCAACTGAGAAAGGACCGACAGGG
TACTCTCCAGGGCATGAAGCAGGCTCTCGCTTCTCTTT
CTGAGGCTGAGCGGGCTGAGCTGCTCAAGGGGTTGTG
A
```

>gi|50548503|ref|XP_501721.1| YALI0C11407p
[*Yarrowia lipolytica*] Amino acid sequence
(SEQ ID NO: 56):

```
MRLQLRTLTRRFFSMASGSSTPDVAPLVDPNIHKG
LASHFFGLNSVHTAKPSKVKEFVASHGGHTVINK
VLIANNGIAAVKEIRSVRKWAYETFGDERAISFTVMAT
PEDLAANADYIRMADQYVEVPGGTNNNNYANVELIVD
VAERFGVDAVWAGWGHASENPLLPESLAASPRKIVFIG
PPGAAMRSLGDKISSTIVAQHAKVPCIPWSGTGVDEV
VVDKSTNLVSVSEEVYTKGCTTGPKQGLEKAKQIGFPV
MIKASEGGGGKGIRKVEREEDFEAAYHQVEGEIPGSP
IFIMQLAGNARHLEVQLLADQYGNNISLFGRDCSVQRR
HQKIIEEAPVTVAGQQTFTAMEKAAVRLGKLVGYVSA
GTVEYLYSHEDDKFYFLELNPRLQVEHPTTEMVTGVNL
PAAQLQIAMGIPLDRIKDIRLFYGVNPHTTTPIDFDF
SGEDADKTQRRPVPRGHTTACRITSEDPGEGFKPSGGT
MHELNFRSSSNVWGYFSVGNQGGIHSFSDSQFGHIFA
FGENRSASRKHMVVALKELSIRGDFRTTVEYLIKLLET
PDFEDNTITTGWLDELISNKLTAERPDSFLAVVCGAA
TKAHRASEDSIATYMASLEKGQVPARDILKTLFPVDFI
YEGQRYKFTATRSSEDSYTLFINGSRCDIGVRPLSDG
GILCLVGGRSHNVYWKEEVGATRLSVDSKTCLLEVEND
PTQLRSPSPGKLVKFLVENGDHVRANQPYAEIEVMKM
YMTLTAQEDGIVQLMKQPGSTIEAGDILGILALDDPSK
VKHAKPFEGQLPELGPPTLSGNKPHQRYEHCQNVLHN
ILLGFDNQVVMKSTLQEMVGLLRNPELPYLQWAHQVSS
LHTRMSAKLDATLAGLIDKAKQRGGEFPAKQLLRALE
KEASSGEVDALFQQTLAPLFDLAREYQDGLAIHELQVA
AGLLQAYYDSEARFCGPNVRDEDVILKLREENRDSLR
KVVMAQLSHSRVGAKNNLVLALLDEYKVADQAGTDSPA
SNVHVAKYLRPVLRKIVELESRASAKVSLKAREILIQ
CALPSLKERTDQLEHILRSSVVESRYGEVGLEHRTPRA
DILKEVVDSKYIVFDVLAQFFAHDDPWIVLAALELYI
RRACKAYSILDINYHQDSDLPPVISWRFRLPTMSSALY
NSVVSSGSKTPTSPSVSRADSVSDFSYTVERDSAPAR
TGAIVAVPHLDOLEDALTRVLENLPKRGAGLAISVGAS
NKSAAASARDAAAAASSVDTGLSNICNVMIGRVDES
DDDDTLIARISQVIEDFKEDFEACSLRRITFSFGNSRG
```

-continued

```
TYPKYFTFRGPAYEEDPTIRHIEPALAFQLELARLSN

FDIKPVHTDNRNIHVYEATGKNAASDKRFFTRGIVRPG

RLRENIPTSEYLISEADRLMSDILDALEVIGTTNSDL

NHIFINFSAVFALKPEEVEAAFGGFLERFGRRLWRLRV

TGAEIRMMVSDPETGSAFPLRAMINNVSGYVVQSELY

AEAKNDKGQWIFKSLGKPGSMHMRSINTPYPTKEWLQP

KRYKAHLMGTTYCYDFPELFRQSIFSDWKKYDGKAPD

DLMTCNELILDEDSGELQEVNREPGANNVGMVAWKFEA

KTPEYPRGRSFIVVANDITFQIGSFGPAEDQFFFKVT

ELARKLGIPRIYLSANSGARIGIADELVGKYKVAWNDE

TDPSKGFKYLYFTPESLATLKPDTVVTTEIEEEGPNG

VEKRHVIDYIVGEKDGLGVECLRGSGLIAGATSRAYKD

IFTLTLVTCRSVGIGAYLVRLGQRAIQIEGQPIILTG

APAINKLLGREVYSSNLQLGGTQIMYNNGVSHLTARDD

LNGVHKIMQWLSYIPASRGLPVPVLPHKTDVWDRDVT

FQPVRGEQYDVRWLISGRTLEDGAFESGLFDKDSFQET

LSGWAKGVVVGRARLGGIPFGVIGVETATVDNTTPAD

PANPDSIEMSTSEAGQVWYPNSAFKTSQAINDFNHGEA

LPLMILANWRGFSGGQRDMYNEVLKYGSFIVDALVDY

KQPINIVYIPPTGELRGGSWVVVDPTINSDMMEMYADV

ESRGGVLEPEGMVGIKYRRDKLLDTMARLDPEYSSLKK

QLEESPDSEELKVKLSVREKSLMPIYQQISVQFADLHD

RAGRMEAKGVIREALVWKDARRFFFWRIRRRLVEEYL

ITKINSILPSCTRLECLARIKSWKPATLDQGSDRGVAE

WFDENSDAVSARLSELKKDASAQSFASQLRKDRQGTL

QGMKQALASLSEAERAELLKGL
```

Some aspects provide oleaginous microbes for oil production comprising any of the modifications described herein. Some aspects provide nucleic acids coding for a gene product conferring a required and/or desired phenotype for biofuel or biofuel precursor production to a microbe, such as an oleaginous yeast, for example, *Y. lipolytica*. In some embodiments, the nucleic acid is a nucleic acid derived from *Y. lipolytica*. In some embodiments, the nucleic acid encodes an acetyl-CoA carboxylase gene product, such as an ACC1 gene product, for example, an ACC1 protein. In some embodiments, the nucleic acid encodes a diacylglyceride acyltransferase gene product, such as a DGA1 gene product, for example, a DGA1 protein. In some embodiments, the nucleic acid encodes a a NADPH-dependent malic enzyme gene product, such as the MCE2 gene product of *Mucor circinelloides*, for example a MCE2 protein. In some embodiments, the nucleic acid encodes a glyceraldehyde-3-phosphate dehydrogenase gene product, such as a GapC gene product of *Clostridium acetobutylicum* or a GPD1 gene product of *Kluyveromyces lactis*, for example, a GapC protein or a GPD1. In some embodiments, the nucleic acid encodes an aldehyde dehydrogenase gene product, such as an AldH gene product of *E. coli* gene product, for example, an AldH protein. In some embodiments, the nucleic acid encodes a glutathione disulfide reductase gene product, such as a GSR gene product of *Yarrowia lipolytica*, for example, a GSR protein. In some embodiments, the nucleic acid encodes a glutathione peroxidase gene product, such as a GPO gene product of *Yarrowia lipolytica*, for example, a GPO protein. In some embodiments, the nucleic acid encodes a glucose-6-phosphate dehydrogenase gene product, such as a ZWF gene product of *Saccharomyces cerevisiae*, for example, a ZWF protein. In some embodiments, the nucleic acid encodes a thioredoxin reductase gene product, such as a TRX gene product of *Yarrowia lipolytica*, for example, a TRX protein. In some embodiments, a nucleic acid is provided that encodes a combination of gene products, for example in multiple cistrons.

The term "nucleic acid" refers to a molecule comprising multiple linked nucleotides. "Nucleic acid" and "nucleic acid molecule" are used interchangeably and refer to oligoribonucleotides as well as oligodeoxyribonucleotides. The terms also include polynucleosides (i.e., a polynucleotide minus a phosphate) and any other organic base containing nucleic acid. The organic bases include adenine, uracil, guanine, thymine, cytosine and inosine. The nucleic acids may be single or double stranded. The nucleic acid may be naturally or non-naturally occurring. Nucleic acids can be obtained from natural sources, or can be synthesized using a nucleic acid synthesizer (i.e., synthetic). Isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, PNA or LNA, or a combination thereof, as described herein. Non-naturally occurring nucleic acids such as bacterial artificial chromosomes (BACs) and yeast artificial chromosomes (YACs) can also be used in accordance with some aspects.

Some aspects relate to the use of nucleic acid derivatives. The use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages. Nucleic acid derivatives according to some aspects may contain backbone modifications such as but not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives according to some aspects may contain substitutions or modifications in the sugars and/or bases. For example, some nucleic acid derivatives may include nucleic acids having backbone sugars which are covalently attached to low molecular weight organic groups other than a hydroxyl group at the 3' position and other than a phosphate group at the 5' position (e.g., an 2'-O-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine.

In some embodiments, a nucleic acid may comprise a peptide nucleic acid (PNA), a locked nucleic acid (LNA), DNA, RNA, or a co-nucleic acids of the above such as DNA-LNA co-nucleic acid.

As used herein the term "isolated nucleic acid molecule" refers to a nucleic acid that is not in its natural environment, for example a nucleic acid that has been (i) extracted and/or purified from a cell or microbe, for example, a bacteria or yeast, by methods known in the art, for example, by alkaline lysis of the host cell and subsequent purification of the nucleic acid, for example, by a silica adsorption procedure; (ii) amplified in vitro, for example, by polymerase chain reaction (PCR); (iii) recombinantly produced by cloning, for example, a nucleic acid cloned into an expression vector; (iv) fragmented and size separated, for example, by enzymatic digest in vitro or by shearing and subsequent gel separation; or (v) synthesized by, for example, chemical synthesis. In some embodiments, the term "isolated nucleic acid molecule" refers to (vi) an nucleic acid that is chemically markedly different from any naturally occurring nucleic acid. In some embodiments, an isolated nucleic acid can readily be manipulated by recombinant DNA techniques well known in the art. Accordingly, a nucleic acid cloned into a vector, or a nucleic acid delivered to a host cell and integrated into the host genome is considered isolated but a nucleic acid in its native state in its natural host, for example, in the genome of the host, is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein.

Some aspects relate to nucleic acids encoding a gene product conferring a required or desirable phenotype to a microbe for biofuel or biofuel precursor production which are linked to a promoter or other transcription activating element. In some embodiments, the nucleic acid encoding the gene product and linked to a promoter is comprised in an expression vector or expression construct. As used herein, the terms "expression vector" or "expression construct" refer to a nucleic acid construct, generated recombinantly or synthetically, with a series of specified nucleic acid elements that permit transcription of a particular nucleic acid in a host microbe, for example, an oleaginous yeast. In some embodiments, the expression vector may be part of a plasmid, virus, or nucleic acid fragment. In some embodiments, the expression vector includes the coding nucleic acid to be transcribed operably linked to a promoter. A promoter is a nucleic acid element that facilitates transcription of a nucleic acid to be transcribed. A promoter is typically located on the same strand and upstream (or 5') of the nucleic acid sequence the transcription of which it controls. In some embodiments, the expression vector includes the coding nucleic acid to be transcribed operably linked to a heterologous promoter. A heterologous promoter is a promoter not naturally operably linked to a given nucleic acid sequence. For example, the DGA1 gene in Y. lipolytica is naturally operably linked to the Y. lipolytica DGA1 gene promoter. Any promoter other than the wildtype Y. lipolytica DGA1 gene promoter operably linked to the DGA1 gene, or parts thereof, for example in an expression construct, would, therefore, be a heterologous promoter in this context. For example, a TEF1 promoter linked to a nucleic acid encoding a DGA1 gene product is a heterologous promoter in the DGA1 context.

In some embodiments, the expression vector includes a coding nucleic acid, for example, a nucleic acid encoding any of the gene products described herein, operably linked to a constitutive promoter. The term "constitutive promoter" refers to a promoter that allows for continual transcription of its associated gene. In some embodiments, the expression vector includes a coding nucleic acid, for example, a nucleic acid encoding any of the gene products described herein, operably linked to an inducible promoter. The term "inducible promoter", interchangeably used herein with the term "conditional promoter", refers to a promoter that allows transcription of its associated gene only in the presence or absence of biotic or abiotic factors. Drug-inducible promoters, for example tetracycline/doxycycline inducible promoters, tamoxifen-inducible promoters, as well as promoters that depend on a recombination event in order to be active, for example the cre-mediated recombination of loxP sites, are examples of inducible promoters that are well known in the art.

Some aspects of this disclosure provide an intron-enhanced constitutive promoter for gene overexpression in oleaginous microbes and expression constructs and vectors comprising this intron-enhanced promoter. In some embodiments, an intron-enhanced TEF promoter is provided, that comprises a TEF promoter sequence, a transcription start site, an intronic sequence downstream of the transcription start site, and a coding nucleic acid sequence, for example, a nucleic acid sequence encoding any of the gene products described herein. In some embodiments, the intron is positioned downstream of the translation start site, yet within the open reading frame of the gene sequence, e.g., after the start codon, but before the termination site of the nucleic acid sequence encoding the gene product. In some embodiments, the intron is positioned immediately downstream of the translation start site, e.g., an ATG start codon, yet upstream of the remainder of the coding sequence. For illustration purposes, a non-limiting, exemplary structure of an intron-enhanced expression construct is provided as follows, using DGA1 coding sequence as the exemplary coding nucleic acid:

5'-TEF promoter-transcription start site-intron-DGA1 coding sequence-3'. Another non-limiting, exemplary structure of an intron-enhanced expression construct is provided as follows:

5'-TEF promoter-transcription start site-start codon-intron-DGA1 coding sequence-stop codon-3'. Expression constructs for ACC1 and SCD gene products would have the DGA1 coding sequence substituted for an ACC or SCD coding sequence, respectively.

Suitable TEF promoter sequences as well as suitable intron sequences will be apparent to those of skill in the art. Some intron-less TEF promoter sequences are disclosed, for example, in U.S. Pat. No. 6,265,185. Some exemplary, representative sequences are provided below. However, it will be understood that the invention is not limited in this respect.

```
Exemplary TEF promoter sequence (SEQ ID NO: 57):
AGAGACCGGGTTGGCGGCGCATTTGTGTCCCAAAAAACAGCCCCAATTGC

CCCAATTGACCCCAAATTGACCCAGTAGCGGGCCCAACCCCGGCGAGAGC

CCCCTTCTCCCCACATATCAAACCTCCCCCGGTTCCCACACTTGCCGTTA
```

```
-continued
AGGGCGTAGGGTACTGCAGTCTGGAATCTACGCTTGTTCAGACTTTGTAC

TAGTTTCTTTGTCTGGCCATCCGGGTAACCCATGCCGGACGCAAAATAGA

CTACTGAAAATTTTTTGCTTTGTGGTTGGGACTTTAGCCAAGGGTATAA

AAGACCACCGTCCCCGAATTACCTTTCCTCTTCTTTTCTCTCTCTCCTTG

TCAACTCACACCCGAAATCGTTAAGCATTTCCTTCTGAGTATAAGAATCA

TTCAAA

Exemplary intron sequence (SEQ ID NO: 58):
GTGAGTTTCAGAGGCAGCAGCAATTGCCACGGGCTTTGAGCACACGGCCG
GGTGTGGTCCCATTCCCATCGACACAAGACGCCACGTCATCCGACCAGCA
CTTTTTGCAGTACTAACCGCAG Exemplary TEF promoter-intron sequence comprising
a start codon (ATG) between the promoter and the
intron sequences (SEQ ID NO: 59):
AGAGACCGGGTTGGCGGCGCATTTGTGTCCCAAAAAACAGCCCCAATTGC

CCCAATTGACCCCAAATTGACCCAGTAGCGGGCCCAACCCCGGCGAGAGC

CCCCTTCTCCCCACATATCAAACCTCCCCCGGTTCCCACACTTGCCGTTA

AGGGCGTAGGGTACTGCAGTCTGGAATCTACGCTTGTTCAGACTTTGTAC

TAGTTTCTTTGTCTGGCCATCCGGGTAACCCATGCCGGACGCAAAATAGA

CTACTGAAAATTTTTTGCTTTGTGGTTGGGACTTTAGCCAAGGGTATAA

AAGACCACCGTCCCCGAATTACCTTTCCTCTTCTTTTCTCTCTCTCCTTG

TCAACTCACACCCGAAATCGTTAAGCATTTCCTTCTGAGTATAAGAATCA

TTCAAAATGGTGAGTTTCAGAGGCAGCAGCAATTGCCACGGGCTTTGAGC

ACACGGCCGGGTGTGGTCCCATTCCCATCGACACAAGACGCCACGTCATC

CGACCAGCACTTTTTGCAGTACTAACCGCAG
```

Methods to deliver expression vectors or expression constructs into microbes, for example, into yeast cells, are well known to those of skill in the art. Nucleic acids, including expression vectors, can be delivered to prokaryotic and eukaryotic microbes by various methods well known to those of skill in the relevant biological arts. Methods for the delivery of nucleic acids to a microbe in accordance to some aspects, include, but are not limited to, different chemical, electrochemical and biological approaches, for example, heat shock transformation, electroporation, transfection, for example liposome-mediated transfection, DEAE-Dextran-mediated transfection or calcium phosphate transfection. In some embodiments, a nucleic acid construct, for example an expression construct comprising a combination of nucleic acid sequences encoding the gene products described herein, is introduced into the host microbe using a vehicle, or vector, for transferring genetic material. Vectors for transferring genetic material to microbes are well known to those of skill in the art and include, for example, plasmids, artificial chromosomes, and viral vectors. Methods for the construction of nucleic acid constructs, including expression constructs comprising constitutive or inducible heterologous promoters, knockout and knockdown constructs, as well as methods and vectors for the delivery of a nucleic acid or nucleic acid construct to a microbe are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); Christine Guthrie and Gerald R. Fink, *Guide to Yeast Genetics and Molecular and Cell Biology, Part C, Volume* 351, Academic Press; 1st edition (Jul. 9, 2002); Gregory N. Stephanopoulos, Aristos A. Aristidou and Jens Nielsen, *Metabolic Engineering: Principles and Methodologies*, Academic Press; 1 edition (Oct. 16, 1998); and Christina Smolke, *The Metabolic Pathway Engineering Handbook: Fundamentals*, CRC Press; 1 edition (Jul. 28, 2009), all of which are incorporated by reference herein.

In some embodiments, the native promoter of a gene encoding a gene product conferring a required or desirable phenotype to a microbe, for example, the native promoter of a gene encoding a gene product described herein, is modified in the microbe to alter the regulation of its transcriptional activity. In some embodiment, the modified promoter exhibits an increased transcriptional activity as compared to its unmodified counterpart. The term "modified promoter", as used herein, refers to a promoter the nucleotide sequence of which has been artificially altered. Nucleotide deletion(s), insertion(s) or mutation(s), alone or in combination, are examples of such artificial alterations. Artificial promoter alterations can be effected in a targeted fashion, for example by homologous recombination approaches, such as gene targeting, knockout, knock in, site-directed mutagenesis, or artificial zinc finger nuclease-mediated strategies. Alternatively, such alterations may be effected by a random or quasi-random event, such as irradiation or non-targeted nucleotide integration and subsequent selection. Promoter modifications, in general, are fashioned in order to modulate the transcriptional activation properties of the respective promoter. For example, the disruption or deletion of a regulatory element mediating the repression of a promoter of a gene encoding a gene product described herein in response to elevated intracellular fatty acid levels would lead to continued transcriptional activation of the respective gene even under conditions of elevated intracellular fatty acid levels. Similarly, the insertion of a constitutively active transcriptional activator element into a conditional promoter region may effect overexpression of the respective gene under normally inhibitory conditions. Methods for the targeted disruption of a native promoter, for example, a native promoter of a gene encoding a gene product described herein, in a microbe, for example, for targeted disruption resulting in an increased transcription rate, are well known to those of skill in the art.

Some aspects relate to engineering of a microbe, such as an oleaginous yeast, for example, *Y. lipolytica*, to exhibit a required and/or desirable phenotype for large-scale production of a biofuel or biofuel precursor. Some aspects relate to the metabolic engineering of the lipid synthesis pathway in order to yield a microbe optimized for biofuel production. Some aspects relate to metabolic engineering that comprises a combination of genetic modifications modulating the expression of genes regulating carbon flux into a lipid synthesis pathway in order to yield a microbe optimized for biofuel production. In some embodiments, the modification comprises a genetic modification that increases the level of metabolites, acetyl-CoA, ATP, or NADPH for lipid synthesis in a cell. In some embodiments, the modification is a genetic modification that decreases the level of a product or intermediary of lipid synthesis that exhibits a feedback inhibitory function, for example, a fatty acid.

Some aspects provide methods to greatly increase the efficiency of *Y. lipolytica* mediated carbon source to lipid conversion by modulating *Y. lipolytica*'s native lipid metabolism. Remarkably and unexpectedly, combinations of modifications of lipid metabolism as described herein confers significantly increased lipid production, yield, etc. as compared to individual modifications.

Some aspects relate to a microbe engineered and/or optimized for large-scale biofuel or biofuel precursor production. In some embodiments, an engineered microbe is provided that has been manipulated by a method or using a nucleic acid or protein as described herein, for example, an expression construct or a combination of expression constructs as provided herein, resulting in the overexpression of a combination of a gene products The term "increased synthesis rate" or "increased rate of synthesis" as used herein in the context of microbial lipid synthesis, e.g., in the context of a fatty acid synthesis rate of an oil-producing microbe described herein, refers to a rate of synthesis in an engineered microbe that is increased as compared to the corresponding rate of synthesis in a wild-type microbe of the same species. For example, an increased rate of lipid synthesis in an engineered *Y. lipolytica* microbe described herein refers to rate of lipid synthesis that is increased as compared to the rate of lipid synthesis in a wild-type *Y. lipolytica*. In some embodiments, an increased rate of lipid synthesis, e.g., of TAG or of total lipid synthesis, refers to a rate of fatty acid synthesis of a culture of cells, e.g., of a culture of engineered microbes. In some embodiments, an increased rate of lipid synthesis is a rate of lipid synthesis, e.g., of TAG synthesis or total lipid synthesis of at least at least 0.50 g/L/h (grams of lipid per liter of culture per hour), at least 0.55 g/L/h, at least 0.60 g/L/h, at least 0.65 g/L/h, at least 0.70 g/L/h, at least 0.75 g/L/h, at least 0.80 g/L/h, at least 0.85 g/L/h, at least 0.90 g/L/h, at least 0.95 g/L/h, at least 1.0 g/L/h, at least 1.1 g/L/h, at least 1.2 g/L/h, at least 1.3 g/L/h, at least 1.4 g/L/h, at least 1.5 g/L/h, at least 1.6 g/L/h, at least 1.7 g/L/h, at least 1.8 g/L/h, at least 1.9 g/L/h, at least 2 g/L/h, at least 3 g/L/h, at least 4 g/L/h, at least 5 g/L/h, at least 6 g/L/h, at least 7 g/L/h, at least 8 g/L/h, at least 9 g/L/h, at least 10 g/L/h, at least 25 g/L/h, 0.50 g/L/h to 1.5 g/L/h, 0.60 g/L/h to 1.4 g/L/h, 0.70 g/L/h to 1.3 g/L/h, 0.75 g/L/h to 1.2 g/L/h, 0.80 g/L/h to 1.2 g/L/h, 0.90 g/L/h to 1.2 g/L/h, 1.0 g/L/h to 1.2 g/L/h, 1.0 g/L/h to 1.1 g/L/h or 1.1 g/L/h to 1.2 g/L/h.

In some embodiments, the rate of synthesis in this context is the rate of synthesis measured over a complete run of a bioreactor, e.g., calculating the rate of synthesis from the total amount of lipid, e.g., TAG, synthesized over the total time that the bioreactor was run or the total time lipid production was measured over. This type of synthesis rate is also referred to herein sometimes as "lipid productivity," "total lipid productivity" or "overall lipid productivity," and it is typically provided in g/L/h (grams of lipid produced per liter of culture medium per run time in hours). In some embodiments, an engineered microbe is provided, as described herein that exhibits lipid productivity of at least 0.50 g/L/h (grams of lipid per liter of culture per hour), at least 0.55 g/L/h, at least 0.60 g/L/h, at least 0.65 g/L/h, at least 0.70 g/L/h, at least 0.75 g/L/h, at least 0.80 g/L/h, at least 0.85 g/L/h, at least 0.90 g/L/h, at least 0.95 g/L/h, at least 1.0 g/L/h, at least 1.1 g/L/h, at least 1.2 g/L/h, at least 1.3 g/L/h, at least 1.4 g/L/h, at least 1.5 g/L/h, at least 1.6 g/L/h, at least 1.7 g/L/h, at least 1.8 g/L/h, at least 1.9 g/L/h, at least 2 g/L/h, at least 3 g/L/h, at least 4 g/L/h, at least 5 g/L/h, at least 6 g/L/h, at least 7 g/L/h, at least 8 g/L/h, at least 9 g/L/h, at least 10 g/L/h, at least 25 g/L/h, 0.50 g/L/h to 1.5 g/L/h, 0.60 g/L/h to 1.4 g/L/h, 0.70 g/L/h to 1.3 g/L/h, 0.75 g/L/h to 1.2 g/L/h, 0.80 g/L/h to 1.2 g/L/h, 0.90 g/L/h to 1.2 g/L/h, 1.0 g/L/h to 1.2 g/L/h, 1.0 g/L/h to 1.1 g/L/h, or 1.1 g/L/h to 1.2 g/L/h. In some embodiments, an engineered microbe is provided, as described herein that exhibits at least a 5-fold increase, at least a 6-fold increase, at least a 7-fold increase, at least an 8-fold increase, at least a 9-fold increase, at least a 10-fold increase, at least a 12-fold increase, at least a 10-fold increase, at least a 12.5-fold increase, at least a 15-fold increase, at least a 20-fold increase, at least a 30-fold increase, at least a 40-fold increase, at least a 50-fold increase, at least a 60-fold increase, at least a 70-fold increase, at least an 80-fold increase, at least a 90-fold increase, at least a 100-fold increase, at least a 500-fold increase, or at least a 1000-fold increase in total lipid productivity as compared to a wild-type microbe, e.g., a wild-type *Y. lipolytica*, or *Y. lipolytica* overexpressing ACC and DGA (see PCT/US2012/061101).

In some embodiments, an increased rate of total lipid synthesis or an increased total lipid productivity is at least 0.01 g/L/h, at least 0.04 g/L/h, at least 0.05 g/L/h, at least 0.1 g/L/h, at least 0.14 g/L/h, at least 0.15 g/L/h, at least 0.2 g/L/h, at least 0.3 g/L/h, at least 0.4 g/L/h, at least 0.5 g/L/h, at least 0.6 g/L/h, at least 0.7 g/L/h, at least 0.8 g/L/h, at least 0.9 g/L/h, at least 1 g/L/h, at least 2 g/L/h, at least 3 g/L/h, at least 4 g/L/h, or at least 5 g/L/h as compared to a wild-type microbe, e.g., a wild-type *Y. lipolytica*.

In some embodiments, the rate of synthesis is the maximum rate of synthesis, or the peak rate of synthesis, measured, e.g., under optimal growth conditions and exposure to nutrients. This type of synthesis rate is also referred to herein sometimes as "maximum lipid productivity". In some embodiments, an increased maximum rate of lipid synthesis is a rate of lipid synthesis, e.g., of TAG synthesis, of at least 0.50 g/L/h, at least 0.55 g/L/h, at least 0.60 g/L/h, at least 0.65 g/L/h, at least 0.70 g/L/h, at least 0.75 g/L/h, at least 0.80 g/L/h, at least 0.85 g/L/h, at least 0.90 g/L/h, at least 0.95 g/L/h, at least 1.0 g/L/h, at least 1.1 g/L/h, at least 1.2 g/L/h, at least 1.3 g/L/h, at least 1.4 g/L/h, at least 1.5 g/L/h, at least 1.6 g/L/h, at least 1.7 g/L/h, at least 1.8 g/L/h, at least 1.9 g/L/h, at least 2 g/L/h, at least 3 g/L/h, at least 4 g/L/h, at least 5 g/L/h, at least 6 g/L/h, at least 7 g/L/h, at least 8 g/L/h, at least 9 g/L/h, at least 10 g/L/h, at least 25 g/L/h 0.50 g/L/h to 1.5 g/L/h, 0.60 g/L/h to 1.4 g/L/h, 0.70 g/L/h to 1.3 g/L/h, 0.75 g/L/h to 1.2 g/L/h, 0.80 g/L/h to 1.2 g/L/h, 0.90 g/L/h to 1.2 g/L/h, 1.0 g/L/h to 1.2 g/L/h, 1.0 g/L/h to 1.1 g/L/h, or 1.1 g/L/h to 1.2 g/L/h.

In some embodiments, the engineered microbe is an oleaginous yeast, for example, *Y. lipolytica*. In some embodiments, an engineered yeast provided by this invention exhibits one or more highly desirable and unexpected phenotypic characteristics, for example: increased carbon to oil conversion rate or efficiency, increased lipid accumulation in a lipid body.

In some embodiments, an engineered microbe, for example, an engineered yeast, provided herein exhibits a carbon to oil conversion rate, also referred to herein as "lipid yield," within the range of about 0.02 g/g (g oil, lipid, fatty acid methyl esters or TAG produced/g carbon, e.g., glucose, acetate, or acetic acid consumed) to about 0.3 g/g. In some embodiments, the engineered microbe, for example, the engineered yeast, provided by aspects of this invention exhibits a carbon to oil conversion rate of about 0.01 g/g, about 0.02 g/g, about 0.03 g/g, about 0.04 g/g, about 0.05 g/g, about 0.06 g/g, about 0.07 g/g, about 0.08 g/g, about 0.09 g/g, about 0.10 g/g, about 0.11 g/g, about 0.12 g/g, about 0.13 g/g, about 0.14 g/g, about 0.15 g/g, about 0.16 g/g, about 0.17 g/g, about 0.18 g/g, about 0.19 g/g, about 0.20 g/g, about 0.21 g/g, about 0.22 g/g, about 0.23 g/g, about 0.24 g/g, about 0.25 g/g, about 0.26 g/g, about 0.27 g/g, about 0.28 g/g, about 0.29 g/g, about 0.30 g/g, about 0.31 g/g, about 0.32 g/g, or approaching theoretical values. In some embodiments, the engineered microbe, for example, the engineered yeast, provided by aspects of this invention exhibits a carbon to oil conversion rate of 0.20 g/g to 0.32 g/g, 0.21 g/g to 0.31 g/g, 0.25 g/g to 0.30 g/g, 0.25 g/g to 0.29 g/g, 0.25 g/g to 0.28 g/g, or 0.25 g/g to 0.274 g/g.

The term "lipid titer" as used herein in the context of microbial lipid synthesis, e.g., in the context of a fatty acid synthesis by an oil-producing microbe described herein, refers to an amount of lipid synthesized per volume of a microbial culture comprising the oil-producing microbe. In some embodiments, an engineered microbe, e.g., an engineered Y. lipolytica microbe described herein, can achieve or does achieve a lipid titer of at least 10 g/L (grams of lipid per liter of microbial culture), at least 15 g/L, at least 20 g/L, at least 25 g/L, at least 30 g/L, at least 35 g/L, at least 40 g/L, at least 45 g/L, at least 50 g/L, at least 55 g/L, at least 60 g/L, at least 65 g/L, at least 70 g/L, at least 75 g/L, at least 80 g/L, at least 85 g/L, at least 90 g/L, at least 91 g/L, at least 92 g/L, at least 93 g/L, at least 94 g/L, at least 95 g/L, at least 96 g/L, at least 97 g/L, at least 98 g/L, at least 99 g/L, at least 100 g/L, at least 101 g/L, at least 102 g/L, at least 103 g/L, at least 104 g/L, at least 105 g/L, at least 106 g/L, at least 107 g/L, at least 108 g/L, at least 109 g/L, at least 110 g/L, at least 120 g/L, at least 130 g/L, at least 140 g/L, at least 150 g/L, at least 160 g/L, at least 170 g/L, at least 180 g/L, at least 190 g/L, at least 200 g/L, or at least 250 g/L. In some embodiments, the lipid titer is 40 g/L to 110 g/L, 50 g/L to 105 g/L, 50 g/L to 100 g/L, 50 g/L to 99 g/L, 60 g/L to 99 g/L, 70 g/L to 99 g/L, 80 g/L to 99 g/L, 90 g/L to 99 g/L, or 95 g/L to 99 g/L In some embodiments, an engineered microbe as provided herein exhibits an increased lipid titer during carbon to oil conversion. The term "increased lipid titer" as used herein in the context of microbial lipid synthesis, e.g., in the context of a fatty acid synthesis by an oil-producing microbe described herein, refers to an amount of lipid synthesized per volume of a microbial culture comprising the oil-producing microbe that is increased as compared to the corresponding lipid titer of a wild-type microbe of the same species and under the same conditions (e.g., in the same growth medium, with the same C/N ratio, the same amount of oxygen, the same pH, the same nutrients, and so forth). For example, an increased lipid titer achieved by an engineered Y. lipolytica microbe described herein refers to a lipid titer that is increased as compared to the lipid titer that can be achieved by a wild-type Y. lipolytica under identical conditions. In some embodiments, an increased lipid titer refers to a lipid titer of at least 1 g/L (grams of lipid per liter of microbial culture), at least 2 g/L, at least 3 g/L, at least 4 g/L, at least 5 g/L, at least 6 g/L, at least 7 g/L, at least 8 g/L, at least 9 g/L, at least 10 g/L, at least 11 g/L, at least 12 g/L, at least 13 g/L, at least 14 g/L, at least 15 g/L, at least 20 g/L, at least 25 g/L, at least 30 g/L, at least 40 g/L, at least 50 g/L, at least 60 g/L, at least 70 g/L, at least 80 g/L, at least 90 g/L, at least 100 g/L, at least 200 g/L, or at least 250 g/L. In some embodiments, an increased lipid titer is 1 g/L to 100 g/L, 2 g/L to 100 g/L, 5 g/L to 100 g/L, 5 g/L to 95 g/L, 5 g/L to 90 g/L, 5 g/L to 80 g/L, 5 g/L to 70 g/L, 5 g/L to 0 g/L, 5 g/L to 50 g/L, 10 g/L to 100 g/L, 10 g/L to 90 g/L, 10 g/L to 80 g/L, 10 g/L to 70 g/L, 10 g/L to 60 g/L, or 10 g/L to 50 g/L.

Some aspects provide engineered microbes for oil production that can use a variety of carbon sources, including, but not limited to fermentable sugars, for example, C6 sugars, such as glucose, and organic acids, e.g., acetic acid, and/or their salts, e.g., acetate.

Some aspects relate to cultures of genetically modified microbes provided herein. In some embodiments, the culture comprises a genetically modified microbe provided herein and a medium, for example, a liquid medium. In some embodiments, the culture comprises a genetically modified microbe provided herein and a carbon source, for example, a fermentable carbohydrate source, or an organic acid or salt thereof. In some embodiments, the culture comprises a genetically modified microbe provided herein and a salt and/or buffer establishing conditions of salinity, osmolarity, dissolved oxygen ($dO_2$), and pH, that are amenable to survival, growth, and/or carbohydrate to biofuel or biofuel precursor conversion by the microbe. In some embodiments, the culture comprises an additional component, for example, an additive. Non-limiting examples of additives are nutrients, enzymes, amino acids, albumin, growth factors, enzyme inhibitors (for example protease inhibitors), fatty acids, lipids, hormones (e.g., dexamethasone and gibberellic acid), trace elements, inorganic compounds (e.g., reducing agents, such as manganese), redox-regulators (e.g., antioxidants), stabilizing agents (e.g., dimethylsulfoxide), polyethylene glycol, polyvinylpyrrolidone (PVP), gelatin, antibiotics (e.g., Brefeldin A), salts (e.g., NaCl), chelating agents (e.g., EDTA, EGTA), and enzymes (e.g., cellulase, dispase, hyaluronidase, or DNase). In some embodiments, the culture may comprise a drug inducing or inhibiting transcription from a conditional or inducible promoter, for example doxicycline, tetracycline, tamoxifen, IPTG, hormones, or metal ions.

While the specific culture conditions, for example, the concentration of the carbon source, will depend upon the respective engineered microorganism to be cultured, general methods and culture conditions for the generation of microbial cultures are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); and Christine Guthrie and Gerald R. Fink, *Guide to Yeast Genetics and Molecular and Cell Biology, Part C, Volume* 351, Academic Press; 1st edition (Jul. 9, 2002), all of which are incorporated by reference herein. For oil production, the cultures of engineered microbes described herein are cultured under conditions suitable for oil accumulation, as known in the art.

In some embodiments, the genetically modified microbe exhibits a growth advantage over wild type microbes of the same kind and/or over other microbes, for example, microbes commonly found to contaminate microbial cultures for carbon source to biofuel or biofuel precursor conversion. In some embodiments, the growth and/or proliferation advantage of an engineered microbe provided by aspects of this invention translates into the possibility of using non-sterile culturing and fermentation conditions for biofuel or biofuel precursor production, because the problem of culture overgrowth by contaminating microbes is mitigated or completely abolished. In some embodiments, an engineered microbe provided by aspects of this invention is cultured under non-sterile conditions for biofuel or biofuel precursor production. For example, in some embodiments, non-sterilized feedstock, non-sterilized culture media, non-sterilized supplements, or a non-sterilized bioreactor (e.g. an open reactor under non-sterile conditions) is used for biofuel or biofuel precursor production. A variety of different microbes can be genetically modified according to some aspects and used for industrial-scale biofuel or biofuel precursor production, for example, microbes from various sources of yeast, such as oleaginous yeast, bacteria, algae and fungi. Non-limiting examples of suitable yeast cells are cells from *Yarrowia lipolytica, Hansenula polymorpha, Pichia pastoris, Saccharomyces cerevisiae, S. bayanus, S. K. lactis, Waltomyces lipofer, Mortierella alpine, Mortierella isabellina, Hansenula polymorpha, Mucor rouxii, Trichosporon cutaneu, Rhodotorula glutinis Saccharomyces diastasicus, Schwanniomyces occidentalis, S. cerevisiae, Pichia stipitis*, and *Schizosaccharomyces pombe*. Non-limiting examples of suitable bacteria are *Bacillus subtilis, Salmonella, Escherichia coli, Vibrio cholerae, Streptomyces, Pseudomonas fluorescens, Pseudomonas putida, Pseudomonas* sp, *Rhodococcus* sp, *Streptomyces* sp, and *Alcaligenes* sp. Non-limiting examples of suitable fungal cells can, for example, be cultured from species such as *Aspergillus shirousamii, Aspergillus niger* and *Trichoderma reesei*. Non-limiting examples of suitable algal cells are cells from *Neochloris oleoabundans, Scenedesmus obliquus, Nannochloropsis* sp., *Dunaliella tertiolecta, Chlorella vulgaris, Chlorella emersonii*, and *Spirulina maxima*.

Some aspects provide methods for the production of biofuel or biofuel precursors using genetically modified microbes provided herein. In some embodiments, methods for biofuel or biofuel precursor production on an industrial scale are provided.

A variety of carbon sources can be converted into a biofuel or biofuel precursor using a method and/or a genetically modified microbe provided herein. In some embodiments, the carbon source comprises a carbohydrate. Sugars, starches, and fibers are non-limiting examples of carbohydrate sources suitable for conversion methods provided herein. According to some aspects, a carbohydrate source may comprise a refined and/or unrefined sugar, starch, and/or fiber, or a combination of any of these. Non-limiting examples of sugars are fermentable sugars, such as glucose, fructose, sucrose, xylose, and lactose. Non-limiting examples of starches are amylase and amylopectin. Non-limiting examples of fibers are plant fibers, such as cellulose, hemicellulose and wood fibers. Some aspects relate to the use of industrial byproducts, intermediates, or waste products, for example raw plant extracts, molasses, stover, or sewage as a carbon source. In some embodiments, the carbon source is derived from algae. In some embodiments, algal biomass is produced specifically for use as a carbon source in microbe-mediated biofuel or biofuel precursor production.

In some embodiments, methods for the production of biofuel or biofuel precursor are provided that include the use of a cheap, abundant, and readily available carbon source feedstock as the carbon source. In some embodiments, cellulose or hemicellulose is used as the carbon source. In some embodiments, the cellulose or hemicellulose is derived from industrial by- or waste products. In some embodiments, the cellulose or hemicellulose is derived directly from plant or algal biomass. Plant or algal biomass is one of the most abundant feedstocks and comprises a significant amount of non-fermentable sugars and fibers, for example, cellulose and hemi-cellulose. In some embodiments, biomass feedstock is pretreated to convert a non-fermentable sugar or fiber into a fermentable sugar, thus making them available for microbe growth and microbe-mediated biofuel or biofuel precursor production. In some embodiments, the pretreatment of biomass feedstock includes depolymerizing cellulose and/or hemicellulose components to monomeric sugars using a pretreatment method known to those of skill in the art, for example, a dilute acid or ammonia fiber expansion (AFEX) method (see, e.g., Yang B, Wyman C E. *Dilute acid and autohydrolysis pretreatment*. Methods Mol Biol. 2009; 581:103-14; Balan V, Bals B, Chundawat S P, Marshall D, Dale B E, *Lignocellulosic biomass pretreatment using AFEX Methods* Mol Biol. 2009; 581:61-77). Other methods for depolymerization of biomass polymers to monomeric sugars are well known to those of skill in the art and are contemplated to be used in some embodiments of this invention.

In some embodiments, a biomass feedstock containing non-fermentable sugars is pretreated using a dilute acid method to depolymerize a non-fermentable sugar to a monomeric, fermentable sugar. In some embodiments, biomass is treated with dilute sulphuric acid at moderately mild temperatures for a defined period of time. For example, in some embodiments, the biomass is treated with about 0.5%, about 1%, about 2%, about 3%, about 4%, about 5%, or about 6% sulphuric acid. In some embodiments, the biomass is treated at about 30° C., at about 37° C., at about 40° C., at about 50° C., at about 60° C., at about 70° C., at about 80° C., at about 90° C., at about 100° C., at about 110° C., at about 120° C., at about 130° C., at about 140° C., at about 150° C., at about 175° C., at about 200° C., or at above about 200° C.

In some embodiments, the resulting hydrolysate contains insoluble lignin and solubilized cellulosic and hemicellulosic polymers. The latter products can be further treated to generate hexose and pentose sugars such as glucose and xylose monomers by methods well known to those of skill in the art, for example, by treatment with cellulase or other hydrolyzing enzymes. In some embodiments, the pretreatment of non-fermentable sugars with dilute acid results in the generation of by-products that include toxic compounds which inhibit growth, decrease viability, and/or inhibit biofuel or biofuel precursor production of microbes not engineered according to aspects of this invention. In some embodiments, the pre-treated feedstock is washed, supplemented with media supporting microbial growth and biofuel or biofuel precursor production, and/or over-limed for detoxification.

In some embodiments, a biomass feedstock containing non-fermentable sugars is pretreated using an AFEX method to depolymerize a non-fermentable sugar to a monomeric, fermentable sugar. In some embodiments, biomass is treated with liquid ammonia at high temperature and pressure for a defined period of time. In some embodiments, biomass is treated for about 10 minutes, about 20 minutes, about 30 minutes, about 40 minutes, about 50 minutes, about 60 minutes, about 70 minutes, about 80 minutes, about 90 minutes, or longer. In some embodiments, biomass is treated at about 30° C., at about 37° C., at about 40° C., at about 50° C., at about 60° C., at about 70° C., at about 80° C., at about 90° C., at about 100° C., at about 110° C., at about 120° C., at about 130° C., at about 140° C., at about 150° C., at about 175° C., at about 200° C., or at above about 200° C. In some embodiments, the AFEX pretreatment results in the conversion of crystalline cellulose contained in the feedstock into an amorphous, fermentable form. In some embodiments, the AFEX pre-treated biomass feedstock does not contain significant amounts of toxic byproducts that inhibit microbial growth and/or biofuel or biofuel precursor production, and is used without prior detoxification for microbial biofuel or biofuel precursor production.

In some embodiments, biomass feedstock, with or without pre-treatment, is treated with an enzyme that hydrolyzes or depolymerizes sugar polymers, for example, with a cellulase or hemicellulase enzyme. In some embodiments, the feedstock is contacted with the enzyme in a liquid phase and incubated at a temperature allowing for the enzyme to catalyze a depolymerization or hydrolyzation reaction for a time sufficient to hydrolyze or depolymerize a significant amount of the non-fermentable sugar or fiber in the biomass feedstock. In some embodiments, the liquid phase of the feedstock contacted with the enzyme, which contains the soluble, fermentable sugar fraction, is separated from the solid phase, including non-fermentable sugars and fibers, after incubation for hydrolyzation and depolymerization, for example, by centrifugation. In some embodiments, the liquid fraction of the feedstock is subsequently contacted with a microbe, for example, a microbe provided by aspects of this invention, for conversion to biofuel or biofuel precursor. In some embodiments, enzymatic conversion of non-fermentable sugars or fiber occurs in a consolidated bioprocess, for example, at the same time and/or in the same reactor as microbial conversion of the produced fermentable sugars to biofuel or biofuel precursor. In some embodiments, the enzymatic conversion is performed first, and the feedstock contacted with enzyme is subsequently contacted with the microbe for biofuel or biofuel precursor production. In some embodiments, enzymatic and microbial conversion are performed at the same time and in the same reactor.

In some embodiments, an engineered microbe as provided herein is grown on a carbon source that is replenished during the growth process or culture period, e.g., by contacting the microbe or culture thereof with an additional amount of the carbon source, or with an amount of an additional carbon source, after a period of time in culture, e.g., after 8 hours, after 24 hours, or after 48 hours. In some embodiments, the carbon source or the additional carbon source is added by step-wise exponential addition as is described in more detail elsewhere herein.

In some embodiments, an engineered microbe as provided herein is grown initially, e.g., for the first 6, 12, 18, 24, 30, 36, 42, 48, 54, 60, 66, or 72 hours in a culture medium that comprises a low carbon to nitrogen (C/N) ratio, e.g., a C/N ratio of about 10, of about 20, of about 25, of about 30, of less than 30, of less than 25, or of less than 20. In some embodiments, a low C/N ratio is achieved by supplementing the culture media with a nitrogen source, e.g., with ammonia, to achieve the desired C/N ratio. In some embodiments, e.g., in embodiments, where carbon source is fed into a culture of lipid-producing microbes as described herein, the carbon source is supplemented with a nitrogen source, e.g., ammonia, such as ammonium sulfate. In some embodiments, the supplementation with a nitrogen source is ceased after an initial period of time in culture, e.g., after for the first 6, 12, 18, 24, 30, 36, 42, 48, 54, 60, 66, or 72 hours in culture, thus allowing the engineered microbes in culture to consume the nitrogen source, which, in turn, results in an increase of the C/N ratio. This shift in C/N ratio can be enhanced or sped up by feeding additional carbon source into the culture that is not supplemented with a nitrogen source. In some embodiments, the optimal C/N ratio for oil production by an engineered microbe described herein is within the range of 80-120, such as 80, 805, 90, 905, 100, 105, 110, 115, or 120.

In some embodiments, fermentation processes for large-scale microbe-mediated carbohydrate to lipid conversion may be carried out in bioreactors. As used herein, the terms "bioreactor" and "fermentor", which are interchangeably used, refer to an enclosure, or partial enclosure, in which a biological and/or chemical reaction takes place, at least part of which involves a living organism or part of a living organism. A "large-scale bioreactor" or "industrial-scale bioreactor" is a bioreactor that is used to generate a product, for example a biofuel or biofuel precursor, for example a lipid, fatty acid and/or TAG, on a commercial or quasi-commercial scale. Large scale bioreactors typically have volumes in the range of liters, hundreds of liters, thousands of liters, or more.

A bioreactor in accordance with aspects of this invention may comprise a microbe or a microbe culture. In some embodiments, a bioreactor may comprise a spore and/or any kind of dormant cell type of any isolated microbe provided by aspects of this invention, for example, in a dry state. In some embodiments, addition of a suitable carbohydrate source to such bioreactors may lead to activation of the dormant cell, for example to germination of a yeast spore, and subsequent conversion of the carbohydrate source, at least in part, to a biofuel or biofuel precursor.

Some bioreactors according to aspects of this invention may include cell culture systems where microbes are in contact with moving liquids and/or gas bubbles. Microbes or microbe cultures in accordance with aspects of this invention may be grown in suspension or attached to solid phase carriers. Non-limiting examples of carrier systems include microcarriers (e.g., polymer spheres, microbeads, and microdisks that can be porous or nonporous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, encapsulation cells, capillaries, and aggregates. Carriers can be fabricated from materials such as dextran, gelatin, glass, and cellulose.

Industrial-scale carbohydrate to lipid conversion processes in accordance with aspects of this invention may be operated in continuous, semi-continuous or non-continuous modes. Non-limiting examples of operation modes in accordance with this invention are batch, fed batch, extended batch, repetitive batch, draw/fill, rotating-wall, spinning flask, and/or perfusion mode of operation.

In some embodiments, bioreactors may be used that allow continuous or semi-continuous replenishment of the substrate stock, for example a carbohydrate source and/or continuous or semi-continuous separation of the product, for example a secreted lipid, an organic phase comprising a lipid, and/or cells exhibiting a desired lipid content, from the reactor.

Non-limiting examples of bioreactors in accordance with this invention are: stirred tank fermentors, bioreactors agitated by rotating mixing devices, chemostats, bioreactors agitated by shaking devices, airlift fermentors, packed-bed reactors, fixed-bed reactors, fluidized bed bioreactors, bioreactors employing wave induced agitation, centrifugal bioreactors, roller bottles, and hollow fiber bioreactors, roller apparatuses (for example benchtop, cart-mounted, and/or automated varieties), vertically-stacked plates, spinner flasks, stirring or rocking flasks, shaken multiwell plates, MD bottles, T-flasks, Roux bottles, multiple-surface tissue culture propagators, modified fermentors, and coated beads (e.g., beads coated with serum proteins, nitrocellulose, or carboxymethyl cellulose to prevent cell attachment).

Bioreactors and fermentors according to aspects of this invention may, optionally, comprise a sensor and/or a control system to measure and/or adjust reaction parameters. Non-limiting examples of reaction parameters are: biological parameters, for example growth rate, cell size, cell number, cell density, cell type, or cell state, chemical parameters, for example pH, redox-potential, concentration of reaction substrate and/or product, concentration of dissolved gases, such as oxygen concentration and $CO_2$ concentration, nutrient concentrations, metabolite concentrations, glucose concentration, glutamine concentration, pyruvate concentration, apatite concentration, concentration of an oligopeptide, concentration of an amino acid, concentration of a vitamin, concentration of a hormone, concentration of an additive, serum concentration, ionic strength, concentration of an ion, relative humidity, molarity, osmolarity, concentration of other chemicals, for example buffering agents, adjuvants, or reaction by-products, physical/mechanical parameters, for example density, conductivity, degree of agitation, pressure, and flow rate, shear stress, shear rate, viscosity, color, turbidity, light absorption, mixing rate, conversion rate, as well as thermodynamic parameters, such as temperature, light intensity/quality etc.

Sensors able to measure parameters as described herein are well known to those of skill in the relevant mechanical and electronic arts. Control systems able to adjust the parameters in a bioreactor based on the inputs from a sensor as described herein are well known to those of skill in the art of bioreactor engineering.

The type of carbon source to be employed for conversion to a biofuel or biofuel precursor according to aspects of this invention depends on the specific microbe employed. Some microbes provided by aspects of this invention may be able to efficiently convert a specific carbohydrate source, while a different carbohydrate source may not be processed by the same microbe at high efficiency or at all. According to certain aspects, the oleaginous yeast *Y. lipolytica*, for example, can efficiently convert sugars, such as glucose, fructose, sucrose, and/or lactose, and carbohydrate sources high in sugars, for example molasses, and plant fibers into fatty acids and their derivatives.

In some embodiments, a biofuel or biofuel precursor, for example, a lipid, a fatty acid or a triacylglycerol, generated from a carbon source feedstock is secreted, at least partially, by a microbe provided by aspects of this invention, for example, an oleaginous yeast, such as a *Y. lipolytica* cell. In some embodiments, a microbe provided as described herein is contacted with a carbohydrate source in an aqueous solution in a bioreactor, and secreted biofuel or biofuel precursor forms an organic phase that can be separated from the aqueous phase. The term organic phase, as used herein, refers to a liquid phase comprising a non-polar, organic compound, for example a fatty acid, TAG, and/or other non-polar lipid. And organic phase in accordance to this invention might further contain a microbe, a carbohydrate, or other compound found in other phases found in a respective bioreactor. Methods useful for industrial scale phase separation are well known to those of ordinary skill in the art. In some embodiments, the organic phase is continuously or semi-continuously siphoned off. In some embodiments, a bioreactor is employed, comprising a separator, which continuously or semi-continuously extracts the organic phase.

In some embodiments, a biofuel or biofuel precursor is accumulated in cells according to aspects of this invention. In some embodiments, cells that have accumulated a desirable amount of biofuel or biofuel precursor, are separated continuously or semi-continuously from a bioreactor, for example, by centrifugation, sedimentation, or filtration. Cell separation can further be effected, for example, based on a change in physical cell characteristics, such as cell size or density, by methods well known to those skilled in the art. The accumulated biofuel or biofuel precursor can subsequently be extracted from the respective cells using standard methods of extraction well known to those skilled in the art, for example, solvent hexane extraction. In some embodiments, microbial cells are collected and extracted with 3 times the collected cell volume of hexane. In some embodiments, the extracted biofuel or biofuel precursor are further refined. In some embodiments, a biofuel precursor, for example a triacylglycerol is converted to a biofuel, for example, biodiesel, using a method well known to those of skill in the art, for example, a transesterification procedure.

The function and advantage of these and other embodiments will be more fully understood from the examples below. The following examples are intended to illustrate the benefits of the present invention, but do not exemplify the full scope of the invention. Accordingly, it will be understood that the example section is not meant to limit the scope of the invention.

EXAMPLES

Example 1

Rewiring Metabolism for Maximum Lipid Production in *Yarrowia lipolytica*

Lipids, in particular fatty acids derived lipids, play a significant role in modern industries as feedstock for fuel and oleo-chemicals. With the pressing need to mitigate concerns over the depletion of fossil fuels, climate change and energy security, fatty acid derived lipids are extensively explored as renewable resources for production of biodiesel. Biodiesel is considered a superior gasoline alternative given its high energy density, thermal efficiency, and compatibility with current engines and fuel infrastructure[1]. At present, biodiesel is primarily produced from plant oil and animal fats[2]. However, availability and productivity of crop oils is rather limited, and use of edible oils for biodiesel production considerably conflicts with foods supply[3]. On the other hand, carbohydrates, including starches, cellulosic and hemicellulosic biomass, represent the most abundant sustainable feedstock that can be harnessed to develop second-generation biofuel. Encouraged by the success of production of alcohols by microbial fermentations, microbial conversion of carbohydrates to lipids has emerged as favorable option to harness carbohydrates for biodiesel production[4]. Consequently, over the past two decades, extensive efforts have been made to engineer industrially-relevant microorganisms including *Escherichia coli*[5,6], *Saccharomyces cerevisiae*[7], microalgae[8] and cyanobacteria[9] for productions of fatty acids and fatty acids derived chemicals.

Of all the microorganisms, oleaginous yeasts are of particular interest due to their naturally high storage capability of neutral lipids (primarily triacylglycerides, content 20%-70%), fast growth rate (doubling time 2-4 hours) and lipid production rate, capability of assimilating a variety of substrates and amenability to genetic modifications[3]. In particular, *Yarrowia lipolytica*, the model oleaginous yeast, has been extensively studied and metabolically engineered in the past decades[10-12]. The fatty acid production in *Y. lipolytica* was greatly improved by increasing the carbon lipogenic pathway flux[13], shutting down the degradation pathways including lipolysis[14] and β-oxidations[15], and removal of negative regulation from transcriptional factors[16] or toxic intermediates[17]. Despite these tremendous advancements, the commercialization of microbial oils is still restricted to high-value commodity chemicals[3,18,19] Techno-economic analysis has shown that for biodiesel production the cost of substrates frequently accounts for two thirds of the total cost[20]. Therefore, the conversion yield of carbohydrates to lipids is the key to realizing an economically viable process for biodiesel production.

Although improvement of process yield is clearly associated with elevation of titer or lipid content, to our knowledge, the fundamental limits of the process yield in a given biochemical conversion and the key parameters affecting process yield are still unclear. To address these issues, here we reported the development of a mathematical model that establishes a quantitative relationship between process yield and three key parameters—non-lipid biomass yield, lipid content, and yield of lipid synthesis pathway $Y_L$. Importantly, in silico analysis of the model allows us to identify $Y_L$ as the key driver of process yield maximization. To experimentally verify the theoretical conclusion, we rationally designed and engineered *Y. lipolytica* metabolism for a higher $Y_L$. This is achieved by the introduction of synthetic pathways that are capable of substituting cytosolic NADH with NADPH, which can be directly used to support de novo fatty acid synthesis. In total, thirteen strains were evaluated in shake flask and bioreactor experiments to identify the best strain that achieved a titer of 99 g/L with a productivity of 1.3 g/L/h and an overall process yield 0.274 g FAME/g glucose. Our study presented here will serve as the basis for cost-effective bioconversion of carbohydrates to biodiesel.

Materials and Methods

Constructions of Plasmids and *Y. lipolytica* Strains

All the plasmids constructed in this study were validated via DNA sequencing and are summarized in Table 1.

TABLE 1

Plasmids and strains used in the study

| Strains (host strain) | Genotype or plasmid characteristics | Origin |
|---|---|---|
| *E. coli* | | |
| DH5α | fhuA2 Δ(argF-lacZ) U169 phoA glnV44 Φ80 Δ(lacZ)M15 gyrA96 recA1 relA1 endA1 thi-1 hsdR17 | Invitrogen |
| Plasmid | | |
| YLEX | pINA1269-LEU | Yeastern[4] |
| pMT15 | YLEX derivative replacing hp4d promoter with TEF intron promoter | [5] |
| pMT91 | pACYC derivative with URA3 marker targeting ylLip2 region | [6] |
| pQK7 | pMT15 derivative replacing LEU2 with hygromycin resistance marker | |
| pQkj1 | pUC19 derivative containing markerless URA3 knock-out cassette | This work |
| pQkj2 | pMT91 derivative with TEF intron promoter and XPR2 terminator inserted upstream of URA3 marker | This work |

TABLE 1-continued

Plasmids and strains used in the study

| Strains (host strain) | Genotype or plasmid characteristics | Origin |
|---|---|---|
| pQkj3 | pQkj2 derivative expressing *E. coli* soluble pyridine nucleotide transhydrogenase UdhA | This work |
| pKJ1 | pUC19 derivative with *Y. lipolytica* GPD promoter and LIP1 terminator | This work |
| pKJ2 | pKJ1 derivative expressing *E. coli* membrane-bound pyridine nucleotide transhydrogenase PntA | This work |
| pQkj4 | pQkj2 derivative expressing *E. coli* pyridine nucleotide PntB and PntA (cloned from pKJ2) | This work |
| pQkj5 | pQkj2 derviative expressing *C. acetobutylicum* GAP dehydrogenase GapC | This work |
| pQkj6 | pQkj2 derivative expressing *K. lactis* GAP dehydrogenase GPD1 | This work |
| pQkj7 | pQkj2 derivative expressing *M. circinelloides* malic enzyme MCE2 | This work |
| pKJ3 | pKJ1 derivative expressing synthetic *C. kluyveri* phosphotransacetylase PTA | This work |
| pQkj8 | pQkj2 derivative expressing synthetic *L. mesenteroides* phosphoketolase PK and PTA (cloned from pKJ3) | This work |
| pQkj9 | pQK7 derivative expressing *C. acetobutylicum* GAP dehydrogenase GapC | This work |
| pQkj10 | pQkj2 derivative expressing *Y. lipolytica* NAD⁺ kinase YEF | This work |
| pQkj11 | pQkj2 derivative expressing *Y. lipolytica* NAD⁺/NADH kinase POS5 | This work |
| pQkj12 | pQkj2 derivative expressing *Y. lipolytica* NAD⁺ kinase UTR1 | This work |
| pKJ4 | pKJ1 derivative expressing *C. acetobutylicum* GAP dehydrogenase GapC | This work |
| pQkj13 | pQkj2 derivative expressing *Y. lipolytica* NAD⁺ kinase YEF and *C. acetobutylicum* GAP dehydrogenase GapC (cloned from pKJ4) | This work |
| pQkj14 | pQkj2 derivative expressing *M. circinelloides* malic enzyme MCE2 and *C. acetobutylicum* GAP dehydrogenase GapC (cloned from pKJ4) | This work |
| *Y. lipolytica* | | |
| po1g | MATa, leu2-270, ura3-302::URA3, xpr2-3 | Yeastern |
| YL-wt | Po1g, ylex (LEU2) | [6] |
| MTYL065 | Po1g, pMT065 (LEU2, h4pd-ACC1, TEFin-DGA1) | [4] |
| ADΔura3 | MTYL065, ΔURA3 | This work |
| AD[a] | ADΔura3, pQkj2 (URA3, TEFin-XPR2t) | This work |
| ADudhA | ADΔura3, pQkj3 (URA3, TEFin-UdhA-XPR2t) | This work |
| ADpntAB | ADΔura3, pQkj4 (URA3, TEFin-PntA-XPR2t, GPDp-PntB-LIP1t) | This work |
| ADgapc | ADΔura3, pQkj5 (URA3, TEFin-GapC-XPR2t) | This work |
| ADgpd | ADΔura3, pQkj6 (URA3, TEFin-GPD1-XPR2t) | This work |
| ADme | ADΔura3, pQkj7 (URA3, TEFin-MCE2-XPR2t) | This work |
| ADpp | ADΔura3, pQkj8 (URA3, TEFin-PK-XPR2t, GPDp-PTA-LIP1t) | This work |
| ADgapc2 | ADgapc, pQkj9 (Hygromycin, TEFin-GapC-XPR2t) | This work |
| ADgg | ADgpd, pQkj9 (Hygromycin, TEFin-GapC-XPR2t) | This work |
| ADyef | ADΔura3, pQkj10 (URA3, TEFin-YEF-XPR2t) | This work |
| ADpos5 | ADΔura3, pQkj11 (URA3, TEFin-POS5-XPR2t) | This work |
| ADutr | ADΔura3, pQkj12 (URA3, TEFin-UTR-XPR2t) | This work |
| ADgy | ADΔura3, pQkj13 (URA3, TEFin-YEF-XPRt, GPDp-GapC-LIP1t) | This work |
| ADgm | ADΔura3, pQkj14 (URA3, TEFin-MCE-XPRt, GPDp-GapC-LIP1t) | This work | a: The plasmids pQkj series are all linearized and transform into *Y. lipolytica*, the expression cassettes were all integrated into the genome.

All the primers used in this study were purchased from Integrated DNA Technologies and are listed in Table 2.

TABLE 2

Sequences of primers used in the study

| No. | Primers | SEQ ID NO | Sequences |
|---|---|---|---|
| P1 | URA3-KO1 | 60 | GCCCCAGATAAGGTTCCGA |
| P2 | URA3-KO2 | 61 | AGTGAATTCGAGCTCGGTACCCATGCCCTCCTACGAAGCTCG |
| P3 | URA3-KO3 | 62 | CTGCGAACTTTCTGTCCTCGAA |
| P4 | URA3-KO4 | 63 | TTCGAGGACAGAAAGTTCGCAGTACTCCAAGCAGACCATTGAGCT |
| P5 | URA3-KO5 | 64 | GGTCGACTCTAGAGGATCCCCCTAACAGTTAATCTTCTGGTAAGCCTC |
| P6 | URA3-KO6 | 65 | AAGCTGAACAAGCGCTCCATA |
| P7 | pUC19-v-r | 66 | GGGTACCGAGCTCGAATTCACT |
| P8 | pUC19-v-f | 67 | GGGGATCCTCTAGAGTCGACC |
| P9 | pMT91-15-f | 68 | GAGATATACATATGGCAGATCTCAATTGAGAGACCGGGTTGGCGG |
| P10 | pMT91-15-r | 69 | TCGCGTGGCCGGCCGATATCGGACACGGGCATCTCACTTG |
| P11 | pMT15-91-f | 70 | CAAGTGAGATGCCCGTGTCCGATATCGGCCGGCCACGCGA |
| P12 | pMT15-91-r | 71 | CCGCCAACCCGGTCTCTCAATTGAGATCTGCCATATGTATATCTC |
| P13 | TEF-UdhA-f | 72 | CGACCAGCACTTTTTGCAGTACTAACCGCAGCCACATTCCTACGATTACGATG |
| P14 | TEF-UdhA-r | 73 | CAAGACCGGCAACGTGGGGTTAAAACAGGCGGTTTAAACC |
| P15 | TEF-f | 74 | CCCCACGTTGCCGGTCTTG |
| P16 | TEF-r | 75 | CTGCGGTTAGTACTGCAAAAAGTGCTGGTCG |
| P17 | pKJ1-1f | 76 | AGTGAATTCGAGCTCGGTACCCCGCAGTAGGATGTCCTGCAC |
| P18 | pKJ1-2f | 77 | AGATGCATAGCACGCGTGTAGATACTGTTGATGTGTGTTTAATTCAAGAATGAAT |
| P19 | pKJ1-3f | 78 | TACACGCGTGCTATGCATCTGGTTCATGAGAAGATAAATATATAAATACATTGAGA |
| P20 | pKJ1-4f | 79 | GGTCGACTCTAGAGGATCCCCCTACCTTGCTCGAATGACTTATTG |
| P21 | pKJ1-v-f | 80 | GTATCTACACGCGTGCTATGCA |
| P22 | pKJ1-v-r | 81 | TGTTGATGTGTGTTTAATTCAAGAATGAATATAGAG |
| P23 | pKJ1-PntA-f | 82 | CATTCTTGAATTAAACACACATCAACAATGCGAATTGGCATACCAAGAGAACG |
| P24 | pKJ1-PntA-r | 83 | TGCATAGCACGCGTGTAGATACTTAATTTTTGCGGAACATTTTCAGCATGCGCTG |
| P25 | TEF-PntB-f | 84 | CGACCAGCACTTTTTGCAGTACTAACCGCAGTCTGGAGGATTAGTTACAGCTGCATAC |
| P26 | TEF-PntB-r | 85 | CAAGACCGGCAACGTGGGGTTACAGAGCTTTCAGGATTGCATCCA |
| P27 | Qkj2-KJ1-f | 86 | CGTATTGTACACGGCCGCATAGAATTCGAGCTCGGTACCC |
| P28 | Qkj2-KJ1-r | 87 | CAATTGAGATCTGCCATATGTATATCTCGTCGACTCTAGAGGATCCCC |

TABLE 2-continued

Sequences of primers used in the study

| No. | Primers | SEQ ID NO | Sequences |
|---|---|---|---|
| P29 | Qkj2-v-f | 88 | GAGATATACATATGGCAGATCTCAATTG |
| P30 | Qkj2-v-r | 89 | TATGCGGCCGTGTACAATACG |
| P31 | TEF-GapC-f | 90 | CGACCAGCACTTTTTGCAGTACTAACCGCAGGCAAAGATAGCTATTAATGGTTTTGG |
| P32 | TEF-GapC-r | 91 | CAAGACCGGCAACGTGGGGCTATTTTGCTATTTTTGCAAAGTAAGCT |
| P33 | TEF-Gpd1-f | 92 | CGACCAGCACTTTTTGCAGTACTAACCGCAGCCCGATATGACCAACGAGTCC |
| P34 | TEF-Gpd1-r | 93 | CAAGACCGGCAACGTGGGGTTACACGCCGGCCTCGAA |
| P35 | TEF-Mce2-f | 94 | CGACCAGCACTTTTTGCAGTACTAACCGCAGTCGCCTATTATTGATTTGTTCGTCG |
| P36 | TEF-Mce2-r | 95 | CAAGACCGGCAACGTGGGGCTACAATTTACCAGCTTGCTGATTGCT |
| P37 | pKJ1-PTA-f | 96 | CATTCTTGAATTAAACACACATCAACAATGAAGTTGATGGAAAACATCTTCGGT |
| P38 | pKJ1-PTA-r | 97 | TGCATAGCACGCGTGTAGATACTTAACCTTGTGCTTGAGCTTGAAC |
| P39 | TEF-PK-f | 98 | CGACCAGCACTTTTTGCAGTACTAACCGCAGGCCGATTTCGACTCTAAAGAATAC |
| P40 | TEF-PK-r | 99 | CAAGACCGGCAACGTGGGGTTATTTCAATGGGACCAAGTCCAATC |
| P41 | pQK7-TEF-f | 100 | CCGGAGCTTGCAGGATCGCCAGAGACCGGGTTGGCGGCGC |
| P42 | pQK7-XPR-r | 101 | GAGCGAGTGTTACACATGGAATTGGACACGGGCATCTCACTTG |
| P43 | pQK7-v-f | 102 | AATTCCATGTGTAACACTCGCTC |
| P44 | pQK7-v-r | 103 | GGCGATCCTGCAAGCTCCGG |
| P45 | TEF-YEF-f | 104 | CGACCAGCACTTTTTGCAGTACTAACCGCAGGCCCGCAACACAACGGA |
| P46 | TEF-YEF-r | 105 | CAAGACCGGCAACGTGGGGTTAAATGTTGGTGAACCGCTTCTGT |
| P47 | TEF-POS5-f | 106 | CGACCAGCACTTTTTGCAGTACTAACCGCAGCGACTACTCATCCGCCGAAC |
| P48 | TEF-POS5-r | 107 | CAAGACCGGCAACGTGGGGCTAAGCAACATCGCCTGACG |
| P49 | TEF-UTR1-f | 108 | CGACCAGCACTTTTTGCAGTACTAACCGCAGAGCACTCCGGTCAGCGAGTC |
| P50 | TEF-UTR1-r | 109 | CAAGACCGGCAACGTGGGGTTACTTCGTGTCCTCCTGCTCG |
| P51 | pKJ1-GapC-f | 110 | CATTCTTGAATTAAACACACATCAACAATGGCAAAGATAGCTATTAATGGTTTTGG |
| P52 | pKJ1-GapC-r | 111 | TGCATAGCACGCGTGTAGATACCTATTTTGCTATTTTTGCAAAGTAAGCT |

Plasmids were constructed exclusively via Gibson Assembly[48]. Genomic DNA isolations from bacteria (*E. coli* and *Clostridium acetobutylicum*) and fungi (*Yarrowia lipolytica*) were performed using Wizard Genomic DNA purification kit according to manufacturer's protocol (Promega, USA). Total RNAs from *Mucor circinelloides* and *E lipolytica* were isolated using Ribopure-Yeast RNA Kit (Life Technologies) and RT-PCR was performed using ImProm-II Reverse Transcription Kit according to manufacturer's protocol (Promega, UAS). Polymerase chain reactions were performed using KAPA HiFi PCR Kit (KAPAbiosystems). Synthetic genes were codon optimized using Optimizer[49] and assembled from the 500 bp or 1 kb DNA strings purchased from GeneArt (Table 3 for detailed sequences). All the engineered *Y. lipolytica* strains were constructed by transforming the corresponding plasmids, which were linearized by restriction enzymatic digestion using either NotI or AseI. The transformation protocol has been reported previously[17].

TABLE 3

Sequences of synthetic genes used in this study

| Synthetic gene | SEQ ID NO | Sequences |
|---|---|---|
| GAP Dehydrogenase (GPD), originated from *Kluyveromyces lactis*, codon optimized toward *Y. lipolytica* | 5 | atgcccgatatgaccaacgagtcctcttcgaagcccgcccagat caacatcggcatcaacggcttcggccgaatcggacgactggtgc tgcgagccgccctgacccaccccgaggtgaaggtgcgactgatc aacaaccccctctaccaccccgagtacgccgcctacctgttcaa gtacgactctacccacggcaagtaccgaggcgaggtcgagttcg acgacgagcgaatcatcatccagaacgaccacgtgtctgcccac atcccccctgtctcacttccgagagcccgagcgaatcccctgggc ctcttacaacgtggactacgtgatcgactctaccggcgtgttca aggaagtggacaccgcctctcgacacaagggcgtgaagaaggtg atcatcaccgcccctctaagaccgcccccatgtacgtgtacgg cgtgaaccacgtgaagtacaacccctgaccgaccacgtggtgt ctaacgcctcttgcaccaccaactgcctggcccccctggtgaag gccctggacgacgagttcggcatcgaagaggccctgatgaccac catccacgccaccaccgcctctcagaagactgtcgacggcacct cttctggcggcaaggactggcgaggcggccgatcttgccagggc aacatcatcccctcttctaccggcgctgccaaggccgtgggcaa gatcctgcccgagctgaacggcaagatcaccggcatgtctatcc gagtgccaccatcaacatctccctggtggacctgaccttccga accgccaagaagacctcttacgacgacatcatgaaggccctcga gcagcgatctcgatctgacatgaagggcgtcctgggcgtgacca aggacgccgtggtgtcctctgacttcacctctgactctcgatct tctatcgtggacgccaaggccggcatcgagctgaacgaccactt cttcaaggtgctgtcttggtacgacaacgagtacggctactctt ctcgagtggtcgacctgtctatcttcatggcccagaaggacttc gaggccggcgtgtaa |
| Phosphoketolase (PK), originated from *Leuconostoc mesenteroides*, codon optimized toward *Y. lipolytica* | 7 | atggccgatttcgactctaaagaatacttggaattggttgacaa atggtggagagctaccaattatttgtctgccggtatgatcttct tgaagtctaatcctttgttctccgttaccaacactccaatcaaa gctgaagatgttaaggttaagccaattggtcattgggtactat ttctggtcaaactttcttgtacgctcatgccaacagattgatta acaagtacggtttgaatatgttctacgttggtggtccaggtcat ggtggtcaagttatggttactaatgcttatttggatggtgccta cactgaagattacccagaaattacccaagacatcgaaggtatgt ctcacttgtttaagagattctcattcccaggtggtatcggttct catatgactgctcaaactccaggttctttacatgaaggtggtga attgggttactctttgtctcatgcttttggtgctgttttggata acccagatcaagttgcttttgctgttgttggtgatggtgaagct gaaactggtccatctatggcttcatggcattctattaagttctt gaacgctaagaatgatggtgccgttttgccagttttggatttga atggtttcaagatctccaacccaaccatcttctctagaatgtcc gatgaagaaatcaccaagttctttgaaggtttgggttacagtcc aagattcatcgaaaacgatgatatccatgattacgccacctatc atcaattggctgctaacattttggatcaagccatcgaagatatc caagccattcaaaatgatgccagagaaaacggtaaataccaaga tggtgaaattccagcttggccagttattattgctagattgccaa aaggttgggtggtccaactcatgatgcttctaacaatccaatc gaaaactctttcagagcccatcaagttccattgccattggaaca acatgatttggctactttgccagaattcgaagattggatgaatt cctacaagcctgaagaattattcaacgccgatggttccttgaag gatgaattgaaagctattgctccaaagggtgacaaaagaatgtc tgctaatccaattactaatggtggtgccgatagatccgatttga aattgccaaattggagagaattcgccaacgatattaacgatgac accagaggtaaagaattcgctgattctaagagaaacatggatat ggctaccttgtctaattacttgggtgcagtttctcaattgaacc ctactagattcagatttttcggtccagacgaaccatgtctaat agattgtgggtttgttcaacgttactccaagacaatggatgga agaaatcaaagaaccacaagatcaattattgtccccaaccggta gaatcattgactctcaattgtctgaacatcaagctgaaggttgg ttggaaggttatactttgactggtagagttggtattttcgcctc ttacgaatctttcttgagagttgttgataccatggttacccaac atttcaagtggttgagacatgcttcagaacaagcttggagaaat gattacccatccttgaacttgattgctacttctactgctttcca |

TABLE 3-continued

Sequences of synthetic genes used in this study

| Synthetic gene | SEQ ID NO | Sequences |
|---|---|---|
| | | acaagatcataacggttacactcatcaagatccaggtatgttga<br>ctcatttggctgaaaagaagtccaacttcatcagagaatatttg<br>ccagctgatggtaactctttgttggctgtccaagaaagagcttt<br>ttccgaaagacataaggtcaacttgttgatcgcttctaagcaac<br>ctagacaacaatggttcactgttgaagaagctgaagttttggct<br>aacgaaggtttgaagattattgattgggcttctacagctccatc<br>ctccgatgttgatattacttttgcttctgctggtactgaaccta<br>ccattgaaactttggctgctttgtggttgatcaatcaagctttt<br>ccagatgtcaagttcagatacgttaatgtcgtcgaattattgag<br>attgcaaaaaaagtccgaacctaacatgaacgacgaaagagaat<br>tgtctgcagaagaattcaacaagtacttccaagctgataccccca<br>gttattttggtttccatgcttacgaaaacttgatcgaatcatt<br>cttcttcgaacgtaaattcactggtgatgtttacgttcacggtt<br>acagagaagatggtgatattaccactacctacgatatgagagtt<br>tactcccatttggatagattccaccaagctaaagaagctgccga<br>aattttgtctgcaaacggtaagatagatcaagctgctgctgata<br>ctttcattgccaagatggatgataccttggctaagcactttcaa<br>gttactagaaacgaaggtagagatatcgaagaattcacagattg<br>gacttggtccccattgaaataa |
| Phosphotrans ace tylase (PTA), originated from *Clostridium kluyveri*, codon optimized toward *Y. lipolytica* | 9 | atgaagttgatggaaaacatcttcggtttggctaaggctgataa<br>gaagaaaatcgttttggctgaaggtgaagaagaaagaaacatta<br>gagcctccgaagaaatcatcagagatggtattgctgatatcatc<br>ttggtcggttctgaatccgttatcaaagaaaatgctgctaagtt<br>cggtgttaacttggctggtgttgaaatagttgatccagaaactt<br>cttctaagactgctggttacgctaatgccttctacgaaattaga<br>aagaacaagggtgttaccttggaaaaggcagataagatagttag<br>agatccaatctacttcgctaccatgatggttaagttgggtgatg<br>ctgatggtttggtttctggtgctattcataccaaccggtgatttg<br>ttaagaccaggtttacaaatcgttaagactgttccaggtgcttc<br>cgttgtttcttctgttttttgatgtctgttccagactgcgaat<br>atggtgaagatggttttttgttgttcgctgattgtgctgttaac<br>gtttgtccaactgctgaagaattgtcctctattgctattactac<br>tgctgaaaccgctaagaacttgtgcaaaattgaacctagagttg<br>ccatgttgtctttctctactatgggttctgcttcccatgaattg<br>gttgataaggttactaaggctaccaagttggctaaagaagctag<br>accagatttggatatcgatggtgaattacaattggatgcctcct<br>tggttaagaaggttgctgatttgaaagctccaggttctaaagtt<br>gctggtaaggctaatgttttgatcttcccagatattcaagccgg<br>taacattggttacaagttggttcaaagatttgctaaggcagaag<br>ccattggtccaatttgtcaaggttttgctaagccaatcaacgac<br>ttgtctagaggttgttctgttgatgatatcgttaaggttgttgc<br>cgttactgctgttcaagctcaagcacaaggttaa |

The parent strain in this study is MTYL065, which was previously constructed by overexpressing acetyl-CoA carboxylase 1 (ACC1) and diacylglyceride acyltransferase 1 (DGA1) in the parent *Y. lipolytica* polg (Yeastern, Taiwan). An auxotrophic marker URA3 was introduced by knocking out~250 bp in the center of URA3 CDS region by knock-out cassettes from pQkj1 (primers P2-P5 and P7-P8 used). The transformants were pre-selected using 5-Fluoorotic acid followed by PCR verifications (primers P1 and P6 used). To express genes of interest in the strain ADAura3, a compatible vector pQkj2 was created by combining TEF intron promoter and XPR2 terminator into pMT91 (primers P9-P12 used). The control strain AD was constructed by transforming pQkj2 into ADAura3 to serve as a baseline control for all the experiments. Furthermore, another gene expression vector was created by combining *Y. lipolytica* GPD promoter and LIP1 terminator in cloning vector pUC19 to give pKJ1 (primers P18-P20 used). Plasmid pKJ1 was primarily used as a cloning vector to express a second gene of interest.

To construct *Y. lipolytica* strains with increased cytosolic NADPH availability, a series of genes, including UdhA and PntAB from *E. coli*, glyceraldehyde-3-phosphate (GAP) dehydrogenase from *C. acetobutylicum* and malic enzyme from *M. circinelloides* were cloned from genomic DNAs of *E. coli* and *C. acetobutylicum* and cDNA library prepared from mRNA extracted from *M. circinelloides*. The GAP dehydrogenase from *Kluyveromyces lactis* was codon optimized and synthesized. All the genes were cloned into pQkj2 vector (primer pair P15-P16) to respectively give pQkj3, pQkj4, pQkj5, pQkj7 and pQkj6 (primers P13-14, P21-30, P33-P34, P35-P36 and P33-P34 used). The engineered *Y. lipolytica* strains ADudhA, ADpntAB, ADgapc, ADgpd and ADme were constructed by transforming linearized plasmids from pQkj3 to pQkj7, respectively. To activate the non-oxidative glycolysis pathway in yeast, phosphoketolase (PK) from *Leuconostoc mesenteroides* and phosphotransacetylase (PTA) from *Clostridium kluyveri* were synthesized and cloned into pQkj2 vector to yield pQkj8. The strain ADpp was created by integrating pQkj8 into ADAura3.

To create the *Y. lipolytica* strains with enhanced GAP dehydrogenase activity, pQkj9 was constructed in pQK7 backbone (Hygromycin resistance). The pQkj9 was transformed into ADgapc and ADgpd to afford ADgapc2 and ADgg, respectively. To functionally characterize endogenous $NAD^+$/NADH kinases from *Y. lipolytica*, three candidate genes in the *Y. lipolytica* genome were identified by BLASTX using three previously characterized *Saccharomyces cerevisiae* $NAD^+$/NADH kinase sequences (Table 4). The corresponding genes encoding ylYEF, ylPOS5, ylUTR1 were cloned into pQkj2 vector to yield pQkj10, pQkj11 and pQkj12 (primers P45-P50 used). Subsequently, ADyef, ADpos5 and ADutr were constructed. Finally, pQkj13 and pQkj14 (primers P27-P30, P51-P52) were individually constructed to co-express GapC and ylYEF; GapC and MCE2 in ADAura3 (strains ADgy and ADgm).

TABLE 4

Proteins in *Y. lipolytica* catalyzing the phosphorylation of NADH to form NADPH.

| Y. lipolytica accession number | protein name | S. cerevisiae homolog | EC no. | % amino acid identity/similarity | Deduced function | Ref |
|---|---|---|---|---|---|---|
| YALI0E17963p | ylPOS5 | POS5; YPL188W | 2.7.1.86 | 47/60 | Mitochondrial NADH kinase | 1 |
| YALI0E27874p | ylUTR1 | UTR1; YJR049C | 2.7.1.23 | 50/68 | ATP-NADH kinase, cytosol | 2, 3 |
| YALI0E23991p | ylYEF1 | YEF1; YEL041W | 2.7.1.86 | 37/58 | ATP-NADH kinase, cytosol | 3 |

Culture Media, Chemicals and Conditions

*E. coli* was grown in Luria-Bertani (LB) medium with appropriate antibiotics at 37° C./250 rpm. The antibiotics were added at the concentrations: carbenicillin, 50 µg/mL; kanamycin, 50 µg/mL; chloramphenicol, 34 µg/mL. *Y. lipolytica* was selected in defined medium containing 6.7 g/L yeast nitrogen base w/o amino acids and 20 g/L glucose supplemented with appropriate concentrations of CSM dropout mixtures, including CSM-Leu, CSM-Ura, CSM-Leu-Ura (Sunrise Science, USA) or 250 µL hygromycin at 30° C./250 rpm. For genomic DNA extractions, bacteria were grown in LB medium, while all fungal strains were cultured in YPD medium (10 g/L yeast extract, 20 g/L peptone, 20 g/L glucose). 16 g/L Bacto agar was added for petri dish cultivations (BD, USA). All chemicals and substrates were purchased from Sigma-Aldrich unless otherwise indicated.

Shake Flask Culturing of Engineered *Y. lipolytica* Strains

Single colony of *Y. lipolytica* was grown in 2 mL defined medium (6.7 g/L yeast nitrogen base w/o amino acids, complete and 20 g/L glucose) at 250 rpm for 30 h in 10 mL test tubes (Corning). The cells were harvested by centrifugation at 8000 rpm and washed twice with low nitrogen defined medium (1.7 g/L yeast nitrogen base w/o amino acids and ammonium sulfate, 1.1 g/L ammonium sulfate and 50 g/L glucose). The washed cells were inoculated into 50 mL low-nitrogen defined medium (250 mL shake flask) at $OD_{600}$ of 0.05 and grown at 30° C./250 rpm for 120 h.~2 mL of cell suspension was sampled every 24 h (from 48 h to 120 h) for $OD_{600}$, dry cell weight, extracellular metabolite, and lipid measurements as described below. For enzymatic activity and cofactor quantification assays, ~10 mL cell suspension was harvested at exponential growth phase (24 h) and lipid production phase (60 h).

Bioreactor Experiments for Lipid Production by Engineered *Y. lipolytica*

The 3-liter Bioflo bioreactor (New Brunswick) was operated with 1.6 liter working volume for all the bioreactor experiments in this study. The seed cultures of *Y. lipolytica* were prepared by inoculating a single colony of *Y. lipolytica* into YPD medium (10 g/L yeast extract, 20 g/L peptone, 20 g/L glucose) and growing at 30° C./250 rpm for 30 h. The seed culture was harvested by centrifugation at 4000 rpm, washed twice using fermentation medium (3.4 g/L yeast nitrogen base, 2.5 g/L yeast extract, 8.8 g/L ammonium sulfate, 100 g/L glucose) and inoculated into bioreactor containing 1.6 L fermentation medium. The starting $OD_{600}$ of each bioreactor run was ~0.5. During the fermentation, oxygen was supplied by sterile filtered air at 5 vlm and agitation speed was cascaded (200 rpm to 750 rpm) such that dissolved oxygen levels were maintained at 20% during growth phase (typically from 0 h to 36 h) and ~5% during lipid production phase (~36 h to the end of fermentation).

The temperature was constantly controlled at 28° C., and pH was maintained at 5.5. During the course of fermentation, glucose concentration was monitored and glucose was continuously supplemented to the bioreactor. The concentration of glucose in the feed bottle was 600 g/L and the feeding rate was controlled at 6.5 mL/h from 5 h to 55 h.

Enzymatic Activity of GAP Dehydrogenase

Cells were harvested at exponential growth phase (24 h) and lipid production phase (48 h) in shake flask cultures by centrifugation at 8,000 rpm. The supernatants were removed and cell pellets were washed once with and resuspended in Tris-HCl buffer (50 mM Tris-HCl, 1 mM dithiothreitol and 2 mM EDTA, pH=7.5). Cells were disrupted by sonication with 0.7 mm-diameter acid washed glass beads (Sigma) at 0° C. Cell debris was removed by centrifugation at 18,000 g for 20 min at 4° C. The clear supernatant was filtered through 0.45 um syringe filter and loaded onto Nanosep 10K omega (Pall). The flowthrough was collected and analyzed for quantification of intracellular cofactors, while (~25 uL) retentate was resuspended in appropriate buffer and used as the cell extract for enzymatic activity assays. All the operations were carried out at 4° C. The enzymatic assays were performed according to previously established protocol.

Quantification of Cell Density

Cell densities were monitored by measuring optical density at 600 nm wavelength and dry cell weight. For dry cell weight measurement, 800 µL cell suspension was harvested by centrifugation at 18,000 g for 15 min in pre-weighed micro-centrifuge tubes. The cell pellets were washed twice in water and dried at 60° C. until the mass of each tube remained constant over time (typically after ~36 h).

Extractions, Derivatizations and Quantifications of Lipids

Depending on cell density, 50 µL to 1 mL of cell suspension (approximately 2 mg dry cell weight) was sampled and centrifuged at 18,000 g for 10 min and the supernatant was carefully removed. The cell pellets can be stored in a −20° C. freezer until further derivatization. For lipid analysis, 100 µL hexane containing 2 mg/mL methyl tridecanoate (internal standard for volume change) and 2 mg/mL glyceryl triheptadecanoate (Internal standard for transesterification efficiency) was added to the cell pellet. Lipid transesterifications were initiated by addition of 500 µL 0.5 N sodium methoxide (20 g/L sodium hydroxide in anhydrous methanol) followed by vortexing at 1200 rpm for 60 min at room temperature. Then the samples were neutralized with 40 µL sulfuric acid (98% purity) and the synthesized FAMEs were extracted with 500 µL hexane by vortexing for additional 30 min at 1200 rpm. The samples were centrifuged at 8,000 rpm for 1 min and 1 μL of the top hexane layer was analyzed by a Bruker 450-GC Gas Chromatograph equipped with a flame ionization detector (GC-FID). The sample was injected into a HP-INNOWAX capillary column (Agilent Technologies, USA) with split ratio of 10 and injector temperature of 260° C. The flowrate of carrier gas was 1.5 mL/min and the oven temperature was held at a constant temperature of 200° C. for the duration of 13 min to analyze all five major FAME species (C16, C16:1, C18, C18:1 and C18:2).

Quantification of Extracellular Metabolites

At the indicated time points, ~500 μL of cell suspension was sampled and centrifuged at 16,000 g for 10 min. The supernatant was further filtered with a 13 mm syringe filter with 0.2 μm PTFE membrane (VWR international). 100 μL of the filtered supernatant was analyzed using high-performance liquid chromatography (Agilent 1200 HPLC system equipped with G1362A Refractive Index Detector) to quantify the concentrations of metabolites, including glucose, citrate, mannitol, glycerol and erythritol. The mobile phase (14 mM sulfuric acid) was used to flow through a separation column (Bio-Rad HPX-87H column) at a rate of 0.7 mL/min.

Results

Stoichiometry of Lipid Synthesis and a Process Yield Model FIG. 1 depicts the biosynthetic pathways for the synthesis of fatty acids, specifically stearic acid (SA), $C_{17}H_{35}COOH$. Briefly, SA is formed through the fatty acid synthesis pathway initiated by acetyl-CoA with the overall stoichiometry shown. Acetyl-CoA is the product of ATP-citrate lyase (ACL) cleaving citrate into oxaloacetate (OAA, recycled into the TCA cycle) and acetyl-CoA, used primarily for fatty acid synthesis. Citrate, in turn, is the product of acetyl-CoA condensation with OAA, the reaction taking place in the mitochondria. Under conditions of nitrogen starvation, isocitrate dehydrogenase (IDH) is inhibited leading to citrate accumulation, export from the mitochondria and further processing in the lipogenesis pathway. Acetyl-CoA is the product of decarboxylation of pyruvate, the end point metabolite of glycolysis[21].

FIG. 1 also shows the overall stoichiometry of glycolysis, NADPH production in the Pentose Phosphate Pathway (PPP) and glucose oxidation in the TCA cycle. The overall stoichiometry of glucose conversion to SA is, $$4.5\,Glucose + 8\,ATP + 16\,NADPH.c = 1\,C_{17}H_{35}COOH + 9\,NADH.c + 9\,NADH.m \quad (1)$$

Figure 6:
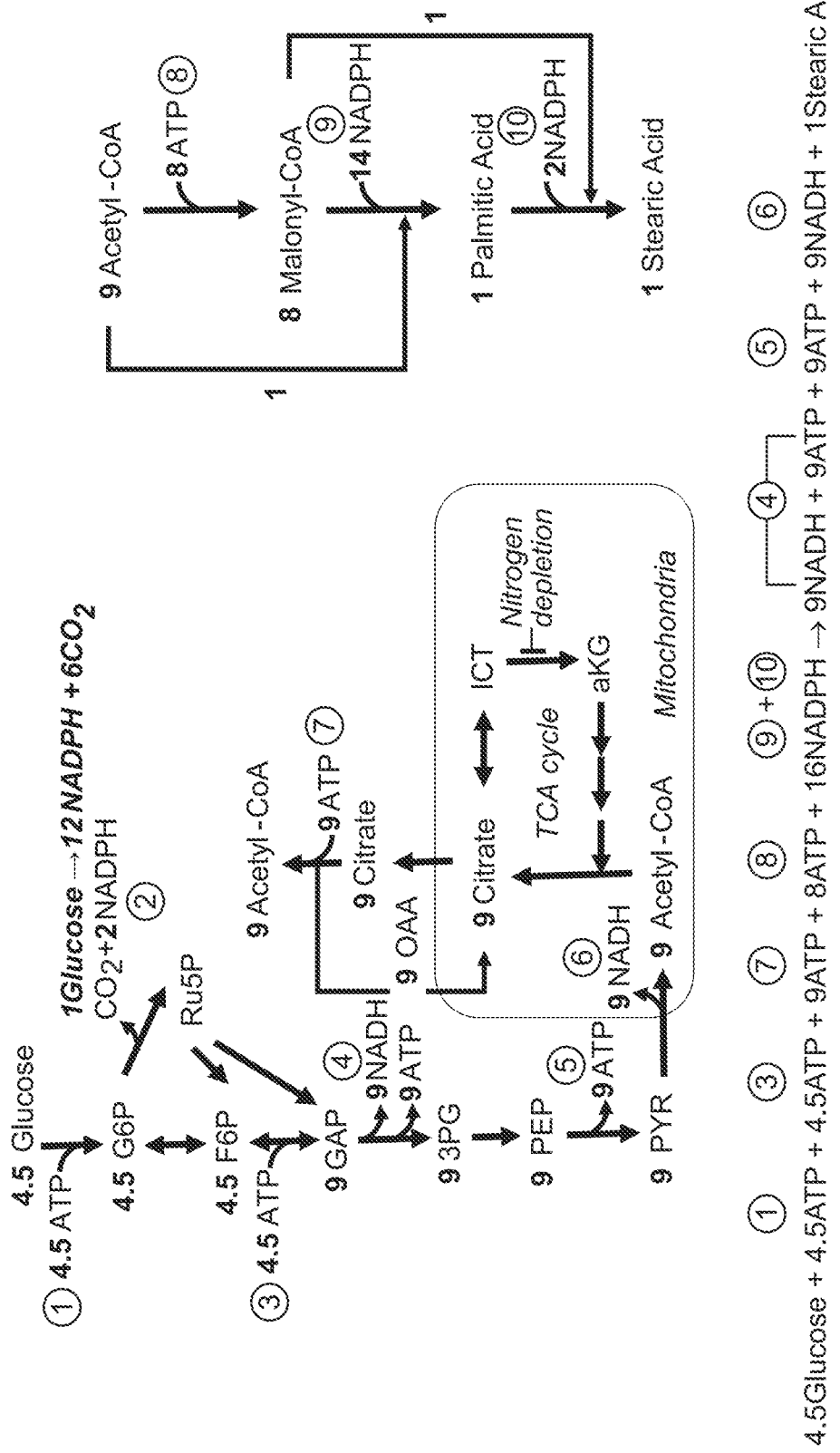
FIG. 6. Overall stoichiometry of biosynthetic pathways involved in lipogenesis in oleaginous yeast *Yarrowia lipolytica* and the calculation of theoretical yield of lipids (as exemplified using stearic acid, SA). SA is biosynthesized by acetyl-CoA (carbon building block) with consumption of ATPs for activating acetyl-CoA to malonyl-CoA and NADPH used to reduce the nascent poly-ketone intermediates. The conversion of glucose to SA is depicted in equation S1 with all the biochemical steps generating or consuming cofactors numbered accordingly. Simplification of equation S1 led to the equation (1) as shown in this figure.

If one assumes that the reducing equivalents generated in the cytosol and mitochondria in the form of NADH (NADH.c and NADH.m, respectively) can be converted to cytosolic NADPH required for fatty acid synthesis, a maximum yield for SA can be calculated as 0.344 g-SA/g-glucose (FIG. 6). If, on the other hand, the above assumption is not invoked and all NADPH required for lipid synthesis is generated from glucose oxidation in the pentose phosphate pathway (the primary source of cytosolic NADPH for biomass synthesis, fatty acid synthesis and other NADPH-requiring pathways), then an extra 1.33 moles of glucose must be oxidized in the PPP, which reduces the yield of stearic acid to 0.271 g-SA/g-glucose (FIG. 6). Clearly, the available NADH.c and NADH.m cannot substitute for NADPH synthesis in yeasts, yet significant lipid yield improvements can be achieved by engineering synthetic pathways that accomplish this. A recent study of flux distributions in a strain of *Y. lipolytica* engineered for lipid overproduction showed that the PPP was the main source of NADPH used for lipid synthesis and indeed lipogenesis was limited by the supply of NADPH[22].

Of course, the above calculations do not include the amount of glucose required for cell growth and maintenance, as well as that consumed for byproduct formation. A mathematical mass balance of glucose allocation into non-lipid biomass (B), lipids (L), by-products (W) and cell maintenance (mB) yields the following equation assuming that each of the corresponding biochemical pathways operates at its maximum efficiency ($Y_B$, $Y_L$ and $Y_w$ are, respectively, the maximal yields of biomass, lipids and by-product):

$$G = \frac{B}{Y_B} + \frac{L}{Y_L} + mB + \frac{W}{Y_w} \quad (2)$$

Neglecting the primary by-product citrate, which was previously minimized to less than 10 g/L in bioreactor studies[13,17], and yeast cell maintenance (contributing less than 10% of total consumed glucose) (see Development of a Mathematical Model of Process Yield, below) simplifies equation (2) to:

$$Y = \frac{\frac{Y_B Y_L}{Y_B - Y_L} C}{\frac{Y_L}{Y_B - Y_L} + C} \quad (3)$$

where C=L/(B+L) is the lipid content and Y=L/G the overall process yield.

Development of a Mathematical Model of Process Yield.

For a given fed-batch fermentation that produce lipids from glucose, the overall process yield Y can be defined as $$Y = \frac{L}{G} \quad (S9)$$

Where L is the lipid titer (g/L) and G represents the total consumed glucose (g/L). Given that glucose is the exclusive carbon source of the fermentation and it is allocated into four major products:

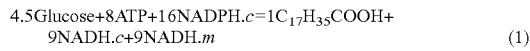

| Total consumed glucose | = | Glucose used to make biomass | + | Glucose used to make lipids | + | Glucose used to maintain cells | + | Glucose used to make byproduct |

It can be rewritten to a mathematical expression:

$$G = \frac{B}{Y_B} + \frac{L}{Y_L} + mB + \frac{W}{Y_w} \quad (2)$$

$$C = \frac{L}{B + L} \quad (S10)$$

B: non-lipid biomass (g/L); m: cell maintenance (g/g dry cell weight); W: byproduct titer (g/L); YB, YL and Yw respectively represent the conversion yield of glucose to the corresponding products-non-lipid biomass, lipids and byproduct(s).

To simplify equation (2), three key assumptions are made on the basis of growth characteristics and data obtained from fed-batch fermentations performed previously[44,46] and in this study: 1. biomass is generated at its maximal yield YB and lipids are biosynthesized at their maximal yield YL. 2. no byproduct formation. 3. cell maintenance is negligible.

As shown in FIG. 12, a fed-batch fermentation of engineered *Y. lipolytica* (for example, baseline strain AD) features a biphasic growth curve. In the growth phase (from 0 h to 36 h), the *Y. lipolytica* cells grow exponentially at a specific growth rate of ~0.25 h−1. After depletion of nitrogen (~40 h), the cells enters lipid production phase, in which cells stop doubling and their metabolism shifts to complete lipogenesis. Therefore, it is reasonable to assume that non-lipid biomass formation in *Y. lipolytica* occurs exclusively in the growth phase. As a result, in the first 36 hour, the non-lipid biomass yield YB is identical to Yx/s, which can be either directly measured or obtained from literature[47]. Besides, the cell maintenance can be neglected in the growth phase.

$$Y_B = Y_{\frac{x}{s}} = \frac{\text{g biomass}}{\text{g substrate}} \quad (S11)$$

During lipid production phase, the increase of dry cell weight almost exclusively results from accumulation of lipids, as evidenced by the unchanged cell numbers and gradual enlargement of lipid bodies. As shown in the AD fermentation, the lipid yield (defined as maximal yield) in this phase is 0.235 g-FA/g-glucose, which is 87% of the stoichiometric maximum theoretical yield (0.271 g/g). Therefore, it is fair to assume that lipids are biosynthesized at their maximum conversion yield. Furthermore, only a small portion (up to 13%) of the substrate contributes to cell maintenance during this phase. Given that about half of the total glucose is consumed in lipid production phase, the glucose consumed for maintenance is ~6.5% of total consumption of glucose, which is neglected due to its small contribution.

Additionally, previous process engineering efforts centered on minimization of the chief byproduct citrate during fermentation have limited the citrate titer to approximately 10 g/L at the end of fermentation by fine-tuning the dissolved oxygen level in the lipid production phase[46]. It is fair to assume that 10 g/L of citrate was derived from 9.4 g/L glucose (theoretical yield 1.07 g-citrate/g-glucose), accounting for less than 3.7% of total consumed glucose (typically >250 g/L).

In summary, the allocation of glucose to cell maintenance and byproduct citrate takes up less than 10% of the total consumed glucose. Furthermore, the cells are making biomass and lipids at high efficiencies (close to 100%) during growth phase and lipid production phase respectively.

The above model was validated using $Y_B$ and C values experimentally determined for a given microbe and $Y_L$ values calculated from the stoichiometry of specific lipid-forming metabolic networks[23] (0.351 g-SA/g-glucose for *E. coli* and 0.271 g-SA/g-glucose for *Y. lipolytica*). Table 5 show less than 5% discrepancy between model predictions and actual values for the overall lipid process yield obtained for *E. coli*[5,24] and *Y. lipolytica*[13,17] for a range of $Y_B$ and C values reported for optimized fermentations.

TABLE 5

Validation of the quantitative yield model using reported fermentation data on two model microorganisms—*E. coli* and *Y. lipolytica*

| | $Y_B$ (g/g) | $Y_L$ (g/g) | Content | Process Y (g/g) | reported yield (g/g) | discrepancy | error |
|---|---|---|---|---|---|---|---|
| *E. coli* (1) | 0.50 | 0.35 | 78.0% | 0.29 | 0.28 | 0.0123 | 4.4% |
| *E. coli* (2) | 0.50 | 0.35 | 21.0% | 0.10 | 0.09 | 0.0041 | 4.4% |
| *Y. lipolytica* (3) | 0.55 | 0.27 | 69.0% | 0.22 | 0.22 | 0.0038 | 1.8% |
| *Y. lipolytica* (4) | 0.17 | 0.27 | 75.0% | 0.17 | 0.17 | −0.0022 | −1.3% |

Using the model we next identified the key parameters that are most influential in driving overall process yield. FIG. 7 shows the results of one-way sensitivity analysis carried out at two different lipid contents C (50% and 70%), which are relevant and were obtained from the two engineered *Y. lipolytica* strains on which we reported previously[13,17]. Lipid content C and lipid pathway yield, $Y_L$, were identified as the most critical parameters, with $Y_L$ being the most important at high lipid contents of 70% in forward engineering strains with high overall process yield.

Physiological range of each parameters. $Y_L$ is solely determined by the metabolic pathway stoichiometry involved in de novo biosynthesis (FIG. 6) and it ranges from the baseline (0.271 g/g according to metabolism in the native *Y. lipolytica*)[49] to the thermodynamic maximum (0.362 g/g) which is calculated by the complete energy conservation[410]. On the other hand, $Y_B$ can be readily measured by experiments (0.55 g-dry cell weight/g-glucose) for *Y. lipolytica* or obtained from literature for different yeasts[47] (if one wanted extend the model to another organism). Of course, a whole genome scale metabolic model can also be used to determine $Y_B$, but its accuracy has to be analyzed before it is used to predict Y. Finally, lipid content C simply ranges from 0% to 100%. It is important to notice that the definition of C is not restricted to intracellular products like lipids in the study but also can be extended to all biochemical products, such as ethanol, butanol or other natural products. Furthermore, all three key parameters are dimensionless, allowing the full transformation of equations related to the model.

Dependence of process yield Y on parameters. The above derived mathematical model (Equation 3 and Development of a Mathematical Model of Process Yield) demonstrates that Y is determined by $Y_B$, $Y_L$ and C. However, it is not obvious how each parameter affects the optimization target Y. To address this issue, we performed full optimization for a series of values within the physiological ranges of each parameter.

In FIG. 7a, we show how Y as a function of the lipid content C responds to increases in the other two yield parameters—$Y_B$ and $Y_L$. As expected, increasing either $Y_B$ or $Y_L$ increases Y, though with different dynamics depending on C. Interestingly, Y is most responsive to $Y_B$ when C is around the mid-point-50%, with only small increments when C is close to either 0% or 100%. On the other hand, $Y_L$ and C seem to have synergistic effects on optimization of Y. The most significant increase in Y occurs when $Y_L$ is increased with C approaching 100%. Considering the practical situation that *Y. lipolytica* has been engineered in our hands to afford C 50%-70%, optimizing $Y_B$ and $Y_L$ could both be good strategies for optimizing Y for production of lipids.

In FIG. 7b, we plotted Y as functions of $Y_B$ and $Y_L$ with three different values of C. We reach similar conclusions as in the previous analysis of FIG. 7a. Firstly, the slopes of the Y as a function of $Y_L$ curves are significantly higher than those of the Y as a function of $Y_B$ curves, indicating $Y_L$ is more effective than $Y_B$ in the range of C (50%-70%) for optimizing Y. Secondly, Y is responsive to C regardless of the values of $Y_L$ or $Y_B$.

Figure 7C:
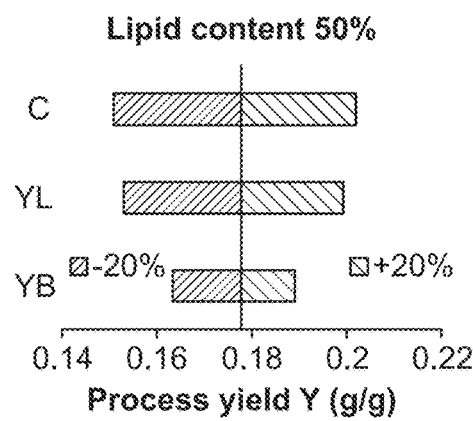
Figure 7D:
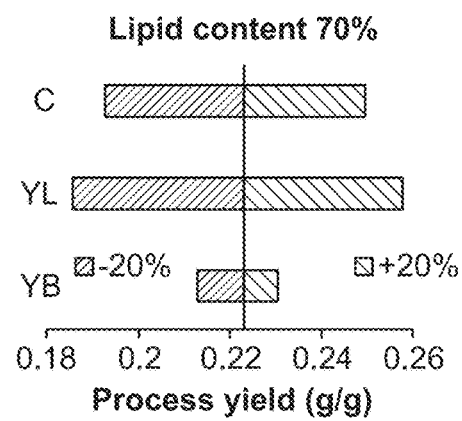

To direct our engineering efforts in elevating the process yield of lipids, it is necessary to identify which parameter is the most effective in optimizing Y. Toward this end, we performed single-point sensitivity analyses at two different C values-50% and 70%, which are, respectively, the lipid contents achieved in our previous experiments[44,46] and previously reported by others in the oleaginous yeasts literature[411-413]. The results are shown in FIG. 7c and FIG. 7d. Both C and $Y_L$ were identified to be very influential on Y at both values of C, while Y is considerably less sensitive to $Y_B$. Although C is slightly more influential than $Y_L$ at C=50%, $Y_L$ becomes the dominant parameter at C=70%. The sensitivity analyses demonstrated that although all three parameters positively contribute to the optimization of Y, we should most likely focus on optimization of C and $Y_L$ in order to engineer strains with high lipid yields.

Figure 1B:
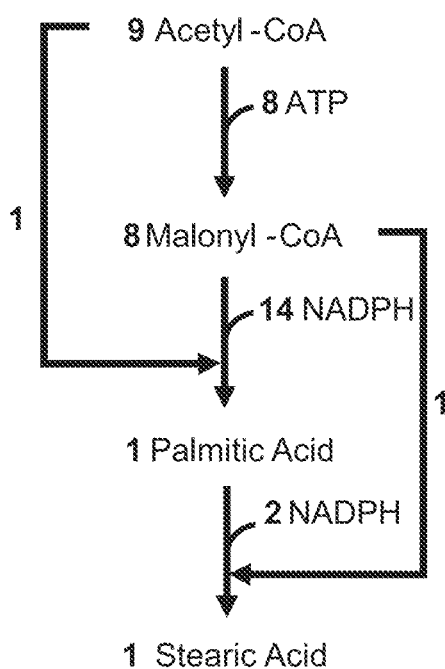
Figure 2A:
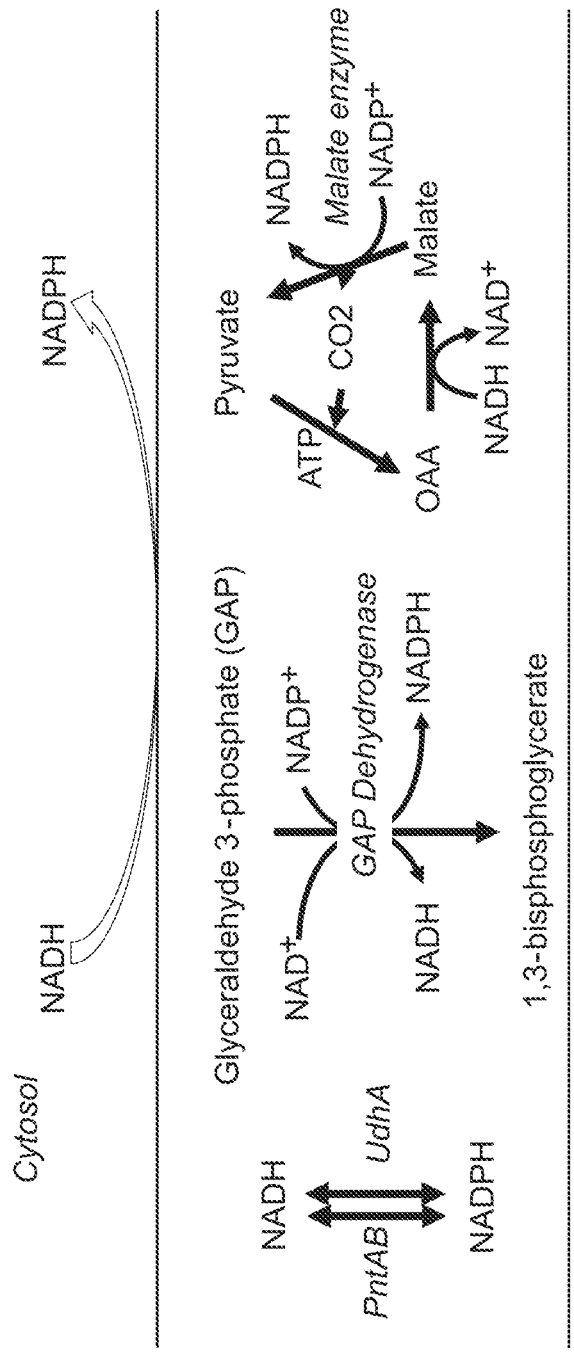
FIGS. 2A-2D. Regeneration of cytosolic NADPH by harvesting NADH.c generated from glycolysis led to lipid yield improvement.

Improving Overall Process Lipid Yield by Rewiring Metabolism to Recycle Cytosolic NADHs to NADPH or Acetyl-CoA In nature, de novo fatty acids biosynthesis is exclusively powered by acetyl-CoA, NADPH and ATP (FIG. 1b). While cytosolic acetyl-CoA in *Y. lipolytica* is mainly generated via the cleavage of citrate by ACL, ATPs can be produced via the respiration activity of the obligate aerobe. Clearly, $Y_L$ (solely determined by the stoichiometry of the lipid pathway) can be elevated by consuming excess NADHs to produce either NADPH or acetyl-CoA. To test this hypothesis, we examined three strategies that could potentially elevate $Y_L$ to 0.311 g-SA/g-glucose in *Y. lipolytica* by converting all 9 NADH.c into NADPH (FIG. 2a and FIG. 8). All genetic modulations were carried out in the genetic background of ACC-DGA overexpression, which is our control strain indicated by subscripts AD.

Figure 2B:
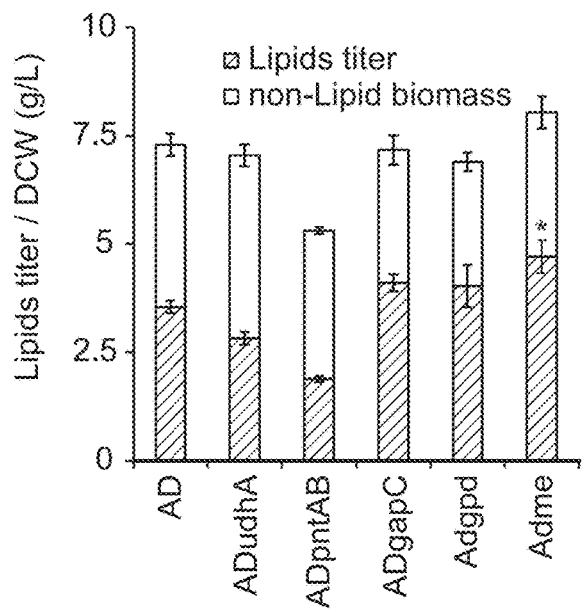
Figure 2C:
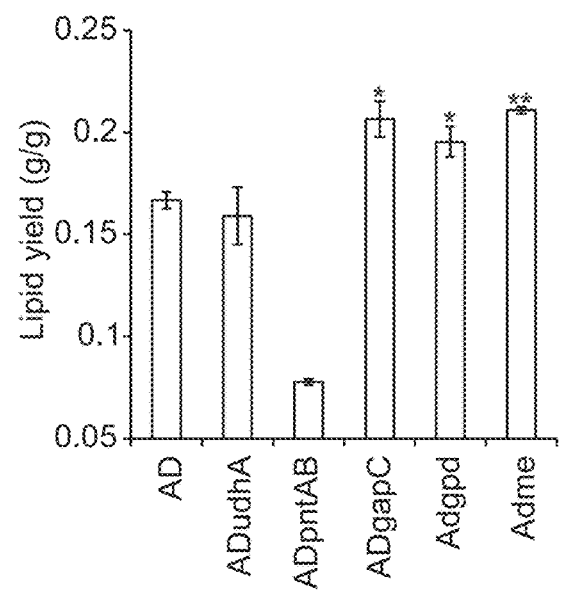

In very few bacteria including *E. coli*, NADPH and NADH can be interconverted by two nucleotide transhydrogenase isoforms-UdhA and PntAB[25]. We hypothesized that the excess cytosolic NADHs can be directly converted to NADPH.c if *E. coli* transhydrogenases were reconstituted in *Y. lipolytica*. Considering the uncertainty about the direction of the enzymatic reactions in yeasts[26], we constructed two strains ADudhA and ADpntAB by expressing *E. coli* UdhA and PntAB respectively. Overexpression of *E. coli* UdhA had no significant effect on lipid yield, titer and biomass, while overexpression of the membrane-bound enzymes PntAB drastically disrupted cell growth and lipid production in *Y. lipolytica* (column 2 and 3 in FIGS. 2b and 2c). Microscopic imaging of ADpntAB revealed that cells developed hyphal morphology, typically observed under stressful culture conditions (FIG. 9).

Figure 2D:
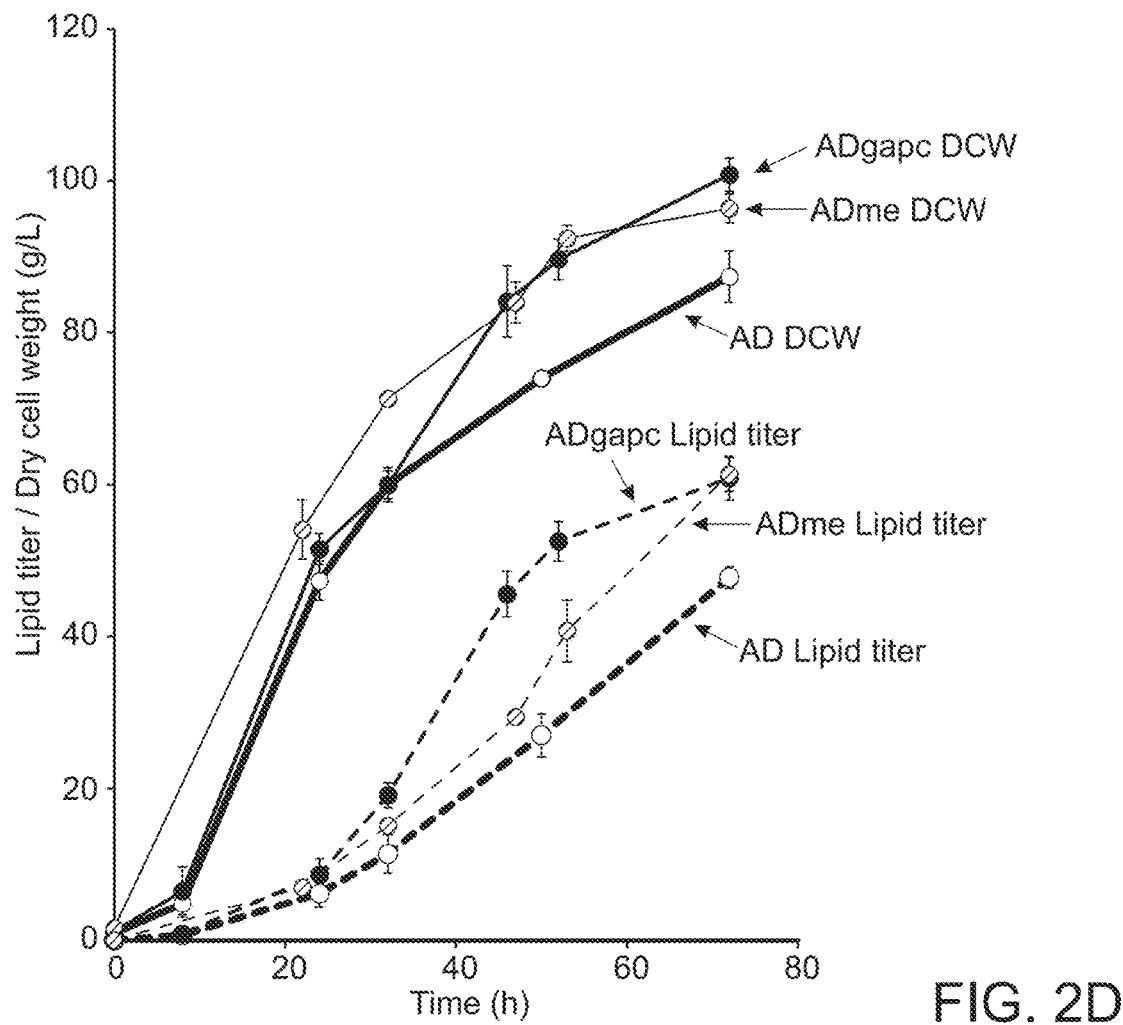

The 9 cytosolic NADHs in the right side of equation (1) are generated at the biochemical reaction catalyzed by glyceraldhyde-3-phosphate dehydrogenase (GPD). *Y. lipolytica* GPD (ylGPD) was hypothesized to favor $NAD^+$ by homology analysis. To biochemically verify its cofactor specificity, we measured the GPD activity using whole cell lysate obtained from AD in the presence of $NAD^+$ and $NADP^+$. As expected, the specific enzymatic activity in the presence of $NAD^+$ is ~10 times higher than that with $NADP^+$ (FIG. 10). To swap the cofactor product of this reaction, we cloned and introduced into the AD strain two NADPH-dependent GPDs: GapC from *Clostridium acetobutylicum*[27] and GPD1 from *Kluyveromyces lactis*[28] to give, respectively, ADgapc and ADgpd. Both engineered *Y. lipolytica* strains showed unchanged lipid titer and dry cell weight, but significant increases in yield relative to that of AD were observed (column 1, 4 and 5 in FIG. 2b and FIG. 2c). In bioreactor cultivations, the best performer ADgapc mirrored the growth of AD and featured a much higher specific productivity in the lipid production phase (FIG. 2d). As a result, the overall lipid process yield of ADgapc was significantly elevated (0.229 g/g) compared to that of AD (0.184 g/g) (Table 6). Notably, the lipids yield in the lipid production phase (36-72 hour) reached 0.279 g/g, exceeding the stoichiometric maximum of AD and thus confirming the contribution of the GPD pathway to NADPH synthesis (FIG. 11).

TABLE 6

Characterization of the engineered *Y. lipolytica* strains lipid production in fed-batch fermentations

| Strain | Cell growth DCW (g/L) | Glucose consumed (g/L) | Lipids (FAMEs) produced[a] | | | | Rationale for genetic modulation(s) |
|---|---|---|---|---|---|---|---|
| | | | Titer (g/L) | Content (%) | Yield (g/g) | Efficiency | |
| AD | 87.4 | 260.3 | 47.8 | 54.7 | 0.184 | n/a | n/a |
| ADgapc | 101.5 | 276.5 | 63.3 | 62.5 | 0.229 | 21.8% | NADH.c → NADPH.c |
| ADme | 96.4 | 248.1 | 61.4 | 63.7 | 0.247 | 50.1% | NADH.c + ATP → NADPH.c |
| ADpp | 93.4 | 260.8 | 56.2 | 52.7 | 0.216 | −11.2% | NADH.c → Acetyl-CoA.c |
| ADgy | 86.3 | 223.2 | 54.6 | 63.2 | 0.244 | 63.5% | $NAD^+$ → $NADP^+$; NADH.c → NADPH.c |
| ADgm | 90.9 | 237.5 | 66.8 | 73.5 | 0.282 | 99.1%/ 64.2% | NADH.c → NADPH.c; NADH.c + ATP → NADPH.c |
| ADgm-hi[b] | 144.5 | 360.9 | 99.3 | 68.6 | 0.274 | 99.0%/ 72.4% | NADH.m → NADPH.c (tbd) |

[a]FAMEs, fatty acid methyl esters.
[b]ADgm-hi represents the strain ADgm cultured in a high density fed-batch fermentation.
[c]Average fermentation characteristics including titer, consumed glucose, lipid titer, content and yield are shown here. Standard deviations and p values are shown in Table 7.

TABLE 7

Model calculated efficiencies of synthetic pathways introduced to *Y. lipolytica*

| | | Cell growth | Glucose consumed | Lipids (FAMEs) produced[a] | | | Synthetic Pathway Efficiency |
|---|---|---|---|---|---|---|---|
| Strain | Batch | DCW (g/L) | (g/L) | Titer (g/L) | Content (%) | Yield (g/g) | |
| AD | 1 | 84.6 | 252.1 | 47.1 | 55.9 | 0.187 | n/a |
| AD | 2 | 90.2 | 268.5 | 48.5 | 53.8 | 0.181 | n/a |
| ADgapc | 1 | 100.8 | 270.4 | 60.9 | 60.4 | 0.225 | 25.1% |
| ADgapc | 2 | 101.9 | 282.6 | 65.7 | 64.5 | 0.232 | 18.4% |
| ADme | 1 | 97.3 | 247.8 | 62.5 | 64.2 | 0.252 | 57.4% |
| ADme | 2 | 95.4 | 248.4 | 60.2 | 63.1 | 0.242 | 42.9% |
| ADpp | 1 | 95.85 | 255.0 | 55.6 | 58.0 | 0.218 | 6.3% |
| ADpp | 2 | 90.9 | 266.6 | 56.8 | 62.4 | 0.213 | −28.7% |
| ADgy | 1 | 85.8 | 216.4 | 52.5 | 61.2 | 0.243 | 66.4% |
| ADgy | 2 | 86.7 | 222.5 | 54.5 | 62.9 | 0.245 | 60.6% |
| ADgm | 1 | 94.4 | 232.4 | 65.5 | 69.4 | 0.279 | 101.4%/62.2% |
| ADgm | 2 | 87.4 | 242.5 | 68.1 | 77.9 | 0.284 | 96.7%/39.1% |
| ADgm-hi | 1 | 140.2 | 365.4 | 98.7 | 70.4 | 0.270 | 98.0%/45.1% |
| ADgm-hi | 2 | 148.8 | 356.3 | 99.3 | 66.7 | 0.279 | 100.0%/69.5% |

The third strategy we adopted was to activate the Pyruvate/Oxaloacetate/Malate (POM) cycle, which can convert 1 mol NADH to 1 mol NADPH at a cost of 1 mol ATP (FIG. 2a). Given that the parental strain polg is a derivative of wild type *Y. lipolytica* W29, which is an excellent citric acid producer, high activities are expected for two enzymes of the POM cycle, namely, pyruvate carboxylase and cytosolic malate dehydrogenase[29]. However, the endogenous malic enzyme (ylMAE) in *Y. lipolytica* was recently found to be a mitochondria-associated NADH-dependent enzyme, whose overexpression and knock-out had very little or no effect on lipid production[30,31]. Therefore, the key to activating the POM cycle was to incorporate a cytosolic NADPH-dependent malic enzyme, as demonstrated to be effective in oleaginous fungi[32-34]. To this end, we cloned and heterologously expressed MCE2 from *Mucor circinelloides* in strain AD to yield strain ADme. The lipid yield of ADme in shake flask was increased to 0.21 g/g with slight increase in both biomass and lipid content (column 1, 6 in FIG. 2b and FIG. 2c). The ADme exhibited a similar time course of growth as AD and ADgapc in bioreactor runs, but much higher lipid titer and yield than those of AD (FIG. 2d and Table 6).

Figure 3A:
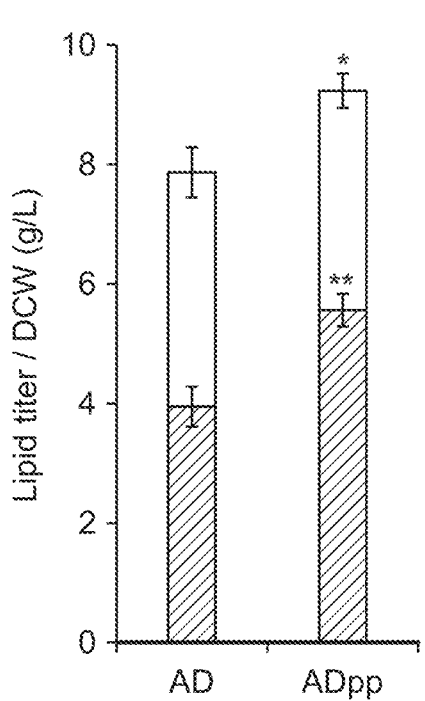
FIGS. 3A-3C. Introduction of non-oxidative glycolytic (NOG) pathway in *Y. lipolytica* benefit the lipids production.
Figure 3B:
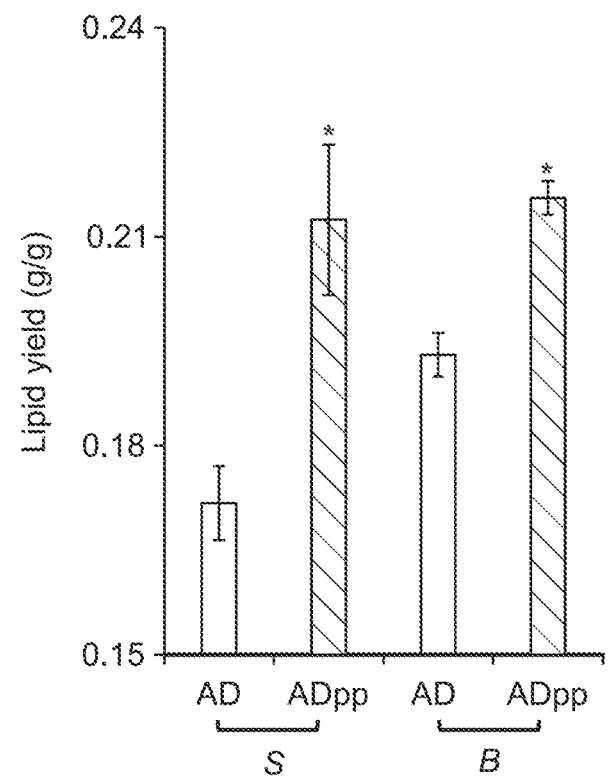
Figure 3C:
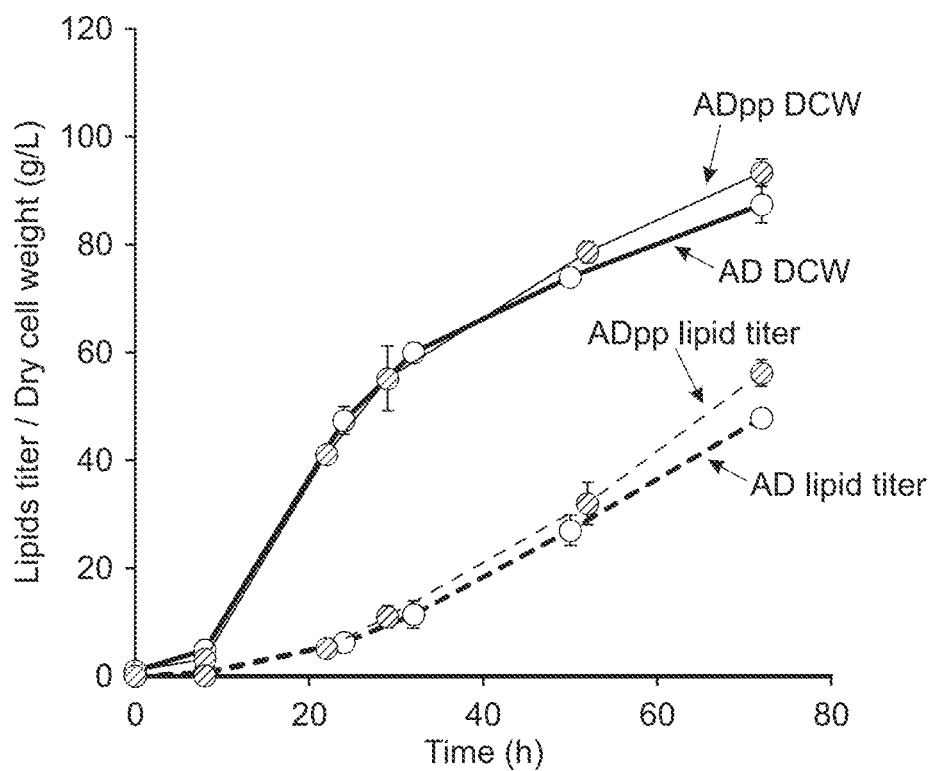

Instead of NADPH, the 9 excess NADH.c can also be utilized to form acetyl-CoA. The recently reported non-oxidative glycolytic (NOG) pathway can be activated to synthesize 3 mol acetyl-CoA from 1 mol glucose, by-passing the Embden-Meyerhof-Parnas (EMP) pathway that generates NADHs and ATPs[35] (FIG. 12). To activate the NOG pathway in *Y. lipolytica*, two enzymes, phosphoketolase from *Leuconostoc mesenteroides* and phosphate acetyltransferase from *Clostridium kluyveri*, were co-expressed in the genetic background of AD[36]. The resultant strain ADpp exhibited accelerated growth and lipid production in shake flask fermentations, as indicated by the elevated dry cell weight and lipid content (FIG. 3a). The ADpp exhibited a slight advantage over AD in terms of cell growth and lipid production in bioreactor fermentations (FIG. 3c). The lipid yields from shake flask and bioreactor runs were moderately increased (FIG. 3b). However, the maximum yield obtained during the lipid production phase remained lower than 0.271 g/g, making it inconclusive whether the NOG pathway actually helped increase $Y_L$ experimentally (FIG. 13).

To further improve the competitiveness of the NADPH-dependent GPD pathway and the carbon flux through the synthetic, NADPH-producing, pathway branch, another copy of GapC or GPD1 was introduced into ADgapc to yield strains ADgapc2 and ADgg. However, despite the higher transcriptional levels of the heterologous GPDs, neither of these strains showed a significant improvement in lipid yield under shake flask culturing conditions (columns 5, 6 and 7 in FIG. 4b and FIG. 4c). We also examined whether increasing the supply of cofactor NADP would strengthen the catalytic efficiency of NADPH-dependent GPDs. The NAD⁺/NADH kinases, which catalyze the final committed step of NADP biosynthesis, were overexpressed. Like *S. cerevisiae*, *Y. lipolytica* harbors three isoforms of NAD⁺/NADH kinases named after their well-characterized *S. cerevisiae* counterparts[37,38]: ylUTR1, ylYEF and ylPOS5 (Table 4). Overexpression of these kinases has been demonstrated previously to benefit the formation of metabolic products, such as polyhydroxybutyrates in *E. coli*[39]. As it was unknown which kinase is functionally involved in the biosynthesis of NADP in the cytosol of *Y. lipolytica*, each of the three kinases were individually overexpressed in the background of AD. This led to the identification of functional cytosolic NAD⁺/NADH kinase ylYEF as the one that can significantly improve lipid yield in *Y. lipolytica* (columns 1 and 3 in FIG. 4c). Co-expression of functional ylYEF and GapC led to a modest increase in process yield (column 8 in FIG. 4c). Finally, co-expression of GapC and MCE2, which enables the combination of the two orthogonally functional synthetic pathways interconverting NADH to NADPH, further increased the yield to 0.231 g/g (column 5, 9 in FIG. 4c).

Bioreactor Fermentation Performance and Optimization of Engineered *Y. lipolytica*

We proceeded to characterize the two best performers ADgy and ADgm in bioreactors and showed that both strains exhibit similar time courses for growth and elevated lipid production in comparison to the baseline strain AD (FIG. 5a). In the strains with increased supply of cytosolic NADPH, not only the specific productivity but also the lipid content was improved, leading to significantly increased overall process yields (FIG. 5c). Notably, the final process yield of strain ADgm was approximately 0.284 g/g, exceeding the theoretical maximum $Y_L$ of baseline strain AD. A yield above the theoretical maximum is possible only through the partial use of the pathways that increases NADH utilization.

We hypothesized that during the lipid production phase, nearly half of NADHs in strain ADgm are converted to NADPH, which is consumed in fatty acid synthesis instead of cellular respiration. This hypothesis was evidenced by the gradually elevated dissolved oxygen level in the lipid production phase of ADgm in comparison to AD while maintaining constant air supply and agitation speed (FIGS. 14a and 14b). To match the decreased specific oxygen consumption rate, instead of decreasing agitation speed, we tried to increase the cell concentration by doubling the initial concentration of ammonium sulfate to 17.6 g/L, which would benefit the production of lipids in terms of titer and productivity (FIG. 14c). As a result, a 67.4% increase in biomass was observed, elevating respectively the FAME titer and productivity to 99 g/L and 1.3 g/L/h, both of which are the highest levels reported to date (FIG. 5b). Notably, the yield of ADgm is slightly decreased to 0.274 g/g, which was a result of a decrease in the lipid content from 73.5% to 68.6% (Table 6).

Synthetic Pathway Efficiency

It should be noted that, as with the pentose phosphate pathway, each of the introduced synthetic pathways creates a bypass pathway that competes with the native glycolytic pathway (FIG. 4a). If operated at 100% capacity, or, in other words, if all carbon flux were diverted through the bypass synthetic pathway, the latter would enable complete conversion of NADH from glycolysis to either NADPH or acetyl-CoA, elevating the lipid pathway yield, $Y_L$, to 0.311 g/g and 0.335 g/g, respectively. However, in the presence of the native pathways, only a fraction of the total flux will be captured by the synthetic pathway; hence, only a fraction of the available NADH supply will become available for lipid synthesis. Therefore, the performance of the engineered cells in terms of process yield will depend on the fraction of the carbon flux that has been drawn into the synthetic pathway. We define the fraction of carbon flux into the synthetic pathway as Pathway Efficiency E. Using experimentally determined values for $Y_B$ and C, upper and lower bounds can be calculated for $Y_L$ assuming 100% and 0% capacity of the corresponding synthetic pathway. These would define the maximum and baseline process yields $Y_m$ and $Y_b$, respectively, calculated using the established model (Equation 3). The corresponding pathway efficiency E can then be calculated from equation (4):

$$E = \frac{Y - Y_b}{Y_m - Y_b} \quad (4)$$

Using this equation, the efficiency of each synthetic pathway was determined as shown in Table 6. The E of ADgapc was shown to be 21%, while the engineered POM cycle was demonstrated to operate at above 50%. Interestingly, E of NOG pathway is −11.2%, indicating that the improvement in $Y_B$ and C is more than sufficient to explain the Y improvement. Notably, the two synthetic pathways installed in strain ADgm featured a collective E of 99%, suggesting the POM cycle and GPD recycled nearly 100% of NADH.c into NADPH. Alternatively, NADH.m may also be used to produce NADPH in the POM cycle if malate that is formed by reduction of OAA in the mitochondria is shuttled out of the mitochondria (FIG. 9d). If this is the case, a lower E value of 61.2% is obtained as $Y_L$ is increased to 0.329 g/g. Clearly, a high process yield is indicative of a high pathway efficiency and vice versa.

Discussion

Table 1 summarizes the strain construction and the rationale for each genetic modulation performed, the obtained performance and the calculated pathway efficiency for each strain. Clearly, overall lipid process yield Y is closely correlated with pathway efficiency (FIG. 15). Increasing pathway efficiency is achieved by improving competitiveness of synthetic pathways, as demonstrated by the examples provided in this report. Alternatively, even higher process yields are attainable by deleting the native pathways in *Y. lipolytica* that compete with the synthetic bypasses, assuming that this can be done without impairing the cell growth and physiology.

With the established yield model, $Y_L$ was determined to be the most promising target to optimize Y. Optimizations of $Y_L$ heavily capitalize on the understanding of the cell metabolism—not only anabolism but also, to a greater extent, catabolism. Experiments carried out here provide evidence that improvements of $Y_L$ through recycling the surplus of NADH.c to NADPH significantly benefit Y. On top of reported strategies, further improvements of $Y_L$ are expected from harvesting excess NADH.m (FIG. 6). In contrast to NADH.c, NADH.m needs to be shuttled to the cytosol before it can be converted to NADPH. The inner membrane of the mitochondrion is impermeable to NADH but permeable to metabolites, such as malate or isocitrate, which can be oxidized by $NADP^+$-dependent malic enzyme and isocitrate dehydrogenase, respectively, to yield NADPH.c. Conversion of NADH.m to NADPH.c can therefore be achieved by constructing POM cycle (FIG. 9d) or citrate/isocitrate/2-ketoglutarate (CIK) cycle[40] across the mitochondrial membrane. Though still inconclusive, the E of ADgm (99.1±2.5%) indicates that POM cycle by itself might be sufficient. Undoubtedly, incorporating efficient malate transporters shuttling malate out of mitochondrion will help fully realize POM cycle's potential[41]. Furthermore, generation of NADH.m by pyruvate decarboxylation can be by-passed via the introduction of *E. coli* pyruvate formate lyase (PFL), which cleaves pyruvate into acetyl-CoA and formate in the cytosol. The formate can be subsequently oxidized by $NADP^+$-dependent formate dehydrogenases (FDH) to give NADPH (FIG. 16). However, *E. coli* PFL had been demonstrated to be extremely sensitive to oxygen[42]. To make it compatible with *Y. lipolytica*, the PFL has to be engineered to improve oxygen tolerance. Alternatively, *Y. lipolytica* could be engineered to adapt to anaerobic conditions.

By combining the genetic modifications that enable recycling of NADH.c and NADH.m, a maximum stoichiometric yield of 0.351 g/g, accounting for 96% of the maximum thermodynamic yield (0.364 g/g), could potentially be reached (FIG. 16). The genetic modulations described in this work spanned the full yield $Y_L$ spectrum between 0.20 and 0.351 g/g, which is the theoretical stoichiometric maximum. There may be other modulations that increase the overall lipid yield. However, these other constructs will follow the specified constraints defined by the presented model (Eqn. 2). Besides $Y_L$, the developed model also identified lipid content C as an influential parameter for engineering strains toward high Y (FIG. 7). However, at high lipid contents the catalytic efficiency of *Y. lipolytica* declines due to deteriorated biosynthesis machinery and induced autophagy-related proteolysis of proteins, particularly metabolic enzymes, under nitrogen starvation conditions[13,15,43]. Therefore, after achieving a certain lipid content, the loss in productivity and very long times required for further lipid synthesis become prohibitive. A tradeoff between C and productivity should be considered and analyzed.

The major challenge in aerobic fermentation at industrial scale is maintaining adequate level of dissolved oxygen (dO$_2$) to guarantee the cell growth and productivity. In fed-batch fermentations of *Y. lipolytica*, high dO$_2$ level was found to induce growth and citrate production while de novo fatty acid synthesis was drastically inhibited under microaerobic or anaerobic conditions (FIG. 17). Therefore, to maximize lipid yield in bioreactor, dO$_2$ levels have to be carefully controlled. In a nitrogen-limited culture, the amount of nitrogen in the starting medium determines cell concentration, positively contributing to the lipid titer and productivity. In comparison to wild type or baseline strain AD, another general feature shared by the engineered *Y. lipolytica* strains is reduced oxygen consumption rate, as exemplified by the dO$_2$ level of ADgm (FIG. 14). This is because in the engineered strains with high synthetic pathway efficiencies the majority of NADH is converted to NADPH and therefore less oxygen is required to support oxidative respiration for regeneration of NAD from NADH. To fully take advantage of the strain feature, the starting concentration of nitrogen was titrated and optimized Consequently, in the fed-batch fermentation of the best performer ADgm and resulted in a titer of 99 g/L, productivity of 1.2 g/L/h and yield of 0.274 g/g (Table 6). Those fermentation characteristics reported here are substantially higher than any other work reported in literature (Table 6 and Table 7). The lipid productivity of ADgm in bioreactor is close to doubling the highest reported (0.7 g/L/h) in literature and the titer. Notably, the figures of merit-titer, yield and productivity of FAME, for the first time, fulfill the requirements (90 g/L, 1.3 g/L/h and 0.284 g-FAs/g-sugars) determined by NREL to support the DOE's 2017 cost goal of $5/gallon gasoline equivalent[44]. Undoubtedly, with the technological maturation of hydrolyzing lignocellulosic feedstocks, finally, require engineering *Y. lipolytica* toward efficient utilization of industrial feedstock, in particular, ligocellulosic biomass, will be the next focus to fully realize its potential for commercial application for biodiesel production.

Finally, the model and experimental results reported here can be extended to help build cost-effective processes for bio-manufacturing not only of biodiesel and other fatty acid based lipids, such as eicosapentaenoic acid[19] and biosurfactants[45], but also a variety of other biochemical products, including polyketides, terpenoids, and polyhydroxyalkanoates, whose biosynthesis relies on acetyl-CoA, ATP and NADPH. Moreover, the fortification of NADPH pools can improve the robustness of yeast cells by endogenous defense mechanisms against reactive oxygen species[46] and toxic byproducts released from deconstruction of biomass, for example furfural[47].

REFERENCES

1. Ma, F. R. & Hanna, M. A. Biodiesel production: a review. *Bioresource technology* 70, 1-15 (1999).
2. Hill, J., Nelson, E., Tilman, D., Polasky, S. & Tiffany, D. Environmental, economic, and energetic costs and benefits of biodiesel and ethanol biofuels. *P Natl Acad Sci USA* 103, 11206-11210 (2006).
3. Sitepu, I. R. et al. Oleaginous yeasts for biodiesel: Current and future trends in biology and production. *Biotechnol Adv* 32, 1336-1360 (2014).
4. Jin, M. et al. Microbial lipid-based lignocellulosic biorefinery: feasibility and challenges. *Trends in biotechnology* 33, 43-54 (2015).
5. Dellomonaco, C., Clomburg, J. M., Miller, E. N. & Gonzalez, R. Engineered reversal of the beta-oxidation cycle for the synthesis of fuels and chemicals. *Nature* 476, 355-359 (2011).
6. Steen, E. J. et al. Microbial production of fatty-acid-derived fuels and chemicals from plant biomass. *Nature* 463, 559-562 (2010).
7. Runguphan, W. & Keasling, J. D. Metabolic engineering of *Saccharomyces cerevisiae* for production of fatty acid-derived biofuels and chemicals. *Metabolic engineering* 21, 103-113 (2014).
8. Williams, P. J. L. & Laurens, L. M. L. Microalgae as biodiesel & biomass feedstocks: Review & analysis of the biochemistry, energetics & economics. *Energ Environ Sci* 3, 554-590 (2010).
9. Machado, I. M. & Atsumi, S. Cyanobacterial biofuel production. *Journal of biotechnology* 162, 50-56 (2012).
10. Sheng, J. & Feng, X. Metabolic engineering of yeast to produce fatty acid-derived biofuels: bottlenecks and solutions. *Frontiers in microbiology* 6, 554 (2015).
11. Abghari, A. & Chen, S. *Yarrowia lipolytica* as an oleaginous cell factory platform for the production of fatty acid-based biofuel and bioproducts. *Frontiers in Energy Research* 2 (2014).
12. Liang, M. H. & Jiang, J. G. Advancing oleaginous microorganisms to produce lipid via metabolic engineering technology. *Prog Lipid Res* 52, 395-408 (2013).
13. Tai, M. & Stephanopoulos, G. Engineering the push and pull of lipid biosynthesis in oleaginous yeast *Yarrowia lipolytica* for biofuel production. *Metabolic engineering* 15, 1-9 (2013).
14. Dulermo, T. et al. Characterization of the two intracellular lipases of *Y. lipolytica* encoded by TGL3 and TGL4 genes: New insights into the role of intracellular lipases and lipid body organisation. *Bba-Mol Cell Biol L* 1831, 1486-1495 (2013).
15. Blazeck, J. et al. Harnessing *Yarrowia lipolytica* lipogenesis to create a platform for lipid and biofuel production. *Nature communications* 5, 3131 (2014).
16. Seip, J., Jackson, R., He, H. X., Zhu, Q. & Hong, S. P. Snf1 Is a Regulator of Lipid Accumulation in *Yarrowia lipolytica*. *Appl Environ Microb* 79, 7360-7370 (2013).
17. Qiao, K. et al. Engineering lipid overproduction in the oleaginous yeast *Yarrowia lipolytica*. *Metabolic engineering* 29, 56-65 (2015).
18. Ratledge, C. & Cohen, Z. Microbial and algal oils: Do they have a future for biodiesel or as commodity oils? *Lipid Technology* 20, 155-160 (2008).
19. Xue, Z. X. et al. Production of omega-3 eicosapentaenoic acid by metabolic engineering of *Yarrowia lipolytica*. *Nature biotechnology* 31, 734-+(2013).
20. Ramage, M. & Katzer, J. Liquid transportation fuels from coal and biomass: technological status, costs, and environmental impacts. *America's Energy Future Panel on Alternative Liquid Transportation Fuels, National Research Council* (2009).
21. Ratledge, C. Regulation of lipid accumulation in oleaginous micro-organisms. *Biochemical Society transactions* 30, 1047-1050 (2002).
22. Wasylenko, T. M., Ahn, W. S. & Stephanopoulos, G. The oxidative pentose phosphate pathway is the primary source of NADPH for lipid overproduction from glucose in *Yarrowia lipolytica*. *Metabolic engineering* 30, 27-39 (2015).
23. Dugar, D. & Stephanopoulos, G. Relative potential of biosynthetic pathways for biofuels and bio-based products. *Nature biotechnology* 29, 1074-1078 (2011).

24. Xu, P. et al. Modular optimization of multi-gene pathways for fatty acids production in *E. coli*. *Nature communications* 4, 1409 (2013).
25. Sauer, U., Canonaco, F., Heri, S., Perrenoud, A. & Fischer, E. The soluble and membrane-bound transhydrogenases UdhA and PntAB have divergent functions in NADPH metabolism of *Escherichia coli*. *J Biol Chem* 279, 6613-6619 (2004).
26. Anderlund, M. et al. Expression of the *Escherichia coli* pntA and pntB genes, encoding nicotinamide nucleotide transhydrogenase, in *Saccharomyces cerevisiae* and its effect on product formation during anaerobic glucose fermentation. *Appl Environ Microbiol* 65, 2333-2340 (1999).
27. Martinez, I., Zhu, J., Lin, H., Bennett, G. N. & San, K. Y. Replacing *Escherichia coli* NAD-dependent glyceraldehyde 3-phosphate dehydrogenase (GAPDH) with a NADP-dependent enzyme from *Clostridium acetobutylicum* facilitates NADPH dependent pathways. *Metabolic engineering* 10, 352-359 (2008).
28. Verho, R. et al. Identification of the first fungal NADP-GAPDH from *Kluyveromyces lactis*. *Biochemistry* 41, 13833-13838 (2002).
29. Wojtatowicz, M., Rymowicz, W. & Kautola, H. Comparison of different strains of the yeast *Yarrowia lipolytica* for citric acid production from glucose hydrol. *Applied biochemistry and biotechnology* 31, 165-174 (1991).
30. Zhang, H. et al. Regulatory properties of malic enzyme in the oleaginous yeast, *Yarrowia lipolytica*, and its non-involvement in lipid accumulation. *Biotechnology letters* 35, 2091-2098 (2013).
31. Dulermo, T. et al. Analysis of ATP-citrate lyase and malic enzyme mutants of *Yarrowia lipolytica* points out the importance of mannitol metabolism in fatty acid synthesis. *Biochimica et biophysica acta* (2015).
32. Liang, Y. J. & Jiang, J. G. Characterization of malic enzyme and the regulation of its activity and metabolic engineering on lipid production. *Rsc Adv* 5, 45558-45570 (2015).
33. Li, Z. et al. Overexpression of malic enzyme (ME) of *Mucor circinelloides* improved lipid accumulation in engineered *Rhodotorula glutinis*. *Applied microbiology and biotechnology* 97, 4927-4936 (2013).
34. Hao, G. et al. Role of malic enzyme during fatty acid synthesis in the oleaginous fungus *Mortierella alpina*. *Appl Environ Microbiol* 80, 2672-2678 (2014).
35. Bogorad, I. W., Lin, T. S. & Liao, J. C. Synthetic non-oxidative glycolysis enables complete carbon conservation. *Nature* 502, 693-697 (2013).
36. Lee, J. M. et al. Cloning and characterization of the gene encoding phosphoketolase in *Leuconostoc mesenteroides* isolated from kimchi. *Biotechnology letters* 27, 853-858 (2005).
37. Iwahashi, Y., Hitoshio, A., Tajima, N. & Nakamura, T. Characterization of NADH kinase from *Saccharomyces cerevisiae*. *Journal of biochemistry* 105, 588-593 (1989).
38. Shianna, K. V., Marchuk, D. A. & Strand, M. K. Genomic characterization of POS5, the *Saccharomyces cerevisiae* mitochondrial NADH kinase. *Mitochondrion* 6, 94-101 (2006).
39. Li, Z. J., Cai, L., Wu, Q. & Chen, G. Q. Overexpression of NAD kinase in recombinant *Escherichia coli* harboring the phbCAB operon improves poly(3-hydroxybutyrate) production. *Applied microbiology and biotechnology* 83, 939-947 (2009).
40. Ratledge, C. The role of malic enzyme as the provider of NADPH in oleaginous microorganisms: a reappraisal and unsolved problems. *Biotechnology letters* 36, 1557-1568 (2014).
41. Casal, M., Paiva, S., Queiros, O. & Soares-Silva, I. Transport of carboxylic acids in yeasts. *FEMS microbiology reviews* 32, 974-994 (2008).
42. Wagner, A. et al. The free radical in pyruvate formate-lyase is located on glycine-734. *Proc Natl Acad Sci USA* 89, pp. 996 (1992).
43. Zhu, Z. et al. A multi-omic map of the lipid-producing yeast *Rhodosporidium toruloides*. *Nature communications* 3, 1112 (2012).
44. Davis, R. et al. Process Design and Economics for the Conversion of Lignocellulosic Biomass to Hydrocarbons: Dilute-Acid and Enzymatic. (2015).
45. Banat, I. M. Biosurfactants Production and Possible Uses in Microbial Enhanced Oil-Recovery and Oil Pollution Remediation—a Review. *Bioresource technology* 51, 1-12 (1995).
46. Moradas-Ferreira, P., Costa, V., Piper, P. & Mager, W. The molecular defences against reactive oxygen species in yeast. *Molecular Microbiology* 19, 651-658 (1996).
47. Wang, X. et al. Engineering furfural tolerance in *Escherichia coli* improves the fermentation of lignocellulosic sugars into renewable chemicals. *P Natl Acad Sci USA* 110, 4021-4026 (2013).
48. Gibson, D. G. et al. Enzymatic assembly of DNA molecules up to several hundred kilobases. *Nat Methods* 6, 343-U341 (2009).
49. Puigbo, P., Guzman, E., Romeu, A. & Garcia-Vallve, S. OPTIMIZER: a web server for optimizing the codon usage of DNA sequences. *Nucleic acids research* 35, W126-131 (2007).
A1. Strand, M. K. et al. POS5 gene of *Saccharomyces cerevisiae* encodes a mitochondrial NADH kinase required for stability of mitochondrial DNA. *Eukaryotic cell* 2, 809-820 (2003).
A2. Kawai, S., Suzuki, S., Mori, S. & Murata, K. Molecular cloning and identification of UTR1 of a yeast *Saccharomyces cerevisiae* as a gene encoding an NAD kinase. *Ferns Microbiol Lett* 200, 181-184 (2001).
A3. Shi, F., Kawai, S., Mori, S., Kono, E. & Murata, K. Identification of ATP-NADH kinase isozymes and their contribution to supply of NADP(H) in *Saccharomyces cerevisiae*. *Febs J* 272, 3337-3349 (2005).
A4. Tai, M. & Stephanopoulos, G. Engineering the push and pull of lipid biosynthesis in oleaginous yeast *Yarrowia lipolytica* for biofuel production. *Metabolic engineering* 15, 1-9 (2013).
A5. Tai, M. (Massachusetts Institute of Technology, 2012).
A6. Qiao, K. et al. Engineering lipid overproduction in the oleaginous yeast *Yarrowia lipolytica*. *Metabolic engineering* 29, 56-65 (2015).
A7. Verduyn, C. Physiology of yeasts in relation to biomass yields. *Antonie van Leeuwenhoek* 60, 325-353 (1991).
A8. Wasylenko, T. M., Ahn, W. S. & Stephanopoulos, G. The oxidative pentose phosphate pathway is the primary source of NADPH for lipid overproduction from glucose in *Yarrowia lipolytica*. *Metabolic engineering* 30, 27-39 (2015).
A9. Ratledge, C. The role of malic enzyme as the provider of NADPH in oleaginous microorganisms: a reappraisal and unsolved problems. *Biotechnology letters* 36, 1557-1568 (2014).

A10. Dugar, D. & Stephanopoulos, G. Relative potential of biosynthetic pathways for biofuels and bio-based products. *Nature biotechnology* 29, 1074-1078 (2011).

A11. Liu, L., Pan, A., Spofford, C., Zhou, N. & Alper, H. S. An evolutionary metabolic engineering approach for enhancing lipogenesis in *Yarrowia lipolytica*. *Metabolic engineering* 29, 36-45 (2015).

A12. Li, Y. H., Zhao, Z. B. & Bai, F. W. High-density cultivation of oleaginous yeast Rhodosporidium toruloides Y4 in fed-batch culture. *Enzyme Microb Tech* 41, 312-317 (2007).

A13. Abghari, A. & Chen, S. *Yarrowia lipolytica* as an oleaginous cell factory platform for the production of fatty acid-based biofuel and bioproducts. *Frontiers in Energy Research* 2 (2014).

Example 2

Engineering Redox Homeostasis and Aldehyde Detoxification for Efficient Lipid Production in Oleaginous Yeast Global energy demand and environmental concerns have stimulated increasing efforts to produce carbon-neutral fuels directly from renewable resources. Microbially derived fatty acids fuels, the petroleum-replica fuels, have emerged as promising alternatives to meet this challenge. This is because fatty acid-based fuels offer several unique advantages such as higher energy density, lower hygroscopicity, miscible with diesel fuels, reduced purification costs and compatible with existing infrastructure [B1]. As such, extensive efforts have been made to engineer various microbes to produce lipids[B2, B3], fatty alcohols[B4], fatty acids[B5, B6], fatty alkyl esters[B7-B9] and aliphatic alkanes[B4, B10]. Most of the work involves engineering bacterial or baking yeast with relatively low titer (<8.6 g/L) [B5] and productivity (<0.25 g/L/h) [B11], which to some extent obscures our long-term goals for cost-efficient and large-scale production.

Recently, microbially derived lipids and oils have attracted wide attentions as they may serve as biorefinery platform chemicals for sustainable production of diesel fuels and oleochemicals via simple chemical- or bio-transformation steps[B12, B13]. Particularly, the choice of engineering hosts has been shifting from traditional microbes (*E. coli* and *S. cerevisiae*) to oleaginous microbes. We chose to engineer the oleaginous yeast *Y. lipolytica* as this species is able to naturally accumulate large quantity of neutral lipids, utilize a broad range of carbon resources and has facile genetic tools that allow for reliable pathway modification [B14].

In our previous efforts, engineering the acetyl-CoA carboxylase (ACC), fatty acyl-CoA sequestration pathways and removal of ACC inhibition have resulted in efficient TAG (triacylglycerides) producers with titer and yield up to 55 g/L and 0.23 g/g[B15, B16]. Engineering the lipogenesis and amino acid degradation pathways coupled with flocculation evolution in a similar cell line has led to TAG production up to 39.1 g/L[B17, B18]. Despite of the pathway level achievements, further development of efficient lipid producers hinges upon systematic investigation of lipogenesis mechanisms and improving cellular stress fitness. Specifically, lipogenesis in oleaginous yeast is triggered by nitrogen starvation, which has been linked with global physiological changes and many cellular stress responses[B19, B20]. One primary stress response is associated with elevated level of reactive oxygen species arising from lipid oxidation and peroxidation[B21]. Lipids, the naturally occurring molecules with polyunsaturated fatty acids as major components, are highly susceptible to free radical attack via a chain reaction mechanism (FIGS. 18*a* and 18*b*). Lipid peroxide can undergo further autolysis and generate reactive aldehydes (FIG. 18*c* and FIG. 18*d*). These membrane-permeable, highly electrophilic radicals can attack the nucleophilic center of many bioactive molecules and elicit a serial of cellular events including cell aging[B22], DNA replication damage [B23] and protein modifications (primarily carbonylation caused by reactive aldehyde attacking lysine, histidine, and cysteine residues) [B24]. Consequently, cellular oxidative stress may reduce cell viability, deactivate critical enzymes and lead to pathway inefficiency. Therefore, it is worthwhile to investigate how oleaginous yeast acclimates to high levels of oxidative stress and whether manipulation of oxidative tolerance could inform novel strategies to improve lipid production further.

In this study, we report the reverse engineering of *Y. lipolytica* to improve its oxidative stress fitness and developed phenotypic engineering strategies that are critical to build an efficient microbial oil factory. Up-regulation of oxidative stress defense pathways and detoxification of reactive aldehydes effectively removed lipotoxicity and altered cell morphology, leading to efficient lipid biosynthesis. The engineered yeast cell factory demonstrated superior lipogenic capacity in terms of lipid production and oil content. The phenotypic engineering strategies reported here could be translated to engineering other oleaginous species facilitating the cost-efficient production of lipids and oleochemicals.

Materials and Methods

Yeast Strains, Growth, and Culture Conditions

The *Y. lipolytica* wild type strain W29 was purchased from ATCC (ATCC20460). The auxotrophic Po1g (Leu-) was obtained from Yeastern Biotech Company (Taipei, Taiwan). All strains and plasmids used in this study are listed in Table 8.

TABLE 8

Strains and plasmids used in this study

| Strain or plasmid | Relevant properties or genotype | Source |
|---|---|---|
| Strain | | |
| NEB 5-α | fhuA2 Δ(argF-lacZ)U169 phoA glnV44 Φ80 Δ(lacZ)M15 gyrA96 recA1 relA1 endA1 thi-1 hsdR17 | NEB |
| po1g | MATa, leu2-270, ura3-302::URA3, xpr2-3 | Yeastem |
| YL-wt | Po1g, ylex (LEU2) | [B15] |
| MTYL065 | Po1g with pMT065 (LEU2, h4pd-ACC1, TEFin-DGA1) | [B15] |
| AD Δura3 | MTYL065, ΔURA3 | Lab stock |
| ADS | AD Δura3 with pYLXP-ylUra3-ylSOD1 | This study |
| ADGG | AD Δura3 with pYLXP-ylUra3-ylGSR-ylGPO | This study |
| ADA | AD Δura3 with pYLXP-ylUra3-EcAldH | This study |
| ADAT | AD Δura3 with pYLXP-ylUra3-EcAldH-ylTRX | This study |
| ADZ | AD Δura3 with pYLXP-ylUra3-ScZwf | This study |
| ADAZ | AD Δura3 with pYLXP-ylUra3-EcAldH-ScZwf | This study |
| ADZT | AD Δura3 with pYLXP-ylUra3-ScZwf-ylTRX | This study |
| ADAZT | AD Δura3 with pYLXP-ylUra3-EcAldH-ScZwf-ylTRX | This study |
| ADZGG | AD Δura3 with pYLXP-ylUra3-ScZwf-ylGSR-ylGPO | This study |
| ADAGG | AD Δura3 with pYLXP-ylUra3-EcAldH-ylGSR-ylGPO | This study |
| ALDH | AD Δura3 with pYLXP-ylUra3-EcAldH-ScZwf-ylGSR-ylGPO | This study |

TABLE 8-continued

Strains and plasmids used in this study

| Strain or plasmid | Relevant properties or genotype | Source |
|---|---|---|
| | Plasmid | |
| pMT015 | YLEX derivative with hp4d promoter replaced with TEF intron promoter | [B15] |
| pYLXP' | Modified pMT015 with ePathBrick feature | This study |
| pYLXP | pYLXP' with additional SpeI site mutated | This study |
| pYLXP-ylSOD1 | pYLXP carrying *Y. lipolytica* SOD1 (YALI0E12133p) | This study |
| pYLXP-ylGPO | pYLXP carrying *Y. lipolytica* GPO (YALI0E02310p) | This study |
| pYLXP-ylGSR | pYLXP carrying *Y. lipolytica* GSR (YALI0E18029p) | This study |
| pYLXP-ylTRX | pYLXP carrying *Y. lipolytica* TRX (YALI0D27126p) | This study |
| pYLXP-ScZwf | pYLXP carrying *S. cerevisize* Zwf1 (YNL241C) | This study |
| pYLXP-ylUra3 | pYLXP carrying *Y. lipolytica* Ura3 (YLU40564) | This study |
| pYLXP-EcAldH | pYLXP carrying *E. coli* AldH (EG10036) | This study |
| pYLXP-ylUra3-ylSOD1 | pYLXP carrying ylUra3 and ylSOD1 | This study |
| pYLXP-ylUra3-ylGSR | pYLXP carrying ylUra3 and ylGSR | This study |
| pYLXP-ylUra3-ylGSR-ylGPO | pYLXP carrying ylUra3, ylGSR and ylGPO | This study |
| pYLXP-ylUra3-EcAldH | pYLXP carrying ylUra3 and EcAldH | This study |
| pYLXP-ylUra3-ScZwf | pYLXP carrying ylUra3 and scZwf | This study |
| pYLXP-ylUra3-ylTRX | pYLXP carrying ylUra3 and ylTRX | This study |
| pYLXP-ylUra3-ScZwf-ylTRX | pYLXP carrying ylUra3, ScZwf and ylTRX | This study |
| pYLXP-ylUra3-EcAldH-ScZwf | pYLXP carrying ylUra3, EcAldH and ScZwf | This study |
| pYLXP-ylUra3-EcAldH-ylTRX | pYLXP carrying ylUra3, EcAldH and ylTRX | This study |
| pYLXP-ylUra3-EcAldH-ScZwf-ylTRX | pYLXP carrying ylUra3, EcAldH, ScZwf and ylTRX | This study |
| pYLXP-ylUra3-EcAldH-ylGSR-ylGPO | pYLXP carrying ylUra3, EcAldH, ylGSR and ylGPO | This study |
| pYLXP-ylUra3-EcAldH-ScZwf-ylGSR-ylGPO | pYLXP carrying ylUra3, EcAldH, ScZwf, ylGSR and ylGPO | This study |

LB broth or agar plate with 100 µg/mL ampicillin was used to cultivate *E. coli* strain. Yeast rich medium (YPD) was prepared with 20 g/L Bacto peptone (Difco), 10 g/L yeast extract (Difco), 20 g/L glucose (Sigma-Aldrich). YPD agar plates were YPD liquid media supplemented with 15 g/L Bacto agar (Difco). YNB medium was made with 1.7 g/L yeast nitrogen base (without amino acids and ammonium sulfate) (Difco), 5 g/L Ammonium Sulfate (Sigma-Aldrich), 0.69 g/L CSM-Leu (Sunrise Science Products, Inc.) or 0.67 g/L CSM-Leu-Ura (Sunrise Science), and 20 g/L glucose. Selective YNB plates were YNB liquid media supplemented with 15 g/L Bacto agar (Difco).

Shake flask fermentation media contains 1.7 g/L yeast nitrogen base (without amino acids and ammonium sulfate), 1.32 g/L ammonium sulfate, and 60 g/L glucose. Single *Yarrowia* colonies were picked up from YNB selective pates and inoculated into YPD media and grown at 30° C. overnight. Overnight cultures were inoculated into 40 mL of media in 250 mL shake flask with an initial cell density (OD600) of 0.08 and allowed to grow for 125 h (250 rpm, 30° C.). Time series samples were taken for analyzing biomass, sugar content, and lipid titer.

Plasmid and Pathway Construction

All primers are listed in Table 9.

TABLE 9

Primers used in this study. All primers are synthesized from Integrated DNA Technologies (IDT).

| Primer name | SEQ ID NO | Sequence (5' > 3') |
|---|---|---|
| Spe_SF | 112 | GCCGCATAGGCCAATAGTGGATCTGCTG |
| spe_SR | 113 | CAGCAGATCCACTATTGGCCTATGCGGC |
| EcaldH_F | 114 | cgaccagcacttttgcagtactaaccgcagAATTTTCATCATCTGGCTTACTGGC |
| EcaldH_R | 115 | ggccatggaactagtcggtaccTCAGGCCTCCAGGCTTATCC |
| EcaldH_V | 116 | CCAGACGCGTTTCATGTTGCT |
| ylGPO_F | 117 | ccgaccagcacttttgcagtactaaccgcagtccgccgagaaaaccaataccg |
| ylGPO_R | 118 | GGACAGGCCATGGAACTAGTCGGTACCTAGGGCTTTTTGAGGAGGGTCTC |
| ylGPO_Vf | 119 | GGGCCTTGAGGAGGTCTACCAGAAGT |
| Y1GPO_Vr | 120 | ACTTCTGGTAGACCTCCTCAAGGCCC |
| ylGSR_F | 121 | ccgaccagcacttttgcagtactaaccgcaggcttctatccccattatgactatc |

TABLE 9-continued

Primers used in this study. All primers are synthesized from Integrated DNA Technologies (IDT).

| Primer name | SEQ ID NO | Sequence (5' > 3') |
|---|---|---|
| y1GSR_R | 122 | GGACAGGCCATGGAACTAGTCGGTACCCTATCTCA TGGTCACCAGCTCC |
| y1GSR_Vr | 123 | AGCTCGCCATTGTCCTTCTTGAC |
| Y1GSR_Vf | 124 | AGGAGGCTACATTGGCGTGGAG |
| y1SOD_F | 125 | cgaccagcactttttgcagtactaaccgcaggtcaaggctgtcgctgttcttcgaggaga |
| y1SOD1_R | 126 | GGACAGGCCATGGAACTAGTCGGTACCTTAGGCGG TAAGACCAATGACA |
| y1SOD1_Vr | 127 | CAACACCCTCAGAGTCAGTCTTGACG |
| y1TRX_F | 128 | ccgaccagcactttttgcagtactaaccgcagacccacagcccagttgttatcat |
| y1TRX_R | 129 | GGACAGGCCATGGAACTAGTCGGTACCCTATTCCTC CTCAGCAAGCAGCTTC |
| ScZwf_F | 130 | ccgaccagcactttttgcagtactaaccgcagagtgaaggccccgtcaaattcgaa |
| ScZwf_R | 131 | GGACAGGCCATGGAACTAGTCGGTACCCTAATTATCC TTCGTATCTTCTGGCTTAG |
| ScZwf_Vf | 132 | CCATTACTTGGGTAAAGAGTTGGTC |
| Y1Ura3_F | 133 | cgaccagcactttttgcagtactaaccgcagCCCTCCTACGAAGCT CGAGCTAACG |
| Y1Ura3_R | 134 | gacaggccatggaactagtggtaccCTAACAGTTAATCTTCTGGT AAGCCTCCCAG |

All restriction enzymes were purchased from Fisher Fast-Digest enzymes. Pfu Ultra (Agilent) DNA polymerase was used for site-directed mutagenesis PCR. Plasmid miniprep, PCR clean-up and gel DNA recovery were using Zyppy and Zymoclean kits purchased from Zymo research. *Escherichia coli* NEB 5-alpha (New England Biolab, NEB) was used for cloning and plasmid propagation. To facilitate gene cloning and assembly, *Yarrowia* vector pMT015 was modified to contain the ePathBrick vector feature [B54]. Specifically, a gene fragment (FIG. 29) containing TEF promoter, exon, incomplete intron, multiple cloning sites and XPR2 terminator with compatible enzyme sites (AvrII, XbaI, SpeI and NheI) interspaced between these elements was synthesized by Invitrogen. Then this synthetic fragment was digested with ClaI and XhoI and cloned into the ClaI and SalI digested pMT015 (note: XhoI and SalI are compatible ends) to give vector pYLXP'. Then the additional SpeI on pYLXP' were mutated with primers Spe_SF and Spe_SR using site-directed mutagenesis PCR to give vector pYLXP.

All candidate genes were amplified either from *E. coli* K-12, *S. cerevisiae* or *E lipolytica* W29 genomic DNA with Q5 hot start DNA polymerase (NEB). Primer pairs EcAldH_F and EcAldH_R, ylGPO_F and ylGPO_R, ylGSR_F and ylGSR_R, ylSOD1_F and ylSOD1_R, ylTRX_F and ylTRX_R, ScZwf_F and ScZwf_R, YlUra3_F and YlUra3_R were used to amplify aldehyde dehydrogenase (EcAldH), glutathione peroxidase (ylGPO), glutathione disulfide reductase (ylGSR), superoxide reductase (yl-SOD1), thioredoxin reductase (ylTRX), glucose-6-phosphate dehydrogenase (ScZwf) and orotidine 5-phosphate decarboxylase (ylUra3), respectively. PCR amplified genes were cleaned with Zymoclean kits and assembled into the SnaB1 and KpnI digested pYLXP vector using Gibson isothermal assembly. Positive transformants were verified by double digestion and further confirmed by DNA sequencing by Quintara Bioscience. Monocistronic gene organization with combinations of AldH, SOD1, GPO, GSR, TRX and/or ZWF1 and Ura3 were assembled following the ePathBrick assembly protocol [B55]. Specifically, AvrII and SalI digested donor vector (i.e. pYLXP-EcAldH) was inserted into the NheI and SalI digested recipient vector (i.e. pYLXP-ylUra3) to give the construct co-expressing two genes. Occasionally, BgIII, NotI or ClaI sites may be used to substitute SalI in case SalI cuts the structural gene. This assembly procedure can be iteratively used to create constructs with expression of multiple genes (up to seven or more).

All plasmids used in this study are listed in Table 8. Constructed vectors were transformed into *Y. lipolytica* AD Aura3 strain following the protocol reported by Chen et al [B56] and grown on CSM-leu-ura plates for transformants screening. Single colonies were grown in YPD media and genomic DNA was purified with Wizard genomic DNA kits (Promega) from the overnight culture. Verification PCR using GoTaq Green polymerase (Promega) was performed with purified genomic DNA as template to confirm the successful integration of candidate gene or pathway. All verification primers have also been listed in Table 9.

Bench-Top Bioreactor Optimization

Fermenter experiments were carried out in a 3-liter Bio-Flo stirred-tank bioreactor equipped with New Brunswick Biocommand control systems (Eppendorf). The media contained 3.4 g/L yeast nitrogen base (without amino acids and ammonium sulfate), 2.8 g/L ammonium sulfate, and 100 g/L glucose. *Yarrowia* frozen stock culture was inoculated into YPD media (250 rpm, 30° C.) and grown overnight to prepare seed culture. Exponential seed culture was aseptically transferred into bioreactor to an optical density (OD600) of 0.2 in the 3-L reactor (3 vvm, pH 6.8, 28° C. and 250 rpm). Dissolved oxygen was cascaded to the agitation and set as 20% throughout the fermentation (with 100% output set as 600 rpm). 50 mL 400 g/L sterile glucose was pulsed into bioreactor at 60 hour and 84 hour. Stepwise exponential feeding fermentation was performed with the initial media consisting of 3.4 g/L yeast nitrogen base, 4.4 g/L ammonium sulfate and 100 g/L glucose. Inoculation OD was adjusted to 0.5 with overnight seed culture. A mixture of carbon (400 g/L glucose) and nitrogen (8.8 g/L ammonium sulfate) source was fed into the bioreactor following a stepwise exponential pattern detailed in Table 10. All other operational procedures were the same as the batch bioreactor.

Table 10. Time profile of step-wise exponential glucose feeding pattern in the optimized bioreactor. Biocommand software systems response time is 16.67 s. Every hour the systems automatically multiple by 216 times. The feeding profile should follow the pattern $F(t)=F_0 \times K^{216t}$ (here t is hour and $F_0$ is the pump output, FIG. 27). 1% pump output corresponds to 3.2 mL/hour so the volume integration should follow $V(t)=3.2F_0 \times \int_0^t K^{216t} dt$. By manually control the doubling time (specific growth rate), we calculated the multiplication factor K.

| Time periods | Doubling time (1/hour) | Multiplication factor K |
|---|---|---|
| 20 h-32 h | 4 | 1.000802576 |
| 32 h-60 h | 8 | 1.000401207 |
| 60 h-90 h | 12 | 1.000267454 |
| 90 h-120 h | 20 | 1.000160464 |

Metabolites Extraction and Analysis

Time point samples were stored at −20° C. for lipid titer and glucose analysis. Sugar and organic acid content was quantified by Agilent 1260 HPLC equipped with a BioRad Aminex HPX-87h column and refractive index detector eluted with 14 mM sulfuric acid. Dry cell weight was determined using a Mettler analytical balance from samples dried at 60° C. for two nights. Four OD units of *Yarrowia* culture were taken for each sample to measure lipid titer. Lipid extraction and GC-FID quantification were carried out following a protocol reported by Qiao et al [B16].

Reactive oxygen species and total aldehydes quantification

Time Series *Yarrowia* Culture was Taken and Diluted to 0.3 OD Units in 1 mL PBS buffer. 2 μL of 2.5 mM CellRox green (Life Technologies) staining dye (contains DCFH-DA oxidative stress staining dye dissolved in DMSO, roughly 5 nmole of DCFH-DA for each sample) was added to the diluted cell and vortex and incubate at 37° C. for 1 hour. 300 μL of sample were used to quantify the relative level of reactive oxygen species with Molecular Device Multifunctional plate reader following the protocol described by Yilancioglu et al [B57]. Fluorescence data was read with the filter settings: excitation at 495 nm and emission at 530 nm.

To quantify reactive aldehyde species, cell pellets were collected by refrigerated centrifuge and resuspended in PBS buffer. Then a hand-hold electronic tissue disrupter was used to homogenize *Yarrowia* pellet. Then the homogenized culture were centrifuged at 4° C. and intracellular reactive aldehydes were measured from the supernatant with a fluorometric aldehyde assay kit from Sigma (MAK141-1KT) followed the instructions described with the kits. A standard aldehyde curve has been generated with this kit (FIG. 30).

Results

Validation of Oxidative Stress During Lipogenesis in Oleaginous Yeast

Our previous metabolic engineering efforts centering on the enhancement of malonyl-CoA flux and sequestration of fatty acyl-CoAs have led to efficient lipid producers with relatively high titer and yield[B15, B16]. Surprisingly, extracellular metabolites analysis revealed the concomitant secretion of mannitol (up to 10 to 40 mM) accompanying with lipid accumulation and glucose consumption (FIG. 23). Mannitol, a more reduced carbon resource contrasting with glucose, has been implicated in plant and fungal physiology as an oxidative stress and osmoprotectant signaling molecule[B25-B28]. It has been proposed that the stress-protective role of mannitol is to shield susceptible thiol-regulated enzymes from hydroxyl radical-induced inactivation and maintain redox homeostasis[B26]. Given the fact that fungal fermentation is highly aerobic in nature and lipids are our target molecule, we speculated that cellular reactive oxygen/aldehyde species arising from lipid oxidation and peroxidation may profoundly impact the lipogenic process in *Y. lipolytica*. Therefore, combating oxidative stress and elimination of lipotoxicity might be the critical control points to improve pathway efficiency.

Yeast cells utilize a number of universal defense pathways to scavenge reactive oxygen and aldehydes compounds [B29]. First we sought to screen a panel of metabolites and enzymes that have been reported to modulate the level of reactive oxygen and aldehyde species [B30]. Acetate, a C2 molecule that is primarily assimilated through peroxisomal glyoxylate pathway and the resulting C4 carboxylic acids (succinate and malate) are further oxidized through TCA cycle, has been reported to stimulate ROS generation in cell metabolism [B31]. Mannitol, an oxidative stress defense molecule that eliminates excess hydroxyl radical [B26], was also tested. Generally, the lipogenic potential of the engineered strain is reversely correlated with the level of reactive oxygen and aldehyde species (FIGS. 19c and 19d). For example, addition of 0.3 M sodium acetate (NaAC) elevated the level of ROS (FIG. 19d) and resulted in decreased lipid level and oil content (FIG. 19c). On the contrary, supplementation with 60 mM mannitol decreased the level of ROS (FIG. 19d) and led to increased lipid level and oil content (FIG. 19c). Expression of putative ROS-scavenging enzymes, superoxide dismutase (SOD1) and glutathione disulfide reductase (GSR) and glutathione peroxidase (GPO), improves both the lipid level and oil content in *Yarrowia* (FIG. 19c) up to 25-54%. Interestingly, expression of a heterologous aldehyde dehydrogenase (AldH), efficiently removed reactive aldehyde species (FIG. 19f) and remarkably improved lipid titer to 10.4 g/L and oil content to 90.5% in shake flasks (FIG. 19c), representing about 260% increase in titer and 230% increase in oil content when compared to the previously engineered AD strain [B15].

Both glutathione disulfide reductase (GSR) and thioredoxin reductase (Trx) require the coupling of NADPH as cofactors (FIGS. 19a and 19b). The oxidative pentose phosphate pathway has been implicated as the primary source of NADPH pathway in both *Y. lipolytica* and *S. cerevisiae*[B32, B33]. Coupling glucose-6-phosphate dehydrogenase (ZWF1) with AldH improves both lipid titer and oil content about 85% and 76% (FIG. 19e), respectively. Combined expression of AldH and ROS-scavenging pathways (ZWF1, Trx or GSR-GPO) further improved lipid titer and oil content by 15-28% (FIG. 19e). Hereafter, we denote the strain carrying both the aldehyde detoxification pathway AldH and ROS defense pathway ZWF-GSR-GPO as strain ALDH. Indeed, aldehyde dehydrogenase, which presumably detoxifies aldehydes to harmless carboxylic acids, has been shown to be the major player to prevent free radical elicited lipotoxicity in both *Arabidopsis* [B23] and mammalian cells [B34]. These results demonstrate that managing reactive oxygen and aldehyde levels is a promising strategy to improve the efficiency of the lipid biosynthetic pathway.

Increased Productivity and Yield Upon Removal of Oxidative Stress

Then we investigated the metabolic performance of the engineered AD strain and AldH strain. GC-FID (Gas chromatography-flame ionization detector) profiling of the wild type, AD and AldH strain (FIG. 24) indicates that the lipids obtained in the three strains have similar fatty acid compositions with oleic acid as the major components (>50%). In the original AD strain (FIG. 20), lipid accumulation and cell growth exhibits rather large discrepancy after 60 hours, possibly due to the elevated level of ROS (FIG. 19d) and toxic aldehydes (FIG. 19f) that prevent the further accumulation of lipids; in contrast, lipid accumulation almost coincided with cell growth throughout the fermentation process in AldH strain (FIG. 20b), possibly due to less ROS (FIG. 19d) and reduced reactive aldehydes (FIG. 19f) formed when AldH and GSR-GPO are expressed. It's also observed that glucose is rapidly consumed in AldH strain (FIG. 20b) comparing with that the slow uptake of glucose in AD strain (FIG. 20a). Glucose along with the relative level of ROS, recently, have been suggested to act synergistically on repressing respiration in proliferating yeast and cancer cells [B35]. Our results, therefore, emphasized the notion that ROS and glucose-sensing mechanisms may have a profound effect on regulating lipid metabolism in oleaginous yeast.

Figure 20C:
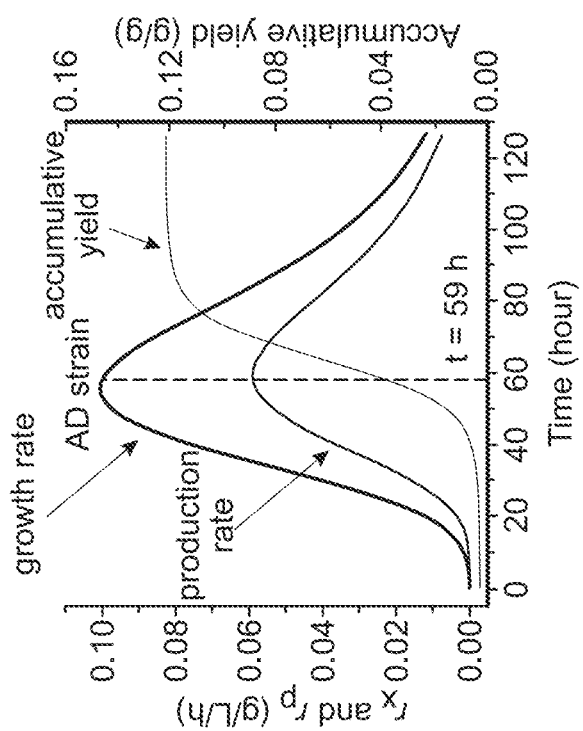

Fermentation kinetics analysis indicates that lipid accumulation is well correlated with cell growth in both the AD strain and AldH strain (FIGS. 20c and 20d). Interestingly, AD strain exhibits a peak cell growth rate and lipid production rate at around 59 hour (FIG. 20c), whereas AldH strain shows a peak cell growth and lipid production at around 31 hour (FIG. 20d). By removing excess reactive oxygen and aldehyde species, the lipid production phase is shifted forward about 28 hours. As a result, the maximal lipid production rate (productivity, 0.265 g/L/h, FIG. 20d) is improved more than 5-fold compared with AD strain (0.052 g/L/h, FIG. 20c). After around 45 hours, the lipid accumulation accounts for almost all the biomass increase in AldH strain as seen that the lipid production rate is perfectly overlapped with cell growth rate (FIG. 20d). In comparison, cell growth continues outcompeting lipid production throughout the fermentation process in AD strain (FIGS. 20a and 20c), suggesting that a large portion of carbon flux is directed towards non-lipid biomass in AD strain. As a result, the lipid accumulative yield is increased to 0.227 g/g in AldH strain (FIG. 20d), representing a 32% increase comparing with AD strain (0.182 g/g, FIG. 20c). Lipid accumulation almost synchronizes with cell growth in AldH strain, as shown that the 20 hour to 80 hour period accounts for more than 80% of biomass and lipid increase (FIGS. 20b and 20d). However, 2/3 of the lipids are produced after 60 hours in the AD strain (FIGS. 20a and 20c), a significant lagging behind the cell growth. Oil content was also increased from 41% in the AD strain to 87% in AldH strain. Analysis of the specific lipid yield suggests that AD strain and AldH strain have distinct lipogenic capacity. The maximal lipid specific yield is above one in AldH strain (FIG. 25), which may support the fact that biomass components (i.e. protein and amino acids) could be degraded and converted to lipids [B17]. Overall, the synchronized lipid production, improved productivity, yield and oil content, reinforced the fact that engineering oxidative stress tolerance are important steps to develop a cost-economic process for large scale production of lipids from renewable resources.

Pseudohypha to Yeast Morphology Change in Engineered Strain

One major character of AldH strain is the rapid cell growth and lipid production due to reduced oxidative stress and aldehyde levels. Cell morphology change is an important stress-response indicator in fungal metabolism [B36]. It is well known that *Yarrowia* undergoes dimorphic transition upon challenging with different environmental stressors. We next investigated the morphology change in both the AD strain and AldH strain. It is not surprising that AD strain, with relatively higher level of ROS and aldehydes (FIG. 19), exhibits considerable amount of pseudohyphal and mycelial microstructure and relatively less oil droplets (FIG. 21a). In contrast, AldH strain develops round, isolated and singular cell morphism and contains large amount of oil droplets (FIG. 21b). This singular, isolated and round cell shape, to a large extent, accounts for the rapid glucose consumption rate in AldH strain (FIG. 20b) as sphere cells have relatively large surface area to capture and access the nutrients in the media. Indeed, hexose sugar uptake has been recently proposed as the major factor limiting lipid production when fructose is used as carbon source in *Yarrowia* yeast [B37]. Challenging the AldH strain with 5 mM $H_2O_2$ led to elongated and pseudohyphal structure and less oil droplets (FIG. 21c), partially corroborating that oxidative stress is closely intertwined with cell morphology and lipid metabolism. Under cultivation in oxygen-intensive bioreactors, AldH strain still maintains singular and round cell morphism and contains large portion of lipid bodies (FIG. 21d and FIG. 28), indicating the robust nature of this strain. These results indicate that manipulating oxidative stress and aldehyde levels are critical steps to establish an efficient microbial lipid factory in industrially-relevant settings.

Bioprocess Optimization to Improve Lipid Production

At the end, lipid production with AldH strain was scaled to a 3-liter bioreactor. Citrate is a major byproduct secreted from the cell due to the overflow of glycolytic flux that cannot be accommodated by the downstream lipid pathway. To minimize citrate overflow, we adopted a stepwise exponential feeding strategy to restrict the level of glucose exposed to the cell [B38]. Glucose and ammonium (C/N=100) were exponentially fed into the bioreactor to adjust carbon-nitrogen ratio and elicit lipid production (FIG. 26). We compared the lipid production process by using two glucose feeding patterns: pulse-feeding (FIG. 27) and step-wise exponential feeding (FIG. 22). A summary of the fermentation metrics has been listed in Table 10. In the stepwise-exponential feeding bioreactor, we achieved a final lipid titer around 72.7 g/L with a process yield 0.252 g/g (FIGS. 22a and 22b), which is about 93% of the theoretical yield (0.271 g/g). Maximal lipid productivity achieved 0.97 g/L/h (FIG. 21b), which is an industrially-relevant level that could prospect an economical-viable process for large-scale production. The final oil content is about 82.5%, representing a more than 2-fold increase compared with the AD strain (around 40.6%). In addition, the citrate level is remarkably decreased to 3.9 g/L in the optimized bioreactor, comparing with more than 31 g/L citrate in the pulse-feeding bioreactor (Table 10). Cell still maintains singular and round shape in the optimized bioreactor (FIG. 28), an indicator for high lipogenic capacity. Taken together, bioprocess optimization further improves both lipid titer and productivity, albeit the lipid content is slightly dropped probably due to disproportional scale-up.

TABLE 10

Comparison of glucose feeding patterns in optimized bioreactors

| Feeding pattern | Pulse feeding | Stepwise exponential feeding |
|---|---|---|
| Lipid titer | 31.86 g/L | 72.67 g/L |
| Maximal productivity | 0.32 g/L/h | 0.97 g/L/h |
| Process yield | 0.215 g/g | 0.252 g/g |
| Oil content | 76.2% | 82.5% |
| Dry cell weight | 42.1 g/L | 89.3 g/L |
| Glucose consumed | 195.8 g/L | 288.4 g/L |
| Citrate level | 31.5 g/L | 3.9 g/L |

Discussion

Given the distinct character of lipid accumulation in oleaginous yeast, nitrogen starvation conditions that trigger the onset of lipogenesis are linked with many cellular stress responses. Lipid is synthesized in the endoplasmic reticulum (ER) and further agglomerated and stored in the lipid bodies [B39]. Under normal physiological conditions, these lipids are stable and used as energy source to maintain cell metabolism. Under stress conditions, lipids that are composed of long alkyl saturated or unsaturated fatty acids could be easily oxidized through either enzyme (acyl-CoA oxidase FIG. 18a and lipoxygenase FIG. 18b) or hydroxyl radical induced (FIG. 18b) lipooxidation process. Apart from reactive oxygen species, lipid peroxidation also generates reactive aldehyde species (i.e. malonyl semialdehyde and 4-hydroxynonenal). These reactive radicals are highly electrophilic in nature and capable of attacking the nucleophilic center of bioactive molecules, deactivating of critical enzymes and eventually leading to pathway inefficiency. In fact, lipid peroxidation induced free radical has been implicated as the culprit molecule responsible for cell aging, programmed cell death and altered cell fate in both cancer cell and adipose cell [B24, B40].

Previous biochemical studies on lipogenic phenotype have confirmed that *Y. lipolytica* contains six acyl-CoA oxidase (POX1 through POX6) that are responsible for lipid oxidation [B41, B42]. Recent efforts working on fatty acyl-CoA elongation and desaturation pathways along with the deletion of five acyl-CoA oxidases have prompted *Yarrowia* strains efficiently produce dietary polyunsaturated fatty acids EPA and DHA [B43, B44]. All these studies suggest that lipid oxidation is one of the critical control points regulating lipid biosynthesis in oleaginous yeast. Intracellular reactive radical assay indicates that our previously engineered strain contains considerably high level of reactive oxygen and aldehyde species. In this study, we seek alternative approaches targeting the cellular oxidative defense pathways and aldehyde detoxification pathways to further improve lipid biosynthesis.

The majority of cellular reactive radicals are generated from unsaturated fatty acids peroxidation that is readily triggered by reactive oxygen radicals [B22], but propagate without further input of ROS (FIG. 18). A distinct character of chain reaction mechanism. As such, the formation of lipid peroxidation-derived aldehyde is relatively independent to the level of initiating ROS, but rely mainly on the availability of unsaturated fatty acids. *Y. lipolytica* is well known to synthesize large quantity of unsaturated fatty acids (generally more than 50% oleic acids C18:1 and 10% linoleic acid C18:2). It is not surprising that *Y. lipolytica* cell contains sufficient amount of endogenous aldehydes (FIG. 19f) and expression of a broad substrate range aldehyde dehydrogenase led to the most significant production improvement. Indeed, a recent study indicates that several unique aldehyde dehydrogenases such as ALDH3B2 is localized onto the surface of lipid body of mouse cell to detoxify lipid-derived aldehydes and serve as a quality control mechanism to maintain lipid-membrane homeostasis [B34].

At the pathway level, numerous studies have shown that lipid biosynthetic enzymes such as ATP-citrate lyase [B45], acetyl-CoA carboxylase [B46], α-keto-glutarate dehydrogenase [B47] and malic enzyme [B48] are subject to redox regulation in various cell lines. To this end, the improved lipid production and oil content could possibly be ascribed to the detoxification effects that protect these enzymes from free radical induced modification and inactivation. Interestingly, studies have shown that nitrogen fasting condition activates alternative oxidase in *Y. lipolytica* [B49] and these alternative oxidases may transfer electrons that are superfluous for the cytochrome respiratory chain [B50]. Another study indicates that *Y. lipolytica* mitochondria exists alternative NADH dehydrogenase that could interact specifically with the cytochrome complexes of the classic respiratory pathway [B51]. These findings suggest that redox level may alter the mitochondrial respiration state and lead to profound effect on central metabolic activity including lipid biosynthesis. Taken together, upon engineering redox homeostasis and removing toxic reactive aldehydes, our engineered strain is capable of producing large quantity of neutral lipids (73 g/L) with high yield (0.252 g/g) and a final oil content around 83%.

Conclusion

Recently, there is considerable awareness that phenotypic engineering targeting on stress tolerance pathways might be the critical steps to deliver efficient microbial biocatalysts to achieve high titer, yield and production rate [B52,B53]. In this work, we solved one major obstacle for efficient production of lipids in oleaginous yeast. Efficient lipid production is pertinent to the unique nitrogen deprivation conditions which distinctly separate the production phase from cell growth phase. A prolonged fermentation period inevitably limits the productivity and scalability and increases the operational cost for industrial application. Here we report maintaining redox homeostasis and detoxifying reactive aldehydes are important strategies to synchronize cell growth and lipid production. The engineered strain demonstrated superior lipogenic capacity and the high titer (72.7 g/L), high yield (0.252 g/g, 93% of theoretical yield), productivity (0.97 g/L/h) and oil content (82.5% in bioreactor) represent exciting potentials of engineering *Yarrowia* as a biorefinery platform to upgrade low-value renewable carbons to high value oleochemicals and biofuels.

REFERENCES

B1. Knothe, G., *Biodiesel and renewable diesel: A comparison*. Progress in Energy and Combustion Science, 2010. 36(3): p. 364-373.

B2. Zhou, Y. J., et al., *Fatty Acid-Derived Biofuels and Chemicals Production in Saccharomyces cerevisiae*. Front Bioeng Biotechnol, 2014. 2: p. 32.

B3. Kamisaka, Y., et al., *Overexpression of the active diacylglycerol acyltransferase variant transforms Saccharomyces cerevisiae into an oleaginous yeast.* Appl Microbiol Biotechnol, 2013. 97(16): p. 7345-55.

B4. Runguphan, W. and J. D. Keasling, *Metabolic engineering of Saccharomyces cerevisiae for production of fatty acid-derived biofuels and chemicals.* Metab Eng, 2014. 21: p. 103-13.

B5. Xu, P., et al., *Modular optimization of multi-gene pathways for fatty acids production in E. coli.* Nature Communications, 2013. 4: p. 1409.

B6. Xu, P., et al., *Improving fatty acids production by engineering dynamic pathway regulation and metabolic control.* Proceedings of the National Academy of Sciences of the United States of America, 2014. 111(31): p. 11299-11304.

B7. de Jong, B. W., et al., *Improved production of fatty acid ethyl esters in Saccharomyces cerevisiae through up-regulation of the ethanol degradation pathway and expression of the heterologous phosphoketolase pathway.* Microb Cell Fact, 2014. 13(1): p. 39.

B8. Shi, S., et al., *Engineering of chromosomal wax ester synthase integrated Saccharomyces cerevisiae mutants for improved biosynthesis of fatty acid ethyl esters.* Biotechnol Bioeng, 2014. 111(9): p. 1740-7.

B9. Tai, Y. S., M. Xiong, and K. Zhang, *Engineered biosynthesis of medium-chain esters in Escherichia coli.* Metab Eng, 2015. 27: p. 20-8.

B10. Blazeck, J., et al., *Heterologous production of pentane in the oleaginous yeast Yarrowia lipolytica.* J Biotechnol, 2013. 165(3-4): p. 184-94.

B11. Dellomonaco, C., et al., *Engineered reversal of the β-oxidation cycle for the synthesis of fuels and chemicals.* Nature, 2011. 476(7360): p. 355-9.

B12. Lennen, R. M. and B. F. Pfleger, *Microbial production of fatty acid-derived fuels and chemicals.* Curr Opin Biotechnol, 2013. 24(6): p. 1044-53.

B13. Pfleger, B. F., M. Gossing, and J. Nielsen, *Metabolic engineering strategies for microbial synthesis of oleochemicals.* Metab Eng, 2015. 29: p. 1-11.

B14. Nicaud, J. M., *Yarrowia lipolytica.* Yeast, 2012. 29(10): p. 409-18.

B15. Tai, M. and G. Stephanopoulos, *Engineering the push and pull of lipid biosynthesis in oleaginous yeast Yarrowia lipolytica for biofuel production.* Metab Eng, 2013. 15: p. 1-9.

B16. Qiao, K., et al., *Engineering lipid overproduction in the oleaginous yeast Yarrowia lipolytica.* Metab Eng, 2015. 29: p. 56-65.

B17. Blazeck, J., et al., *Harnessing Yarrowia lipolytica lipogenesis to create a platform for lipid and biofuel production.* Nat Commun, 2014. 5: p. 3131.

B18. Liu, L., et al., *An evolutionary metabolic engineering approach for enhancing lipogenesis in Yarrowia lipolytica.* Metab Eng, 2015. 29: p. 36-45.

B19. Morin, N., et al., *Transcriptomic analyses during the transition from biomass production to lipid accumulation in the oleaginous yeast Yarrowia lipolytica.* PLoS One, 2011. 6(11): p. e27966.

B20. Rosenwasser, S., et al., *Mapping the diatom redox-sensitive proteome provides insight into response to nitrogen stress in the marine environment.* Proc Natl Acad Sci USA, 2014. 111(7): p. 2740-5.

B21. Li, Q., et al., *Oxidative stress in fungal fermentation processes: the roles of alternative respiration.* Biotechnol Lett, 2011. 33(3): p. 457-67.

B22. Zimniak, P., *Relationship of electrophilic stress to aging.* Free Radic Biol Med, 2011. 51(6): p. 1087-105.

B23. Mano, J., et al., *The NADPH:quinone oxidoreductase P1-zeta-crystallin in Arabidopsis catalyzes the alpha, beta-hydrogenation of 2-alkenals: detoxication of the lipid peroxide-derived reactive aldehydes.* Plant Cell Physiol, 2002. 43(12): p. 1445-55.

B24. Grimsrud, P. A., et al., *Oxidative stress and covalent modification of protein with bioactive aldehydes.* J Biol Chem, 2008. 283(32): p. 21837-41.

B25. Shen, B., R. G. Jensen, and H. J. Bohnert, *Increased resistance to oxidative stress in transgenic plants by targeting mannitol biosynthesis to chloroplasts.* Plant Physiol, 1997. 113(4): p. 1177-83.

B26. Shen, B., R. G. Jensen, and H. J. Bohnert, *Mannitol Protects against Oxidation by Hydroxyl Radicals.* Plant Physiol, 1997. 115(2): p. 527-532.

B27. Ruijter, G. J., et al., *Mannitol is required for stress tolerance in Aspergillus niger conidiospores.* Eukaryot Cell, 2003. 2(4): p. 690-8.

B28. Rathinasabapathi, B., *Metabolic Engineering for Stress Tolerance: Installing Osmoprotectant Synthesis Pathways.* Annals of Botany, 2000. 86(4): p. 709-716.

B29. Jamieson, D. J., *Oxidative stress responses of the yeast Saccharomyces cerevisiae.* Yeast, 1998. 14(16): p. 1511-27.

B30. Lopes, M., M. Mota, and I. Belo, *Comparison of Yarrowia lipolytica and Pichia pastoris cellular response to different agents of oxidative stress.* Appl Biochem Biotechnol, 2013. 170(2): p. 448-58.

B31. Lamonte, G., et al., *Acidosis induces reprogramming of cellular metabolism to mitigate oxidative stress.* Cancer Metab, 2013. 1(1): p. 23.

B32. Wasylenko, T. M., W. S. Ahn, and G. Stephanopoulos, *The oxidative pentose phosphate pathway is the primary source of NADPH for lipid overproduction from glucose in Yarrowia lipolytica.* Metab Eng, 2015. 30: p. 27-39.

B33. Minard, K. I., et al., *Sources of NADPH and expression of mammalian NADP+-specific isocitrate dehydrogenases in Saccharomyces cerevisiae.* J Biol Chem, 1998. 273(47): p. 31486-93.

B34. Kitamura, T., et al., *Mouse aldehyde dehydrogenase ALDH3B2 is localized to lipid droplets via two C-terminal tryptophan residues and lipid modification.* Biochemical Journal, 2015. 465(1): p. 79-87.

B35. Reddi, A. R. and V. C. Culotta, *SOD1 integrates signals from oxygen and glucose to repress respiration.* Cell, 2013. 152(1-2): p. 224-35.

B36. Morano, K. A., C. M. Grant, and W. S. Moye-Rowley, *The response to heat shock and oxidative stress in Saccharomyces cerevisiae.* Genetics, 2012. 190(4): p. 1157-95.

B37. Lazar, Z., et al., *Hexokinase—A limiting factor in lipid production from fructose in Yarrowia lipolytica.* Metab Eng, 2014. 26C: p. 89-99.

B38. Ochoa-Estopier, A. and S. E. Guillouet, *D-stat culture for studying the metabolic shifts from oxidative metabolism to lipid accumulation and citric acid production in Yarrowia lipolytica.* J Biotechnol, 2014. 170: p. 35-41.

B39. Li-Beisson, Y., et al., *Acyl-Lipid Metabolism.* The Arabidopsis Book, 2010: p. e0133.

B40. Wallace, D. C., *Mitochondria and cancer.* Nat Rev Cancer, 2012. 12(10): p. 685-98.

B41. Mlíčková, K., et al., *Lipid accumulation, lipid body formation, and acyl coenzyme A oxidases of the yeast Yarrowia lipolytica.* Appl Environ Microbiol, 2004. 70(7): p. 3918-24.

B42. Beopoulos, A., et al., *Control of lipid accumulation in the yeast Yarrowia lipolytica*. Appl Environ Microbiol, 2008. 74(24): p. 7779-89.

B43. Xue, Z., et al., *Production of omega-3 eicosapentaenoic acid by metabolic engineering of Yarrowia lipolytica*. Nat Biotechnol, 2013. 31(8): p. 734-40.

B44. Xie, D., E. N. Jackson, and Q. Zhu, *Sustainable source of omega-3 eicosapentaenoic acid from metabolically engineered Yarrowia lipolytica: from fundamental research to commercial production*. Appl Microbiol Biotechnol, 2015. 99(4): p. 1599-610.

B45. Wells, T. N. C. and B. A. Saxty, *Redox control of catalysis in ATP-citrate lyase from rat liver*. European Journal of Biochemistry, 1992. 204(1): p. 249-255.

B46. Sasaki, Y., A. Kozaki, and M. Hatano, *Link between light and fatty acid synthesis: Thioredoxin-linked reductive activation of plastidic acetyl-CoA carboxylase*. Proceedings of the National Academy of Sciences, 1997. 94(20): p. 11096-11101.

B47. McLain, A. L., P. A. Szweda, and L. I. Szweda, *α-Ketoglutarate dehydrogenase: A mitochondrial redox sensor*. Free Radical Research, 2011. 45(1): p. 29-36.

B48. Drincovich, M. F. and C. S. Andreo, *Redox regulation of maize NADP-malic enzyme by thiol-disulfide interchange: effect of reduced thioredoxin on activity*. Biochimica et Biophysica Acta (BBA)—Protein Structure and Molecular Enzymology, 1994. 1206(1): p. 10-16.

B49. Medentse, A. G., et al., *Activation of the Alternative Oxidase of Yarrowia lipolytica by Adenosine Monophosphate*. Microbiology, 2004. 73(2): p. 117-123.

B50. Medentsev, A. G., et al., *Involvement of the alternative oxidase in respiration of Yarrowia lipolytica mitochondria is controlled by the activity of the cytochrome pathway*. FEMS Yeast Research, 2002. 2(4): p. 519-524.

B51. Guerrero-Castillo, S., et al., *In Yarrowia lipolytica mitochondria, the alternative NADH dehydrogenase interacts specifically with the cytochrome complexes of the classic respiratory pathway*. Biochimica et Biophysica Acta (BBA)—Bioenergetics, 2009. 1787(2): p. 75-85.

B52. Lam, F. H., et al., *Biofuels. Engineering alcohol tolerance in yeast*. Science, 2014. 346(6205): p. 71-5.

B53. Andre, C., et al., *Fusing catalase to an alkane-producing enzyme maintains enzymatic activity by converting the inhibitory byproduct $H_2O_2$ to the cosubstrate $O_2$*. Proceedings of the National Academy of Sciences, 2013. 110(8): p. 3191-3196.

B54. Xu, P., et al., *ePathBrick.—A Synthetic Biology Platform for Engineering Metabolic Pathways in E-coli*. ACS Synth. Biol., 2012. 1(7): p. 256-266.

B55. Xu, P. and M. G. Koffas, *Assembly of Multi-gene Pathways and Combinatorial Pathway Libraries Through ePathBrick Vectors*, in *Synthetic Biology*, K. M. Polizzi and C. Kontoravdi, Editors. 2013, Humana Press. p. 107-129.

B56. Chen, D. C., J. M. Beckerich, and C. Gaillardin, *One-step transformation of the dimorphic yeast Yarrowia lipolytica*. Applied Microbiology and Biotechnology, 1997. 48(2): p. 232-235.

B57. Yilancioglu, K., et al., *Oxidative stress is a mediator for increased lipid accumulation in a newly isolated Dunaliella salina strain*. PLoS One, 2014. 9(3): p. e91957.

All publications, patents and sequence database entries mentioned in the specification herein are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

---

What is claimed is:

1. An isolated *Yarrowia lipolytica* cell comprising:
   (a) a nucleic acid construct comprising an expression cassette comprising a nucleic acid sequence encoding a cytosolic $NADP^+$-dependent malic enzyme having the amino acid sequence of SEQ ID NO: 2 under the control of a heterologous promoter; and
   (b) a nucleic acid construct comprising an expression cassette comprising a nucleic acid sequence encoding a $NADP^+$-dependent glyceraldehyde-3-phosphate dehydrogenase having the amino acid sequence of SEQ ID NO: 4 or SEQ ID NO: 6 under the control of a heterologous promoter,
   wherein the heterologous promoter is an intron-enhanced TEF promoter or an intron-enhanced *Yarrowia lipolytica* glyceraldehyde-3-phosphate dehydrogenase promoter.

2. The isolated *Yarrowia lipolytica* cell of claim 1, wherein the cell further comprises a nucleic acid construct comprising an expression cassette comprising a nucleic acid sequence encoding an acetyl-CoA carboxylase (ACC1) having the amino acid sequence of SEQ ID NO: 56 under the control of a heterologous promoter, and a nucleic acid construct comprising an expression cassette comprising a nucleic acid sequence encoding a diacylglyceraldehyde acyltransferase (DGA1) having the amino acid sequence of SEQ ID NO: 54 under the control of a heterologous promoter, and wherein the heterologous promoter is an intron-enhanced TEF promoter or an intron-enhanced *Yarrowia lipolytica* glyceraldehyde-3-phosphate dehydrogenase promoter.

3. An isolated *Yarrowia lipolytica* cell comprising:
   a nucleic acid construct comprising an expression cassette comprising a nucleic acid sequence encoding an aldehyde dehydrogenase (AldH) having the amino acid sequence of SEQ ID NO: 30, SEQ ID NO: 32, SEQ ID NO: 34, SEQ ID NO: 36, or SEQ ID NO: 38 under the control of a heterologous promoter,
   wherein the heterologous promoter is an intron-enhanced TEF promoter or an intron-enhanced *Yarrowia lipolytica* glyceraldehyde-3-phosphate dehydrogenase promoter.

4. The isolated *Yarrowia lipolytica* cell of claim 3, wherein the cell further comprises a nucleic acid construct comprising an expression cassette comprising a nucleic acid sequence encoding an acetyl-CoA carboxylase (ACC1) having the amino acid sequence of SEQ ID NO: 56 under the control of a heterologous promoter, and a nucleic acid construct comprising an expression cassette comprising a nucleic acid sequence encoding a diacylglyceraldehyde acyltransferase (DGA1) having the amino acid sequence of SEQ ID NO: 54 under the control of a heterologous promoter, and wherein the heterologous promoter is an intron-enhanced TEF promoter or an intron-enhanced *Yarrowia lipolytica* glyceraldehyde-3-phosphate dehydrogenase promoter.

5. The isolated *Yarrowia lipolytica* cell of claim 4, wherein the acetyl-CoA carboxylase (ACC1) is encoded by SEQ ID NO: 55.

6. The isolated *Yarrowia lipolytica* cell of claim 4, wherein the diacylglyceride acyltransferase (DGA1) is encoded by SEQ ID NO: 53.

7. A culture comprising the isolated *Yarrowia lipolytica* cell of claim 1.

8. A method comprising culturing the isolated *Yarrowia lipolytica* cell of claim 1 with a carbon source.

9. The isolated *Yarrowia lipolytica* cell of claim 1, wherein the cytosolic NADP+-dependent malic enzyme is encoded by SEQ ID NO: 1 or wherein the NADP+-dependent glyceraldehyde-3-phosphate dehydrogenase is encoded by SEQ ID NO: 3 or SEQ ID NO: 5.

10. The isolated *Yarrowia lipolytica* cell of claim 3, wherein the aldehyde dehydrogenase is encoded by SEQ ID NO: 29, SEQ ID NO: 31, SEQ ID NO: 33, SEQ ID NO: 35, or SEQ ID NO: 37.

11. The isolated *Yarrowia lipolytica* cell of claim 1, wherein the nucleic acid construct is inserted into the genome of the cell.

12. The isolated *Yarrowia lipolytica* cell of claim 1, wherein the lipid titer is at least 25 g/L or 25-150 g/L; or wherein the lipid productivity is at least 0.25 g/L/h or 0.25 g/L/h to 1.5 g/L/h.

13. The isolated *Yarrowia lipolytica* cell of claim 3, wherein the lipid titer is at least 25 g/L or 25-150 g/L; or wherein the lipid productivity is at least 0.25 g/L/h or 0.25 g/L/h to 1.5 g/L/h.

14. The isolated *Yarrowia lipolytica* cell of claim 2, wherein the acetyl-CoA carboxylase (ACC1) is encoded by SEQ ID NO: 55.

15. The isolated *Yarrowia lipolytica* cell of claim 2, wherein the diacylglyceride acyltransferase (DGA1) is encoded by SEQ ID NO: 53.

* * * * *

SEQUENCE LISTING

<160> NUMBER OF SEQ ID NOS: 135

<210> SEQ ID NO 1
<211> LENGTH: 1863
<212> TYPE: DNA
<213> ORGANISM: Mucor circinelloides

<400> SEQUENCE: 1

```
atgtcgccta ttattgattt tgttcgtcgc caattgtcct ctacaaagtt gcatgaagag      60
cagcaaacag caactacaaa tgatttggtc tctagatcag gctatctaaa tgaaggcaag     120
tatgaggtcc gcttgaattg tatcaatgct ggctgcttac aaaaaaaact aaactatata     180
ggtactgcca tggatcctgc taaacgtcaa agacttggat tgaacggtct tttacctgct     240
ggtgtagaga cattggaaat tcaaaaagct cgcgccctca gagtgcttcg ttcaaaacac     300
aatttattag aaaaatacat tttaatggct caacttcgta ccaccaacgt ccgcttattt     360
tacaagattg tcattgatga attagagacc gttcaattgg ctcctgttat ctataccccg     420
actgttggta ccgcatgctt ggaatactct accatctatc ccttcttggc tgcccctggt     480
gtgccggatg gtctttacct caccaaagcc gaattaccgg aactgtgtca aaccattcgt     540
aactatcgtc ctacggatac tgagggtttt gagccagaga ttgctgtgat ttctgatggg     600
tctcgaattt tgggtctggg tgatttggga acaaatggca tgggtattcc aatgggtaaa     660
cttcagctct atgttgctgg tgctggtatt gatcctcgtc gtacgttacc catcatttg      720 gatttgggta caaacaatga aaagttgctc aatgatgagt tttatattgg tcttcgtcaa     780
aagcgaccca atgatgagga gttttatcaa acagttgata cagtcttgac agcattacat     840
accgtgtacc ccaacctact catccagttt gaagattggt cttctgaaca cgcatttggc     900
ctcttggaaa agtaccaaaa tcaaatgctt tgttttaacg acgacataca gggcacaggt     960
gctgtcatat tatctggtgt cattaatgct attcgcaagg ttgagaaaga gaatcaagtg    1020
tctcctcgtg atcatcgtat cgtgttctac ggtgctggtt ctgctgctat cggtgttgct    1080
cgtcaaattc aaagctactt ccaaattgaa cacaacatga ctgaggaaga agctaagcat    1140
gtgttctgga ttgttgattc caagggtctt gttactacta cacgaggcga taaattagct    1200
caacacaagg tgtattacgc acgaggcgat aatgaaggcc aacagtacaa ggaattgatt    1260
gatattgtca actataatct ctacagtttg attggtttat catctactac aggtgccttt    1320
aatactcaag tccttgagcg tcttgcctca ctcaatgagc aacctattgt tttccctctt    1380
tccaatccag ccacacaagc agaatgtaca tttgagcaag ccatggaagc taccaacaac    1440
aaggttattt ttgcatctgg tactgctttc cctgcatata ccatcaaatc cactggcgaa    1500 gtaaatatccc ctggtcaagg caacaacatg tacatcttcc ctggtttggg tctgggtgct    1560
tgtctggcta acccagcaca tttcgatcgc atgatctacg aagcatccaa agcacttgct    1620
gactcactta cagaggaaga aatcagtaag gcctggttat atccatcttt aaactatcgt    1680
```

```
agcgtatcag ccatcgttgc agcagctgta tgtcaagaga ctttgaatga aaacctagca    1740
acgtctcaag ctatgatgac gcagtgtaaa tcacatgaag atattctaga ttatgttagt    1800
gctcatatgt ggtctcccga ctatggaaac aacaacagca atcagcaagc tggtaaattg    1860
tag                                                                   1863

<210> SEQ ID NO 2
<211> LENGTH: 620
<212> TYPE: PRT
<213> ORGANISM: Mucor circinelloides

<400> SEQUENCE: 2

Met Ser Pro Ile Ile Asp Phe Val Arg Arg Gln Leu Ser Ser Thr Lys
1               5                   10                  15

Leu His Glu Glu Gln Gln Thr Ala Thr Thr Asn Asp Leu Val Ser Arg
            20                  25                  30

Ser Gly Tyr Leu Asn Glu Gly Lys Tyr Glu Val Arg Leu Asn Cys Ile
        35                  40                  45

Asn Ala Gly Cys Leu Gln Lys Lys Leu Asn Tyr Ile Gly Thr Ala Met
    50                  55                  60

Asp Pro Ala Lys Arg Gln Arg Leu Gly Leu Asn Gly Leu Leu Pro Ala
65                  70                  75                  80

Gly Val Glu Thr Leu Glu Ile Gln Lys Ala Arg Ala Leu Arg Val Leu
                85                  90                  95

Arg Ser Lys His Asn Leu Leu Glu Lys Tyr Ile Leu Met Ala Gln Leu
            100                 105                 110

Arg Thr Thr Asn Val Arg Leu Phe Tyr Lys Ile Val Ile Asp Glu Leu
        115                 120                 125

Glu Thr Val Gln Leu Ala Pro Val Ile Tyr Thr Pro Thr Val Gly Thr
130                 135                 140

Ala Cys Leu Glu Tyr Ser Thr Ile Tyr Pro Phe Leu Ala Ala Pro Gly
145                 150                 155                 160

Val Pro Asp Gly Leu Tyr Leu Thr Lys Ala Glu Leu Pro Glu Leu Cys
                165                 170                 175

Gln Thr Ile Arg Asn Tyr Arg Pro Thr Asp Thr Glu Gly Phe Glu Pro
            180                 185                 190

Glu Ile Ala Val Ile Ser Asp Gly Ser Arg Ile Leu Gly Leu Gly Asp
        195                 200                 205

Leu Gly Thr Asn Gly Met Gly Ile Pro Met Gly Lys Leu Gln Leu Tyr
210                 215                 220

Val Ala Gly Ala Gly Ile Asp Pro Arg Arg Thr Leu Pro Ile Ile Leu
225                 230                 235                 240

Asp Leu Gly Thr Asn Asn Glu Lys Leu Leu Asn Asp Glu Phe Tyr Ile
                245                 250                 255

Gly Leu Arg Gln Lys Arg Pro Asn Asp Glu Glu Phe Tyr Gln Thr Val
            260                 265                 270

Asp Thr Val Leu Thr Ala Leu His Thr Val Tyr Pro Asn Leu Leu Ile
        275                 280                 285

Gln Phe Glu Asp Trp Ser Ser Glu His Ala Phe Gly Leu Leu Glu Lys
290                 295                 300

Tyr Gln Asn Gln Met Leu Cys Phe Asn Asp Asp Ile Gln Gly Thr Gly
305                 310                 315                 320

Ala Val Ile Leu Ser Gly Val Ile Asn Ala Ile Arg Lys Val Glu Lys
                325                 330                 335
```

```
Glu Asn Gln Val Ser Pro Arg Asp His Arg Ile Val Phe Tyr Gly Ala
                340                 345                 350
Gly Ser Ala Ala Ile Gly Val Ala Arg Gln Ile Gln Ser Tyr Phe Gln
            355                 360                 365
Ile Glu His Asn Met Thr Glu Glu Ala Lys His Val Phe Trp Ile
    370                 375                 380
Val Asp Ser Lys Gly Leu Val Thr Thr Thr Arg Gly Asp Lys Leu Ala
385                 390                 395                 400
Gln His Lys Val Tyr Tyr Ala Arg Gly Asp Asn Glu Gly Gln Gln Tyr
                405                 410                 415
Lys Glu Leu Ile Asp Ile Val Asn Tyr Asn Leu Tyr Ser Leu Ile Gly
            420                 425                 430
Leu Ser Ser Thr Thr Gly Ala Phe Asn Thr Gln Val Leu Glu Arg Leu
            435                 440                 445
Ala Ser Leu Asn Glu Gln Pro Ile Val Phe Pro Leu Ser Asn Pro Ala
        450                 455                 460
Thr Gln Ala Glu Cys Thr Phe Glu Gln Ala Met Glu Ala Thr Asn Asn
465                 470                 475                 480
Lys Val Ile Phe Ala Ser Gly Thr Ala Phe Pro Ala Tyr Thr Ile Lys
                485                 490                 495
Ser Thr Gly Glu Val Asn Thr Pro Gly Gln Gly Asn Asn Met Tyr Ile
            500                 505                 510
Phe Pro Gly Leu Gly Leu Gly Ala Cys Leu Ala Asn Pro Ala His Phe
        515                 520                 525
Asp Arg Met Ile Tyr Glu Ala Ser Lys Ala Leu Ala Asp Ser Leu Thr
530                 535                 540
Glu Glu Glu Ile Ser Lys Ala Trp Leu Tyr Pro Ser Leu Asn Tyr Arg
545                 550                 555                 560
Ser Val Ser Ala Ile Val Ala Ala Val Cys Gln Glu Thr Leu Asn
                565                 570                 575
Glu Asn Leu Ala Thr Ser Gln Ala Met Met Thr Gln Cys Lys Ser His
            580                 585                 590
Glu Asp Ile Leu Asp Tyr Val Ser Ala His Met Trp Ser Pro Asp Tyr
        595                 600                 605
Gly Asn Asn Asn Ser Asn Gln Gln Ala Gly Lys Leu
    610                 615                 620

<210> SEQ ID NO 3
<211> LENGTH: 1005
<212> TYPE: DNA
<213> ORGANISM: Clostridium acetobutylicum

<400> SEQUENCE: 3
atggcaaaga tagctattaa tggttttgga agaataggaa gattagcttt aagaagaatt      60
cttgaagtac ctggattgga agttgttgca ataaacgact taactgatgc aaaaatgtta     120
gcacacttat ttaaatatga ttcatcacaa ggaagattca atgagaaaat tgaagttaaa     180
gaaggagctt tcgtagtaaa cggaaaagaa gttaaagttt cgctgaagc agatcctgaa      240 aaattacctt gggagatct tggaatagac gttgttcttg agtgcacagg tttcttcaca      300
aagaaagaaa aagcagaagc tcacgtaaga gcaggcgcta aaaagttgt tatatcagct     360 ccagctggaa cgacttaaa gacaatagtt ttcaacgtta ataatgaaga tcttgatgga      420
acagaaacag ttatatcagg tgcatcatgc acaactaact gcttagctcc aatggctaaa     480
gtattaaatg ataaatttgg aatagaaaaa ggattcatga ctacaattca tgcgttcact     540
```

-continued

```
aatgaccaaa acacattaga tggtccacac agaaaaggag atttaagaag agctagagct    600
gctgctgtaa gtatcatccc taactcaact ggtgctgcta agctataag ccaagttatt    660 cctgacttag ctggaaaatt agacggaaac gctcaaagag ttccagttcc aactggttca    720
ataactgaat tagtttcagt tcttaagaaa aagttacag ttgaagaaat caacgctgct    780
atgaaagaag ctgctgatga atcatttgga tacactgaag atccaatcgt ttcagctgac    840
gtagtaggaa tcaactacgg atcattattt gatgcaactt taactaaaat tgttgatgtt    900
aacggatcac aattagttaa aacagctgct tggtatgata atgaaatgtc atacacttca    960
caattagtta gaacttttagc ttactttgca aaaatagcaa aatag                 1005
```

<210> SEQ ID NO 4
<211> LENGTH: 333
<212> TYPE: PRT
<213> ORGANISM: Clostridium acetobutylicum

<400> SEQUENCE: 4

```
Ala Lys Ile Ala Ile Asn Gly Phe Gly Arg Ile Gly Arg Leu Ala Leu
1               5                   10                  15

Arg Arg Ile Leu Glu Val Pro Gly Leu Glu Val Val Ala Ile Asn Asp
            20                  25                  30

Leu Thr Asp Ala Lys Met Leu Ala His Leu Phe Lys Tyr Asp Ser Ser
        35                  40                  45

Gln Gly Arg Phe Asn Gly Glu Ile Glu Val Lys Glu Gly Ala Phe Val
    50                  55                  60

Val Asn Gly Lys Glu Val Lys Val Phe Ala Glu Ala Asp Pro Glu Lys
65                  70                  75                  80

Leu Pro Trp Gly Asp Leu Gly Ile Asp Val Val Leu Glu Cys Thr Gly
                85                  90                  95

Phe Phe Thr Lys Lys Glu Lys Ala Glu Ala His Val Arg Ala Gly Ala
            100                 105                 110

Lys Lys Val Val Ile Ser Ala Pro Ala Gly Asn Asp Leu Lys Thr Ile
        115                 120                 125

Val Phe Asn Val Asn Asn Glu Asp Leu Asp Gly Thr Glu Thr Val Ile
    130                 135                 140

Ser Gly Ala Ser Cys Thr Thr Asn Cys Leu Ala Pro Met Ala Lys Val
145                 150                 155                 160

Leu Asn Asp Lys Phe Gly Ile Glu Lys Gly Phe Met Thr Thr Ile His
                165                 170                 175

Ala Phe Thr Asn Asp Gln Asn Thr Leu Asp Gly Pro His Arg Lys Gly
            180                 185                 190

Asp Leu Arg Arg Ala Arg Ala Ala Val Ser Ile Ile Pro Asn Ser
        195                 200                 205

Thr Gly Ala Ala Lys Ala Ile Ser Gln Val Ile Pro Asp Leu Ala Gly
    210                 215                 220

Lys Leu Asp Gly Asn Ala Gln Arg Val Pro Val Pro Thr Gly Ser Ile
225                 230                 235                 240

Thr Glu Leu Val Ser Val Leu Lys Lys Val Thr Val Glu Glu Ile
                245                 250                 255

Asn Ala Ala Met Lys Glu Ala Ala Asp Glu Ser Phe Gly Tyr Thr Glu
            260                 265                 270

Asp Pro Ile Val Ser Ala Asp Val Val Gly Ile Asn Tyr Gly Ser Leu
        275                 280                 285
```

```
Phe Asp Ala Thr Leu Thr Lys Ile Val Asp Val Asn Gly Ser Gln Leu
        290                 295                 300

Val Lys Thr Ala Ala Trp Tyr Asp Asn Glu Met Ser Tyr Thr Ser Gln
305                 310                 315                 320

Leu Val Arg Thr Leu Ala Tyr Phe Ala Lys Ile Ala Lys
                325                 330
```

<210> SEQ ID NO 5
<211> LENGTH: 1071
<212> TYPE: DNA
<213> ORGANISM: Kluyveromyces lactis

<400> SEQUENCE: 5

```
atgcccgata tgaccaacga gtcctcttcg aagcccgccc agatcaacat cggcatcaac    60
ggcttcggcc gaatcggacg actggtgctg cgagccgccc tgacccaccc cgaggtgaag   120
gtgcgactga tcaacaaccc ctctaccacc cccgagtacg ccgcctacct gttcaagtac   180
gactctaccc acggcaagta ccgaggcgag gtcgagttcg acgacgagcg aatcatcatc   240
cagaacgacc acgtgtctgc ccacatcccc ctgtctcact ccgagagccc cgagcgaatc   300
ccctgggcct cttacaacgt ggactacgtg atcgactcta ccggcgtgtt caaggaagtg   360
gacaccgcct ctcgacacaa gggcgtgaag aaggtgatca tcaccgcccc ctctaagacc   420
gcccccatgt acgtgtacgg cgtgaaccac gtgaagtaca ccccctgac cgaccacgtg    480
gtgtctaacg cctcttgcac caccaactgc ctggcccccc tggtgaaggc cctggacgac   540
gagttcggca tcgaagaggc cctgatgacc accatccacg ccaccaccgc ctctcagaag   600
actgtcgacg gcacctcttc tggcggcaag gactggcgag gcggccgatc ttgccagggc   660
aacatcatcc cctcttctac cggcgctgcc aaggccgtgg gcaagatcct gcccgagctg   720
aacggcaaga tcaccggcat gtctatccga gtgcccacca tcaacatctc cctggtggac   780
ctgaccttcc gaaccgccaa gaagacctct tacgacgaca tcatgaaggc cctcgagcag   840
cgatctcgat ctgacatgaa gggcgtcctg ggcgtgacca aggacgccgt ggtgtcctct   900
gacttcacct ctgactctcg atcttctatc gtggacgcca aggccggcat cgagctgaac   960
gaccacttct tcaaggtgct gtcttggtac gacaacgagt acggctactc ttctcgagtg  1020
gtcgacctgt ctatcttcat ggcccagaag gacttcgagg ccggcgtgta a           1071
```

<210> SEQ ID NO 6
<211> LENGTH: 356
<212> TYPE: PRT
<213> ORGANISM: Kluyveromyces lactis

<400> SEQUENCE: 6

```
Met Pro Asp Met Thr Asn Glu Ser Ser Ser Lys Pro Ala Gln Ile Asn
1               5                   10                  15

Ile Gly Ile Asn Gly Phe Gly Arg Ile Gly Arg Leu Val Leu Arg Ala
            20                  25                  30

Ala Leu Thr His Pro Glu Val Lys Val Arg Leu Ile Asn Asn Pro Ser
        35                  40                  45

Thr Thr Pro Glu Tyr Ala Ala Tyr Leu Phe Lys Tyr Asp Ser Thr His
    50                  55                  60

Gly Lys Tyr Arg Gly Glu Val Glu Phe Asp Asp Glu Arg Ile Ile Ile
65                  70                  75                  80

Gln Asn Asp His Val Ser Ala His Ile Pro Leu Ser His Ser Arg Glu
                85                  90                  95
```

Pro Glu Arg Ile Pro Trp Ala Ser Tyr Asn Val Asp Tyr Val Ile Asp
            100                 105                 110

Ser Thr Gly Val Phe Lys Glu Val Asp Thr Ala Ser Arg His Lys Gly
        115                 120                 125

Val Lys Lys Val Ile Ile Thr Ala Pro Ser Lys Thr Ala Pro Met Tyr
130                 135                 140

Val Tyr Gly Val Asn His Val Lys Tyr Asn Pro Leu Thr Asp His Val
145                 150                 155                 160

Val Ser Asn Ala Ser Cys Thr Thr Asn Cys Leu Ala Pro Leu Val Lys
                165                 170                 175

Ala Leu Asp Asp Glu Phe Gly Ile Glu Glu Ala Leu Met Thr Thr Ile
            180                 185                 190

His Ala Thr Thr Ala Ser Gln Lys Thr Val Asp Gly Thr Ser Ser Gly
        195                 200                 205

Gly Lys Asp Trp Arg Gly Gly Arg Ser Cys Gln Gly Asn Ile Ile Pro
210                 215                 220

Ser Ser Thr Gly Ala Ala Lys Ala Val Gly Lys Ile Leu Pro Glu Leu
225                 230                 235                 240

Asn Gly Lys Ile Thr Gly Met Ser Ile Arg Val Pro Thr Ile Asn Ile
                245                 250                 255

Ser Leu Val Asp Leu Thr Phe Arg Thr Ala Lys Lys Thr Ser Tyr Asp
            260                 265                 270

Asp Ile Met Lys Ala Leu Glu Gln Arg Ser Arg Ser Asp Met Lys Gly
        275                 280                 285

Val Leu Gly Val Thr Lys Asp Ala Val Val Ser Ser Asp Phe Thr Ser
290                 295                 300

Asp Ser Arg Ser Ser Ile Val Asp Ala Lys Ala Gly Ile Glu Leu Asn
305                 310                 315                 320

Asp His Phe Phe Lys Val Leu Ser Trp Tyr Asp Asn Glu Tyr Gly Tyr
                325                 330                 335

Ser Ser Arg Val Val Asp Leu Ser Ile Phe Met Ala Gln Lys Asp Phe
            340                 345                 350

Glu Ala Gly Val
        355

<210> SEQ ID NO 7
<211> LENGTH: 2442
<212> TYPE: DNA
<213> ORGANISM: Artificial Sequence
<220> FEATURE:
<223> OTHER INFORMATION: Codon-optimized form of Leuconostoc
      mesenteroides gene

<400> SEQUENCE: 7

```
atggccgatt tcgactctaa agaatacttg gaattggttg acaaatggtg gagagctacc      60
aattatttgt ctgccggtat gatcttcttg aagtctaatc ctttgttctc cgttaccaac     120
actccaatca aagctgaaga tgttaaggtt aagccaattg tcattgggg tactatttct      180 ggtcaaactt tcttgtacgc tcatgccaac agattgatta acaagtacgg tttgaatatg     240
ttctacgttg gtggtccagg tcatggtggt caagttatgg ttactaatgc ttatttggat     300
ggtgcctaca ctgaagatta cccagaaatt acccaagaca tcgaaggtat gtctcacttg     360
tttaagagat tctcattccc aggtggtatc ggttctcata tgactgctca aactccaggt     420
tctttacatt aaggtggtga attgggttac tctttgtctc atgcttttgg tgctgttttg     480
gataacccag atcaagttgc ttttgctgtt gttggtgatg gtgaagctga aactggtcca    540
```

```
tctatggctt catggcattc tattaagttc ttgaacgcta agaatgatgg tgccgttttg    600
ccagttttgg atttgaatgg tttcaagatc tccaacccaa ccatcttctc tagaatgtcc    660
gatgaagaaa tcaccaagtt ctttgaaggt ttgggttaca gtccaagatt catcgaaaac    720
gatgatatcc atgattacgc cacctatcat caattggctg ctaacatttt ggatcaagcc    780
atcgaagata tccaagccat tcaaaatgat gccagagaaa acggtaaata ccaagatggt    840
gaaattccag cttggccagt tattattgct agattgccaa aaggttgggg tggtccaact    900
catgatgctt ctaacaatcc aatcgaaaac tctttcagag cccatcaagt tccattgcca    960
ttggaacaac atgatttggc tactttgcca gaattcgaag attggatgaa ttcctacaag   1020
cctgaagaat tattcaacgc cgatggttcc ttgaaggatg aattgaaagc tattgctcca   1080
aagggtgaca aagaatgtc tgctaatcca attactaatg gtggtgccga tagatccgat   1140
ttgaaattgc caaattggag agaattcgcc aacgatatta cgatgacac cagaggtaaa   1200 gaattcgctg attctaagag aaacatggat atggctacct tgtctaatta cttgggtgca   1260
gtttctcaat tgaaccctac tagattcaga ttttcggtc cagacgaaac catgtctaat   1320
agattgtggg gtttgttcaa cgttactcca agacaatgga tggaagaaat caagaaacca   1380
caagatcaat tattgtcccc aaccggtaga atcattgact ctcaattgtc tgaacatcaa   1440
gctgaaggtt ggtggaagg ttatactttg actggtagag ttggtatttt cgcctcttac   1500
gaatctttct tgagagttgt tgataccatg gttacccaac atttcaagtg ttgagacat   1560 gcttcagaac aagcttggag aaatgattac ccatccttga acttgattgc tacttctact   1620
gctttccaac aagatcataa cggttacact catcaagatc caggtatgtt gactcatttg   1680
gctgaaaaga gtccaactt catcagagaa tatttgccag ctgatggtaa ctctttgttg   1740
gctgtccaag aaagagcttt ttccgaaaga cataaggtca acttgttgat cgcttctaag   1800
caacctagac aacaatggtt cactgttgaa gaagctgaag ttttggctaa cgaaggttg   1860 aagattattg attgggcttc tacagctcca tcctccgatg ttgatattac ttttgcttct   1920
gctggtactg aacctaccat tgaaactttg gctgcttttg gttgatcaa tcaagctttt   1980 ccagatgtca gttcagata cgttaatgtc gtcgaattat tgagattgca aaaaagtcc   2040 gaacctaaca tgaacgacga aagagaattg tctgcagaag aattcaacaa gtacttccaa   2100
gctgataccc cagttatttt tggtttccat gcttacgaaa acttgatcga atcattcttc   2160
ttcgaacgta aattcactgg tgatgtttac gttcacggtt acagagaaga tggtgatatt   2220
accactacct acgatatgag agtttactcc catttggata gattccacca agctaaagaa   2280
gctgccgaaa ttttgtctgc aaacggtaag atagatcaag ctgctgctga tactttcatt   2340
gccaagatgg atgatacctt ggctaagcac tttcaagtta ctagaaacga aggtagagat   2400
atcgaagaat tcacagattg gacttggtcc ccattgaaat aa                      2442
```

<210> SEQ ID NO 8
<211> LENGTH: 813
<212> TYPE: PRT
<213> ORGANISM: Artificial Sequence
<220> FEATURE:
<223> OTHER INFORMATION: Codon-optimized form of Leuconostoc
        mesenteroides protein

<400> SEQUENCE: 8

Met Ala Asp Phe Asp Ser Lys Glu Tyr Leu Glu Leu Val Asp Lys Trp
1               5                   10                  15

-continued

```
Trp Arg Ala Thr Asn Tyr Leu Ser Ala Gly Met Ile Phe Leu Lys Ser
             20                  25                  30
Asn Pro Leu Phe Ser Val Thr Asn Thr Pro Ile Lys Ala Glu Asp Val
         35                  40                  45
Lys Val Lys Pro Ile Gly His Trp Gly Thr Ile Ser Gly Gln Thr Phe
 50                  55                  60
Leu Tyr Ala His Ala Asn Arg Leu Ile Asn Lys Tyr Gly Leu Asn Met
 65                  70                  75                  80
Phe Tyr Val Gly Gly Pro Gly His Gly Gln Val Met Val Thr Asn
                 85                  90                  95
Ala Tyr Leu Asp Gly Ala Tyr Thr Glu Asp Tyr Pro Glu Ile Thr Gln
             100                 105                 110
Asp Ile Glu Gly Met Ser His Leu Phe Lys Arg Phe Ser Phe Pro Gly
         115                 120                 125
Gly Ile Gly Ser His Met Thr Ala Gln Thr Pro Gly Ser Leu His Glu
 130                 135                 140
Gly Gly Glu Leu Gly Tyr Ser Leu Ser His Ala Phe Gly Ala Val Leu
145                 150                 155                 160
Asp Asn Pro Asp Gln Val Ala Phe Ala Val Val Gly Asp Gly Glu Ala
             165                 170                 175
Glu Thr Gly Pro Ser Met Ala Ser Trp His Ser Ile Lys Phe Leu Asn
         180                 185                 190
Ala Lys Asn Asp Gly Ala Val Leu Pro Val Leu Asp Leu Asn Gly Phe
     195                 200                 205
Lys Ile Ser Asn Pro Thr Ile Phe Ser Arg Met Ser Asp Glu Glu Ile
210                 215                 220
Thr Lys Phe Phe Glu Gly Leu Gly Tyr Ser Pro Arg Phe Ile Glu Asn
225                 230                 235                 240
Asp Asp Ile His Asp Tyr Ala Thr Tyr His Gln Leu Ala Ala Asn Ile
             245                 250                 255
Leu Asp Gln Ala Ile Glu Asp Ile Gln Ala Ile Gln Asn Asp Ala Arg
         260                 265                 270
Glu Asn Gly Lys Tyr Gln Asp Gly Glu Ile Pro Ala Trp Pro Val Ile
     275                 280                 285
Ile Ala Arg Leu Pro Lys Gly Trp Gly Gly Pro Thr His Asp Ala Ser
290                 295                 300
Asn Asn Pro Ile Glu Asn Ser Phe Arg Ala His Gln Val Pro Leu Pro
305                 310                 315                 320
Leu Glu Gln His Asp Leu Ala Thr Leu Pro Glu Phe Glu Asp Trp Met
             325                 330                 335
Asn Ser Tyr Lys Pro Glu Glu Leu Phe Asn Ala Asp Gly Ser Leu Lys
         340                 345                 350
Asp Glu Leu Lys Ala Ile Ala Pro Lys Gly Asp Lys Arg Met Ser Ala
     355                 360                 365
Asn Pro Ile Thr Asn Gly Gly Ala Asp Arg Ser Asp Leu Lys Leu Pro
370                 375                 380
Asn Trp Arg Glu Phe Ala Asn Asp Ile Asn Asp Thr Arg Gly Lys
385                 390                 395                 400
Glu Phe Ala Asp Ser Lys Arg Asn Met Asp Met Ala Thr Leu Ser Asn
             405                 410                 415
Tyr Leu Gly Ala Val Ser Gln Leu Asn Pro Thr Arg Phe Arg Phe Phe
         420                 425                 430
Gly Pro Asp Glu Thr Met Ser Asn Arg Leu Trp Gly Leu Phe Asn Val
```

```
        435                 440                 445

Thr Pro Arg Gln Trp Met Glu Glu Ile Lys Glu Pro Gln Asp Gln Leu
    450                 455                 460

Leu Ser Pro Thr Gly Arg Ile Ile Asp Ser Gln Leu Ser Glu His Gln
465                 470                 475                 480

Ala Glu Gly Trp Leu Glu Gly Tyr Thr Leu Thr Gly Arg Val Gly Ile
                485                 490                 495

Phe Ala Ser Tyr Glu Ser Phe Leu Arg Val Val Asp Thr Met Val Thr
            500                 505                 510

Gln His Phe Lys Trp Leu Arg His Ala Ser Glu Gln Ala Trp Arg Asn
        515                 520                 525

Asp Tyr Pro Ser Leu Asn Leu Ile Ala Thr Ser Thr Ala Phe Gln Gln
    530                 535                 540

Asp His Asn Gly Tyr Thr His Gln Asp Pro Gly Met Leu Thr His Leu
545                 550                 555                 560

Ala Glu Lys Lys Ser Asn Phe Ile Arg Glu Tyr Leu Pro Ala Asp Gly
                565                 570                 575

Asn Ser Leu Leu Ala Val Gln Glu Arg Ala Phe Ser Glu Arg His Lys
            580                 585                 590

Val Asn Leu Leu Ile Ala Ser Lys Gln Pro Arg Gln Gln Trp Phe Thr
        595                 600                 605

Val Glu Glu Ala Glu Val Leu Ala Asn Glu Gly Leu Lys Ile Ile Asp
    610                 615                 620

Trp Ala Ser Thr Ala Pro Ser Ser Asp Val Asp Ile Thr Phe Ala Ser
625                 630                 635                 640

Ala Gly Thr Glu Pro Thr Ile Glu Thr Leu Ala Ala Leu Trp Leu Ile
                645                 650                 655

Asn Gln Ala Phe Pro Asp Val Lys Phe Arg Tyr Val Asn Val Val Glu
            660                 665                 670

Leu Leu Arg Leu Gln Lys Lys Ser Glu Pro Asn Met Asn Asp Glu Arg
        675                 680                 685

Glu Leu Ser Ala Glu Glu Phe Asn Lys Tyr Phe Gln Ala Asp Thr Pro
    690                 695                 700

Val Ile Phe Gly Phe His Ala Tyr Glu Asn Leu Ile Glu Ser Phe Phe
705                 710                 715                 720

Phe Glu Arg Lys Phe Thr Gly Asp Val Tyr Val His Gly Tyr Arg Glu
                725                 730                 735

Asp Gly Asp Ile Thr Thr Thr Tyr Asp Met Arg Val Tyr Ser His Leu
            740                 745                 750

Asp Arg Phe His Gln Ala Lys Glu Ala Ala Glu Ile Leu Ser Ala Asn
        755                 760                 765

Gly Lys Ile Asp Gln Ala Ala Ala Asp Thr Phe Ile Ala Lys Met Asp
    770                 775                 780

Asp Thr Leu Ala Lys His Phe Gln Val Thr Arg Asn Glu Gly Arg Asp
785                 790                 795                 800

Ile Glu Glu Phe Thr Asp Trp Thr Trp Ser Pro Leu Lys
                805                 810
```

<210> SEQ ID NO 9
<211> LENGTH: 1002
<212> TYPE: DNA
<213> ORGANISM: Artificial Sequence
<220> FEATURE:
<223> OTHER INFORMATION: Codon-optimized form of Clostridium kluyveri
gene

<400> SEQUENCE: 9

```
atgaagttga tggaaaacat cttcggtttg gctaaggctg ataagaagaa aatcgttttg      60
gctgaaggtg aagaagaaag aaacattaga gcctccgaag aaatcatcag agatggtatt     120
gctgatatca tcttggtcgg ttctgaatcc gttatcaaag aaaatgctgc taagttcggt     180
gttaacttgg ctggtgttga aatagttgat ccagaaactt cttctaagac tgctggttac     240
gctaatgcct tctacgaaat tagaaagaac aagggtgtta ccttggaaaa ggcagataag     300
atagttagag atccaatcta cttcgctacc atgatggtta agttgggtga tgctgatggt     360
ttggtttctg gtgctattca tacaaccggt gatttgttaa gaccaggttt acaaatcgtt     420
aagactgttc caggtgcttc cgttgtttct tctgtttttt tgatgtctgt tccagactgc     480
gaatatggtg aagatggttt tttgttgttc gctgattgtg ctgttaacgt tgtccaact      540
gctgaagaat tgtcctctat tgctattact actgctgaaa ccgctaagaa cttgtgcaaa     600
attgaaccta gagttgccat tgttgtcttc tctactatgg ttctgcttc ccatgaattg      660
gttgataagg ttactaaggc taccaagttg gctaagaag ctagaccaga tttggatatc       720
gatggtgaat acaattgga tgcctccttg gttaagaagg ttgctgattt gaaagctcca      780
ggttctaaag ttgctggtaa ggctaatgtt ttgatcttcc cagatattca agccggtaac      840
attggttaca agttggttca aagatttgct aaggcagaag ccattggtcc aatttgtcaa     900
ggttttgcta agccaatcaa cgacttgtct agaggttgtt ctgttgatga tatcgttaag     960
gttgttgccg ttactgctgt tcaagctcaa gcacaaggtt aa                       1002
```

<210> SEQ ID NO 10
<211> LENGTH: 332
<212> TYPE: PRT
<213> ORGANISM: Artificial Sequence
<220> FEATURE:
<223> OTHER INFORMATION: Codon-optimized form of Clostridium kluyveri protein

<400> SEQUENCE: 10

```
Lys Leu Met Glu Asn Ile Phe Gly Leu Ala Lys Ala Asp Lys Lys Lys
1               5                   10                  15

Ile Val Leu Ala Glu Gly Glu Glu Arg Asn Ile Arg Ala Ser Glu
            20                  25                  30

Glu Ile Ile Arg Asp Gly Ile Ala Asp Ile Ile Leu Val Gly Ser Glu
        35                  40                  45

Ser Val Ile Lys Glu Asn Ala Ala Lys Phe Gly Val Asn Leu Ala Gly
    50                  55                  60

Val Glu Ile Val Asp Pro Glu Thr Ser Ser Lys Thr Ala Gly Tyr Ala
65                  70                  75                  80

Asn Ala Phe Tyr Glu Ile Arg Lys Asn Lys Gly Val Thr Leu Glu Lys
                85                  90                  95

Ala Asp Lys Ile Val Arg Asp Pro Ile Tyr Phe Ala Thr Met Met Val
            100                 105                 110

Lys Leu Gly Asp Ala Asp Gly Leu Val Ser Gly Ala Ile His Thr Thr
        115                 120                 125

Gly Asp Leu Leu Arg Pro Gly Leu Gln Ile Val Lys Thr Val Pro Gly
    130                 135                 140

Ala Ser Val Val Ser Ser Val Phe Leu Met Ser Val Pro Asp Cys Glu
145                 150                 155                 160

Tyr Gly Glu Asp Gly Phe Leu Leu Phe Ala Asp Cys Ala Val Asn Val
```

```
            165                 170                 175
Cys Pro Thr Ala Glu Glu Leu Ser Ser Ile Ala Ile Thr Thr Ala Glu
            180                 185                 190

Thr Ala Lys Asn Leu Cys Lys Ile Glu Pro Arg Val Ala Met Leu Ser
        195                 200                 205

Phe Ser Thr Met Gly Ser Ala Ser His Glu Leu Val Asp Lys Val Thr
    210                 215                 220

Lys Ala Thr Lys Leu Ala Lys Glu Ala Arg Pro Asp Leu Asp Ile Asp
225                 230                 235                 240

Gly Glu Leu Gln Leu Asp Ala Ser Leu Val Lys Lys Val Ala Asp Leu
                245                 250                 255

Lys Ala Pro Gly Ser Lys Val Ala Gly Lys Ala Asn Val Leu Ile Phe
            260                 265                 270

Pro Asp Ile Gln Ala Gly Asn Ile Gly Tyr Lys Leu Val Gln Arg Phe
        275                 280                 285

Ala Lys Ala Glu Ala Ile Gly Pro Ile Cys Gln Gly Phe Ala Lys Pro
    290                 295                 300

Ile Asn Asp Leu Ser Arg Gly Cys Ser Val Asp Ile Val Lys Val
305                 310                 315                 320

Val Ala Val Thr Ala Val Gln Ala Gln Ala Gln Gly
                325                 330
```

<210> SEQ ID NO 11
<211> LENGTH: 2283
<212> TYPE: DNA
<213> ORGANISM: Escherichia coli

<400> SEQUENCE: 11

```
atgtccgagc ttaatgaaaa gttagccaca gcctgggaag ttttaccaa aggtgactgg      60
cagaatgaag taaacgtccg tgacttcatt cagaaaaact acactccgta cgagggtgac     120
gagtccttcc tggctggcgc tactgaagcg accaccaccc tgtgggacaa agtaatggaa     180
ggcgttaaac tggaaaaccg cactcacgcg ccagttgact ttgacaccgc tgttgcttcc     240
accatcacct ctcacgacgc tggctacatc aacaagcagc ttgagaaaat cgttggtctg     300
cagactgaag ctccgctgaa acgtgctctt atcccgttcg gtggtatcaa aatgatcgaa     360
ggttcctgca aagcgtacaa ccgcgaactg atcccgatga tcaaaaaaat cttcactgaa     420
taccgtaaaa ctcacaacca gggcgtgttc gacgtttaca ctccggacat cctgcgttgc     480
cgtaaatctg gtgttctgac cggtctgcca gatgcatatg ccgtggccg tatcatcggt     540
gactaccgtc gcgttgcgct gtacggtatc gactacctga tgaaagacaa actggcacag     600
ttcacttctc tgcaggctga tctggaaaac ggcgtaaacc tggaacagac tatccgtctg     660
cgcgaagaaa tcgctgaaca gcaccgcgct ctgggtcaga tgaaagaaat ggctgcgaaa     720
tacggctacg acatctctgg tccggctacc aacgctcagg aagctatcca gtggacttac     780
ttcggctacc tggctgctgt taagtctcag aacggtgctg caatgtcctt cggtcgtacc     840
tccaccttcc tggatgtgta catcgaacgt gacctgaaag ctggcaagat caccgaacaa     900
gaagcgcagg aaatggttga ccacctggtc atgaaactgc gtatggttcg cttcctgcgt     960
actccggaat acgatgaact gttctctggc gacccgatct gggcaaccga atctatcggt    1020
ggtatgggcc tcgacggtcg taccctggtt accaaaaaca gcttccgttt cctgaacacc    1080
ctgtacacca tgggtccgtc tccggaaccg aacatgacca ttctgtggtc tgaaaaactg    1140
ccgctgaact tcaagaaatt cgccgctaaa gtgtccatcg acacctcttc tctgcagtat    1200
```

```
gagaacgatg acctgatgcg tccggacttc aacaacgatg actacgctat tgcttgctgc   1260
gtaagcccga tgatcgttgg taaacaaatg cagttcttcg gtgcgcgtgc aaacctggcg   1320
aaaaccatgc tgtacgcaat caacggcggc gttgacgaaa aactgaaaat gcaggttggt   1380
ccgaagtctg aaccgatcaa aggcgatgtc ctgaactatg atgaagtgat ggagcgcatg   1440
gatcacttca tggactggct ggctaaacag tacatcactg cactgaacat catccactac   1500
atgcacgaca gtacagcta cgaagcctct ctgatggcgc tgcacgaccg tgacgttatc   1560
cgcaccatgg cgtgtggtat cgctggtctg tccgttgctg ctgactccct gtctgcaatc   1620
aaatatgcga aagttaaacc gattcgtgac gaagacggtc tggctatcga cttcgaaatc   1680
gaaggcgaat acccgcagtt tggtaacaat gatccgcgtg tagatgacct ggctgttgac   1740
ctggtagaac gtttcatgaa gaaaattcag aaactgcaca cctaccgtga cgctatcccg   1800
actcagtctg ttctgaccat cacttctaac gttgtgtatg gtaagaaaac gggtaacacc   1860
ccagacggtc gtcgtgctgg cgcgccgttc ggacccgggtg ctaacccgat gcacggtcgt   1920
gaccagaaag gtgcagtagc ctctctgact tccgttgcta aactgccgtt tgcttacgct   1980
aaagatggta tctcctacac cttctctatc gttccgaacg cactgggtaa agacgacgaa   2040
gttcgtaaga ccaacctggc tggtctgatg gatggttact ccaccacga agcatccatc   2100 gaaggtggtc agcaccctgaa cgttaacgtg atgaaccgtg aaatgctgct cgacgcgatg   2160
gaaaacccgg aaaaatatcc gcagctgacc atccgtgtat ctggctacgc agtacgtttc   2220
aactcgctga ctaaagaaca gcagcaggac gttattactc gtaccttcac tcaatctatg   2280
taa                                                                 2283
```

<210> SEQ ID NO 12
<211> LENGTH: 759
<212> TYPE: PRT
<213> ORGANISM: Escherichia coli

<400> SEQUENCE: 12

```
Ser Glu Leu Asn Glu Lys Leu Ala Thr Ala Trp Glu Gly Phe Thr Lys
1               5                   10                  15

Gly Asp Trp Gln Asn Glu Val Asn Val Arg Asp Phe Ile Gln Lys Asn
            20                  25                  30

Tyr Thr Pro Tyr Glu Gly Asp Glu Ser Phe Leu Ala Gly Ala Thr Glu
        35                  40                  45

Ala Thr Thr Thr Leu Trp Asp Lys Val Met Glu Gly Val Lys Leu Glu
    50                  55                  60

Asn Arg Thr His Ala Pro Val Asp Phe Asp Thr Ala Val Ala Ser Thr
65                  70                  75                  80

Ile Thr Ser His Asp Ala Gly Tyr Ile Asn Lys Gln Leu Glu Lys Ile
                85                  90                  95

Val Gly Leu Gln Thr Glu Ala Pro Leu Lys Arg Ala Leu Ile Pro Phe
            100                 105                 110

Gly Gly Ile Lys Met Ile Glu Gly Ser Cys Lys Ala Tyr Asn Arg Glu
        115                 120                 125

Leu Asp Pro Met Ile Lys Lys Ile Phe Thr Glu Tyr Arg Lys Thr His
    130                 135                 140

Asn Gln Gly Val Phe Asp Val Tyr Thr Pro Asp Ile Leu Arg Cys Arg
145                 150                 155                 160

Lys Ser Gly Val Leu Thr Gly Leu Pro Asp Ala Tyr Gly Arg Gly Arg
                165                 170                 175
```

-continued

Ile Ile Gly Asp Tyr Arg Arg Val Ala Leu Tyr Gly Ile Asp Tyr Leu
            180                 185                 190

Met Lys Asp Lys Leu Ala Gln Phe Thr Ser Leu Gln Ala Asp Leu Glu
            195                 200                 205

Asn Gly Val Asn Leu Glu Gln Thr Ile Arg Leu Arg Glu Glu Ile Ala
            210                 215                 220

Glu Gln His Arg Ala Leu Gly Gln Met Lys Glu Met Ala Ala Lys Tyr
225                 230                 235                 240

Gly Tyr Asp Ile Ser Gly Pro Ala Thr Asn Ala Gln Glu Ala Ile Gln
                245                 250                 255

Trp Thr Tyr Phe Gly Tyr Leu Ala Ala Val Lys Ser Gln Asn Gly Ala
            260                 265                 270

Ala Met Ser Phe Gly Arg Thr Ser Thr Phe Leu Asp Val Tyr Ile Glu
            275                 280                 285

Arg Asp Leu Lys Ala Gly Lys Ile Thr Glu Gln Glu Ala Gln Glu Met
            290                 295                 300

Val Asp His Leu Val Met Lys Leu Arg Met Val Arg Phe Leu Arg Thr
305                 310                 315                 320

Pro Glu Tyr Asp Glu Leu Phe Ser Gly Asp Pro Ile Trp Ala Thr Glu
                325                 330                 335

Ser Ile Gly Gly Met Gly Leu Asp Gly Arg Thr Leu Val Thr Lys Asn
            340                 345                 350

Ser Phe Arg Phe Leu Asn Thr Leu Tyr Thr Met Gly Pro Ser Pro Glu
            355                 360                 365

Pro Asn Met Thr Ile Leu Trp Ser Glu Lys Leu Pro Leu Asn Phe Lys
            370                 375                 380

Lys Phe Ala Ala Lys Val Ser Ile Asp Thr Ser Ser Leu Gln Tyr Glu
385                 390                 395                 400

Asn Asp Asp Leu Met Arg Pro Asp Phe Asn Asn Asp Asp Tyr Ala Ile
                405                 410                 415

Ala Cys Cys Val Ser Pro Met Ile Val Gly Lys Gln Met Gln Phe Phe
            420                 425                 430

Gly Ala Arg Ala Asn Leu Ala Lys Thr Met Leu Tyr Ala Ile Asn Gly
            435                 440                 445

Gly Val Asp Glu Lys Leu Lys Met Gln Val Gly Pro Lys Ser Glu Pro
            450                 455                 460

Ile Lys Gly Asp Val Leu Asn Tyr Asp Glu Val Met Glu Arg Met Asp
465                 470                 475                 480

His Phe Met Asp Trp Leu Ala Lys Gln Tyr Ile Thr Ala Leu Asn Ile
                485                 490                 495

Ile His Tyr Met His Asp Lys Tyr Ser Tyr Glu Ala Ser Leu Met Ala
            500                 505                 510

Leu His Asp Arg Asp Val Ile Arg Thr Met Ala Cys Gly Ile Ala Gly
            515                 520                 525

Leu Ser Val Ala Ala Asp Ser Leu Ser Ala Ile Lys Tyr Ala Lys Val
            530                 535                 540

Lys Pro Ile Arg Asp Glu Asp Gly Leu Ala Ile Asp Phe Glu Ile Glu
545                 550                 555                 560

Gly Glu Tyr Pro Gln Phe Gly Asn Asn Asp Pro Arg Val Asp Asp Leu
                565                 570                 575

Ala Val Asp Leu Val Glu Arg Phe Met Lys Lys Ile Gln Lys Leu His
            580                 585                 590

Thr Tyr Arg Asp Ala Ile Pro Thr Gln Ser Val Leu Thr Ile Thr Ser
            595                 600                 605

Asn Val Val Tyr Gly Lys Lys Thr Gly Asn Thr Pro Asp Gly Arg Arg
        610                 615                 620

Ala Gly Ala Pro Phe Gly Pro Gly Ala Asn Pro Met His Gly Arg Asp
625                 630                 635                 640

Gln Lys Gly Ala Val Ala Ser Leu Thr Ser Val Ala Lys Leu Pro Phe
                645                 650                 655

Ala Tyr Ala Lys Asp Gly Ile Ser Tyr Thr Phe Ser Ile Val Pro Asn
            660                 665                 670

Ala Leu Gly Lys Asp Asp Glu Val Arg Lys Thr Asn Leu Ala Gly Leu
        675                 680                 685

Met Asp Gly Tyr Phe His His Glu Ala Ser Ile Glu Gly Gln His
    690                 695                 700

Leu Asn Val Asn Val Met Asn Arg Glu Met Leu Leu Asp Ala Met Glu
705                 710                 715                 720

Asn Pro Glu Lys Tyr Pro Gln Leu Thr Ile Arg Val Ser Gly Tyr Ala
                725                 730                 735

Val Arg Phe Asn Ser Leu Thr Lys Glu Gln Gln Gln Asp Val Ile Thr
            740                 745                 750

Arg Thr Phe Thr Gln Ser Met
        755

<210> SEQ ID NO 13
<211> LENGTH: 741
<212> TYPE: DNA
<213> ORGANISM: Escherichia coli

<400> SEQUENCE: 13
atgtcagtta ttggtcgcat tcactccttt gaatcctgtg gaaccgtaga cggcccaggt      60
attcgcttta tcaccttttt ccagggctgc ctgatgcgct gcctgtattg tcataaccgc     120
gacacctggg acacgcatgg cggtaaagaa gttaccgttg aagatttgat gaaggaagtg     180
gtgacctatc gccactttat gaacgcttcc ggcggcggcg ttaccgcatc cggcggtgaa     240
gcaatcctgc aagctgagtt tgttcgtgac tggttccgcg cctgcaaaaa agaaggcatt     300
catacctgtc tggacaccaa cggttttgtt cgtcgttacg atccggtgat tgatgaactg     360
ctggaagtaa ccgacctggt aatgctcgat ctcaaacaga tgaacgacga gatccaccaa     420
aatctggttg gagtttccaa ccaccgcacg ctggagttcg ctaaatatct ggcgaacaaa     480
aatgtgaagg tgtggatccg ctacgttgtt gtcccaggct ggtctgacga tgacgattca     540
gcgcatcgcc tcggtgaatt tacccgtgat atgggcaacg ttgagaaaat cgagcttctc     600
ccctaccacg agctgggcaa acacaaatgg gtggcaatgg gtgaagagta caaactcgac     660
ggtgttaaac caccgaagaa agagaccatg gaacgcgtga aggcattctc tgagcagtac     720
ggtcataagg taatgttcta a                                              741

<210> SEQ ID NO 14
<211> LENGTH: 246
<212> TYPE: PRT
<213> ORGANISM: Escherichia coli

<400> SEQUENCE: 14

Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met

```
                    20                  25                  30
Arg Cys Leu Tyr Cys His Asn Arg Asp Thr Trp Asp Thr His Gly Gly
            35                  40                  45

Lys Glu Val Thr Val Glu Asp Leu Met Lys Glu Val Val Thr Tyr Arg
 50                  55                  60

His Phe Met Asn Ala Ser Gly Gly Val Thr Ala Ser Gly Gly Glu
 65                  70                  75                  80

Ala Ile Leu Gln Ala Glu Phe Val Arg Asp Trp Phe Arg Ala Cys Lys
            85                  90                  95

Lys Glu Gly Ile His Thr Cys Leu Asp Thr Asn Gly Phe Val Arg Arg
            100                 105                 110

Tyr Asp Pro Val Ile Asp Glu Leu Leu Glu Val Thr Asp Leu Val Met
            115                 120                 125

Leu Asp Leu Lys Gln Met Asn Asp Glu Ile His Gln Asn Leu Val Gly
            130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Pro Gly Trp Ser Asp
            165                 170                 175

Asp Asp Asp Ser Ala His Arg Leu Gly Glu Phe Thr Arg Asp Met Gly
            180                 185                 190

Asn Val Glu Lys Ile Glu Leu Leu Pro Tyr His Glu Leu Gly Lys His
            195                 200                 205

Lys Trp Val Ala Met Gly Glu Glu Tyr Lys Leu Asp Gly Val Lys Pro
            210                 215                 220

Pro Lys Lys Glu Thr Met Glu Arg Val Lys Gly Ile Leu Glu Gln Tyr
225                 230                 235                 240

Gly His Lys Val Met Phe
            245

<210> SEQ ID NO 15
<211> LENGTH: 1161
<212> TYPE: DNA
<213> ORGANISM: Artificial Sequence
<220> FEATURE:
<223> OTHER INFORMATION: Codon-optimized form of Burkholderia stabilis
      gene

<400> SEQUENCE: 15
atggctactg ttttgtgtgt cttgtatcca gatccagttg atggttatcc accacattat    60
gttagagata ccattccagt tattaccaga tacgctgatg tcaaactgc tccaactcca   120 gctggtccac caggttttag accaggtgaa ttggttggtt ctgtttctgg tgctttgggt   180
ttgagaggtt atttggaagc tcatggtcat actttgatcg ttacctctga taaggatggt   240
ccagattctg aattcgaaag aagattgcca gacgccgatg ttgttatttc tcaaccattt   300
tggccagctt acttgaccgc tgaaagaatt gctagcac caaaattgag attggctttg   360
actgctggta ttggttctga tcatgttgat ttggatgctg ctgctagagc ccatattact   420
gttgctgaag ttactggttc caactctatt tcagttgccg aacacgttgt tatgactact   480
ttggctttgg tcagaaacta cttgccatct catgctattg ctcaacaagg tggttggaat   540
attgctgatt gtgtctctag atcctacgat gttgaaggta tgcattttgg tactgttggt   600
gctggtagaa ttggtttggc tgttttgaga agattgaagc catttggttt acacttgcac   660
tacacccaaa gacatagatt ggatgcagct atcgaacaag aattggggttt aacttatcat   720
```

```
gctgatccag cttcattggc tgctgctgtt gatatagtta acttgcaaat cccattatac    780
ccatccaccg aacatttgtt tgatgctgct atgattgcta gaatgaagag aggtgcatac    840
ttgattaaca ccgctagagc taaattggtt gatagagatg ctgttgttag agctgttact    900
tctggtcatt tggctggtta tggtggtgat gtttggtttc cacaaccagc tccagctgat    960
catccttgga gagctatgcc ttttaatggt atgactccac atatctccgg tacatctttg   1020
tctgctcaag ctagatatgc tgctggtact ttggaaatat tgcaatgttg gtttgacggt   1080
agaccaatca gaaacgaata tttgattgtc gacggtggta ctttagctgg tactggtgct   1140
caatcttaca gattaactta a                                              1161
```

```
<210> SEQ ID NO 16
<211> LENGTH: 386
<212> TYPE: PRT
<213> ORGANISM: Artificial Sequence
<220> FEATURE:
<223> OTHER INFORMATION: Codon-optimized form of Burkholderia stabilis
      protein

<400> SEQUENCE: 16
```

| Met | Ala | Thr | Val | Leu | Cys | Val | Leu | Tyr | Pro | Asp | Pro | Val | Asp | Gly | Tyr |
|---|---|---|---|---|---|---|---|---|---|---|---|---|---|---|---|
| 1 | | | | 5 | | | | | 10 | | | | | 15 | |

| Pro | Pro | His | Tyr | Val | Arg | Asp | Thr | Ile | Pro | Val | Ile | Thr | Arg | Tyr | Ala |
| | | | 20 | | | | | 25 | | | | | 30 | | |

| Asp | Gly | Gln | Thr | Ala | Pro | Thr | Pro | Ala | Gly | Pro | Pro | Gly | Phe | Arg | Pro |
| | | | 35 | | | | | 40 | | | | | 45 | | |

| Gly | Glu | Leu | Val | Gly | Ser | Val | Ser | Gly | Ala | Leu | Gly | Leu | Arg | Gly | Tyr |
| | 50 | | | | | 55 | | | | | 60 | | | | |

| Leu | Glu | Ala | His | Gly | His | Thr | Leu | Ile | Val | Thr | Ser | Asp | Lys | Asp | Gly |
| 65 | | | | | 70 | | | | | 75 | | | | | 80 |

| Pro | Asp | Ser | Glu | Phe | Glu | Arg | Arg | Leu | Pro | Asp | Ala | Asp | Val | Val | Ile |
| | | | | 85 | | | | | 90 | | | | | 95 | |

| Ser | Gln | Pro | Phe | Trp | Pro | Ala | Tyr | Leu | Thr | Ala | Glu | Arg | Ile | Ala | Arg |
| | | | 100 | | | | | 105 | | | | | 110 | | |

| Ala | Pro | Lys | Leu | Arg | Leu | Ala | Leu | Thr | Ala | Gly | Ile | Gly | Ser | Asp | His |
| | | | 115 | | | | | 120 | | | | | 125 | | |

| Val | Asp | Leu | Asp | Ala | Ala | Ala | Arg | Ala | His | Ile | Thr | Val | Ala | Glu | Val |
| | 130 | | | | | 135 | | | | | 140 | | | | |

| Thr | Gly | Ser | Asn | Ser | Ile | Ser | Val | Ala | Glu | His | Val | Val | Met | Thr | Thr |
| 145 | | | | | 150 | | | | | 155 | | | | | 160 |

| Leu | Ala | Leu | Val | Arg | Asn | Tyr | Leu | Pro | Ser | His | Ala | Ile | Ala | Gln | Gln |
| | | | | 165 | | | | | 170 | | | | | 175 | |

| Gly | Gly | Trp | Asn | Ile | Ala | Asp | Cys | Val | Ser | Arg | Ser | Tyr | Asp | Val | Glu |
| | | | 180 | | | | | 185 | | | | | 190 | | |

| Gly | Met | His | Phe | Gly | Thr | Val | Gly | Ala | Gly | Arg | Ile | Gly | Leu | Ala | Val |
| | | | 195 | | | | | 200 | | | | | 205 | | |

| Leu | Arg | Arg | Leu | Lys | Pro | Phe | Gly | Leu | His | Leu | His | Tyr | Thr | Gln | Arg |
| | 210 | | | | | 215 | | | | | 220 | | | | |

| His | Arg | Leu | Asp | Ala | Ala | Ile | Glu | Gln | Glu | Leu | Gly | Leu | Thr | Tyr | His |
| 225 | | | | | 230 | | | | | 235 | | | | | 240 |

| Ala | Asp | Pro | Ala | Ser | Leu | Ala | Ala | Val | Asp | Ile | Val | Asn | Leu | Gln |
| | | | | 245 | | | | | 250 | | | | | 255 |

| Ile | Pro | Leu | Tyr | Pro | Ser | Thr | Glu | His | Leu | Phe | Asp | Ala | Ala | Met | Ile |
| | | | 260 | | | | | 265 | | | | | 270 | | |

| Ala | Arg | Met | Lys | Arg | Gly | Ala | Tyr | Leu | Ile | Asn | Thr | Ala | Arg | Ala | Lys |

```
                275                 280                 285
Leu Val Asp Arg Asp Ala Val Arg Ala Val Thr Ser Gly His Leu
                    290                 295                 300
Ala Gly Tyr Gly Gly Asp Val Trp Phe Pro Gln Pro Ala Pro Ala Asp
305                 310                 315                 320
His Pro Trp Arg Ala Met Pro Phe Asn Gly Met Thr Pro His Ile Ser
                325                 330                 335
Gly Thr Ser Leu Ser Ala Gln Ala Arg Tyr Ala Ala Gly Thr Leu Glu
                    340                 345                 350
Ile Leu Gln Cys Trp Phe Asp Gly Arg Pro Ile Arg Asn Glu Tyr Leu
                355                 360                 365
Ile Val Asp Gly Gly Thr Leu Ala Gly Thr Gly Ala Gln Ser Tyr Arg
                    370                 375                 380
Leu Thr
385
```

<210> SEQ ID NO 17
<211> LENGTH: 2664
<212> TYPE: DNA
<213> ORGANISM: Escherichia coli

<400> SEQUENCE: 17

```
atgtcagaac gtttcccaaa tgacgtggat ccgatcgaaa ctcgcgactg gctccaggcg      60
atcgaatcgg tcatccgtga agaaggtgtt gagcgtgctc agtatctgat cgaccaactg     120
cttgctgaag cccgcaaagg cggtgtaaac gtagccgcag gcacaggtat cagcaactac     180
atcaacacca tccccgttga agaacaaccg gagtatccgg gtaatctgga actggaacgc     240
cgtattcgtt cagctatccg ctggaacgcc atcatgacgg tgctgcgtgc gtcgaaaaaa     300
gacctcgaac tgggcggcca tatggcgtcc ttccagtctt ccgcaaccat ttatgatgtg     360
tgctttaacc acttcttccg tgcacgcaac gagcaggatg cggcgacct ggtttacttc      420
cagggccaca tctccccggg cgtgtacgct cgtgctttcc tggaaggtcg tctgactcag     480
gagcagctgg ataacttccg tcaggaagtt cacggcaatg ccctctcttc ctatccgcac     540
ccgaaactga tgccggaatt ctggcagttc ccgaccgtat ctatgggtct gggtccgatt     600
ggtgctattt accaggctaa attcctgaaa tatctggaac accgtggcct gaaagatacc     660
tctaaacaaa ccgtttacgc gttcctcggt gacggtgaaa tggacgaacc ggaatccaaa     720
ggtgcgatca ccatcgctac ccgtgaaaaa ctggataacc tggtcttcgt tatcaactgt     780
aacctgcagc gtcttgacgg cccggtcacc ggtaacggca gatcatcaa cgaactggaa      840
ggcatcttcg aaggtgctgg ctggaacgtg atcaaagtga tgtggggtag ccgttgggat     900
gaactgctgc gtaaggatac cagcggtaaa ctgatccagc tgatgaacga accgttgac      960
ggcgactacc agaccttcaa atcgaaagat ggtgcgtacg ttcgtgaaca cttcttcggt    1020
aaatatcctg aaaccgcagc actggttgca gactggacctg acgagcagat ctgggcactg   1080
aaccgtggtg gtcacgatcc gaagaaaatc tacgctgcat tcaagaaagc gcaggaaacc    1140
aaaggcaaag cgacagtaat ccttgctcat accattaaag gttacggcat gggcgacgcg    1200
gctgaaggta aaacatcgc gcaccaggtt aagaaaatga acatggacgg tgtgcgtcat     1260
atccgcgacc gtttcaatgt gccggtgtct gatgcagata tcgaaaaact gccgtacatc    1320
accttcccgg aaggttctga agagcatacc tatctgcacg ctcagcgtca gaaactgcac    1380
ggttatctgc caagccgtca gccgaacttc acgagaagc ttgagctgcc gagcctgcaa     1440
```

```
gacttcggcg cgctgttgga agagcagagc aaagagatct ctaccactat cgctttcgtt   1500
cgtgctctga acgtgatgct gaagaacaag tcgatcaaag atcgtctggt accgatcatc   1560
gccgacgaag cgcgtacttt cggtatggaa ggtctgttcc gtcagattgg tatttacagc   1620
ccgaacggtc agcagtacac cccgcaggac cgcgagcagg ttgcttacta taaagaagac   1680
gagaaaggtc agattctgca ggaagggatc aacgagctgg gcgcaggttg ttcctggctg   1740
gcagcggcga cctcttacag caccaacaat ctgccgatga tcccgttcta catctattac   1800
tcgatgttcg gcttccagcg tattggcgat ctgtgctggg cggctggcga ccagcaagcg   1860
cgtggcttcc tgatcggcgg tacttccggt cgtaccaccc tgaacggcga aggtctgcag   1920
cacgaagatg gtcacagcca cattcagtcg ctgactatcc gaactgtat ctcttacgac     1980 ccggcttacg cttacgaagt tgctgtcatc atgcatgacg gtctggagcg tatgtacggt   2040
gaaaaacaag agaacgttta ctactacatc actacgctga cgaaaactac cacatgccg    2100 gcaatgccgg aaggtgctga ggaaggtatc cgtaaaggta tctacaaact cgaaactatt   2160
gaaggtagca aaggtaaagt tcagctgctc ggctccggtt ctatcctgcg tcacgtccgt   2220
gaagcagctg agatcctggc gaaagattac ggcgtaggtt ctgacgttta tagcgtgacc   2280
tccttcaccg agctggcgcg tgatggtcag gattgtgaac gctggaacat gctgcacccg   2340
ctggaaactc cgcgcgttcc gtatatcgct caggtgatga acgacgctcc ggcagtggca   2400
tctaccgact atatgaaact gttcgctgag caggtccgta cttacgtacc ggctgacgac   2460
taccgcgtac tgggtactga tggcttcggt cgttccgaca gccgtgagaa cctgcgtcac   2520
cacttcgaag ttgatgcttc ttatgtcgtg gttgcggcgc tgggcgaact ggctaaacgt   2580
ggcgaaatcg ataagaaagt ggttgctgac gcaatcgcca aattcaacat cgatgcagat   2640
aaagttaacc cgcgtctggc gtaa                                          2664
```

<210> SEQ ID NO 18
<211> LENGTH: 813
<212> TYPE: PRT
<213> ORGANISM: Escherichia coli

<400> SEQUENCE: 18

```
Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
            20                  25                  30

Asn Pro Leu Phe Ser Val Thr Asn Thr Pro Ile Lys Ala Glu Asp Val
        35                  40                  45

Lys Val Lys Pro Ile Gly His Trp Gly Thr Ile Ser Gly Gln Thr Phe
    50                  55                  60

Leu Tyr Ala His Ala Asn Arg Leu Ile Asn Lys Tyr Gly Leu Asn Met
65                  70                  75                  80

Phe Tyr Val Gly Gly Pro Gly His Gly Gln Val Met Val Thr Asn
                85                  90                  95

Ala Tyr Leu Asp Gly Ala Tyr Thr Glu Asp Tyr Pro Glu Ile Thr Gln
            100                 105                 110

Asp Ile Glu Gly Met Ser His Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Ser Leu Ser His Ala Phe Gly Ala Val Leu
145                 150                 155                 160
```

```
Asp Asn Pro Asp Gln Val Ala Phe Ala Val Val Gly Asp Gly Glu Ala
            165                 170                 175

Glu Thr Gly Pro Ser Met Ala Ser Trp His Ser Ile Lys Phe Leu Asn
        180                 185                 190

Ala Lys Asn Asp Gly Ala Val Leu Pro Val Leu Asp Leu Asn Gly Phe
            195                 200                 205

Lys Ile Ser Asn Pro Thr Ile Phe Ser Arg Met Ser Asp Glu Glu Ile
        210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Thr Tyr His Gln Leu Ala Ala Asn Ile
            245                 250                 255

Leu Asp Gln Ala Ile Glu Asp Ile Gln Ala Ile Gln Asn Asp Ala Arg
        260                 265                 270

Glu Asn Gly Lys Tyr Gln Asp Gly Glu Ile Pro Ala Trp Pro Val Ile
        275                 280                 285

Ile Ala Arg Leu Pro Lys Gly Trp Gly Gly Pro Thr His Asp Ala Ser
290                 295                 300

Asn Asn Pro Ile Glu Asn Ser Phe Arg Ala His Gln Val Pro Leu Pro
305                 310                 315                 320

Leu Glu Gln His Asp Leu Ala Thr Leu Pro Glu Phe Glu Asp Trp Met
            325                 330                 335

Asn Ser Tyr Lys Pro Glu Glu Leu Phe Asn Ala Asp Gly Ser Leu Lys
        340                 345                 350

Asp Glu Leu Lys Ala Ile Ala Pro Lys Gly Asp Lys Arg Met Ser Ala
            355                 360                 365

Asn Pro Ile Thr Asn Gly Gly Ala Asp Arg Ser Asp Leu Lys Leu Pro
        370                 375                 380

Asn Trp Arg Glu Phe Ala Asn Asp Ile Asn Asp Asp Thr Arg Gly Lys
385                 390                 395                 400

Glu Phe Ala Asp Ser Lys Arg Asn Met Asp Met Ala Thr Leu Ser Asn
            405                 410                 415

Tyr Leu Gly Ala Val Ser Gln Leu Asn Pro Thr Arg Phe Arg Phe Phe
        420                 425                 430

Gly Pro Asp Glu Thr Met Ser Asn Arg Leu Trp Gly Leu Phe Asn Val
        435                 440                 445

Thr Pro Arg Gln Trp Met Glu Glu Ile Lys Glu Pro Gln Asp Gln Leu
        450                 455                 460

Leu Ser Pro Thr Gly Arg Ile Ile Asp Ser Gln Leu Ser Glu His Gln
465                 470                 475                 480

Ala Glu Gly Trp Leu Glu Gly Tyr Thr Leu Thr Gly Arg Val Gly Ile
            485                 490                 495

Phe Ala Ser Tyr Glu Ser Phe Leu Arg Val Val Asp Thr Met Val Thr
        500                 505                 510

Gln His Phe Lys Trp Leu Arg His Ala Ser Glu Gln Ala Trp Arg Asn
        515                 520                 525

Asp Tyr Pro Ser Leu Asn Leu Ile Ala Thr Ser Thr Ala Phe Gln Gln
        530                 535                 540

Asp His Asn Gly Tyr Thr His Gln Asp Pro Gly Met Leu Thr His Leu
545                 550                 555                 560

Ala Glu Lys Lys Ser Asn Phe Ile Arg Glu Tyr Leu Pro Ala Asp Gly
            565                 570                 575
```

```
Asn Ser Leu Leu Ala Val Gln Glu Arg Ala Phe Ser Glu Arg His Lys
            580                 585                 590

Val Asn Leu Leu Ile Ala Ser Lys Gln Pro Arg Gln Gln Trp Phe Thr
        595                 600                 605

Val Glu Glu Ala Glu Val Leu Ala Asn Glu Gly Leu Lys Ile Ile Asp
    610                 615                 620

Trp Ala Ser Thr Ala Pro Ser Ser Asp Val Asp Ile Thr Phe Ala Ser
625                 630                 635                 640

Ala Gly Thr Glu Pro Thr Ile Glu Thr Leu Ala Ala Leu Trp Leu Ile
                645                 650                 655

Asn Gln Ala Phe Pro Asp Val Lys Phe Arg Tyr Val Asn Val Val Glu
            660                 665                 670

Leu Leu Arg Leu Gln Lys Lys Ser Glu Pro Asn Met Asn Asp Glu Arg
        675                 680                 685

Glu Leu Ser Ala Glu Glu Phe Asn Lys Tyr Phe Gln Ala Asp Thr Pro
    690                 695                 700

Val Ile Phe Gly Phe His Ala Tyr Glu Asn Leu Ile Glu Ser Phe Phe
705                 710                 715                 720

Phe Glu Arg Lys Phe Thr Gly Asp Val Tyr Val His Gly Tyr Arg Glu
                725                 730                 735

Asp Gly Asp Ile Thr Thr Thr Tyr Asp Met Arg Val Tyr Ser His Leu
            740                 745                 750

Asp Arg Phe His Gln Ala Lys Glu Ala Ala Glu Ile Leu Ser Ala Asn
        755                 760                 765

Gly Lys Ile Asp Gln Ala Ala Ala Asp Thr Phe Ile Ala Lys Met Asp
    770                 775                 780

Asp Thr Leu Ala Lys His Phe Gln Val Thr Arg Asn Glu Gly Arg Asp
785                 790                 795                 800

Ile Glu Glu Phe Thr Asp Trp Thr Trp Ser Pro Leu Lys
                805                 810

<210> SEQ ID NO 19
<211> LENGTH: 1893
<212> TYPE: DNA
<213> ORGANISM: Escherichia coli

<400> SEQUENCE: 19
atggctatcg aaatcaaagt accggacatc ggggctgatg aagttgaaat caccgagatc      60
ctggtcaaag tgggcgacaa agttgaagcc gaacagtcgc tgatcaccgt agaaggcgac     120
aaagcctcta tggaagttcc gtctccgcag gcgggtatcg ttaaagagat caaagtctct     180
gttggcgata aacccagac cggcgcactg attatgattt cgattccgc cgacggtgca       240 gcagacgctg cacctgctca ggcagaagag aagaaagaag cagctccggc agcagcacca     300
gcggctgcgg cggcaaaaga cgttaacgtt ccggatatcg cagcgacga gttgaagtg       360 accgaaatcc tggtgaaagt tggcgataaa gttgaagctg aacagtcgct gatcaccgta     420
gaaggcgaca aggcttctat ggaagttccg gctccgtttg ctggcaccgt gaaagagatc     480
aaagtgaacg tgggtgacaa agtgtctacc ggctcgctga ttatggtctt cgaagtcgcg     540
ggtgaagcag gcgcggcagc tccggccgct aaacaggaag cagctccggc agcggccct     600 gcaccagcgg ctggcgtgaa agaagttaac gttccggata tcgcggtga cgaagttgaa     660 gtgactgaag tgatggtgaa agtgggcgac aaagttgccg ctgaacagtc actgatcacc     720
gtagaaggcg acaaagcttc tatggaagtt ccggcgccgt ttgcaggcgt cgtgaaggaa     780
```

-continued

```
ctgaaagtca acgttggcga taaagtgaaa actggctcgc tgattatgat cttcgaagtt    840
gaaggcgcag cgcctgcggc agctcctgcg aaacaggaag cggcagcgcc ggcaccggca    900
gcaaaagctg aagccccggc agcagcacca gctgcgaaag cggaaggcaa atctgaattt    960
gctgaaaacg acgcttatgt tcacgcgact ccgctgatcc gccgtctggc acgcgagttt   1020
ggtgttaacc ttgcgaaagt gaagggcact ggccgtaaag gtcgtatcct gcgcgaagac   1080
gttcaggctt acgtgaaaga agctatcaaa cgtgcagaag cagctccggc agcgactggc   1140
ggtggtatcc ctggcatgct gccgtggccg aaggtggact cagcaagtt tggtgaaatc    1200
gaagaagtgg aactgggccg catccagaaa atctctggtg cgaacctgag ccgtaactgg   1260
gtaatgatcc cgcatgttac tcacttcgac aaaaccgata tcaccgagtt ggaagcgttc   1320
cgtaaacagc agaacgaaga agcggcgaaa cgtaagctgg atgtgaagat caccccggtt   1380
gtcttcatca tgaaagccgt tgctgcagct cttgagcaga tgcctcgctt caatagttcg   1440
ctgtcggaag acggtcagcg tctgaccctg aagaaataca tcaacatcgg tgtggcggtg   1500
gataccccga acggtctggt tgttccggta ttcaaagacg tcaacaagaa aggcatcatc   1560
gagctgtctc gcgagctgat gactatttct aagaaagcgc gtgacggtaa gctgactgcg   1620
ggcgaaatgc agggcggttg cttcaccatc tccagcatcg gcggcctggg tactaccac   1680
ttcgcgccga ttgtgaacgc gccggaagtg gctatcctcg gcgtttccaa gtccgcgatg   1740
gagccggtgt ggaatggtaa agagttcgtg ccgcgtctga tgctgccgat ttctctctcc   1800
ttcgaccacc gcgtgatcga cggtgctgat ggtgcccgtt tcattaccat cattaacaac   1860
acgctgtctg acattcgccg tctggtgatg taa                                1893
```

<210> SEQ ID NO 20
<211> LENGTH: 630
<212> TYPE: PRT
<213> ORGANISM: Escherichia coli

<400> SEQUENCE: 20

```
Met Ala Ile Glu Ile Lys Val Pro Asp Ile Gly Ala Asp Glu Val Glu
1               5                   10                  15

Ile Thr Glu Ile Leu Val Lys Val Gly Asp Lys Val Glu Ala Glu Gln
            20                  25                  30

Ser Leu Ile Thr Val Glu Gly Asp Lys Ala Ser Met Glu Val Pro Ser
        35                  40                  45

Pro Gln Ala Gly Ile Val Lys Glu Ile Lys Val Ser Val Gly Asp Lys
    50                  55                  60

Thr Gln Thr Gly Ala Leu Ile Met Ile Phe Asp Ser Ala Asp Gly Ala
65                  70                  75                  80

Ala Asp Ala Ala Pro Ala Gln Ala Glu Glu Lys Lys Glu Ala Ala Pro
                85                  90                  95

Ala Ala Ala Pro Ala Ala Ala Ala Lys Asp Val Asn Val Pro Asp
            100                 105                 110

Ile Gly Ser Asp Glu Val Glu Val Thr Glu Ile Leu Val Lys Val Gly
        115                 120                 125

Asp Lys Val Glu Ala Glu Gln Ser Leu Ile Thr Val Glu Gly Asp Lys
    130                 135                 140

Ala Ser Met Glu Val Pro Ala Pro Phe Ala Gly Thr Val Lys Glu Ile
145                 150                 155                 160

Lys Val Asn Val Gly Asp Lys Val Ser Thr Gly Ser Leu Ile Met Val
                165                 170                 175
```

```
Phe Glu Val Ala Gly Glu Gly Ala Ala Pro Ala Ala Lys Gln
            180                 185                 190

Glu Ala Ala Pro Ala Ala Pro Ala Pro Ala Ala Gly Val Lys Glu
        195                 200                 205

Val Asn Val Pro Asp Ile Gly Gly Asp Glu Val Glu Val Thr Glu Val
        210                 215                 220

Met Val Lys Val Gly Asp Lys Val Ala Ala Glu Gln Ser Leu Ile Thr
225                 230                 235                 240

Val Glu Gly Asp Lys Ala Ser Met Glu Val Pro Ala Pro Phe Ala Gly
                245                 250                 255

Val Val Lys Glu Leu Lys Val Asn Val Gly Asp Lys Val Lys Thr Gly
                260                 265                 270

Ser Leu Ile Met Ile Phe Glu Val Glu Gly Ala Ala Pro Ala Ala Ala
                275                 280                 285

Pro Ala Lys Gln Glu Ala Ala Ala Pro Ala Pro Ala Ala Lys Ala Glu
        290                 295                 300

Ala Pro Ala Ala Ala Pro Ala Ala Lys Ala Glu Gly Lys Ser Glu Phe
305                 310                 315                 320

Ala Glu Asn Asp Ala Tyr Val His Ala Thr Pro Leu Ile Arg Arg Leu
                325                 330                 335

Ala Arg Glu Phe Gly Val Asn Leu Ala Lys Val Lys Gly Thr Gly Arg
                340                 345                 350

Lys Gly Arg Ile Leu Arg Glu Asp Val Gln Ala Tyr Val Lys Glu Ala
                355                 360                 365

Ile Lys Arg Ala Glu Ala Ala Pro Ala Ala Thr Gly Gly Gly Ile Pro
                370                 375                 380

Gly Met Leu Pro Trp Pro Lys Val Asp Phe Ser Lys Phe Gly Glu Ile
385                 390                 395                 400

Glu Glu Val Glu Leu Gly Arg Ile Gln Lys Ile Ser Gly Ala Asn Leu
                405                 410                 415

Ser Arg Asn Trp Val Met Ile Pro His Val Thr His Phe Asp Lys Thr
                420                 425                 430

Asp Ile Thr Glu Leu Glu Ala Phe Arg Lys Gln Gln Asn Glu Glu Ala
                435                 440                 445

Ala Lys Arg Lys Leu Asp Val Lys Ile Thr Pro Val Val Phe Ile Met
450                 455                 460

Lys Ala Val Ala Ala Ala Leu Glu Gln Met Pro Arg Phe Asn Ser Ser
465                 470                 475                 480

Leu Ser Glu Asp Gly Gln Arg Leu Thr Leu Lys Lys Tyr Ile Asn Ile
                485                 490                 495

Gly Val Ala Val Asp Thr Pro Asn Gly Leu Val Val Pro Val Phe Lys
                500                 505                 510

Asp Val Asn Lys Lys Gly Ile Ile Glu Leu Ser Arg Glu Leu Met Thr
                515                 520                 525

Ile Ser Lys Lys Ala Arg Asp Gly Lys Leu Thr Ala Gly Glu Met Gln
                530                 535                 540

Gly Gly Cys Phe Thr Ile Ser Ser Ile Gly Gly Leu Gly Thr Thr His
545                 550                 555                 560

Phe Ala Pro Ile Val Asn Ala Pro Glu Val Ala Ile Leu Gly Val Ser
                565                 570                 575

Lys Ser Ala Met Glu Pro Val Trp Asn Gly Lys Glu Phe Val Pro Arg
                580                 585                 590

Leu Met Leu Pro Ile Ser Leu Ser Phe Asp His Arg Val Ile Asp Gly
```

Ala Asp Gly Ala Arg Phe Ile Thr Ile Ile Asn Asn Thr Leu Ser Asp
610                 615                 620

Ile Arg Arg Leu Val Met
625             630

<210> SEQ ID NO 21
<211> LENGTH: 1425
<212> TYPE: DNA
<213> ORGANISM: Escherichia coli

<400> SEQUENCE: 21

| | |
|---|---|
| atgagtactg aaatcaaaac tcaggtcgtg gtacttgggg caggccccgc aggttactcc | 60 |
| gctgccttcc gttgcgctga tttaggtctg gaaaccgtaa tcgtagaacg ttacaacacc | 120 |
| cttggcggtg tttgcctgaa cgtcggctgt atcccttcta agcactgct gcacgtagca | 180 |
| aaagttatcg aagaagccaa agcgctggct gaacacggta tcgtcttcgg cgaaccgaaa | 240 |
| accgatatcg acaagattcg tacctggaaa gagaaagtga tcaatcagct gaccggtggt | 300 |
| ctggctggta tggcgaaagg ccgcaaagtc aaagtggtca acggtctggg taaattcacc | 360 |
| ggggctaaca ccctggaagt tgaaggtgag aacggcaaaa ccgtgatcaa cttcgacaac | 420 |
| gcgatcattg cagcgggttc tcgcccgatc caactgccgt ttattccgca tgaagatccg | 480 |
| cgtatctggg actccactga cgcgctggaa ctgaaagaag taccagaacg cctgctggta | 540 |
| atgggtggcg gtatcatcgg tctggaaatg ggcaccgttt accacgcgct gggttcacag | 600 |
| attgacgtgg ttgaaatgtt cgaccaggtt atcccggcag ctgacaaaga catcgttaaa | 660 |
| gtcttcacca gcgtatcag caagaaattc aacctgatgc tggaaaccaa agttaccgcc | 720 |
| gttgaagcga agaagacgg catttatgtg acgatggaag cgaaaaaagc acccgctgaa | 780 |
| ccgcagcgtt acgacgccgt gctggtagcg attggtcgtg tgccgaacgg taaaaacctc | 840 |
| gacgcaggca agcaggcgt ggaagttgac gaccgtggtt tcatccgcgt tgacaaacag | 900 |
| ctgcgtacca acgtaccgca tatctttgct atcggcgata tcgtcggtca accgatgctg | 960 |
| gcacacaaag tgttcacga aggtcacgtt gccgctgaag ttatcgccgg taagaaacac | 1020 |
| tacttcgatc cgaaagttat cccgtccatc gcctataccg aaccagaagt tgcatgggtg | 1080 |
| ggtctgactg agaagaagc gaaagagaaa ggcatcagct atgaaaccgc caccttcccg | 1140 |
| tgggctgctt ctggtcgtgc tatcgcttcc gactgcgcag acggtatgac caagctgatt | 1200 |
| ttcgacaaag aatctcaccg tgtgatcggt ggtgcgattg tcggtactaa cggcggcgag | 1260 |
| ctgctgggtg aaatcggcct ggcaatcgaa atgggttgtg atgctgaaga catcgcactg | 1320 |
| accatccacg cgcaccccgac tctgcacgag tctgtgggcc tggcggcaga agtgttcgaa | 1380 |
| ggtagcatta ccgacctgcc gaacccgaaa gcgaagaaga gtaa | 1425 |

<210> SEQ ID NO 22
<211> LENGTH: 474
<212> TYPE: PRT
<213> ORGANISM: Escherichia coli

<400> SEQUENCE: 22

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val

```
                35                  40                  45
Gly Cys Ile Pro Ser Lys Ala Leu Leu His Val Ala Lys Val Ile Glu
 50                  55                  60
Glu Ala Lys Ala Leu Ala Glu His Gly Ile Val Phe Gly Glu Pro Lys
 65                  70                  75                  80
Thr Asp Ile Asp Lys Ile Arg Thr Trp Lys Glu Lys Val Ile Asn Gln
                 85                  90                  95
Leu Thr Gly Gly Leu Ala Gly Met Ala Lys Gly Arg Lys Val Lys Val
                100                 105                 110
Val Asn Gly Leu Gly Lys Phe Thr Gly Ala Asn Thr Leu Glu Val Glu
                115                 120                 125
Gly Glu Asn Gly Lys Thr Val Ile Asn Phe Asp Asn Ala Ile Ile Ala
                130                 135                 140
Ala Gly Ser Arg Pro Ile Gln Leu Pro Phe Ile Pro His Glu Asp Pro
145                 150                 155                 160
Arg Ile Trp Asp Ser Thr Asp Ala Leu Glu Leu Lys Glu Val Pro Glu
                165                 170                 175
Arg Leu Leu Val Met Gly Gly Gly Ile Ile Gly Leu Glu Met Gly Thr
                180                 185                 190
Val Tyr His Ala Leu Gly Ser Gln Ile Asp Val Val Glu Met Phe Asp
                195                 200                 205
Gln Val Ile Pro Ala Ala Asp Lys Asp Ile Val Lys Val Phe Thr Lys
210                 215                 220
Arg Ile Ser Lys Lys Phe Asn Leu Met Leu Glu Thr Lys Val Thr Ala
225                 230                 235                 240
Val Glu Ala Lys Glu Asp Gly Ile Tyr Val Thr Met Glu Gly Lys Lys
                245                 250                 255
Ala Pro Ala Glu Pro Gln Arg Tyr Asp Ala Val Leu Val Ala Ile Gly
                260                 265                 270
Arg Val Pro Asn Gly Lys Asn Leu Asp Ala Gly Lys Ala Gly Val Glu
                275                 280                 285
Val Asp Asp Arg Gly Phe Ile Arg Val Asp Lys Gln Leu Arg Thr Asn
                290                 295                 300
Val Pro His Ile Phe Ala Ile Gly Asp Ile Val Gly Gln Pro Met Leu
305                 310                 315                 320
Ala His Lys Gly Val His Glu Gly His Val Ala Ala Glu Val Ile Ala
                325                 330                 335
Gly Lys Lys His Tyr Phe Asp Pro Lys Val Ile Pro Ser Ile Ala Tyr
                340                 345                 350
Thr Glu Pro Glu Val Ala Trp Val Gly Leu Thr Glu Lys Glu Ala Lys
                355                 360                 365
Glu Lys Gly Ile Ser Tyr Glu Thr Ala Thr Phe Pro Trp Ala Ala Ser
                370                 375                 380
Gly Arg Ala Ile Ala Ser Asp Cys Ala Asp Gly Met Thr Lys Leu Ile
385                 390                 395                 400
Phe Asp Lys Glu Ser His Arg Val Ile Gly Gly Ala Ile Val Gly Thr
                405                 410                 415
Asn Gly Gly Glu Leu Leu Gly Glu Ile Gly Leu Ala Ile Glu Met Gly
                420                 425                 430
Cys Asp Ala Glu Asp Ile Ala Leu Thr Ile His Ala His Pro Thr Leu
                435                 440                 445
His Glu Ser Val Gly Leu Ala Ala Glu Val Phe Glu Gly Ser Ile Thr
                450                 455                 460
```

Asp Leu Pro Asn Pro Lys Ala Lys Lys Lys
465                 470

<210> SEQ ID NO 23
<211> LENGTH: 1425
<212> TYPE: DNA
<213> ORGANISM: Escherichia coli

<400> SEQUENCE: 23

```
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta agcactgct gcacgtagca     180
aaagttatcg aagaagccaa agcgctggct gaacacggta tcgtcttcgg cgaaccgaaa     240
accgatatcg acaagattcg tacctggaaa gagaaagtga tcaatcagct gaccggtggt     300
ctggctggta tggcgaaagg ccgcaaagtc aaagtggtca acggtctggg taaattcacc     360
ggggctaaca ccctggaagt tgaaggtgag aacggcaaaa ccgtgatcaa cttcgacaac     420
gcgatcattg cagcgggttc tcgcccgatc caactgccgt ttattccgca tgaagatccg     480
cgtatctggg actccactga cgcgctgaa ctgaaagaag taccagaacg cctgctggta     540
atgggtggcg gtatcatcgc tctggaaatg gctaccgttt accacgcgct gggttcacag     600
attgacgtgg ttgttcgtaa acatcaggtt atccgtgcag ctgacaaaga catcgttaaa     660
gtcttcacca gcgtatcag caagaaattc aacctgatgc tggaaaccaa agttaccgcc     720
gttgaagcga agaagacgg catttatgtg acgatggaag gcaaaaagc acccgctgaa     780
ccgcagcgtt acgacgccgt gctggtagcg attggtcgtg tgccgaacgg taaaaacctc     840
gacgcaggca agcaggcgt ggaagttgac gaccgtggtt tcatccgcgt tgacaaacag     900
ctgcgtacca acgtaccgca tctctttgct atcggcgata tcgtcggtca accgatgctg     960
gcacacaaag tgttcacga aggtcacgtt gccgctgaag ttatcgccgg taagaaacac    1020
tacttcgatc cgaaagttat cccgtccatc gcctataccg aaccagaagt tgcatgggtg    1080
ggtctgactg agaagaagc gaaagagaaa ggcatcagct atgaaaccgc caccttcccg    1140
tgggctgctt ctggtcgtgc tatcgcttcc gactgcgcag acggtatgac caagctgatt    1200
ttcgacaaag aatctcaccg tgtgatcggt ggtgcgattg tcggtactaa cggcggcgag    1260
ctgctgggtg aaatcggcct ggcaatcgaa atgggttgtg atgctgaaga catcgcactg    1320
accatccacg cgcaccccgac tctgcacgag tctgtgggcc tggcggcaga agtgttcgaa    1380
ggtagcatta ccgacctgcc gaacccgaaa gcgaagaaga agtaa              1425
```

<210> SEQ ID NO 24
<211> LENGTH: 474
<212> TYPE: PRT
<213> ORGANISM: Escherichia coli

<400> SEQUENCE: 24

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

```
Glu Ala Lys Ala Leu Ala Glu His Gly Ile Val Phe Gly Glu Pro Lys
 65                  70                  75                  80

Thr Asp Ile Asp Lys Ile Arg Thr Trp Lys Glu Lys Val Ile Asn Gln
                 85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Ile Ile Ala Leu Glu Met Ala Thr
            180                 185                 190

Val Tyr His Ala Leu Gly Ser Gln Ile Asp Val Val Arg Lys His
        195                 200                 205

Gln Val Ile Arg Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470
```

<210> SEQ ID NO 25
<211> LENGTH: 1200
<212> TYPE: DNA
<213> ORGANISM: Yarrowia lipolytica

<400> SEQUENCE: 25

```
atgcgactac tcatccgccg aaccggtata acacggcccc acagcgtgca agcgcgccga    60
tccacatgga ttcggcttct ctcgaccgag atattgcatg cagaactgct tcccgaccgc   120
cagtcgcccc actacgtcca ggagtcgacc tctctgtcat ctctggtgtg ggacaagcct   180
ctggaaaacg ttctgatcgt caaaaaaccc tgggaccaca atgtgcgcga gtcgctcatc   240
cagatggcat ctcacatcca gcgccggtac ccccgagtca acattctggt ggaggaacat   300
gtggccgacg aggtccagaa gcagattgga gccgcaggcg tgaccgccat ccacacgggg   360
ccaggagagg tgctgagaaa caagacggat ctgctcgtga ctctgggagg cgacggaact   420
attctacatg ccacctccat gtttgcttcc ggagaagtgc cgccggtgct gtccttttcg   480
ctggggactc tgggttttcct gctgccgttt gatttcaagg acttcaaaac tgcattcgac   540
atggtgtact cgtcgcaggc ctcggtggtc aaccgcgccc gcctagcatg tcagaaaatg   600
tccattcgca aggaaatcac ccacttgccc tcccaatcgc acattgaaca caactcaacc   660
catgtctacg gcaatcccga cgactacaat cttagcccac taacctacgc atgaacgac   720
atcaacatcc accgtggagc tgagccgcat ctccaccaag tcgacatcca cgttgacggc   780
gagttcatca cccgagccat tgctgacggt gtcaccatcg ccacacccac gggctccacg   840
gcctactcgc tgtcgtctgg cggctccatt gtgcatcccc gagtcgcctg cattctgctg   900
acccccatct gtccgcgatc gctgtcattc cggcctctca tttttcccagc cacctccaaa   960
atatgcatca ccgcctcgtc cgaatctcga ggtagaggcg ccgagctgtc tgtcgacgga  1020
atcgccaagg gtctggttcg acccagcgac aagattctgg tcgaaagcga aaccggccac  1080
aactcgggca tctggtgcgt ggccaagaca gacagagact gggtcagtgg cctcaacggg  1140
ttactgggct tcaatagcag ttttggcaag ggcggggagg cgtcaggcga tgttgcttag  1200
```

<210> SEQ ID NO 26
<211> LENGTH: 398
<212> TYPE: PRT
<213> ORGANISM: Yarrowia lipolytica

<400> SEQUENCE: 26

```
Arg Leu Leu Ile Arg Arg Thr Gly Ile Thr Arg Pro His Ser Val Gln
 1               5                  10                  15

Ala Arg Arg Ser Thr Trp Ile Arg Leu Leu Ser Thr Glu Ile Leu His
            20                  25                  30

Ala Glu Leu Leu Pro Asp Arg Gln Ser Pro His Tyr Val Gln Glu Ser
        35                  40                  45

Thr Ser Leu Ser Ser Leu Val Trp Asp Lys Pro Leu Glu Asn Val Leu
    50                  55                  60

Ile Val Lys Lys Pro Trp Asp His Asn Val Arg Glu Ser Leu Ile Gln
65                  70                  75                  80

Met Ala Ser His Ile Gln Arg Arg Tyr Pro Arg Val Asn Ile Leu Val
                85                  90                  95

Glu Glu His Val Ala Asp Glu Val Gln Lys Gln Ile Gly Ala Ala Gly
            100                 105                 110

Val Thr Ala Ile His Thr Gly Pro Gly Glu Val Leu Arg Asn Lys Thr
        115                 120                 125
```

Asp Leu Leu Val Thr Leu Gly Gly Asp Gly Thr Ile Leu His Ala Thr
130                 135                 140

Ser Met Phe Ala Ser Gly Glu Val Pro Pro Val Leu Ser Phe Ser Leu
145                 150                 155                 160

Gly Thr Leu Gly Phe Leu Leu Pro Phe Asp Phe Lys Asp Phe Lys Thr
                165                 170                 175

Ala Phe Asp Met Val Tyr Ser Ser Gln Ala Ser Val Val Asn Arg Ala
            180                 185                 190

Arg Leu Ala Cys Gln Lys Met Ser Ile Arg Lys Glu Ile Thr His Leu
        195                 200                 205

Pro Ser Gln Ser His Ile Glu His Asn Ser Thr His Val Tyr Gly Asn
    210                 215                 220

Pro Asp Asp Tyr Asn Leu Ser Pro Leu Thr Tyr Ala Met Asn Asp Ile
225                 230                 235                 240

Asn Ile His Arg Gly Ala Glu Pro His Leu Thr Lys Leu Asp Ile His
                245                 250                 255

Val Asp Gly Glu Phe Ile Thr Arg Ala Ile Ala Asp Gly Val Thr Ile
            260                 265                 270

Ala Thr Pro Thr Gly Ser Thr Ala Tyr Ser Leu Ser Ser Gly Gly Ser
        275                 280                 285

Ile Val His Pro Arg Val Ala Cys Ile Leu Leu Thr Pro Ile Cys Pro
    290                 295                 300

Arg Ser Leu Ser Phe Arg Pro Leu Ile Phe Pro Ala Thr Ser Lys Ile
305                 310                 315                 320

Cys Ile Thr Ala Ser Ser Glu Ser Arg Gly Arg Gly Ala Glu Leu Ser
                325                 330                 335

Val Asp Gly Ile Ala Lys Gly Leu Val Arg Pro Ser Asp Lys Ile Leu
            340                 345                 350

Val Glu Ser Glu Thr Gly His Asn Ser Gly Ile Trp Cys Val Ala Lys
        355                 360                 365

Thr Asp Arg Asp Trp Val Ser Gly Leu Asn Gly Leu Leu Gly Phe Asn
    370                 375                 380

Ser Ser Phe Gly Lys Gly Gly Glu Ala Ser Gly Asp Val Ala
385                 390                 395

<210> SEQ ID NO 27
<211> LENGTH: 1281
<212> TYPE: DNA
<213> ORGANISM: Yarrowia lipolytica

<400> SEQUENCE: 27
atggcccgca acacaacgga ccgccatctc accgtgcttg tccatgatct gctaaacatt     60
gccgacgagc ataccggcag ctcgctgctg agcaccaacc aggctcgcgc ggaggcgaca    120
ggccacattc tgtgcgaaaa gtcgcgccac tctcgagagg agctcaacga gtttgtcatg    180
aacgtccggg gtctgtccaa ccggctgagc aacctcaagt tgaagccgca gctgcgacaa    240
gtgatgattg tagcgaaact gcaggataaa gacatcattg ccaagacgcg cgactttgcg    300
tcgctgctga tgaaacgtgg aatctccgtc tacgtgcaga agagctggc ggcccatcct    360 ctgttcaacc tcaatggact tgagggagac gccaaaaacg ccgacacaaa gttccacact    420
tggtccgagg tggctctgcc ggaccccaac aaactggacc tggtcgtgac ccttggggc    480 gacggaacgt gctatttgt gtcctggctg ttccagcaga ttgtgccacc ggtggtctcc    540
tttggcctgg gctctctggg attcctcacc gagtacgagt gggacagacg tgaggagacg    600

```
atcgattcga tcgacaaaaa cggcatctat ctgtcgttga gaatgcggtt cgagtgccgc    660
gtcatccgag ctgtcaagga cgacggagag gactggatga cccgagactt ggacgacgaa    720
attcgttcca tggttacctc ccacaactcg accgacaacc tggacgagta ctcgtacgac    780
aagcattacg tggacgccac gcactcgatt ctcaacgact ggtggttga ccgaggcaca     840 aactccacca tgaccaccac agagctgtac acggactttg atcacctgac caccgtacag    900
gccgatggac tggtgattgc cactccttct ggatccacgg cgtactccct gtccgcagga    960
ggatctcttg ttcaccccga tatccccggc attctcattt ccccatttg tccccatact    1020 ctgagtttcc ggccggttgt tgtgcccgat aatactacga ttcgaatcgg agtgccatac    1080
gatgctcggg cgtcggcgta ctgctcgttc gacggccgat cgagggtgga actgacgcct    1140
ggagacttta tcaccgtcac cgcgtcgcga ttcccattcc ccaaggtgca gtcggaggct    1200
gggtccgagt ggtattctgg tttgtccaat acgttgaact ggaaccagcg aaagcgacag    1260
aagcggttca ccaacattta a                                             1281

<210> SEQ ID NO 28
<211> LENGTH: 426
<212> TYPE: PRT
<213> ORGANISM: Yarrowia lipolytica

<400> SEQUENCE: 28

Met Ala Arg Asn Thr Thr Asp Arg His Leu Thr Val Leu Val His Asp
1               5                  10                  15

Leu Leu Asn Ile Ala Asp Glu His Thr Gly Ser Ser Leu Leu Ser Thr
            20                  25                  30

Asn Gln Ala Arg Ala Glu Ala Thr Gly His Ile Leu Cys Glu Lys Ser
        35                  40                  45

Arg His Ser Arg Glu Glu Leu Asn Glu Phe Val Met Asn Val Arg Gly
    50                  55                  60

Leu Ser Asn Arg Leu Ser Asn Leu Lys Leu Lys Pro Gln Leu Arg Gln
65                  70                  75                  80

Val Met Ile Val Ala Lys Leu Gln Asp Lys Asp Ile Ile Ala Lys Thr
                85                  90                  95

Arg Asp Phe Ala Ser Leu Leu Met Lys Arg Gly Ile Ser Val Tyr Val
            100                 105                 110

Gln Lys Glu Leu Ala Ala His Pro Leu Phe Asn Leu Asn Gly Leu Glu
        115                 120                 125

Gly Asp Ala Lys Asn Ala Asp Thr Lys Phe His Thr Trp Ser Glu Val
    130                 135                 140

Ala Leu Pro Asp Pro Asn Lys Leu Asp Leu Val Val Thr Leu Gly Gly
145                 150                 155                 160

Asp Gly Thr Val Leu Phe Val Ser Trp Leu Phe Gln Gln Ile Val Pro
                165                 170                 175

Pro Val Val Ser Phe Gly Leu Gly Ser Leu Gly Phe Leu Thr Glu Tyr
            180                 185                 190

Glu Trp Asp Arg Arg Glu Glu Thr Ile Asp Ser Ile Asp Lys Asn Gly
        195                 200                 205

Ile Tyr Leu Ser Leu Arg Met Arg Phe Glu Cys Arg Val Ile Arg Ala
    210                 215                 220

Val Lys Asp Asp Gly Glu Asp Trp Met Thr Arg Asp Leu Asp Asp Glu
225                 230                 235                 240

Ile Arg Ser Met Val Thr Ser His Asn Ser Thr Asp Asn Leu Asp Glu
```

```
                    245                 250                 255
Tyr Ser Tyr Asp Lys His Tyr Val Asp Ala Thr His Ser Ile Leu Asn
            260                 265                 270

Asp Leu Val Val Asp Arg Gly Thr Asn Ser Thr Met Thr Thr Thr Glu
        275                 280                 285

Leu Tyr Thr Asp Phe Asp His Leu Thr Thr Val Gln Ala Asp Gly Leu
    290                 295                 300

Val Ile Ala Thr Pro Ser Gly Ser Thr Ala Tyr Ser Leu Ser Ala Gly
305                 310                 315                 320

Gly Ser Leu Val His Pro Asp Ile Pro Gly Ile Leu Ile Ser Pro Ile
                325                 330                 335

Cys Pro His Thr Leu Ser Phe Arg Pro Val Val Pro Asp Asn Thr
                340                 345                 350

Thr Ile Arg Ile Gly Val Pro Tyr Asp Ala Arg Ala Ser Ala Tyr Cys
            355                 360                 365

Ser Phe Asp Gly Arg Ser Arg Val Glu Leu Thr Pro Gly Asp Phe Ile
370                 375                 380

Thr Val Thr Ala Ser Arg Phe Pro Phe Pro Lys Val Gln Ser Glu Ala
385                 390                 395                 400

Gly Ser Glu Trp Tyr Ser Gly Leu Ser Asn Thr Leu Asn Trp Asn Gln
                405                 410                 415

Arg Lys Arg Gln Lys Arg Phe Thr Asn Ile
                420                 425

<210> SEQ ID NO 29
<211> LENGTH: 1488
<212> TYPE: DNA
<213> ORGANISM: Escherichia coli

<400> SEQUENCE: 29
atgaattttc atcatctggc ttactggcag gataaagcgt taagtctcgc cattgaaaac      60
cgcttattta ttaacggtga atatactgct gcggcggaaa atgaaacctt tgaaaccgtt     120
gatccggtca cccaggcacc gctggcgaaa attgcccgcg caagagcgt cgatatcgac      180 cgtgcgatga gcgcagcacg cggcgtattt gaacgcggcg actggtcact ctcttctccg     240
gctaaacgta aagcggtact gaataaactc gccgatttaa tggaagccca cgccgaagag     300
ctggcactgc tggaaactct cgacaccggc aaaccgattc gtcacagtct gcgtgatgat     360
attcccggcg cggcgcgcgc cattcgctgg tacgccgaag cgatcgacaa agtgtatggc     420
gaagtggcga ccaccagtag ccatgagctg gcgatgatcg tgcgtgaacc ggtcggcgtg     480
attgccgcca tcgtgccgtg gaacttcccg ctgttgctga cttgctggaa actcggcccg     540
gcgctggcgg cgggaaacag cgtgattcta aaaccgtctg aaaaatcacc gctcagtgcg     600
attcgtctcg cggggctggc gaaagaagca ggcttgccgg atggtgtgtt gaacgtggtg     660
acgggttttg gtcatgaagc cgggcaggcg ctgtcgcgtc ataacgatat cgacgccatt     720
gcctttaccg gttcaacccg taccgggaaa cagctgctga agatgcgggc gacagcaac     780 atgaaacgcg tctggctgga agcgggcggc aaaagcgcca acatcgtttt cgctgactgc     840
ccggatttgc aacaggcggc aagcgccacc gcagcaggca ttttctacaa ccagggacag     900
gtgtgcatcg ccggaacgcg cctgttgctg aagagagca tcgccgatga attcttagcc     960
ctgttaaaaa cagcaggcgc aaaactggca gccgggccat cacttgatcc gcaaccacc     1020 atgggcacct taatcgactg cgcccacgcc gactcggtcc atagctttat tcgggaaggc     1080
```

```
gaaagcaaag ggcaactgtt gttggatggc cgtaacgccg ggctggctgc cgccatcggc    1140
ccgaccatct ttgtggatgt ggacccgaat gcgtccttaa gtcgcgaaga gattttcggt    1200
ccggtgctgg tggtcacgcg tttcacatca aagaacagg cgctacagct tgccaacgac     1260
agccagtacg gccttggcgc ggcggtatgg acgcgcgacc tctcccgcgc gcaccgcatg    1320
agccgacgcc tgaaagccgg ttccgtcttc gtcaataact acaacgacgg cgatatgacc    1380
gtgccgtttg gcggctataa gcagagcggc aacggtcgcg acaaatccct gcatgccctt    1440
gaaaaattca ctgaactgaa aaccatctgg ataagcctgg aggcctga                 1488
```

<210> SEQ ID NO 30
<211> LENGTH: 495
<212> TYPE: PRT
<213> ORGANISM: Escherichia coli

<400> SEQUENCE: 30

```
Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
        115                 120                 125

Arg Trp Tyr Ala Glu Ala Ile Asp Lys Val Tyr Gly Glu Val Ala Thr
    130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
        195                 200                 205

Glu Ala Gly Leu Pro Asp Gly Val Leu Asn Val Thr Gly Phe Gly
    210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
    290                 295                 300
```

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
            325                 330                 335

Pro Ala Thr Thr Met Gly Thr Leu Ile Asp Cys Ala His Ala Asp Ser
        340                 345                 350

Val His Ser Phe Ile Arg Glu Gly Glu Ser Lys Gly Gln Leu Leu Leu
    355                 360                 365

Asp Gly Arg Asn Ala Gly Leu Ala Ala Ile Gly Pro Thr Ile Phe
370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
                405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
            435                 440                 445

Val Phe Val Asn Asn Tyr Asn Asp Gly Asp Met Thr Val Pro Phe Gly
450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
            485                 490                 495

<210> SEQ ID NO 31
<211> LENGTH: 1491
<212> TYPE: DNA
<213> ORGANISM: Yarrowia lipolytica

<400> SEQUENCE: 31
atgtctcttt tcagcaaact taccctagcc aacggccttg aggtcgatca gcccactggc        60
cttttcatta cggcgaatt cgttgccgcg aagtctggca aaacgtttga aaccatcaac       120
cctaccaccg aggaagtgat tgttccgtt tctgaggcag atgaggaaga tgtgaatgct       180
gctgttgacg ctgctgctgc tgctttcaag acctggggtt tcaagactgc tcccagtgct       240
cgaggtgcgg ctctattcaa gctggcggac ctcattgagc gagacctcga tatcatcgct       300
gcgattgaaa cgactgacaa cggtaaggtg tacgcccatg ccaagggtga tgttgctctg       360
gttgtcaagg tcattcgatt ttatgcagga tatgctgaca agatctacgg agacgttatc       420
catggtaacg atggacactt ttcctacact cgaaaggagc ccattggagt tgtggacaa       480 atcattccct ggaacttccc cttggtcatg tggtcctgga agattgctcc tgctctggct       540
accggtaaca ctgtggttct caagagtgcc gagtctactc ctctgtctgc tctgtacgcg       600
gccaagctcg cccaggaagc aggtattccc gcaggcgtgc tcaacattgt ttcaggttac       660
ggaaaggtcg gcgctttgat gactaaccac cccaagatcc gaaggtggc tttcacaggc       720 tcgactgcta ccggcaagca ggttctcaag ggtgcagctc tgtccaacct gaagaagatc       780
tcccttgagc ttggaggaaa gtctcccaac atcatctttg atgatgccaa cctgcccaac       840
gccatctcct gggctgctct tggtatcttc ttcaactctg agaagtctg tgctgctgcc       900 tctcgtctct atgttcagga gggagtctac cacgaagtcg ttgctgctct caaacagcga       960
gctgaggcat tggttgtggg cgatcccttt gaccagcaga ccttccaggg ggcccagacc      1020
tccaagattc agttcgaccg agtcatgagc ttcattgagg ccggaaaggc cgagggagct      1080

```
actctgctga ccggaggctg ccgagcaaag gacaagggct atttcatccg gcccactgtc    1140
ttcaccgacg ttaaaaagga catgaagatt gtgcaggaag agatctttgg ccccgttgtc    1200
gttgtgacca agttcaagac tcttgaggag gtcattgagc ttgccaacga ctctgagtac    1260
ggcctggctg cgggtgtgca cacccaggac atttctcgag cccactattt ggcagagaac    1320
ctccatgccg gaactgtgtg ggttaatacc tacaactcgt ttcacatctc gcttcctttt    1380
ggaggtttca accagagtgg tttcggtaag gagatgggca aggacggact ggacagttat    1440
attcagacca aggctgttcg aatcatgttt gaccaggcca agctgcagta a             1491
```

```
<210> SEQ ID NO 32
<211> LENGTH: 496
<212> TYPE: PRT
<213> ORGANISM: Yarrowia lipolytica

<400> SEQUENCE: 32

Met Ser Leu Phe Ser Lys Leu Thr Leu Ala Asn Gly Leu Glu Val Asp
1               5                   10                  15

Gln Pro Thr Gly Leu Phe Ile Asn Gly Glu Phe Val Ala Ala Lys Ser
            20                  25                  30

Gly Lys Thr Phe Glu Thr Ile Asn Pro Thr Thr Glu Val Ile Cys
        35                  40                  45

Ser Val Ser Glu Ala Asp Glu Glu Asp Val Asn Ala Ala Val Asp Ala
    50                  55                  60

Ala Ala Ala Ala Phe Lys Thr Trp Gly Phe Lys Thr Ala Pro Ser Ala
65                  70                  75                  80

Arg Gly Ala Ala Leu Phe Lys Leu Ala Asp Leu Ile Glu Arg Asp Leu
                85                  90                  95

Asp Ile Ile Ala Ala Ile Glu Thr Thr Asp Asn Gly Lys Val Tyr Ala
            100                 105                 110

His Ala Lys Gly Asp Val Ala Leu Val Val Lys Val Ile Arg Phe Tyr
        115                 120                 125

Ala Gly Tyr Ala Asp Lys Ile Tyr Gly Asp Val Ile His Gly Asn Asp
    130                 135                 140

Gly His Phe Ser Tyr Thr Arg Lys Glu Pro Ile Gly Val Cys Gly Gln
145                 150                 155                 160

Ile Ile Pro Trp Asn Phe Pro Leu Val Met Trp Ser Trp Lys Ile Ala
                165                 170                 175

Pro Ala Leu Ala Thr Gly Asn Thr Val Val Leu Lys Ser Ala Glu Ser
            180                 185                 190

Thr Pro Leu Ser Ala Leu Tyr Ala Ala Lys Leu Ala Gln Glu Ala Gly
        195                 200                 205

Ile Pro Ala Gly Val Leu Asn Ile Val Ser Gly Tyr Gly Lys Val Gly
    210                 215                 220

Ala Leu Met Thr Asn His Pro Lys Ile Arg Lys Val Ala Phe Thr Gly
225                 230                 235                 240

Ser Thr Ala Thr Gly Lys Gln Val Leu Lys Gly Ala Ala Leu Ser Asn
                245                 250                 255

Leu Lys Lys Ile Ser Leu Glu Leu Gly Gly Lys Ser Pro Asn Ile Ile
            260                 265                 270

Phe Asp Asp Ala Asn Leu Pro Asn Ala Ile Ser Trp Ala Ala Leu Gly
        275                 280                 285

Ile Phe Phe Asn Ser Gly Glu Val Cys Ala Ala Ala Ser Arg Leu Tyr
    290                 295                 300
```

| | | | | | | | | | | | | | | | |
|---|---|---|---|---|---|---|---|---|---|---|---|---|---|---|---|
| Val | Gln | Glu | Gly | Val | Tyr | His | Glu | Val | Val | Ala | Ala | Leu | Lys | Gln | Arg |
| 305 | | | | 310 | | | | 315 | | | | 320 | | | |
| Ala | Glu | Ala | Leu | Val | Val | Gly | Asp | Pro | Phe | Asp | Gln | Gln | Thr | Phe | Gln |
| | | | | 325 | | | | | 330 | | | | | 335 | |
| Gly | Ala | Gln | Thr | Ser | Lys | Ile | Gln | Phe | Asp | Arg | Val | Met | Ser | Phe | Ile |
| | | | 340 | | | | | 345 | | | | | 350 | | |
| Glu | Ala | Gly | Lys | Ala | Glu | Gly | Ala | Thr | Leu | Leu | Thr | Gly | Gly | Cys | Arg |
| | | 355 | | | | | 360 | | | | | 365 | | | |
| Ala | Lys | Asp | Lys | Gly | Tyr | Phe | Ile | Arg | Pro | Thr | Val | Phe | Thr | Asp | Val |
| | 370 | | | | | 375 | | | | | 380 | | | | |
| Lys | Lys | Asp | Met | Lys | Ile | Val | Gln | Glu | Glu | Ile | Phe | Gly | Pro | Val | Val |
| 385 | | | | | 390 | | | | | 395 | | | | | 400 |
| Val | Val | Thr | Lys | Phe | Lys | Thr | Leu | Glu | Glu | Val | Ile | Glu | Leu | Ala | Asn |
| | | | | 405 | | | | | 410 | | | | | 415 | |
| Asp | Ser | Glu | Tyr | Gly | Leu | Ala | Ala | Gly | Val | His | Thr | Gln | Asp | Ile | Ser |
| | | | 420 | | | | | 425 | | | | | 430 | | |
| Arg | Ala | His | Tyr | Leu | Ala | Glu | Asn | Leu | His | Ala | Gly | Thr | Val | Trp | Val |
| | | | 435 | | | | | 440 | | | | | 445 | | |
| Asn | Thr | Tyr | Asn | Ser | Phe | His | Ile | Ser | Leu | Pro | Phe | Gly | Gly | Phe | Asn |
| | | | 450 | | | | | 455 | | | | | 460 | | |
| Gln | Ser | Gly | Phe | Gly | Lys | Glu | Met | Gly | Lys | Asp | Gly | Leu | Asp | Ser | Tyr |
| 465 | | | | | 470 | | | | | 475 | | | | | 480 |
| Ile | Gln | Thr | Lys | Ala | Val | Arg | Ile | Met | Phe | Asp | Gln | Ala | Lys | Leu | Gln |
| | | | | 485 | | | | | 490 | | | | | 495 | |

<210> SEQ ID NO 33
<211> LENGTH: 1548
<212> TYPE: DNA
<213> ORGANISM: Yarrowia lipolytica

<400> SEQUENCE: 33

```
atgccatata tacggtgtct gggggactgt atcggtccca tcaaccaatt gctcaacatg     60
tccatctcca tttcgctgcc aacggaaac aagtacgaac agcccacggg cattttcatc    120
aacaacgagt ggtccgaggc ctccgacaag ggtaccattc ccgtctacaa cccgtcgacc    180
ggcgacgagg tggtgcaggt ggcggctgct actgctgagg acgtggatcg ggcagtagtt    240
gctgctcgaa aggcgttcca gagctggcga gatgtccccg tgaggagcg tgccaagttg    300
ctggacaact tcatcaatct ggtgtccaag aacctcgaca cggtggctgc catcgaggct    360
ctcgattccg gcaagcctct tcagctcaat gctcggggtg acatcgccgg cggcctggcc    420
gtctacaagt actacgcagg gtgggcggac aaggtgtttg gtaagaccat tgtcaacacc    480
accaagaagc tggcgtacac tcttcacgag ccccatggag tgtgtggtca gatcattccc    540
tggaactatc cgtttctgat ggccgcgtgg aagattgcgc tgcaattgc ggctggcaac    600
gtggtggtga tgaagctcgc ggaaaacacc cctctgtcga tgctgtatct gtgcaatctg    660
ttcaaggagg ccgggttccc tcccggagtg atcaacatct tcactggcca cggcgccaag    720
gctggctcgc gactggctga gcaccccggat gtcgacaaga ttgccttcac cggctccacc    780
gccaccggcc gaatcatcat gaagctggcc gctaccaacc tcaaggccat cactctggaa    840
tgtggaggca agtcgcccat gattgttctg ggagatgccg atctcgacca ggccaccaaa    900
tgggcccatg ccgtattat gaccaaccag ggccagatct gctgcggtgt gtcgcgagtg    960
ctggttcacg agtccatcta cgaccagttt gtcgacaagt acgtcgaggt ggtcaagcag   1020
```

```
cggtctcgag tcggagacat gttccaggac aagattctcc aaggccccca ggtctccaag    1080
gtccagcagg agaaggtgct tggctacatt gagaagggca aggaggaggg cgccaagctg    1140
gtctactctg gcgctgtggc tgccgaggcg ctcgaaaagg gctactttgt gccccccact    1200
gtgtttgctg acgtcagaga cgacatggtg atttctcgag aggagatttt cggacctgtg    1260
gttgccatcg ccaagttctc cgacgtggaa gacgccatca accgagccaa cgactccgag    1320
tacggtttgg ccgcgtccgt ctacaccaag gacctgaccg aggcccaccg aatctcccga    1380
cggctcgaaa gtggccaggt gttcatcaac atggcccata tgggcgacta ccgaatgcct    1440
tttggaggat acaaacagag tggaattgga cgagagttgg gcgagtatgg tctcgatact    1500
tatactcagt gcaaggcggt gcatattaac atgggtatga agttgtag                1548
```

<210> SEQ ID NO 34
<211> LENGTH: 515
<212> TYPE: PRT
<213> ORGANISM: Yarrowia lipolytica

<400> SEQUENCE: 34

```
Met Pro Tyr Ile Arg Cys Leu Gly Asp Cys Ile Gly Pro Ile Asn Gln
1               5                   10                  15

Leu Leu Asn Met Ser Ile Ser Ile Ser Leu Pro Asn Gly Asn Lys Tyr
            20                  25                  30

Glu Gln Pro Thr Gly Ile Phe Ile Asn Asn Glu Trp Ser Glu Ala Ser
        35                  40                  45

Asp Lys Gly Thr Ile Pro Val Tyr Asn Pro Ser Thr Gly Asp Glu Val
    50                  55                  60

Val Gln Val Ala Ala Ala Thr Ala Glu Asp Val Asp Arg Ala Val Val
65                  70                  75                  80

Ala Ala Arg Lys Ala Phe Gln Ser Trp Arg Asp Val Pro Gly Glu Glu
                85                  90                  95

Arg Ala Lys Leu Leu Asp Asn Phe Ile Asn Leu Val Ser Lys Asn Leu
            100                 105                 110

Asp Thr Val Ala Ala Ile Glu Ala Leu Asp Ser Gly Lys Pro Leu Gln
        115                 120                 125

Leu Asn Ala Arg Gly Asp Ile Ala Gly Gly Leu Ala Val Tyr Lys Tyr
    130                 135                 140

Tyr Ala Gly Trp Ala Asp Lys Val Phe Gly Lys Thr Ile Val Asn Thr
145                 150                 155                 160

Thr Lys Lys Leu Ala Tyr Thr Leu His Glu Pro His Gly Val Cys Gly
                165                 170                 175

Gln Ile Ile Pro Trp Asn Tyr Pro Phe Leu Met Ala Ala Trp Lys Ile
            180                 185                 190

Ala Pro Ala Ile Ala Ala Gly Asn Val Val Met Lys Leu Ala Glu
        195                 200                 205

Asn Thr Pro Leu Ser Met Leu Tyr Leu Cys Asn Leu Phe Lys Glu Ala
    210                 215                 220

Gly Phe Pro Pro Gly Val Ile Asn Ile Phe Thr Gly His Gly Ala Lys
225                 230                 235                 240

Ala Gly Ser Arg Leu Ala Glu His Pro Asp Val Asp Lys Ile Ala Phe
                245                 250                 255

Thr Gly Ser Thr Ala Thr Gly Arg Ile Ile Met Lys Leu Ala Ala Thr
            260                 265                 270

Asn Leu Lys Ala Ile Thr Leu Glu Cys Gly Gly Lys Ser Pro Met Ile
        275                 280                 285
```

```
Val Leu Gly Asp Ala Asp Leu Asp Gln Ala Thr Lys Trp Ala His Ala
    290                 295                 300
Gly Ile Met Thr Asn Gln Gly Gln Ile Cys Cys Gly Val Ser Arg Val
305                 310                 315                 320
Leu Val His Glu Ser Ile Tyr Asp Gln Phe Val Asp Lys Tyr Val Glu
                325                 330                 335
Val Val Lys Gln Arg Ser Arg Val Gly Asp Met Phe Gln Asp Lys Ile
            340                 345                 350
Leu Gln Gly Pro Gln Val Ser Lys Val Gln Gln Glu Lys Val Leu Gly
        355                 360                 365
Tyr Ile Glu Lys Gly Lys Glu Gly Ala Lys Leu Val Tyr Ser Gly
    370                 375                 380
Ala Val Ala Ala Glu Ala Leu Glu Lys Gly Tyr Phe Val Pro Pro Thr
385                 390                 395                 400
Val Phe Ala Asp Val Arg Asp Asp Met Val Ile Ser Arg Glu Glu Ile
                405                 410                 415
Phe Gly Pro Val Val Ala Ile Ala Lys Phe Ser Asp Val Glu Asp Ala
            420                 425                 430
Ile Asn Arg Ala Asn Asp Ser Glu Tyr Gly Leu Ala Ala Ser Val Tyr
        435                 440                 445
Thr Lys Asp Leu Thr Glu Ala His Arg Ile Ser Arg Arg Leu Glu Ser
    450                 455                 460
Gly Gln Val Phe Ile Asn Met Ala His Met Gly Asp Tyr Arg Met Pro
465                 470                 475                 480
Phe Gly Gly Tyr Lys Gln Ser Gly Ile Gly Arg Glu Leu Gly Glu Tyr
                485                 490                 495
Gly Leu Asp Thr Tyr Thr Gln Cys Lys Ala Val His Ile Asn Met Gly
            500                 505                 510
Met Lys Leu
        515

<210> SEQ ID NO 35
<211> LENGTH: 1569
<212> TYPE: DNA
<213> ORGANISM: Yarrowia lipolytica

<400> SEQUENCE: 35
atgctccgac gaatcactct caaccagttt aagggcggcc tgcgacggct gtccacccct      60 accccccgtca agaacgaacc tctgaccctg cccaacggcg ccaagtacga gcagcccgtc     120
ggtctcttca tcaacggcga gttcgtcaag tctcagtccg aaagcgattc gagaccgag      180 aaccccacca ccgagacccc catcatctcc gtttacgagg ctggtgaggc tgatgccaac     240
gcagctgtcg aggctgccaa gatgccttc aagaactggg gcttcaagac cgctccttcc     300
gagcgaggag tcctgctcaa caagctcgct gatctcattg agcgagatct cgacctcatt     360
tctgccattg agaccaccga caacggtaag gtctttgccc aggcccaggg tgacgtcgcc     420
ctcgtcgtca aggtgctccg atactacgct ggatttgccg acaagattgg cggcgaccttc    480 gtccagacca cgacggctt cttcaactac acccgaaagg agcctctcgg agtgtgtggc     540
cagatcatcc cctggaactt ccctctgctc atgtgggcct ggaagattgc ccccgctctg     600
accactggta acaccgtggt cttaagacc gccgagtcca cccctctgtc cgccctgtac     660
gcctgtaagc tctcccagga ggctggcttc cccaaggggtg ttctcaacgt tgtgtccggt    720
tatggccccg ttggaggcgt tctgtccgcc caccccgaca tcaagaagat tgcttttcacc   780
```

-continued

```
ggctccaccg ccactggtaa gcaggttgct aagaccgccc tgacctccaa cctcaagaag    840
accaccatgg agctcggtgg taagtccccc aacattatct tcgacgacgc caacctcgag    900
gacgctcttt ctgccgccgc tctcggtatc ttcttcaact ccggagaggt ctgctgcgcc    960
ggctctcgac tctttgtcca agccggtgtc tacgaccagg ttgtcgaggc cttcaagaag   1020
aaggctgagt ccgtcaaggt cggtgatccc ttcgacccca actctctcca gggtccccag   1080
cagaacaaga accagttcaa gaagattctg gatacattg agcagggcca agaggagggc    1140
gcccatctcc tgtgtggagg atctgcccag gccggtccta caagggata cttcatccag     1200 cccaccgttt tcaccgacgt gaacaacgat atgtccattg tgcgagagga gattttcggc   1260
cccgtcctga ccatcaccaa gttcaacacc gttgacgaag tgattgacat ggccaacgac   1320
tccgagtacg tcttgccgc tggtatccac accactgata tcaacaaggc ccactatgtt    1380
gctgagaaca ttgcctccgg taccatctgg gtcaactgct acaacgcctt ccacgaggcc   1440 gttcccttg gaggatacaa gcagtctggt ttcggtaagg agatgggtcg agatggtctt    1500
gagaactacc tccagaccaa ggcagttcga gtcaagcttg atgagcgaaa gtgggctgac   1560
aagcagtga                                                            1569
```

<210> SEQ ID NO 36
<211> LENGTH: 522
<212> TYPE: PRT
<213> ORGANISM: Yarrowia lipolytica

<400> SEQUENCE: 36

```
Met Leu Arg Arg Ile Thr Leu Asn Gln Phe Lys Gly Gly Leu Arg Arg
1               5                   10                  15

Leu Ser Thr Leu Thr Pro Val Lys Asn Glu Pro Leu Thr Leu Pro Asn
            20                  25                  30

Gly Ala Lys Tyr Glu Gln Pro Val Gly Leu Phe Ile Asn Gly Glu Phe
        35                  40                  45

Val Lys Ser Gln Ser Gly Lys Arg Phe Glu Thr Glu Asn Pro Thr Thr
    50                  55                  60

Glu Thr Pro Ile Ile Ser Val Tyr Glu Ala Gly Glu Ala Asp Ala Asn
65                  70                  75                  80

Ala Ala Val Glu Ala Lys Asn Ala Phe Lys Asn Trp Gly Phe Lys
                85                  90                  95

Thr Ala Pro Ser Glu Arg Gly Val Leu Leu Asn Lys Leu Ala Asp Leu
            100                 105                 110

Ile Glu Arg Asp Leu Asp Leu Ile Ser Ala Ile Glu Thr Thr Asp Asn
        115                 120                 125

Gly Lys Val Phe Ala Gln Ala Gln Gly Asp Val Ala Leu Val Val Lys
    130                 135                 140

Val Leu Arg Tyr Tyr Ala Gly Phe Ala Asp Lys Ile Gly Gly Asp Leu
145                 150                 155                 160

Val Gln Thr Asn Asp Gly Phe Phe Asn Tyr Thr Arg Lys Glu Pro Leu
                165                 170                 175

Gly Val Cys Gly Gln Ile Ile Pro Trp Asn Phe Pro Leu Leu Met Trp
            180                 185                 190

Ala Trp Lys Ile Ala Pro Ala Leu Thr Thr Gly Asn Thr Val Val Leu
        195                 200                 205

Lys Thr Ala Glu Ser Thr Pro Leu Ser Ala Leu Tyr Ala Cys Lys Leu
    210                 215                 220
```

-continued

| | | | | | | | | | | | | | | |
|---|---|---|---|---|---|---|---|---|---|---|---|---|---|---|
| Ser | Gln | Glu | Ala | Gly | Phe | Pro | Lys | Gly | Val | Leu | Asn | Val | Val | Ser | Gly |
| 225 | | | | 230 | | | | | 235 | | | | | 240 | |
| Tyr | Gly | Pro | Val | Gly | Gly | Val | Leu | Ser | Ala | His | Pro | Asp | Ile | Lys | Lys |
| | | | 245 | | | | | 250 | | | | | 255 | | |
| Ile | Ala | Phe | Thr | Gly | Ser | Thr | Ala | Thr | Gly | Lys | Gln | Val | Ala | Lys | Thr |
| | | | 260 | | | | | 265 | | | | | 270 | | |
| Ala | Leu | Thr | Ser | Asn | Leu | Lys | Lys | Thr | Thr | Met | Glu | Leu | Gly | Gly | Lys |
| | | 275 | | | | | 280 | | | | | 285 | | | |
| Ser | Pro | Asn | Ile | Ile | Phe | Asp | Asp | Ala | Asn | Leu | Glu | Asp | Ala | Leu | Ser |
| | 290 | | | | | 295 | | | | | 300 | | | | |
| Ala | Ala | Ala | Leu | Gly | Ile | Phe | Phe | Asn | Ser | Gly | Glu | Val | Cys | Cys | Ala |
| 305 | | | | | 310 | | | | | 315 | | | | | 320 |
| Gly | Ser | Arg | Leu | Phe | Val | Gln | Ala | Gly | Val | Tyr | Asp | Gln | Val | Val | Glu |
| | | | 325 | | | | | 330 | | | | | 335 | | |
| Ala | Phe | Lys | Lys | Lys | Ala | Glu | Ser | Val | Lys | Val | Gly | Asp | Pro | Phe | Asp |
| | | | 340 | | | | | 345 | | | | | 350 | | |
| Pro | Asn | Ser | Leu | Gln | Gly | Pro | Gln | Gln | Asn | Lys | Asn | Gln | Phe | Lys | Lys |
| | | 355 | | | | | 360 | | | | | 365 | | | |
| Ile | Leu | Gly | Tyr | Ile | Glu | Gln | Gly | Gln | Lys | Glu | Gly | Ala | His | Leu | Leu |
| | 370 | | | | | 375 | | | | | 380 | | | | |
| Cys | Gly | Gly | Ser | Ala | Gln | Ala | Gly | Pro | Asn | Lys | Gly | Tyr | Phe | Ile | Gln |
| 385 | | | | | 390 | | | | | 395 | | | | | 400 |
| Pro | Thr | Val | Phe | Thr | Asp | Val | Asn | Asn | Asp | Met | Ser | Ile | Val | Arg | Glu |
| | | | 405 | | | | | 410 | | | | | 415 | | |
| Glu | Ile | Phe | Gly | Pro | Val | Leu | Thr | Ile | Thr | Lys | Phe | Asn | Thr | Val | Asp |
| | | | 420 | | | | | 425 | | | | | 430 | | |
| Glu | Val | Ile | Asp | Met | Ala | Asn | Asp | Ser | Glu | Tyr | Gly | Leu | Ala | Ala | Gly |
| | | | 435 | | | | | 440 | | | | | 445 | | |
| Ile | His | Thr | Thr | Asp | Ile | Asn | Lys | Ala | His | Tyr | Val | Ala | Glu | Asn | Ile |
| | 450 | | | | | 455 | | | | | 460 | | | | |
| Ala | Ser | Gly | Thr | Ile | Trp | Val | Asn | Cys | Tyr | Asn | Ala | Phe | His | Glu | Ala |
| 465 | | | | | 470 | | | | | 475 | | | | | 480 |
| Val | Pro | Phe | Gly | Gly | Tyr | Lys | Gln | Ser | Gly | Phe | Gly | Lys | Glu | Met | Gly |
| | | | 485 | | | | | 490 | | | | | 495 | | |
| Arg | Asp | Gly | Leu | Glu | Asn | Tyr | Leu | Gln | Thr | Lys | Ala | Val | Arg | Val | Lys |
| | | | 500 | | | | | 505 | | | | | 510 | | |
| Leu | Asp | Glu | Arg | Lys | Trp | Ala | Asp | Lys | Gln |
| | | | 515 | | | | | 520 | |

<210> SEQ ID NO 37
<211> LENGTH: 1766
<212> TYPE: DNA
<213> ORGANISM: Yarrowia lipolytica

<400> SEQUENCE: 37

```
agtgagtatt aatatggagg acaccagttg cacagattca gatacagctc ttacattctg    60
ttgtctcaga ctcgattcga tcactgtcgt ctacactcct cgataaccga taaccgacac   120
gtactgataa cgatctcaac cccatagcat agatcgtcca acaacgccac ccaaaatatt   180
cccacaacat gtaccgacta tcacaactcc acgccacatt gcgcccaatt acgtcgtttg   240
ccatctataa ggcgcccaag aaggccgctc ctgccgtcgc tgctaaccta gtgcaagtta   300
ctcttcccga cggaaagtcc tacgaccagc caccaagct  cttcatcaac aacgagtggg   360
tcgatggtca cggcggctca attgagtctg tcaaccccgc caccgagcag gtcatctgct   420
```

| | | |
|---|---|---|
| ccgttgaggc cgctgacgag agtgatgtcg acaaggctgt tcaggccgct cgaaactgct | 480 |
| acgagaacgt ctggcgaaag gtcaccggtg ccgagcgagc acagctcatg cgcaagcttg | 540 |
| ccgaccttgt cgagaagaac aaggacctgc tcacctccat tgaggctgcc gactctggaa | 600 |
| agcccaagta cggcaactgt gacggagacg tggacgagct catctacgtc ctgcgatact | 660 |
| actccggcct ggctgagaag gctggcaatg gagtcaccat ttctacctcc aacgaaaagt | 720 |
| ttgcctacac catccacgag ccttacggag tctgtggcca gatcatcccc tggaactacc | 780 |
| ccattgctat ggctgcctgg aagctaggtc cctgtctcgc tgccggtaac gtgctggtca | 840 |
| tgaagctttc cgaatacacc cctctgtcca tgctggtcat ctgcaacctg gtcaaggagg | 900 |
| ctggtttccc ccctggcgtg gtgaacgtgg ttaacggcta cggcgccaag gccggcaacc | 960 |
| gactggctga gcaccccgac gttgacaaga ttgccttcac cggttctacc gctaccggtc | 1020 |
| gatctgtcat gaaggctgct accggaaaca tgaaggccgt gaccatggag cttggaggaa | 1080 |
| agtctcctct gctcattttc gacgactgcg atctcgccaa ggccatcgag tgggcccaca | 1140 |
| ttggcatcat gtacaacatg gccaggtgt gttccgccac ctctcgaatc ctggtgcaag | 1200 |
| aaggcattgc cgacaagttc gtcgagggtt tcatcaagca gtgtaatgag gcctccattc | 1260 |
| tgggttgtcc tttggaccag aagacctctc acgtcctca ggtcaacaag atccagtatg | 1320 |
| agaaggtgct cggatacatt gagaagggta aggctgaggg agccaagtgc attctgggag | 1380 |
| gtgaggctgc cccccaaaac ggcaaggct atttcattaa gcccaccgcc ttcaccaacg | 1440 |
| tcaacaagga catgaccatc tggaaggagg agattttcgg ccctgtcgtg gtaattgaca | 1500 |
| ccttcaagac cgaggaggag gccattgcca aggccaacga tactccgtac ggtctggctg | 1560 |
| ccgctctgtt taccgagaac attcggcgag cccaccgggt tgtcaaggag ctgcgagctg | 1620 |
| gtcaggtctg ggtcaactct gataacgact ccgatcctcg agttcccttt ggtggtgtca | 1680 |
| agcagagtgg tattggtcga gagcttggtg agtatggtct ttctatttac acccaggcca | 1740 |
| aggccgtcca cattaacctg gattag | 1766 |

<210> SEQ ID NO 38
<211> LENGTH: 491
<212> TYPE: PRT
<213> ORGANISM: Yarrowia lipolytica

<400> SEQUENCE: 38

Met Gln Val Thr Leu Pro Asp Gly Lys Ser Tyr Asp Gln Pro Thr Lys
1               5                   10                  15

Leu Phe Ile Asn Asn Glu Trp Val Asp Gly His Gly Gly Ser Ile Glu
            20                  25                  30

Ser Val Asn Pro Ala Thr Glu Gln Val Ile Cys Ser Val Glu Ala Ala
        35                  40                  45

Asp Glu Ser Asp Val Asp Lys Ala Val Gln Ala Ala Arg Asn Cys Tyr
    50                  55                  60

Glu Asn Val Trp Arg Lys Val Thr Gly Ala Glu Arg Ala Gln Leu Met
65                  70                  75                  80

Arg Lys Leu Ala Asp Leu Val Glu Lys Asn Lys Asp Leu Leu Thr Ser
                85                  90                  95

Ile Glu Ala Ala Asp Ser Gly Lys Pro Lys Tyr Gly Asn Cys Asp Gly
            100                 105                 110

Asp Val Asp Glu Leu Ile Tyr Val Leu Arg Tyr Tyr Ser Gly Leu Ala
        115                 120                 125

Glu Lys Ala Gly Asn Gly Val Thr Ile Ser Thr Ser Asn Glu Lys Phe

| | | | | | | | | | | | | | | |
|---|---|---|---|---|---|---|---|---|---|---|---|---|---|---|
| | | 130 | | | | | 135 | | | | | 140 | | |
| Ala | Tyr | Thr | Ile | His | Glu | Pro | Tyr | Gly | Val | Cys | Gly | Gln | Ile | Ile | Pro |
| 145 | | | | | 150 | | | | | 155 | | | | | 160 |
| Trp | Asn | Tyr | Pro | Ile | Ala | Met | Ala | Ala | Trp | Lys | Leu | Gly | Pro | Cys | Leu |
| | | | | 165 | | | | | 170 | | | | | 175 | |
| Ala | Ala | Gly | Asn | Val | Leu | Val | Met | Lys | Leu | Ser | Glu | Tyr | Thr | Pro | Leu |
| | | | 180 | | | | | 185 | | | | | 190 | | |
| Ser | Met | Leu | Val | Ile | Cys | Asn | Leu | Val | Lys | Glu | Ala | Gly | Phe | Pro | Pro |
| | | 195 | | | | | 200 | | | | | 205 | | | |
| Gly | Val | Val | Asn | Val | Val | Asn | Gly | Tyr | Gly | Ala | Lys | Ala | Gly | Asn | Arg |
| | 210 | | | | | 215 | | | | | 220 | | | | |
| Leu | Ala | Glu | His | Pro | Asp | Val | Asp | Lys | Ile | Ala | Phe | Thr | Gly | Ser | Thr |
| 225 | | | | | 230 | | | | | 235 | | | | | 240 |
| Ala | Thr | Gly | Arg | Ser | Val | Met | Lys | Ala | Ala | Thr | Gly | Asn | Met | Lys | Ala |
| | | | 245 | | | | | 250 | | | | | 255 | | |
| Val | Thr | Met | Glu | Leu | Gly | Gly | Lys | Ser | Pro | Leu | Leu | Ile | Phe | Asp | Asp |
| | | | 260 | | | | | 265 | | | | | 270 | | |
| Cys | Asp | Leu | Ala | Lys | Ala | Ile | Glu | Trp | Ala | His | Ile | Gly | Ile | Met | Tyr |
| | | 275 | | | | | 280 | | | | | 285 | | | |
| Asn | Met | Gly | Gln | Val | Cys | Ser | Ala | Thr | Ser | Arg | Ile | Leu | Val | Gln | Glu |
| | 290 | | | | | 295 | | | | | 300 | | | | |
| Gly | Ile | Ala | Asp | Lys | Phe | Val | Glu | Gly | Phe | Ile | Lys | Gln | Cys | Asn | Glu |
| 305 | | | | | 310 | | | | | 315 | | | | | 320 |
| Ala | Ser | Ile | Leu | Gly | Cys | Pro | Leu | Asp | Gln | Lys | Thr | Ser | His | Gly | Pro |
| | | | 325 | | | | | 330 | | | | | 335 | | |
| Gln | Val | Asn | Lys | Ile | Gln | Tyr | Glu | Lys | Val | Leu | Gly | Tyr | Ile | Glu | Lys |
| | | | 340 | | | | | 345 | | | | | 350 | | |
| Gly | Lys | Ala | Glu | Gly | Ala | Lys | Cys | Ile | Leu | Gly | Gly | Glu | Ala | Ala | Pro |
| | | 355 | | | | | 360 | | | | | 365 | | | |
| Gln | Asn | Gly | Lys | Gly | Tyr | Phe | Ile | Lys | Pro | Thr | Ala | Phe | Thr | Asn | Val |
| | 370 | | | | | 375 | | | | | 380 | | | | |
| Asn | Lys | Asp | Met | Thr | Ile | Trp | Lys | Glu | Glu | Ile | Phe | Gly | Pro | Val | Val |
| 385 | | | | | 390 | | | | | 395 | | | | | 400 |
| Val | Ile | Asp | Thr | Phe | Lys | Thr | Glu | Glu | Glu | Ala | Ile | Ala | Lys | Ala | Asn |
| | | | 405 | | | | | 410 | | | | | 415 | | |
| Asp | Thr | Pro | Tyr | Gly | Leu | Ala | Ala | Ala | Leu | Phe | Thr | Glu | Asn | Ile | Arg |
| | | | 420 | | | | | 425 | | | | | 430 | | |
| Arg | Ala | His | Arg | Val | Val | Lys | Glu | Leu | Arg | Ala | Gly | Gln | Val | Trp | Val |
| | | 435 | | | | | 440 | | | | | 445 | | | |
| Asn | Ser | Asp | Asn | Asp | Ser | Asp | Pro | Arg | Val | Pro | Phe | Gly | Gly | Val | Lys |
| | 450 | | | | | 455 | | | | | 460 | | | | |
| Gln | Ser | Gly | Ile | Gly | Arg | Glu | Leu | Gly | Glu | Tyr | Gly | Leu | Ser | Ile | Tyr |
| 465 | | | | | 470 | | | | | 475 | | | | | 480 |
| Thr | Gln | Ala | Lys | Ala | Val | His | Ile | Asn | Leu | Asp | | | | | |
| | | | 485 | | | | | 490 | | | | | | | |

<210> SEQ ID NO 39
<211> LENGTH: 1413
<212> TYPE: DNA
<213> ORGANISM: Yarrowia lipolytica

<400> SEQUENCE: 39

```
atggcttcta tccccattat tgactatctg gttatcggcg gaggctctgg aggtgttgct    60
tctgctcgtc gagccgcctc gtacggcgcc aaaacactgc tgatcgaggg caaggcgctg   120
```

```
ggaggcacct gcgtcaacgt gggctgtgtg cccaaaaagg tcatgtggaa cgcgtccgat      180
ctggcgggcc gaatccgaca ggccaaggag tacggcttcc ccgacgtgga ccccaagtac      240
gccgacaact tgactggtc cggattcaag gccaagcgag acgcttacgt caagcgactc       300
aatggaatct acgaacgaaa cctccagaag gagggcgtcg agtacgtgtt tggctgggcc      360
accctctaca gcaggaggg ccaggagttc ccctggtac atgtcaagag cgacgacggc        420
aataccaagc tgtattctgc caagaagatt atgattgcca ccggcggaaa gccccgtctg      480
cccgacgtgc ctggagccga gtacggcatt gactccgacg gcttctttgc tctcgagacc     540
cagcccaagc gagtggcggt ggttggagga ggctacattg gcgtggagct ggctggtgtc      600
ttccacggac tcaactccga gaccaccctc ttctgccgag gccagacggt gctccgagcg      660
ttcgacatca tgatccagga caccatcacc gactactacg tcaaggaggg catcaacgtg     720
ctcaagggct ccggcgtcaa gaagattgtc aagaaggaca atggcgagct gctcgtcacc     780
tacgagcagg atggcgccga aaggatatc actcttgact cacttatttg gaccattgga       840
cgagagcctc tcaaggacac cctcaacctc ggcgagtttg gcatcaagac caacaagcgg     900
ggctacattg aggtcgacga gtaccagcga tcgtccgttg acaacattta ctcgcttgga     960
gacgtttgcg gcaaggtcga gctaacccc atggctattg ctgccggacg aaagctgtcc     1020
aaccggctgt ttggtcccac agagttcaag aaccagaagc aggactacac cgatgttcct     1080
tctgccgtct tttcccaccc cgaggttggc tccatcggta tcaccgaggc tgccgccaag    1140
gagcagtatg cgaggagaa cgtcaaggtc tacacctcca gtttgtcgc catgtactac      1200 gccatgctcg aggagaaggc tcccaccgcc tacaagctgg tgtgtgccgg caaggacgag    1260
aaggttgttg gtctgcacat tgttggcgct gactctgccg agattctgca gggtttcggc    1320
gtggccattc gaatgggagc caccaaggcc gatttcgaca tgttgtggc tatccatccc      1380 acttctgccg aggagctggt gaccatgaga tag                                  1413
```

<210> SEQ ID NO 40
<211> LENGTH: 470
<212> TYPE: PRT
<213> ORGANISM: Yarrowia lipolytica

<400> SEQUENCE: 40

```
Met Ala Ser Ile Pro His Tyr Asp Tyr Leu Val Ile Gly Gly Gly Ser
1               5                   10                  15

Gly Gly Val Ala Ser Ala Arg Arg Ala Ala Ser Tyr Gly Ala Lys Thr
                20                  25                  30

Leu Leu Ile Glu Gly Lys Ala Leu Gly Gly Thr Cys Val Asn Val Gly
            35                  40                  45

Cys Val Pro Lys Lys Val Met Trp Asn Ala Ser Asp Leu Ala Gly Arg
        50                  55                  60

Ile Arg Gln Ala Lys Glu Tyr Gly Phe Pro Asp Val Asp Pro Lys Tyr
65                  70                  75                  80

Ala Asp Asn Phe Asp Trp Ser Gly Phe Lys Ala Lys Arg Asp Ala Tyr
                85                  90                  95

Val Lys Arg Leu Asn Gly Ile Tyr Glu Arg Asn Leu Gln Lys Glu Gly
            100                 105                 110

Val Glu Tyr Val Phe Gly Trp Ala Thr Leu Tyr Lys Gln Glu Gly Gln
        115                 120                 125

Glu Phe Pro Leu Val His Val Lys Ser Asp Asp Gly Asn Thr Lys Leu
    130                 135                 140
```

Tyr Ser Ala Lys Lys Ile Met Ile Ala Thr Gly Gly Lys Pro Arg Leu
145                 150                 155                 160

Pro Asp Val Pro Gly Ala Glu Tyr Gly Ile Asp Ser Asp Gly Phe Phe
            165                 170                 175

Ala Leu Glu Thr Gln Pro Lys Arg Val Ala Val Val Gly Gly Gly Tyr
            180                 185                 190

Ile Gly Val Glu Leu Ala Gly Val Phe His Gly Leu Asn Ser Glu Thr
            195                 200                 205

Thr Leu Phe Cys Arg Gly Gln Thr Val Leu Arg Ala Phe Asp Ile Met
210                 215                 220

Ile Gln Asp Thr Ile Thr Asp Tyr Tyr Val Lys Glu Gly Ile Asn Val
225                 230                 235                 240

Leu Lys Gly Ser Gly Val Lys Lys Ile Val Lys Lys Asp Asn Gly Glu
            245                 250                 255

Leu Leu Val Thr Tyr Glu Gln Asp Gly Ala Glu Lys Asp Ile Thr Leu
            260                 265                 270

Asp Ser Leu Ile Trp Thr Ile Gly Arg Glu Pro Leu Lys Asp Thr Leu
            275                 280                 285

Asn Leu Gly Glu Phe Gly Ile Lys Thr Asn Lys Arg Gly Tyr Ile Glu
290                 295                 300

Val Asp Glu Tyr Gln Arg Ser Ser Val Asp Asn Ile Tyr Ser Leu Gly
305                 310                 315                 320

Asp Val Cys Gly Lys Val Glu Leu Thr Pro Met Ala Ile Ala Ala Gly
            325                 330                 335

Arg Lys Leu Ser Asn Arg Leu Phe Gly Pro Thr Glu Phe Lys Asn Gln
            340                 345                 350

Lys Gln Asp Tyr Thr Asp Val Pro Ser Ala Val Phe Ser His Pro Glu
            355                 360                 365

Val Gly Ser Ile Gly Ile Thr Glu Ala Ala Lys Glu Gln Tyr Gly
            370                 375                 380

Glu Glu Asn Val Lys Val Tyr Thr Ser Lys Phe Val Ala Met Tyr Tyr
385                 390                 395                 400

Ala Met Leu Glu Glu Lys Ala Pro Thr Ala Tyr Lys Leu Val Cys Ala
            405                 410                 415

Gly Lys Asp Glu Lys Val Val Gly Leu His Ile Val Gly Ala Asp Ser
            420                 425                 430

Ala Glu Ile Leu Gln Gly Phe Gly Val Ala Ile Arg Met Gly Ala Thr
            435                 440                 445

Lys Ala Asp Phe Asp Asn Val Val Ala Ile His Pro Thr Ser Ala Glu
450                 455                 460

Glu Leu Val Thr Met Arg
465                 470

<210> SEQ ID NO 41
<211> LENGTH: 507
<212> TYPE: DNA
<213> ORGANISM: Yarrowia lipolytica

<400> SEQUENCE: 41
atgtccgccg agaaaaccaa taccgctttc tacaacctcg ctccactcga caagaacgga      60
gagcctttcc ccttcaagca gcttgagggc aaggtcgtgc tcatcgtgaa cgtcgcctcc     120
aagtgtggct ttactcccca atacaagggc cttgaggagg tctaccagaa gtacaaggat     180
cagggattca ccatcatcgg cttcccctgc aaccagtttg gtggccaaga gcctggttcc     240

```
gctgacgaga tctcctcctt ctgtcagctg aactacggcg tcactttccc cgttcttcag    300
aagatcaacg tcaacggcaa cgacgccgac cccgtctacg tctacctgaa ggagcagaag    360
gctggtctgc tgggcttccg aggaatcaag tggaactttg agaagttcct ggttgataag    420
cacggtaacg tcgtcgaccg atatgcttcc ctcaagaccc ccgccggcct cgaatccacc    480
atcgagaccc tcctcaaaaa gccctaa                                        507
```

<210> SEQ ID NO 42
<211> LENGTH: 168
<212> TYPE: PRT
<213> ORGANISM: Yarrowia lipolytica

<400> SEQUENCE: 42

```
Met Ser Ala Glu Lys Thr Asn Thr Ala Phe Tyr Asn Leu Ala Pro Leu
1               5                   10                  15

Asp Lys Asn Gly Glu Pro Phe Pro Phe Lys Gln Leu Glu Gly Lys Val
                20                  25                  30

Val Leu Ile Val Asn Val Ala Ser Lys Cys Gly Phe Thr Pro Gln Tyr
            35                  40                  45

Lys Gly Leu Glu Glu Val Tyr Gln Lys Tyr Lys Asp Gln Gly Phe Thr
        50                  55                  60

Ile Ile Gly Phe Pro Cys Asn Gln Phe Gly Gln Glu Pro Gly Ser
65                  70                  75                  80

Ala Asp Glu Ile Ser Ser Phe Cys Gln Leu Asn Tyr Gly Val Thr Phe
                85                  90                  95

Pro Val Leu Gln Lys Ile Asn Val Asn Gly Asn Asp Ala Asp Pro Val
                100                 105                 110

Tyr Val Tyr Leu Lys Glu Gln Lys Ala Gly Leu Leu Gly Phe Arg Gly
            115                 120                 125

Ile Lys Trp Asn Phe Glu Lys Phe Leu Val Asp Lys His Gly Asn Val
        130                 135                 140

Val Asp Arg Tyr Ala Ser Leu Lys Thr Pro Ala Gly Leu Glu Ser Thr
145                 150                 155                 160

Ile Glu Thr Leu Leu Lys Lys Pro
                165
```

<210> SEQ ID NO 43
<211> LENGTH: 960
<212> TYPE: DNA
<213> ORGANISM: Yarrowia lipolytica

<400> SEQUENCE: 43

```
atgacccaca gcccagttgt tatcatcggt tccggccccg ccgcccacac cgctgccatc    60
tacctttctc gagccgagat caagcccact ctctacgagg aatgatggc caacggcatt    120 gctgccggcg tcagctcac cactaccact gagattgaga acttccccgg cttccccgac    180
ggaatcatgg ctcccagct catggaggac atgcgaaagc agtccatccg attcggcacc    240
gagatcatca ccgagaccgt ctccaaggtc gatctgtccc agcgacccct caagtactgg    300
accgagttca tgaggacga ggagcccac actgccgacg ccattattct tgccaccggt    360
gcctctgcca agcgactctc tctgcccggt gaggaccagt actggcagca gggtatctct    420
gcctgcgctg tctgtgacgg tgctgtcccc attttccgaa acaagcctct cgccgttgtc    480
ggaggaggag actctgccgc tgaggaggcc ctcttcctca ccaagtacgg ctccaaggtc    540
tacgtcattg tccgaaagga caagctgcga gcttccgccg ttatggccaa gcgactggcc    600
```

```
tcccacccca aggtcgagat tctcttcaac cacgtgtcca tcgaggccaa gggagacggc    660
aagctgctga acgccctgga gatcgagaac accctgaccg gcgagaagcg agacctcgag    720
gtcaacggtc tgttctacgc cattggtcac atccccgcca cctccatcgt caagggccag    780
gtcgagaccg acgaggaggg ctacgttgtt accgtcccg gtaccgccaa cacctccgtc    840
aagggtgtct tgccgctgg tgatgtccag gacaagcgat accgacaggc cattacctct    900
gctggtaccg ctgcatggc tgctctcgac tgtgagaagc tgcttgctga ggaggaatag    960
```

<210> SEQ ID NO 44
<211> LENGTH: 319
<212> TYPE: PRT
<213> ORGANISM: Yarrowia lipolytica

<400> SEQUENCE: 44

```
Met Thr His Ser Pro Val Ile Ile Gly Ser Gly Pro Ala Ala His
1               5                   10                  15

Thr Ala Ala Ile Tyr Leu Ser Arg Ala Glu Ile Lys Pro Thr Leu Tyr
            20                  25                  30

Glu Gly Met Met Ala Asn Gly Ile Ala Ala Gly Gly Gln Leu Thr Thr
        35                  40                  45

Thr Thr Glu Ile Glu Asn Phe Pro Gly Phe Pro Asp Gly Ile Met Gly
    50                  55                  60

Ser Gln Leu Met Glu Asp Met Arg Lys Gln Ser Ile Arg Phe Gly Thr
65                  70                  75                  80

Glu Ile Ile Thr Glu Thr Val Ser Lys Val Asp Leu Ser Gln Arg Pro
                85                  90                  95

Phe Lys Tyr Trp Thr Glu Phe Asn Glu Asp Glu Pro His Thr Ala
            100                 105                 110

Asp Ala Ile Ile Leu Ala Thr Gly Ala Ser Ala Lys Arg Leu Ser Leu
        115                 120                 125

Pro Gly Glu Asp Gln Tyr Trp Gln Gln Gly Ile Ser Ala Cys Ala Val
    130                 135                 140

Cys Asp Gly Ala Val Pro Ile Phe Arg Asn Lys Pro Leu Ala Val Val
145                 150                 155                 160

Gly Gly Gly Asp Ser Ala Ala Glu Glu Ala Leu Phe Leu Thr Lys Tyr
                165                 170                 175

Gly Ser Lys Val Tyr Val Ile Val Arg Lys Asp Lys Leu Arg Ala Ser
            180                 185                 190

Ala Val Met Ala Lys Arg Leu Ala Ser His Pro Lys Val Glu Ile Leu
        195                 200                 205

Phe Asn His Val Ser Ile Glu Ala Lys Gly Asp Gly Lys Leu Leu Asn
    210                 215                 220

Ala Leu Glu Ile Glu Asn Thr Leu Thr Gly Glu Lys Arg Asp Leu Glu
225                 230                 235                 240

Val Asn Gly Leu Phe Tyr Ala Ile Gly His Ile Pro Ala Thr Ser Ile
                245                 250                 255

Val Lys Gly Gln Val Glu Thr Asp Glu Glu Gly Tyr Val Val Thr Val
            260                 265                 270

Pro Gly Thr Ala Asn Thr Ser Val Lys Gly Val Phe Ala Gly Asp
        275                 280                 285

Val Gln Asp Lys Arg Tyr Arg Gln Ala Ile Thr Ser Ala Gly Thr Gly
    290                 295                 300

Cys Met Ala Ala Leu Asp Cys Glu Lys Leu Leu Ala Glu Glu Glu
```

<210> SEQ ID NO 45
<211> LENGTH: 761
<212> TYPE: DNA
<213> ORGANISM: Yarrowia lipolytica

<400> SEQUENCE: 45

```
atggtcaagg ctggtgagta cgagagcaag gcccggaatc gggcacattg agcggccagc      60
gggtcaattg aaggccgctc gaccggtcca cacccacagg ttggccgcta cgttgacttc     120
gacaaccgtc tggaaggtgg cggaacgttg cgccgtgtga ggtggcaggt gactcagaag     180
ttgctcattg tttgttgaga tcagaccccca caagcacaat tgcattttag gagggaattg     240
agagccctac ctcacggaat agtccatgtc gttgttcgcc acttgcccac actgcacatt     300
ctaacccagt cgctgttctt cgaggagatt ccaaggtctc cggtactgtc actttcgagc     360
aggactctga gtccggcccc gtcactgtca cctacgacat caagggcaac gatcccaacg     420
ctgagcgagg attccacgtc cacgagtttg gtgacaacac caacggctgc acttctgccg     480
gcccccactt caaccccttc aagaagaacc acggtggtcc caccgactct gagcgacacg     540
ttggtgacct cggaaacgtc aagactgact ctgagggtgt tgccaagggt gttctcaagg     600
actctcttct caagctgact ggtgacaact ccattgttgg ccgaaccgtc gttatccacg     660
gtggtgagga cgatcttgga aagggtggcc atgccgactc tctcaagacc ggaaacgctg     720
gccctcgacc cgcctgcggt gtcattggtc ttaccgccta a                         761
```

<210> SEQ ID NO 46
<211> LENGTH: 154
<212> TYPE: PRT
<213> ORGANISM: Yarrowia lipolytica

<400> SEQUENCE: 46

```
Met Val Lys Ala Val Ala Val Leu Arg Gly Asp Ser Lys Val Ser Gly
 1               5                  10                  15

Thr Val Thr Phe Glu Gln Asp Ser Glu Ser Gly Pro Val Thr Val Thr
             20                  25                  30

Tyr Asp Ile Lys Gly Asn Asp Pro Asn Ala Glu Arg Gly Phe His Val
         35                  40                  45

His Glu Phe Gly Asp Asn Thr Asn Gly Cys Thr Ser Ala Gly Pro His
     50                  55                  60

Phe Asn Pro Phe Lys Lys Asn His Gly Gly Pro Thr Asp Ser Glu Arg
 65                  70                  75                  80

His Val Gly Asp Leu Gly Asn Val Lys Thr Asp Ser Glu Gly Val Ala
                 85                  90                  95

Lys Gly Val Leu Lys Asp Ser Leu Leu Lys Leu Thr Gly Asp Asn Ser
            100                 105                 110

Ile Val Gly Arg Thr Val Val Ile His Gly Gly Glu Asp Asp Leu Gly
        115                 120                 125

Lys Gly Gly His Ala Asp Ser Leu Lys Thr Gly Asn Ala Gly Pro Arg
    130                 135                 140

Pro Ala Cys Gly Val Ile Gly Leu Thr Ala
145                 150
```

<210> SEQ ID NO 47
<211> LENGTH: 1518
<212> TYPE: DNA
<213> ORGANISM: Saccharomyces cerevisiae

<400> SEQUENCE: 47

```
atgagtgaag gccccgtcaa attcgaaaaa aataccgtca tatctgtctt tggtgcgtca      60
ggtgatctgg caaagaagaa gacttttccc gccttatttg gcttttcag agaaggttac     120
cttgatccat ctaccaagat cttcggttat gcccggtcca aattgtccat ggaggaggac    180
ctgaagtccc gtgtcctacc ccacttgaaa aaacctcacg gtgaagccga tgactctaag    240
gtcgaacagt tcttcaagat ggtcagctac atttcgggaa attacgacac agatgaaggc    300
ttcgacgaat taagaacgca gatcgagaaa ttcgagaaaa gtgccaacgt cgatgtccca    360
caccgtctct tctatctggc cttgccgcca agcgtttttt tgacggtggc caagcagatc    420
aagagtcgtg tgtacgcaga gaatggcatc acccgtgtaa tcgtagagaa cctttcggc    480
cacgacctgg cctctgccag ggagctgcaa aaaaacctgg ggcccctctt taaagaagaa    540
gagttgtaca gaattgacca ttacttgggt aaagagttgg tcaagaatct tttagtcttg    600
aggttcggta accagttttt gaatgcctcg tggaatagag acaacattca aagcgttcag    660
atttcgttta agagaggtt cggcaccgaa ggccgtggcg gctatttcga ctctataggc    720
ataatcagag acgtgatgca gaaccatctg ttacaaatca tgactctctt gactatggaa    780
agaccggtgt cttttgaccc ggaatctatt cgtgacgaaa aggttaaggt tctaaaggcc    840
gtggcccca tcgacacgga cgacgtcctc ttgggccagt acggtaaatc tgaggacggg    900
tctaagcccg cctacgtgga tgatgacact gtagacaagg actctaaatg tgtcactttt    960
gcagcaatga ctttcaacat cgaaaacgag cgttgggagg cgtcccat catgatgcgt    1020
gccggtaagg ctttgaatga gtccaaggtg gagatcagac tgcagtacaa agcggtcgca    1080
tcgggtgtct tcaaagacat tccaaataac gaactggtca tcagagtgca gcccgatgcc    1140
gctgtgtacc taagtttaa tgctaagacc cctggtctgt caaatgctac ccaagtcaca    1200
gatctgaatc taacttacgc aagcaggtac caagacttt ggattccaga ggcttacgag    1260
gtgttgataa gagacgccct actgggtgac cattccaact ttgtcagaga tgacgaattg    1320
gatatcagtt ggggcatatt caccccatta ctgaagcaca tagagcgtcc ggacggtcca    1380
acaccggaaa tttaccccta cggatcaaga ggtccaaagg gattgaagga atatatgcaa    1440
aaacacaagt atgttatgcc cgaaaagcac ccttacgctt ggcccgtgac taagccagaa    1500
gatacgaagg ataattag                                                  1518
```

<210> SEQ ID NO 48
<211> LENGTH: 505
<212> TYPE: PRT
<213> ORGANISM: Saccharomyces cerevisiae

<400> SEQUENCE: 48

```
Met Ser Glu Gly Pro Val Lys Phe Glu Lys Asn Thr Val Ile Ser Val
1               5                   10                  15

Phe Gly Ala Ser Gly Asp Leu Ala Lys Lys Thr Phe Pro Ala Leu
            20                  25                  30

Phe Gly Leu Phe Arg Glu Gly Tyr Leu Asp Pro Ser Thr Lys Ile Phe
        35                  40                  45

Gly Tyr Ala Arg Ser Lys Leu Ser Met Glu Glu Asp Leu Lys Ser Arg
    50                  55                  60

Val Leu Pro His Leu Lys Lys Pro His Gly Glu Ala Asp Asp Ser Lys
65                  70                  75                  80

Val Glu Gln Phe Phe Lys Met Val Ser Tyr Ile Ser Gly Asn Tyr Asp
```

```
            85                  90                  95
Thr Asp Glu Gly Phe Asp Glu Leu Arg Thr Gln Ile Glu Lys Phe Glu
            100                 105                 110

Lys Ser Ala Asn Val Asp Val Pro His Arg Leu Phe Tyr Leu Ala Leu
            115                 120                 125

Pro Pro Ser Val Phe Leu Thr Val Ala Lys Gln Ile Lys Ser Arg Val
            130                 135                 140

Tyr Ala Glu Asn Gly Ile Thr Arg Val Ile Val Glu Lys Pro Phe Gly
145                 150                 155                 160

His Asp Leu Ala Ser Ala Arg Glu Leu Gln Lys Asn Leu Gly Pro Leu
            165                 170                 175

Phe Lys Glu Glu Glu Leu Tyr Arg Ile Asp His Tyr Leu Gly Lys Glu
            180                 185                 190

Leu Val Lys Asn Leu Leu Val Leu Arg Phe Gly Asn Gln Phe Leu Asn
            195                 200                 205

Ala Ser Trp Asn Arg Asp Asn Ile Gln Ser Val Gln Ile Ser Phe Lys
            210                 215                 220

Glu Arg Phe Gly Thr Glu Gly Arg Gly Gly Tyr Phe Asp Ser Ile Gly
225                 230                 235                 240

Ile Ile Arg Asp Val Met Gln Asn His Leu Leu Gln Ile Met Thr Leu
            245                 250                 255

Leu Thr Met Glu Arg Pro Val Ser Phe Asp Pro Glu Ser Ile Arg Asp
            260                 265                 270

Glu Lys Val Lys Val Leu Lys Ala Val Ala Pro Ile Asp Thr Asp Asp
            275                 280                 285

Val Leu Leu Gly Gln Tyr Gly Lys Ser Glu Asp Gly Ser Lys Pro Ala
            290                 295                 300

Tyr Val Asp Asp Asp Thr Val Asp Lys Asp Ser Lys Cys Val Thr Phe
305                 310                 315                 320

Ala Ala Met Thr Phe Asn Ile Glu Asn Glu Arg Trp Glu Gly Val Pro
            325                 330                 335

Ile Met Met Arg Ala Gly Lys Ala Leu Asn Glu Ser Lys Val Glu Ile
            340                 345                 350

Arg Leu Gln Tyr Lys Ala Val Ala Ser Gly Val Phe Lys Asp Ile Pro
            355                 360                 365

Asn Asn Glu Leu Val Ile Arg Val Gln Pro Asp Ala Ala Val Tyr Leu
            370                 375                 380

Lys Phe Asn Ala Lys Thr Pro Gly Leu Ser Asn Ala Thr Gln Val Thr
385                 390                 395                 400

Asp Leu Asn Leu Thr Tyr Ala Ser Arg Tyr Gln Asp Phe Trp Ile Pro
            405                 410                 415

Glu Ala Tyr Glu Val Leu Ile Arg Asp Ala Leu Leu Gly Asp His Ser
            420                 425                 430

Asn Phe Val Arg Asp Asp Glu Leu Asp Ile Ser Trp Gly Ile Phe Thr
            435                 440                 445

Pro Leu Leu Lys His Ile Glu Arg Pro Asp Gly Pro Thr Pro Glu Ile
            450                 455                 460

Tyr Pro Tyr Gly Ser Arg Gly Pro Lys Gly Leu Lys Tyr Met Gln
465                 470                 475                 480

Lys His Lys Tyr Val Met Pro Glu Lys His Pro Tyr Ala Trp Pro Val
            485                 490                 495

Thr Lys Pro Glu Asp Thr Lys Asp Asn
            500                 505
```

<210> SEQ ID NO 49
<211> LENGTH: 1937
<212> TYPE: DNA
<213> ORGANISM: Yarrowia lipolytica

<400> SEQUENCE: 49

| | | | | | |
|---|---|---|---|---|---|
| atgactggca | ccttacccaa | gttcggcgac | ggaaccacca | ttgtggttct | tggagcctcc | 60 |
| ggcgacctcg | ctaagaagaa | gaccgtgagt | attgaaccag | actgaggtca | attgaagagt | 120 |
| aggagagtct | gagaacattc | gacggacctg | attgtgctct | ggaccactca | attgactcgt | 180 |
| tgagagcccc | aatgggtctt | ggctagccga | gtcgttgact | tgttgacttg | ttgagcccag | 240 |
| aaccccccaac | ttttgccacc | atacaccgcc | atcaccatga | cacccagatg | tgcgtgcgta | 300 |
| tgtgagagtc | aattgttccg | tggcaaggca | cagcttattc | caccgtgttc | cttgcacagg | 360 |
| tggtctttac | gctctcccac | tctatccgag | caataaaagc | ggaaaaacag | cagcaagtcc | 420 |
| caacagactt | ctgctccgaa | taaggcgtct | agcaagtgtg | cccaaaactc | aattcaaaaa | 480 |
| tgtcagaaac | ctgatatcaa | cccgtcttca | aaagctaacc | ccagttcccc | gccctcttcg | 540 |
| gcctttaccg | aaacggcctg | ctgcccaaaa | atgttgaaat | catcggctac | gcacggtcga | 600 |
| aaatgactca | ggaggagtac | cacgagcgaa | tcagccacta | cttcaagacc | cccgacgacc | 660 |
| agtccaagga | gcaggccaag | aagttccttg | agaacacctg | ctacgtccag | ggcccttacg | 720 |
| acggtgccga | gggctaccag | cgactgaatg | aaaagattga | ggagtttgag | aagaagaagc | 780 |
| ccgagcccca | ctaccgtctt | ttctacctgg | ctctgccccc | cagcgtcttc | cttgaggctg | 840 |
| ccaacggtct | gaagaagtat | gtctaccccg | gcgagggcaa | ggcccgaatc | atcatcgaga | 900 |
| agcccttttgg | ccacgacctg | gcctcgtcac | gagagctcca | ggacggcctt | gctcctctct | 960 |
| ggaaggagtc | tgagatcttc | cgaatcgacc | actacctcgg | aaaggagatg | gtcaagaacc | 1020 |
| tcaacattct | gcgatttggc | aaccagttcc | tgtccgccgt | gtgggacaag | aacaccattt | 1080 |
| ccaacgtcca | gatctccttc | aaggagccct | ttggcactga | gggccgaggt | ggatacttca | 1140 |
| acgacattgg | aatcatccga | gacgttattc | agaaccatct | gttgcaggtt | ctgtccattc | 1200 |
| tagccatgga | gcgacccgtc | actttcggcg | ccgaggacat | tcgagatgag | aaggtcaagg | 1260 |
| tgctccgatg | tgtcgacatt | ctcaacattg | acgacgtcat | tctcggccag | tacggcccct | 1320 |
| ctgaagacgg | aaagaagccc | ggatacaccg | atgacgatgg | cgttcccgat | gactcccgag | 1380 |
| ctgtgacctt | tgctgctctc | catctccaga | tccacaacga | cagatgggag | ggtgttcctt | 1440 |
| tcatcctccg | agccggtaag | gctctggacg | agggcaaggt | cgagatccga | gtgcagttcc | 1500 |
| gagacgtgac | caagggcgtt | gtggaccatc | tgcctcgaaa | tgagctcgtc | atccgaatcc | 1560 |
| agccctccga | gtccatctac | atgaagatga | actccaagct | gcctggcctt | actgccaaga | 1620 |
| acattgtcac | cgacctggat | ctgacctaca | accgacgata | tcggacgtg | cgaatccctg | 1680 |
| aggcttacga | gtctctcatt | ctggactgcc | tcaagggtga | ccacaccaac | tttgtgcgaa | 1740 |
| acgacgagct | ggacatttcc | tggaagattt | tcaccgatct | gctgcacaag | attgacgagg | 1800 |
| acaagagcat | tgtgcccgag | aagtacgcct | acggctctcg | tggccccgag | cgactcaagc | 1860 |
| agtggctccg | agaccgaggc | tacgtgcgaa | acggcaccga | gctgtaccaa | tggcctgtca | 1920 |
| ccaagggctc | ctcgtga | | | | | 1937 |

<210> SEQ ID NO 50
<211> LENGTH: 498
<212> TYPE: PRT

<213> ORGANISM: Yarrowia lipolytica

<400> SEQUENCE: 50

| | | | | | | | | | | | | | | |
|---|---|---|---|---|---|---|---|---|---|---|---|---|---|---|
| Met | Thr | Gly | Thr | Leu | Pro | Lys | Phe | Gly | Asp | Gly | Thr | Ile | Val | Val |
| 1 | | | | 5 | | | | | 10 | | | | | 15 |
| Leu | Gly | Ala | Ser | Gly | Asp | Leu | Ala | Lys | Lys | Thr | Phe | Pro | Ala | Leu |
| | | | 20 | | | | | 25 | | | | | 30 | |
| Phe | Gly | Leu | Tyr | Arg | Asn | Gly | Leu | Leu | Pro | Lys | Asn | Val | Glu | Ile | Ile |
| | | 35 | | | | | 40 | | | | | 45 | | |
| Gly | Tyr | Ala | Arg | Ser | Lys | Met | Thr | Gln | Glu | Glu | Tyr | His | Glu | Arg | Ile |
| | 50 | | | | | 55 | | | | | 60 | | | | |
| Ser | His | Tyr | Phe | Lys | Thr | Pro | Asp | Asp | Gln | Ser | Lys | Glu | Gln | Ala | Lys |
| 65 | | | | | 70 | | | | | 75 | | | | | 80 |
| Lys | Phe | Leu | Glu | Asn | Thr | Cys | Tyr | Val | Gln | Gly | Pro | Tyr | Asp | Gly | Ala |
| | | | | 85 | | | | | 90 | | | | | 95 | |
| Glu | Gly | Tyr | Gln | Arg | Leu | Asn | Glu | Lys | Ile | Glu | Glu | Phe | Glu | Lys | Lys |
| | | | 100 | | | | | 105 | | | | | 110 | | |
| Lys | Pro | Glu | Pro | His | Tyr | Arg | Leu | Phe | Tyr | Leu | Ala | Leu | Pro | Pro | Ser |
| | | 115 | | | | | 120 | | | | | 125 | | | |
| Val | Phe | Leu | Glu | Ala | Ala | Asn | Gly | Leu | Lys | Lys | Tyr | Val | Tyr | Pro | Gly |
| | 130 | | | | | 135 | | | | | 140 | | | | |
| Glu | Gly | Lys | Ala | Arg | Ile | Ile | Ile | Glu | Lys | Pro | Phe | Gly | His | Asp | Leu |
| 145 | | | | | 150 | | | | | 155 | | | | | 160 |
| Ala | Ser | Ser | Arg | Glu | Leu | Gln | Asp | Gly | Leu | Ala | Pro | Leu | Trp | Lys | Glu |
| | | | | 165 | | | | | 170 | | | | | 175 | |
| Ser | Glu | Ile | Phe | Arg | Ile | Asp | His | Tyr | Leu | Gly | Lys | Glu | Met | Val | Lys |
| | | | 180 | | | | | 185 | | | | | 190 | | |
| Asn | Leu | Asn | Ile | Leu | Arg | Phe | Gly | Asn | Gln | Phe | Leu | Ser | Ala | Val | Trp |
| | | 195 | | | | | 200 | | | | | 205 | | | |
| Asp | Lys | Asn | Thr | Ile | Ser | Asn | Val | Gln | Ile | Ser | Phe | Lys | Glu | Pro | Phe |
| | 210 | | | | | 215 | | | | | 220 | | | | |
| Gly | Thr | Glu | Gly | Arg | Gly | Gly | Tyr | Phe | Asn | Asp | Ile | Gly | Ile | Ile | Arg |
| 225 | | | | | 230 | | | | | 235 | | | | | 240 |
| Asp | Val | Ile | Gln | Asn | His | Leu | Leu | Gln | Val | Leu | Ser | Ile | Leu | Ala | Met |
| | | | | 245 | | | | | 250 | | | | | 255 | |
| Glu | Arg | Pro | Val | Thr | Phe | Gly | Ala | Glu | Asp | Ile | Arg | Asp | Glu | Lys | Val |
| | | | 260 | | | | | 265 | | | | | 270 | | |
| Lys | Val | Leu | Arg | Cys | Val | Asp | Ile | Leu | Asn | Ile | Asp | Asp | Val | Ile | Leu |
| | | 275 | | | | | 280 | | | | | 285 | | | |
| Gly | Gln | Tyr | Gly | Pro | Ser | Glu | Asp | Gly | Lys | Lys | Pro | Gly | Tyr | Thr | Asp |
| | 290 | | | | | 295 | | | | | 300 | | | | |
| Asp | Asp | Gly | Val | Pro | Asp | Asp | Ser | Arg | Ala | Val | Thr | Phe | Ala | Ala | Leu |
| 305 | | | | | 310 | | | | | 315 | | | | | 320 |
| His | Leu | Gln | Ile | His | Asn | Asp | Arg | Trp | Glu | Gly | Val | Pro | Phe | Ile | Leu |
| | | | | 325 | | | | | 330 | | | | | 335 | |
| Arg | Ala | Gly | Lys | Ala | Leu | Asp | Glu | Gly | Lys | Val | Glu | Ile | Arg | Val | Gln |
| | | | 340 | | | | | 345 | | | | | 350 | | |
| Phe | Arg | Asp | Val | Thr | Lys | Gly | Val | Val | Asp | His | Leu | Pro | Arg | Asn | Glu |
| | | 355 | | | | | 360 | | | | | 365 | | | |
| Leu | Val | Ile | Arg | Ile | Gln | Pro | Ser | Glu | Ser | Ile | Tyr | Met | Lys | Met | Asn |
| | 370 | | | | | 375 | | | | | 380 | | | | |
| Ser | Lys | Leu | Pro | Gly | Leu | Thr | Ala | Lys | Asn | Ile | Val | Thr | Asp | Leu | Asp |
| 385 | | | | | 390 | | | | | 395 | | | | | 400 |

```
Leu Thr Tyr Asn Arg Arg Tyr Ser Asp Val Arg Ile Pro Glu Ala Tyr
                405                 410                 415

Glu Ser Leu Ile Leu Asp Cys Leu Lys Gly Asp His Thr Asn Phe Val
            420                 425                 430

Arg Asn Asp Glu Leu Asp Ile Ser Trp Lys Ile Phe Thr Asp Leu Leu
        435                 440                 445

His Lys Ile Asp Glu Asp Lys Ser Ile Val Pro Glu Lys Tyr Ala Tyr
    450                 455                 460

Gly Ser Arg Gly Pro Glu Arg Leu Lys Gln Trp Leu Arg Asp Arg Gly
465                 470                 475                 480

Tyr Val Arg Asn Gly Thr Glu Leu Tyr Gln Trp Pro Val Thr Lys Gly
                485                 490                 495

Ser Ser
```

<210> SEQ ID NO 51
<211> LENGTH: 1251
<212> TYPE: DNA
<213> ORGANISM: Yarrowia lipolytica

<400> SEQUENCE: 51

```
atgtccacca ccgctactcg aggcctgtcc accaagatca aggtcaagaa ccccattgtc       60
gagctcgatg gtgatgagat gacccgaatc atctggaagt ccatcaagga caagctcatt      120
ctgccctatc tcgacattga tcttaagtac tacgatctgg catcgagta ccgagaccag       180
actaacgacc aggtgaccat gacgccgcc gaggccatca gaagtacca ggtcggtgtc        240
aagtgcgcca ccatcacccc cgacgaggcc cgagtcaagg agtttggcct caagaagatg     300
tggctgtcgc ccaacggtac catccgaaac attctcggcg gtactgtttt ccgagagccc     360
attgtcattc ccgccgtccc ccggcttgtg cccggatgga aggagcctat catcattggt     420
cgacacgccc acggcgacca gtacaaggcc caggatgccg tcatccccgg cgccggtgag     480
ctgactctta acttcaagcc cgctaacgga ggcgacgagc aggtcatcaa ggtgtacacc     540
tacgacgccc ctggtgtcgc catggccatg tacaacactg acgagtccat caccggcttt   600
gcctactctt cattcaacct ggctctgcag aagaagctgc ccctgtacat gtctaccaag    660
aacaccatcc ttaagaagta cgacggccga ttcaaggaca ttttccagga gatttacgac    720
aaggagtaca aggataagtt tgatgctgcc ggcatttggt acgagcaccg actcattgat    780
gacatggtcg cccagatgat caagtctaag ggaggcttca tcatggccct caagaactac    840
gacggagacg tgcagtccga cattgttgcc cagggctttg ctctctcgg tctcatgacc     900
tctgttctcg tcacccccga cggaaagacc tttgagtccg aggccgccca cggcaccgtg    960
actcgacact accgacagca ccagcagggc aaggagacct ctaccaactc cattgcctcc   1020
atcttcgcct ggacccgagg cctcatccag cgaggcattc tcgacgagac ccctgaggtg   1080
accaagtttg ccgaggctct cgagaaggcc accgtcgaca ctgttgacaa ggacggcatt   1140
atgaccaagg atctggctct ggccggtggc aagaccgacc gatcctcgta tgtgctgacc   1200
gaggagttta tcgacgctgt ggccaacaga ctgaagaagg acctggctta g            1251
```

<210> SEQ ID NO 52
<211> LENGTH: 416
<212> TYPE: PRT
<213> ORGANISM: Yarrowia lipolytica

<400> SEQUENCE: 52

Met Ser Thr Thr Ala Thr Arg Gly Leu Ser Thr Lys Ile Lys Val Lys

|   |   |   |   |   |   |   |   |   |   |
|---|---|---|---|---|---|---|---|---|---|
| 1 |   | 5 |   |   |   | 10 |   |   | 15 |

Asn Pro Ile Val Glu Leu Asp Gly Asp Glu Met Thr Arg Ile Ile Trp
                20                  25                  30

Lys Ser Ile Lys Asp Lys Leu Ile Leu Pro Tyr Leu Asp Ile Asp Leu
            35                  40                  45

Lys Tyr Tyr Asp Leu Gly Ile Glu Tyr Arg Asp Gln Thr Asn Asp Gln
        50                  55                  60

Val Thr Ile Asp Ala Ala Glu Ala Ile Lys Lys Tyr Gln Val Gly Val
65                  70                  75                  80

Lys Cys Ala Thr Ile Thr Pro Asp Glu Ala Arg Val Lys Glu Phe Gly
                85                  90                  95

Leu Lys Lys Met Trp Leu Ser Pro Asn Gly Thr Ile Arg Asn Ile Leu
                100                 105                 110

Gly Gly Thr Val Phe Arg Glu Pro Ile Val Ile Pro Ala Val Pro Arg
            115                 120                 125

Leu Val Pro Gly Trp Lys Glu Pro Ile Ile Gly Arg His Ala His
        130                 135                 140

Gly Asp Gln Tyr Lys Ala Gln Asp Ala Val Ile Pro Gly Ala Gly Glu
145                 150                 155                 160

Leu Thr Leu Asn Phe Lys Pro Ala Asn Gly Gly Asp Glu Gln Val Ile
                165                 170                 175

Lys Val Tyr Thr Tyr Asp Ala Pro Gly Val Ala Met Ala Met Tyr Asn
            180                 185                 190

Thr Asp Glu Ser Ile Thr Gly Phe Ala Tyr Ser Ser Phe Asn Leu Ala
        195                 200                 205

Leu Gln Lys Lys Leu Pro Leu Tyr Met Ser Thr Lys Asn Thr Ile Leu
210                 215                 220

Lys Lys Tyr Asp Gly Arg Phe Lys Asp Ile Phe Gln Glu Ile Tyr Asp
225                 230                 235                 240

Lys Glu Tyr Lys Asp Lys Phe Asp Ala Ala Gly Ile Trp Tyr Glu His
                245                 250                 255

Arg Leu Ile Asp Asp Met Val Ala Gln Met Ile Lys Ser Lys Gly Gly
            260                 265                 270

Phe Ile Met Ala Leu Lys Asn Tyr Asp Gly Asp Val Gln Ser Asp Ile
        275                 280                 285

Val Ala Gln Gly Phe Gly Ser Leu Gly Leu Met Thr Ser Val Leu Val
            290                 295                 300

Thr Pro Asp Gly Lys Thr Phe Glu Ser Glu Ala Ala His Gly Thr Val
305                 310                 315                 320

Thr Arg His Tyr Arg Gln His Gln Gln Gly Lys Glu Thr Ser Thr Asn
                325                 330                 335

Ser Ile Ala Ser Ile Phe Ala Trp Thr Arg Gly Leu Ile Gln Arg Gly
            340                 345                 350

Ile Leu Asp Glu Thr Pro Glu Val Thr Lys Phe Ala Glu Ala Leu Glu
        355                 360                 365

Lys Ala Thr Val Asp Thr Val Asp Lys Asp Gly Ile Met Thr Lys Asp
370                 375                 380

Leu Ala Leu Ala Gly Gly Lys Thr Asp Arg Ser Ser Tyr Val Leu Thr
385                 390                 395                 400

Glu Glu Phe Ile Asp Ala Val Ala Asn Arg Leu Lys Lys Asp Leu Ala
                405                 410                 415

<210> SEQ ID NO 53

<211> LENGTH: 1545
<212> TYPE: DNA
<213> ORGANISM: Yarrowia lipolytica

<400> SEQUENCE: 53

```
atgactatcg actcacaata ctacaagtcg cgagacaaaa acgacacggc acccaaaatc      60
gcgggaatcc gatatgcccc gctatcgaca ccattactca accgatgtga gaccttctct     120
ctggtctggc acattttcag cattcccact ttcctcacaa ttttcatgct atgctgcgca     180
attccactgc tctggccatt tgtgattgcg tatgtagtgt acgctgttaa agacgactcc     240
ccgtccaacg gaggagtggt caagcgatac tcgcctattt caagaaactt cttcatctgg     300
aagctctttg gccgctactt ccccataact ctgcacaaga cggtggatct ggagcccacg     360
cacacatact accctctgga cgtccaggag tatcacctga ttgctgagag atactggccg     420
cagaacaagt acctccgagc aatcatctcc accatcgagt actttctgcc cgccttcatg     480
aaacggtctc tttctatcaa cgagcaggag cagcctgccg agcgagatcc tctcctgtct     540
cccgtttctc ccagctctcc gggttctcaa cctgacaagt ggattaacca cgacagcaga     600
tatagccgtg gagaatcatc tggctccaac ggccacgcct cgggctccga acttaacggc     660
aacggcaaca atggcaccac taaccgacga cctttgtcgt ccgcctctgc tggctccact     720
gcatctgatt ccacgcttct taacgggtcc ctcaactcct acgccaacca gatcattggc     780
gaaaacgacc cacagctgtc gcccacaaaa ctcaagccca ctggcagaaa atacatcttc     840
ggctaccacc cccacggcat tatcggcatg ggagcctttg gtggaattgc accgagggag     900
gctggatggt ccaagctctt tccgggcatc cctgtttctc ttatgactct caccaacaac     960
ttccgagtgc ctctctacag agagtacctc atgagtctgg gagtcgcttc tgtctccaag    1020
aagtcctgca aggccctcct caagcgaaac cagtctatct gcattgtcgt tggtggagca    1080
caggaaagtc ttctggccag acccggtgtc atggacctgg tgctactcaa gcgaaagggt    1140
tttgttcgac ttggtatgga ggtcggaaat gtcgcccttg ttcccatcat ggcctttggt    1200
gagaacgacc tctatgacca ggttagcaac gacaagtcgt ccaagctgta ccgattccag    1260
cagtttgtca agaacttcct tggattcacc cttcctttga tgcatgcccg aggcgtcttc    1320
aactacgatg tcggtcttgt cccctacagg cgacccgtca acattgtggt tggttccccc    1380
attgacttgc cttatctccc acaccccacc gacgaagaag tgtccgaata ccacgaccga    1440
tacatcgccg agctgcagcg aatctacaac gagcacaagg atgaatattt catcgattgg    1500
accgaggagg gcaaaggagc cccagagttc gaatgattg agtaa                     1545
```

<210> SEQ ID NO 54
<211> LENGTH: 514
<212> TYPE: PRT
<213> ORGANISM: Yarrowia lipolytica

<400> SEQUENCE: 54

```
Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
```

-continued

```
                65                  70                  75                  80
Pro Ser Asn Gly Gly Val Val Lys Arg Tyr Ser Pro Ile Ser Arg Asn
                    85                  90                  95

Phe Phe Ile Trp Lys Leu Phe Gly Arg Tyr Phe Pro Ile Thr Leu His
                    100                 105                 110

Lys Thr Val Asp Leu Glu Pro Thr His Thr Tyr Tyr Pro Leu Asp Val
                    115                 120                 125

Gln Glu Tyr His Leu Ile Ala Glu Arg Tyr Trp Pro Gln Asn Lys Tyr
                    130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                    165                 170                 175

Pro Leu Leu Ser Pro Val Ser Pro Ser Pro Gly Ser Gln Pro Asp
                    180                 185                 190

Lys Trp Ile Asn His Asp Ser Arg Tyr Ser Arg Gly Glu Ser Ser Gly
                    195                 200                 205

Ser Asn Gly His Ala Ser Gly Ser Glu Leu Asn Gly Asn Gly Asn Asn
                    210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                    245                 250                 255

Gln Ile Ile Gly Glu Asn Asp Pro Gln Leu Ser Pro Thr Lys Leu Lys
                    260                 265                 270

Pro Thr Gly Arg Lys Tyr Ile Phe Gly Tyr His Pro His Gly Ile Ile
                    275                 280                 285

Gly Met Gly Ala Phe Gly Gly Ile Ala Thr Glu Gly Ala Gly Trp Ser
                    290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                    325                 330                 335

Ser Val Ser Lys Lys Ser Cys Lys Ala Leu Leu Lys Arg Asn Gln Ser
                    340                 345                 350

Ile Cys Ile Val Val Gly Gly Ala Gln Glu Ser Leu Leu Ala Arg Pro
                    355                 360                 365

Gly Val Met Asp Leu Val Leu Leu Lys Arg Lys Gly Phe Val Arg Leu
                    370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                    405                 410                 415

Tyr Arg Phe Gln Gln Phe Val Lys Asn Phe Leu Gly Phe Thr Leu Pro
                    420                 425                 430

Leu Met His Ala Arg Gly Val Phe Asn Tyr Asp Val Gly Leu Val Pro
                    435                 440                 445

Tyr Arg Arg Pro Val Asn Ile Val Val Gly Ser Pro Ile Asp Leu Pro
                    450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                    485                 490                 495
```

Phe Ile Asp Trp Thr Glu Glu Gly Lys Gly Ala Pro Glu Phe Arg Met
        500                 505                 510

Ile Glu

<210> SEQ ID NO 55
<211> LENGTH: 7270
<212> TYPE: DNA
<213> ORGANISM: Yarrowia lipolytica

<400> SEQUENCE: 55

| | |
|---|---:|
| atgcgactgc aattgaggac actaacacgt cggttttca ggtgagtaaa cgacggtggc | 60 |
| cgtggccacg acagccgagg cgtcacgatg ggccagacga gcacattctc gccgccacaa | 120 |
| cctcgccagc acaagaaact aacccagtat ggcttcagga tcttcaacgc agatgtggc | 180 |
| tcccttggtg accccaaca ttcacaaagg tctcgcctct catttctttg gactcaattc | 240 |
| tgtccacaca gccaagccct caaaagtcaa ggagtttgtg gcttctcacg gaggtcatac | 300 |
| agttatcaac aaggtgagta tttgacgttt agactgtata acaggcggcc gcagtgcaac | 360 |
| aacgaccaaa aagggtcgaa aaggggtcga aacggacac aaaagctgga aacaagagt | 420 |
| gtaatacatt cttacacgtc caattgttag acaaacacgg ctgttcggtc ccaaaaccac | 480 |
| cagtatcacc tattttccac ttgtgtctcg gatctgatca taatctgatc tcaagatgaa | 540 |
| atttacgcca ccgacatgat attgtgattt tcggattctc cagaccgagc agattccagc | 600 |
| aataccacca cttgcccacc ttcagcggcc tctcggcgcg attcgccact tccccaacg | 660 |
| agtgttacta acccaggtcc tcatcgctaa caacggtatt gccgcagtaa aggagatccg | 720 |
| ttcagtacga aaatgggcct acgagacctt ggcgacgag cgagcaatct cgttcaccgt | 780 |
| catggccacc cccgaagatc tcgctgccaa cgccgactac attagaatgg ccgatcagta | 840 |
| cgtcgaggtg cccggaggaa ccaacaacaa caactacgcc aacgtcgagc tgattgtcga | 900 |
| cgtggctgag cgattcggcg tcgatgccgt gtgggccgga tggggccatg ccagtgaaaa | 960 |
| tccctgctc cccgagtcgc tagcggcctc tccccgcaag attgtcttca tcggccctcc | 1020 |
| cggagctgcc atgagatctc tgggagacaa aatttcttct accattgtgg cccagcacgc | 1080 |
| aaaggtcccg tgtatcccgt ggtctggaac cggagtggac gaggttgtgg ttgacaagag | 1140 |
| caccaacctc gtgtccgtgt ccgaggaggt gtacaccaag gctgcacca ccggtcccaa | 1200 |
| gcagggtctg gagaaggcta agcagattgg attccccgtg atgatcaagg cttccgaggg | 1260 |
| aggaggagga aagggtattc gaaggttga gcgagaggag gacttcgagg ctgcttacca | 1320 |
| ccaggtcgag ggagagatcc ccggctcgcc catcttcatt atgcagcttg caggcaatgc | 1380 |
| ccggcatttg gaggtgcagc ttctggctga tcagtacggc aacaatattt cactgtttgg | 1440 |
| tcgagattgt tcggttcagc gacggcatca aaagattatt gaggaggctc ctgtgactgt | 1500 |
| ggctggccag cagaccttca ctgccatgga aaggctgcc gtgcgactcg gtaagcttgt | 1560 |
| cggatatgtc tctgcaggta ccgttgaata tctgtattcc catgaggacg acaagttcta | 1620 |
| cttcttggag ctgaatcctc gtcttcaggt cgaacatcct accaccgaga tggtcaccgg | 1680 |
| tgtcaacctg cccgctgccc agcttcagat cgccatgggt atccccctcg atcgaatcaa | 1740 |
| ggacattcgt ctcttttacg gtgttaaccc tcacaccacc actccaattg atttcgactt | 1800 |
| ctcgggcgag gatgctgata agacacagcg acgtcccgtc cccgaggtc acaccactgc | 1860 |
| ttgccgaatc acatccgagg accctggaga gggtttcaag ccctccggag gtactatgca | 1920 |
| cgagctcaac ttccgatcct cgtccaacgt gtggggttac ttctccgttg gtaaccaggg | 1980 |

```
aggtatccat tcgttctcgg attcgcagtt tggtcacatc ttcgccttcg gtgagaaccg    2040
aagtgcgtct cgaaagcaca tggttgttgc tttgaaggaa ctatctattc gaggtgactt    2100
ccgaaccacc gtcgagtacc tcatcaagct gctggagaca ccggacttcg aggacaacac    2160
catcaccacc ggctggctgg atgagcttat ctccaacaag ctgactgccg agcgacccga    2220
ctcgttcctc gctgttgttt gtggtgctgc taccaaggcc catcgagctt ccgaggactc    2280
tattgccacc tacatggctt cgctagagaa gggccaggtc cctgctcgag acattctcaa    2340 gaccctttc cccgttgact tcatctacga gggccagcgg tacaagttca ccgccacccg    2400
gtcgtctgag gactcttaca cgctgttcat caacggttct cgatgcgaca ttggagttag    2460
acctctttct gacggtggta ttctgtgtct tgtaggtggg agatcccaca atgtctactg    2520
gaaggaggag gttggagcca cgcgactgtc tgttgactcc aagacctgcc ttctcgaggt    2580
ggagaacgac cccactcagc ttcgatctcc ctctcccggt aagctggtta agttcctggt    2640
cgagaacggc gaccacgtgc gagccaacca gccctatgcc gagattgagg tcatgaagat    2700
gtacatgact ctcactgctc aggaggacgg tattgtccag ctgatgaagc agcccggttc    2760
caccatcgag gctggcgaca tcctcggtat cttggcccct tgatgatcct tccaaggtcaa   2820 gcatgccaag cccttgagg gccagcttcc cgagcttgga cccccactc tcagcggtaa     2880 caagcctcat cagcgatacg agcactgcca gaacgtgctc cataacattc tgcttggttt    2940
cgataaccag gtggtgatga agtccactct tcaggagatg gttggtctgc tccgaaaccc    3000
tgagcttcct tatctccagt gggctcatca ggtgtcttct ctgcacaccc gaatgagcgc    3060
caagctggat gctactcttg ctggtctcat tgacaaggcc aagcagcgag gtggcgagtt    3120
tcctgccaag cagcttctgc gagcccttga aaggaggcg agctctggcg aggtcgatgc    3180
gctcttccag caaactcttg ctcctctgtt tgaccttgct cgagagtacc aggacggtct    3240
tgctatccac gagcttcagg ttgctgcagg ccttctgcag gcctactacg actctgaggc    3300
ccggttctgc ggacccaacg tacgtgacga ggatgtcatt ctcaagcttc gagaggagaa    3360
ccgagattct cttcgaaagg ttgtgatggc ccagctgtct cattctcgag tcggagccaa    3420 gaacaaccttt gtgctggccc ttctcgatga atacaaggtg gccgaccagg ctggcaccga   3480
ctctcctgcc tccaacgtgc acgttgcaaa gtacttgcga cctgtgctgc gaaagattgt    3540
ggagctggaa tctcgagctt ctgccaaggt atctctgaaa gcccgagaga ttctcatcca    3600
gtgcgctctg ccctctctaa aggagcgaac tgaccagctt gagcacattc tgcgatcttc    3660
tgtcgtcgag tctcgatacg agagggttgg tctggagcac cgaactcccc gagccgatat    3720
tctcaaggag gttgtcgact ccaagtacat tgtctttgat gtgcttgccc agttctttgc    3780
ccacgatgat ccctggatcg tccttgctgc cctggagctg tacatccgac gagcttgcaa    3840
ggcctactcc atcctggaca tcaactacca ccaggactcg gacctgcctc ccgtcatctc    3900
gtggcgattt agactgccta ccatgtcgtc tgctttgtac aactcagtag tgtcttctgg    3960
ctccaaaacc cccacttccc cctcggtgtc tcgagctgat tccgtctccg acttttcgta    4020
caccgttgag cgagactctg ctcccgctcg aaccggagcg attgttgccg tgcctcatct    4080
ggatgatctg gaggatgctc tgactcgtgt tctggagaac ctgccaaac ggggcgctgg     4140 tcttgccatc tctgttggtg ctagcaacaa gagtgccgct gcttctgctc gtgacgctgc    4200
tgctgctgcc gcttcatccg ttgacactgg cctgtccaac atttgcaacg ttatgattgg    4260
tcgggttgat gagtctgatg acgacgacac tctgattgcc cgaatctccc aggtcattga    4320
```

```
ggactttaag gaggactttg aggcctgttc tctgcgacga atcaccttct ccttcggcaa   4380
ctcccgaggt acttatccca agtatttcac gttccgaggc cccgcatacg aggaggaccc   4440
cactatccga cacattgagc ctgctctggc cttccagctg gagctcgccc gtctgtccaa   4500
cttcgacatc aagcctgtcc acaccgacaa ccgaaacatc cacgtgtacg aggctactgg   4560
caagaacgct gcttccgaca gcggttctt cacccgaggt atcgtacgac ctggtcgtct   4620
tcgagagaac atccccacct cggagtatct catttccgag gctgaccggc tcatgagcga   4680
tattttggac gctctagagg tgattggaac caccaactcg gatctcaacc acattttcat   4740
caacttctca gccgtctttg ctctgaagcc cgaggaggtt gaagctgcct ttggcggttt   4800
cctggagcga tttggccgac gtctgtggcg acttcgagtc accggtgccg agatccgaat   4860
gatggtatcc gaccccgaaa ctggctctgc tttccctctg cgagcaatga tcaacaacgt   4920
ctctggttac gttgtgcagt ctgagctgta cgctgaggcc aagaacgaca agggccagtg   4980
gattttcaag tctctgggca agcccggctc catgcacatg cggtctatca acactcccta   5040
ccccaccaag gagtggctgc agcccaagcg gtacaaggcc catctgatgg gtaccaccta   5100
ctgctatgac ttccccgagc tgttccgaca gtccattgag tcggactgga agaagtatga   5160
cggcaaggct cccgacgatc tcatgacttg caacgagctg attctcgatg aggactctgg   5220
cgagctgcag gaggtgaacc gagagcccgg cgccaacaac gtcggtatgg ttgcgtggaa   5280
gtttgaggcc aagaccccg agtacccctcg aggccgatct ttcatcgtgg tggccaacga   5340
tatcaccttc cagattggtt cgtttggccc tgctgaggac cagttcttct tcaaggtgac   5400
ggagctggct cgaaagctcg gtattcctcg aatctatctg tctgccaact ctggtgctcg   5460
aatcggcatt gctgacgagc tcgttggcaa gtacaaggtt gcgtggaacg acgagactga   5520
cccctccaag ggcttcaagt acctttactt caccctgag tctcttgcca ccctcaagcc   5580
cgacactgtt gtcaccactg agattgagga ggagggtccc aacggcgtgg agaagcgtca   5640
tgtgatcgac tacattgtcg gagagaagga cggtctcgga gtcgagtgtc tgcgggctc   5700 tggtctcatt gcaggcgcca cttctcgagc ctacaaggat atcttcactc tcactcttgt   5760
cacctgtcga tccgttggta tcggtgctta ccttgttcgt cttggtcaac gagccatcca   5820
gattgagggc cagcccatca ttctcactgg tgccccgcc atcaacaagc tgcttggtcg   5880
agaggtctac tcttccaact tgcagcttgg tggtactcag atcatgtaca caacggtgt   5940 gtctcatcctg actgccgag atgatctcaa cggtgtccac aagatcatgc agtggctgtc   6000
atacatccct gcttctcgag gtcttccagt gcctgttctc cctcacaaga ccgatgtgtg   6060
ggatcgagac gtgacgttcc agcctgtccg aggcgagcag tacgatgtta gatggcttat   6120
ttctggccga actctcgagg atggtgcttt cgagtctggt ctctttgaca aggactcttt   6180
ccaggagact ctgtctggct gggccaaggg tgttgttgtt ggtcgagctc gtcttggcgg   6240
cattcccttc ggtgtcattg gtgtcgagac tgcgaccgtc gacaatacta cccctgccga   6300 tccccgccaac ccggactcta ttgagatgag cacctctgaa gccggccagg tttggtaccc   6360
caactcggcc ttcaagacct ctcaggccat caacgacttc aaccatggtg aggcgcttcc   6420
tctcatgatt cttgctaact ggcgaggctt ttctggtggt cagcgagaca tgtacaatga   6480
ggttctcaag tacggatctt tcattgttga tgctctggtt gactacaagc agcccatcat   6540
ggtgtacatc cctcccaccg gtgagctgcg aggtggttct tgggttgtgg ttgaccccac   6600
catcaactcg gacatgatgg agatgtacgc tgacgtcgag tctcgaggtg gtgtgctgga   6660
gcccgaggga atggtcggta tcaagtaccg acgagacaag ctactggaca ccatggctcg   6720
```

-continued

```
tctggatccc gagtactcct ctctcaagaa gcagcttgag gagtctcccg attctgagga    6780
gctcaaggtc aagctcagcg tgcgagagaa gtctctcatg cccatctacc agcagatctc    6840
cgtgcagttt gccgacttgc atgaccgagc tggccgaatg gaggccaagg gtgtcattcg    6900
tgaggctctt gtgtggaagg atgctcgtcg attcttcttc tggcgaatcc gacgacgatt    6960
agtcgaggag tacctcatta ccaagatcaa tagcattctg ccctcttgca ctcggcttga    7020
gtgtctggct cgaatcaagt cgtggaagcc tgccactctt gatcagggct ctgaccgggg    7080
tgttgccgag tggtttgacg agaactctga tgccgtctct gctcgactca gcgagctcaa    7140
gaaggacgct tctgcccagt cgtttgcttc tcaactgaga aaggaccgac agggtactct    7200
ccagggcatg aagcaggctc tcgcttctct ttctgaggct gagcgggctg agctgctcaa    7260
ggggttgtga                                                            7270
```

<210> SEQ ID NO 56
<211> LENGTH: 2266
<212> TYPE: PRT
<213> ORGANISM: Yarrowia lipolytica

<400> SEQUENCE: 56

```
Met Arg Leu Gln Leu Arg Thr Leu Thr Arg Arg Phe Phe Ser Met Ala
1               5                   10                  15

Ser Gly Ser Ser Thr Pro Asp Val Ala Pro Leu Val Asp Pro Asn Ile
            20                  25                  30

His Lys Gly Leu Ala Ser His Phe Gly Leu Asn Ser Val His Thr
        35                  40                  45

Ala Lys Pro Ser Lys Val Lys Glu Phe Val Ala Ser His Gly Gly His
    50                  55                  60

Thr Val Ile Asn Lys Val Leu Ile Ala Asn Asn Gly Ile Ala Ala Val
65                  70                  75                  80

Lys Glu Ile Arg Ser Val Arg Lys Trp Ala Tyr Glu Thr Phe Gly Asp
                85                  90                  95

Glu Arg Ala Ile Ser Phe Thr Val Met Ala Thr Pro Glu Asp Leu Ala
            100                 105                 110

Ala Asn Ala Asp Tyr Ile Arg Met Ala Asp Gln Tyr Val Glu Val Pro
        115                 120                 125

Gly Gly Thr Asn Asn Asn Tyr Ala Asn Val Glu Leu Ile Val Asp
    130                 135                 140

Val Ala Glu Arg Phe Gly Val Asp Ala Val Trp Ala Gly Trp Gly His
145                 150                 155                 160

Ala Ser Glu Asn Pro Leu Leu Pro Glu Ser Leu Ala Ala Ser Pro Arg
                165                 170                 175

Lys Ile Val Phe Ile Gly Pro Pro Gly Ala Ala Met Arg Ser Leu Gly
            180                 185                 190

Asp Lys Ile Ser Ser Thr Ile Val Ala Gln His Ala Lys Val Pro Cys
        195                 200                 205

Ile Pro Trp Ser Gly Thr Gly Val Asp Glu Val Val Asp Lys Ser
    210                 215                 220

Thr Asn Leu Val Ser Val Ser Glu Glu Val Tyr Thr Lys Gly Cys Thr
225                 230                 235                 240

Thr Gly Pro Lys Gln Gly Leu Glu Lys Ala Lys Gln Ile Gly Phe Pro
                245                 250                 255

Val Met Ile Lys Ala Ser Glu Gly Gly Gly Gly Lys Gly Ile Arg Lys
            260                 265                 270
```

-continued

```
Val Glu Arg Glu Glu Asp Phe Glu Ala Ala Tyr His Gln Val Glu Gly
            275                 280                 285
Glu Ile Pro Gly Ser Pro Ile Phe Ile Met Gln Leu Ala Gly Asn Ala
290                 295                 300
Arg His Leu Glu Val Gln Leu Leu Ala Asp Gln Tyr Gly Asn Asn Ile
305                 310                 315                 320
Ser Leu Phe Gly Arg Asp Cys Ser Val Gln Arg His Gln Lys Ile
                325                 330                 335
Ile Glu Glu Ala Pro Val Thr Val Ala Gly Gln Gln Thr Phe Thr Ala
            340                 345                 350
Met Glu Lys Ala Ala Val Arg Leu Gly Lys Leu Val Gly Tyr Val Ser
            355                 360                 365
Ala Gly Thr Val Glu Tyr Leu Tyr Ser His Glu Asp Asp Lys Phe Tyr
370                 375                 380
Phe Leu Glu Leu Asn Pro Arg Leu Gln Val Glu His Pro Thr Thr Glu
385                 390                 395                 400
Met Val Thr Gly Val Asn Leu Pro Ala Ala Gln Leu Gln Ile Ala Met
            405                 410                 415
Gly Ile Pro Leu Asp Arg Ile Lys Asp Ile Arg Leu Phe Tyr Gly Val
            420                 425                 430
Asn Pro His Thr Thr Thr Pro Ile Asp Phe Asp Phe Ser Gly Glu Asp
            435                 440                 445
Ala Asp Lys Thr Gln Arg Arg Pro Val Pro Arg Gly His Thr Thr Ala
450                 455                 460
Cys Arg Ile Thr Ser Glu Asp Pro Gly Glu Gly Phe Lys Pro Ser Gly
465                 470                 475                 480
Gly Thr Met His Glu Leu Asn Phe Arg Ser Ser Ser Asn Val Trp Gly
            485                 490                 495
Tyr Phe Ser Val Gly Asn Gln Gly Gly Ile His Ser Phe Ser Asp Ser
            500                 505                 510
Gln Phe Gly His Ile Phe Ala Phe Gly Glu Asn Arg Ser Ala Ser Arg
            515                 520                 525
Lys His Met Val Val Ala Leu Lys Glu Leu Ser Ile Arg Gly Asp Phe
530                 535                 540
Arg Thr Thr Val Glu Tyr Leu Ile Lys Leu Leu Glu Thr Pro Asp Phe
545                 550                 555                 560
Glu Asp Asn Thr Ile Thr Thr Gly Trp Leu Asp Glu Leu Ile Ser Asn
            565                 570                 575
Lys Leu Thr Ala Glu Arg Pro Asp Ser Phe Leu Ala Val Val Cys Gly
            580                 585                 590
Ala Ala Thr Lys Ala His Arg Ala Ser Glu Asp Ser Ile Ala Thr Tyr
            595                 600                 605
Met Ala Ser Leu Glu Lys Gly Gln Val Pro Ala Arg Asp Ile Leu Lys
610                 615                 620
Thr Leu Phe Pro Val Asp Phe Ile Tyr Glu Gly Gln Arg Tyr Lys Phe
625                 630                 635                 640
Thr Ala Thr Arg Ser Ser Glu Asp Ser Tyr Thr Leu Phe Ile Asn Gly
            645                 650                 655
Ser Arg Cys Asp Ile Gly Val Arg Pro Leu Ser Asp Gly Gly Ile Leu
            660                 665                 670
Cys Leu Val Gly Gly Arg Ser His Asn Val Tyr Trp Lys Glu Glu Val
            675                 680                 685
```

```
Gly Ala Thr Arg Leu Ser Val Asp Ser Lys Thr Cys Leu Leu Glu Val
690                 695                 700

Glu Asn Asp Pro Thr Gln Leu Arg Ser Pro Ser Pro Gly Lys Leu Val
705                 710                 715                 720

Lys Phe Leu Val Glu Asn Gly Asp His Val Arg Ala Asn Gln Pro Tyr
            725                 730                 735

Ala Glu Ile Glu Val Met Lys Met Tyr Met Thr Leu Thr Ala Gln Glu
            740                 745                 750

Asp Gly Ile Val Gln Leu Met Lys Gln Pro Gly Ser Thr Ile Glu Ala
            755                 760                 765

Gly Asp Ile Leu Gly Ile Leu Ala Leu Asp Asp Pro Ser Lys Val Lys
770                 775                 780

His Ala Lys Pro Phe Glu Gly Gln Leu Pro Glu Leu Gly Pro Pro Thr
785                 790                 795                 800

Leu Ser Gly Asn Lys Pro His Gln Arg Tyr Glu His Cys Gln Asn Val
                805                 810                 815

Leu His Asn Ile Leu Leu Gly Phe Asp Asn Gln Val Val Met Lys Ser
                820                 825                 830

Thr Leu Gln Glu Met Val Gly Leu Leu Arg Asn Pro Glu Leu Pro Tyr
    835                 840                 845

Leu Gln Trp Ala His Gln Val Ser Ser Leu His Thr Arg Met Ser Ala
850                 855                 860

Lys Leu Asp Ala Thr Leu Ala Gly Leu Ile Asp Lys Ala Lys Gln Arg
865                 870                 875                 880

Gly Gly Glu Phe Pro Ala Lys Gln Leu Leu Arg Ala Leu Glu Lys Glu
                885                 890                 895

Ala Ser Ser Gly Glu Val Asp Ala Leu Phe Gln Gln Thr Leu Ala Pro
            900                 905                 910

Leu Phe Asp Leu Ala Arg Glu Tyr Gln Asp Gly Leu Ala Ile His Glu
    915                 920                 925

Leu Gln Val Ala Ala Gly Leu Leu Gln Ala Tyr Tyr Asp Ser Glu Ala
    930                 935                 940

Arg Phe Cys Gly Pro Asn Val Arg Asp Glu Asp Val Ile Leu Lys Leu
945                 950                 955                 960

Arg Glu Glu Asn Arg Asp Ser Leu Arg Lys Val Val Met Ala Gln Leu
                965                 970                 975

Ser His Ser Arg Val Gly Ala Lys Asn Asn Leu Val Leu Ala Leu Leu
            980                 985                 990

Asp Glu Tyr Lys Val Ala Asp Gln Ala Gly Thr Asp Ser Pro Ala Ser
    995                 1000                1005

Asn Val His Val Ala Lys Tyr Leu Arg Pro Val Leu Arg Lys Ile
    1010                1015                1020

Val Glu Leu Glu Ser Arg Ala Ser Ala Lys Val Ser Leu Lys Ala
    1025                1030                1035

Arg Glu Ile Leu Ile Gln Cys Ala Leu Pro Ser Leu Lys Glu Arg
    1040                1045                1050

Thr Asp Gln Leu Glu His Ile Leu Arg Ser Ser Val Val Glu Ser
    1055                1060                1065

Arg Tyr Gly Glu Val Gly Leu Glu His Arg Thr Pro Arg Ala Asp
    1070                1075                1080

Ile Leu Lys Glu Val Val Asp Ser Lys Tyr Ile Val Phe Asp Val
    1085                1090                1095

Leu Ala Gln Phe Phe Ala His Asp Asp Pro Trp Ile Val Leu Ala
```

```
                 1100              1105              1110
Ala Leu Glu Leu Tyr Ile Arg Arg Ala Cys Lys Ala Tyr Ser Ile
    1115              1120              1125
Leu Asp Ile Asn Tyr His Gln Asp Ser Asp Leu Pro Pro Val Ile
    1130              1135              1140
Ser Trp Arg Phe Arg Leu Pro Thr Met Ser Ser Ala Leu Tyr Asn
    1145              1150              1155
Ser Val Val Ser Ser Gly Ser Lys Thr Pro Thr Ser Pro Ser Val
    1160              1165              1170
Ser Arg Ala Asp Ser Val Ser Asp Phe Ser Tyr Thr Val Glu Arg
    1175              1180              1185
Asp Ser Ala Pro Ala Arg Thr Gly Ala Ile Val Ala Val Pro His
    1190              1195              1200
Leu Asp Asp Leu Glu Asp Ala Leu Thr Arg Val Leu Glu Asn Leu
    1205              1210              1215
Pro Lys Arg Gly Ala Gly Leu Ala Ile Ser Val Gly Ala Ser Asn
    1220              1225              1230
Lys Ser Ala Ala Ser Ala Arg Asp Ala Ala Ala Ala Ala
    1235              1240              1245
Ser Ser Val Asp Thr Gly Leu Ser Asn Ile Cys Asn Val Met Ile
    1250              1255              1260
Gly Arg Val Asp Glu Ser Asp Asp Asp Thr Leu Ile Ala Arg
    1265              1270              1275
Ile Ser Gln Val Ile Glu Asp Phe Lys Glu Asp Phe Glu Ala Cys
    1280              1285              1290
Ser Leu Arg Arg Ile Thr Phe Ser Phe Gly Asn Ser Arg Gly Thr
    1295              1300              1305
Tyr Pro Lys Tyr Phe Thr Phe Arg Gly Pro Ala Tyr Glu Glu Asp
    1310              1315              1320
Pro Thr Ile Arg His Ile Glu Pro Ala Leu Ala Phe Gln Leu Glu
    1325              1330              1335
Leu Ala Arg Leu Ser Asn Phe Asp Ile Lys Pro Val His Thr Asp
    1340              1345              1350
Asn Arg Asn Ile His Val Tyr Glu Ala Thr Gly Lys Asn Ala Ala
    1355              1360              1365
Ser Asp Lys Arg Phe Phe Thr Arg Gly Ile Val Arg Pro Gly Arg
    1370              1375              1380
Leu Arg Glu Asn Ile Pro Thr Ser Glu Tyr Leu Ile Ser Glu Ala
    1385              1390              1395
Asp Arg Leu Met Ser Asp Ile Leu Asp Ala Leu Glu Val Ile Gly
    1400              1405              1410
Thr Thr Asn Ser Asp Leu Asn His Ile Phe Ile Asn Phe Ser Ala
    1415              1420              1425
Val Phe Ala Leu Lys Pro Glu Glu Val Glu Ala Ala Phe Gly Gly
    1430              1435              1440
Phe Leu Glu Arg Phe Gly Arg Arg Leu Trp Arg Leu Arg Val Thr
    1445              1450              1455
Gly Ala Glu Ile Arg Met Met Val Ser Asp Pro Glu Thr Gly Ser
    1460              1465              1470
Ala Phe Pro Leu Arg Ala Met Ile Asn Asn Val Ser Gly Tyr Val
    1475              1480              1485
Val Gln Ser Glu Leu Tyr Ala Glu Ala Lys Asn Asp Lys Gly Gln
    1490              1495              1500
```

-continued

Trp Ile Phe Lys Ser Leu Gly Lys Pro Gly Ser Met His Met Arg
1505                1510                1515

Ser Ile Asn Thr Pro Tyr Pro Thr Lys Glu Trp Leu Gln Pro Lys
1520                1525                1530

Arg Tyr Lys Ala His Leu Met Gly Thr Thr Tyr Cys Tyr Asp Phe
1535                1540                1545

Pro Glu Leu Phe Arg Gln Ser Ile Glu Ser Asp Trp Lys Lys Tyr
1550                1555                1560

Asp Gly Lys Ala Pro Asp Asp Leu Met Thr Cys Asn Glu Leu Ile
1565                1570                1575

Leu Asp Glu Asp Ser Gly Glu Leu Gln Glu Val Asn Arg Glu Pro
1580                1585                1590

Gly Ala Asn Asn Val Gly Met Val Ala Trp Lys Phe Glu Ala Lys
1595                1600                1605

Thr Pro Glu Tyr Pro Arg Gly Arg Ser Phe Ile Val Val Ala Asn
1610                1615                1620

Asp Ile Thr Phe Gln Ile Gly Ser Phe Gly Pro Ala Glu Asp Gln
1625                1630                1635

Phe Phe Phe Lys Val Thr Glu Leu Ala Arg Lys Leu Gly Ile Pro
1640                1645                1650

Arg Ile Tyr Leu Ser Ala Asn Ser Gly Ala Arg Ile Gly Ile Ala
1655                1660                1665

Asp Glu Leu Val Gly Lys Tyr Lys Val Ala Trp Asn Asp Glu Thr
1670                1675                1680

Asp Pro Ser Lys Gly Phe Lys Tyr Leu Tyr Phe Thr Pro Glu Ser
1685                1690                1695

Leu Ala Thr Leu Lys Pro Asp Thr Val Val Thr Thr Glu Ile Glu
1700                1705                1710

Glu Glu Gly Pro Asn Gly Val Glu Lys Arg His Val Ile Asp Tyr
1715                1720                1725

Ile Val Gly Glu Lys Asp Gly Leu Gly Val Glu Cys Leu Arg Gly
1730                1735                1740

Ser Gly Leu Ile Ala Gly Ala Thr Ser Arg Ala Tyr Lys Asp Ile
1745                1750                1755

Phe Thr Leu Thr Leu Val Thr Cys Arg Ser Val Gly Ile Gly Ala
1760                1765                1770

Tyr Leu Val Arg Leu Gly Gln Arg Ala Ile Gln Ile Glu Gly Gln
1775                1780                1785

Pro Ile Ile Leu Thr Gly Ala Pro Ala Ile Asn Lys Leu Leu Gly
1790                1795                1800

Arg Glu Val Tyr Ser Ser Asn Leu Gln Leu Gly Gly Thr Gln Ile
1805                1810                1815

Met Tyr Asn Asn Gly Val Ser His Leu Thr Ala Arg Asp Asp Leu
1820                1825                1830

Asn Gly Val His Lys Ile Met Gln Trp Leu Ser Tyr Ile Pro Ala
1835                1840                1845

Ser Arg Gly Leu Pro Val Pro Val Leu Pro His Lys Thr Asp Val
1850                1855                1860

Trp Asp Arg Asp Val Thr Phe Gln Pro Val Arg Gly Glu Gln Tyr
1865                1870                1875

Asp Val Arg Trp Leu Ile Ser Gly Arg Thr Leu Glu Asp Gly Ala
1880                1885                1890

Phe Glu Ser Gly Leu Phe Asp Lys Asp Ser Phe Gln Glu Thr Leu
1895                1900                1905

Ser Gly Trp Ala Lys Gly Val Val Gly Arg Ala Arg Leu Gly
1910                1915                1920

Gly Ile Pro Phe Gly Val Ile Gly Val Glu Thr Ala Thr Val Asp
1925                1930                1935

Asn Thr Thr Pro Ala Asp Pro Ala Asn Pro Asp Ser Ile Glu Met
1940                1945                1950

Ser Thr Ser Glu Ala Gly Gln Val Trp Tyr Pro Asn Ser Ala Phe
1955                1960                1965

Lys Thr Ser Gln Ala Ile Asn Asp Phe Asn His Gly Glu Ala Leu
1970                1975                1980

Pro Leu Met Ile Leu Ala Asn Trp Arg Gly Phe Ser Gly Gly Gln
1985                1990                1995

Arg Asp Met Tyr Asn Glu Val Leu Lys Tyr Gly Ser Phe Ile Val
2000                2005                2010

Asp Ala Leu Val Asp Tyr Lys Gln Pro Ile Met Val Tyr Ile Pro
2015                2020                2025

Pro Thr Gly Glu Leu Arg Gly Gly Ser Trp Val Val Asp Pro
2030                2035                2040

Thr Ile Asn Ser Asp Met Met Glu Met Tyr Ala Asp Val Glu Ser
2045                2050                2055

Arg Gly Gly Val Leu Glu Pro Glu Gly Met Val Gly Ile Lys Tyr
2060                2065                2070

Arg Arg Asp Lys Leu Leu Asp Thr Met Ala Arg Leu Asp Pro Glu
2075                2080                2085

Tyr Ser Ser Leu Lys Lys Gln Leu Glu Glu Ser Pro Asp Ser Glu
2090                2095                2100

Glu Leu Lys Val Lys Leu Ser Val Arg Glu Lys Ser Leu Met Pro
2105                2110                2115

Ile Tyr Gln Gln Ile Ser Val Gln Phe Ala Asp Leu His Asp Arg
2120                2125                2130

Ala Gly Arg Met Glu Ala Lys Gly Val Ile Arg Glu Ala Leu Val
2135                2140                2145

Trp Lys Asp Ala Arg Arg Phe Phe Phe Trp Arg Ile Arg Arg Arg
2150                2155                2160

Leu Val Glu Glu Tyr Leu Ile Thr Lys Ile Asn Ser Ile Leu Pro
2165                2170                2175

Ser Cys Thr Arg Leu Glu Cys Leu Ala Arg Ile Lys Ser Trp Lys
2180                2185                2190

Pro Ala Thr Leu Asp Gln Gly Ser Asp Arg Gly Val Ala Glu Trp
2195                2200                2205

Phe Asp Glu Asn Ser Asp Ala Val Ser Ala Arg Leu Ser Glu Leu
2210                2215                2220

Lys Lys Asp Ala Ser Ala Gln Ser Phe Ala Ser Gln Leu Arg Lys
2225                2230                2235

Asp Arg Gln Gly Thr Leu Gln Gly Met Lys Gln Ala Leu Ala Ser
2240                2245                2250

Leu Ser Glu Ala Glu Arg Ala Glu Leu Leu Lys Gly Leu
2255                2260                2265

<210> SEQ ID NO 57
<211> LENGTH: 406
<212> TYPE: DNA

```
<213> ORGANISM: Artificial Sequence
<220> FEATURE:
<223> OTHER INFORMATION: Synthetic Polynucleotide

<400> SEQUENCE: 57
agagaccggg ttggcggcgc atttgtgtcc caaaaaacag ccccaattgc cccaattgac      60
cccaaattga cccagtagcg ggcccaaccc cggcgagagc cccttctcc ccacatatca     120
aacctccccc ggttcccaca cttgccgtta agggcgtagg gtactgcagt ctggaatcta    180
cgcttgttca gactttgtac tagtttcttt gtctggccat ccgggtaacc catgccggac    240
gcaaaataga ctactgaaaa ttttttttgct tgtggttgg actttagcc aagggtataa     300
aagaccaccg tccccgaatt acctttcctc ttctttctc tctctccttg tcaactcaca     360
cccgaaatcg ttaagcattt ccttctgagt ataagaatca ttcaaa                    406

<210> SEQ ID NO 58
<211> LENGTH: 122
<212> TYPE: DNA
<213> ORGANISM: Artificial Sequence
<220> FEATURE:
<223> OTHER INFORMATION: Synthetic Polynucleotide

<400> SEQUENCE: 58
gtgagtttca gaggcagcag caattgccac gggctttgag cacacggccg ggtgtggtcc      60
cattcccatc gacacaagac gccacgtcat ccgaccagca cttttgcag tactaaccgc     120
ag                                                                    122

<210> SEQ ID NO 59
<211> LENGTH: 531
<212> TYPE: DNA
<213> ORGANISM: Artificial Sequence
<220> FEATURE:
<223> OTHER INFORMATION: Synthetic Polynucleotide

<400> SEQUENCE: 59
agagaccggg ttggcggcgc atttgtgtcc caaaaaacag ccccaattgc cccaattgac      60
cccaaattga cccagtagcg ggcccaaccc cggcgagagc cccttctcc ccacatatca     120
aacctccccc ggttcccaca cttgccgtta agggcgtagg gtactgcagt ctggaatcta    180
cgcttgttca gactttgtac tagtttcttt gtctggccat ccgggtaacc catgccggac    240
gcaaaataga ctactgaaaa ttttttttgct tgtggttgg actttagcc aagggtataa     300
aagaccaccg tccccgaatt acctttcctc ttctttctc tctctccttg tcaactcaca     360
cccgaaatcg ttaagcattt ccttctgagt ataagaatca ttcaaaatgg tgagtttcag    420
aggcagcagc aattgccacg ggctttgagc acacggccgg gtgtggtccc attcccatcg    480
acacaagacg ccacgtcatc cgaccagcac ttttgcagt actaaccgca g              531

<210> SEQ ID NO 60
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 60
gccccagata aggttccga                                                   19

<210> SEQ ID NO 61
<211> LENGTH: 42
```

```
<212> TYPE: DNA
<213> ORGANISM: Artificial Sequence
<220> FEATURE:
<223> OTHER INFORMATION: Synthetic Polynucleotide

<400> SEQUENCE: 61
agtgaattcg agctcggtac ccatgccctc ctacgaagct cg                         42

<210> SEQ ID NO 62
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 62
ctgcgaactt tctgtcctcg aa                                               22

<210> SEQ ID NO 63
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 63
ttcgaggaca gaaagttcgc agtactccaa gcagaccatt gagct                      45

<210> SEQ ID NO 64
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 64
ggtcgactct agaggatccc cctaacagtt aatcttctgg taagcctc                   48

<210> SEQ ID NO 65
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 65
aagctgaaca agcgctccat a                                                21

<210> SEQ ID NO 66
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 66
gggtaccgag ctcgaattca ct                                               22

<210> SEQ ID NO 67
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 67
```

```
gggatcctc tagagtcgac c                                              21
```

<210> SEQ ID NO 68
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 68

```
gagatataca tatggcagat ctcaattgag agaccgggtt ggcgg                   45
```

<210> SEQ ID NO 69
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 69

```
tcgcgtggcc ggccgatatc ggacacgggc atctcacttg                         40
```

<210> SEQ ID NO 70
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 70

```
caagtgagat gcccgtgtcc gatatcggcc ggccacgcga                         40
```

<210> SEQ ID NO 71
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 71

```
ccgccaaccc ggtctctcaa ttgagatctg ccatatgtat atctc                   45
```

<210> SEQ ID NO 72
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 72

```
cgaccagcac tttttgcagt actaaccgca gccacattcc tacgattacg atg          53
```

<210> SEQ ID NO 73
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 73

```
caagaccggc aacgtggggt taaaacaggc ggtttaaacc                         40
```

<210> SEQ ID NO 74
<211> LENGTH: 19
<212> TYPE: DNA
<213> ORGANISM: Artificial Sequence

```
<220> FEATURE:
<223> OTHER INFORMATION: Synthetic Polynucleotide

<400> SEQUENCE: 74 cccccacgttg ccggtcttg                                                    19

<210> SEQ ID NO 75
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 75
ctgcggttag tactgcaaaa agtgctggtc g                                       31

<210> SEQ ID NO 76
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 76
agtgaattcg agctcggtac cccgcagtag gatgtcctgc ac                           42

<210> SEQ ID NO 77
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 77
agatgcatag cacgcgtgta gatactgttg atgtgtgttt aattcaagaa tgaat            55

<210> SEQ ID NO 78
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 78
tacacgcgtg ctatgcatct ggttcatgag aagataaata tataaataca ttgaga           56

<210> SEQ ID NO 79
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 79
ggtcgactct agaggatccc cctaccttgc tcgaatgact tattg                        45

<210> SEQ ID NO 80
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 80
gtatctacac gcgtgctatg ca                                                 22
```

<210> SEQ ID NO 81
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 81
tgttgatgtg tgtttaattc aagaatgaat atagag                    36

<210> SEQ ID NO 82
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 82
cattcttgaa ttaaacacac atcaacaatg cgaattggca taccaagaga acg    53

<210> SEQ ID NO 83
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 83
tgcatagcac gcgtgtagat acttaatttt tgcggaacat tttcagcatg cgctg    55

<210> SEQ ID NO 84
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 84
cgaccagcac ttttttgcagt actaaccgca gtctggagga ttagttacag ctgcatac    58

<210> SEQ ID NO 85
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 85
caagaccggc aacgtggggt tacagagctt tcaggattgc atcca          45

<210> SEQ ID NO 86
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 86
cgtattgtac acggccgcat agaattcgag ctcggtaccc              40

<210> SEQ ID NO 87
<211> LENGTH: 48
<212> TYPE: DNA
<213> ORGANISM: Artificial Sequence
<220> FEATURE:
<223> OTHER INFORMATION: Synthetic Polynucleotide

```
<400> SEQUENCE: 87
caattgagat ctgccatatg tatatctcgt cgactctaga ggatcccc                48

<210> SEQ ID NO 88
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 88
gagatataca tatggcagat ctcaattg                                      28

<210> SEQ ID NO 89
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 89
tatgcggccg tgtacaatac g                                             21

<210> SEQ ID NO 90
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 90
cgaccagcac tttttgcagt actaaccgca ggcaaagata gctattaatg gttttgg      57

<210> SEQ ID NO 91
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 91
caagaccggc aacgtggggc tattttgcta ttttgcaaa gtaagct                  47

<210> SEQ ID NO 92
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 92
cgaccagcac tttttgcagt actaaccgca gcccgatatg accaacgagt cc           52

<210> SEQ ID NO 93
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 93
caagaccggc aacgtggggt tacacgccgg cctcgaa                            37

<210> SEQ ID NO 94
```

<210> SEQ ID NO 94
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 94
cgaccagcac tttttgcagt actaaccgca gtcgcctatt attgattttg ttcgtcg    57

<210> SEQ ID NO 95
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 95
caagaccggc aacgtggggc tacaatttac cagcttgctg attgct    46

<210> SEQ ID NO 96
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 96
cattcttgaa ttaaacacac atcaacaatg aagttgatgg aaaacatctt cggt    54

<210> SEQ ID NO 97
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 97
tgcatagcac gcgtgtagat acttaacctt gtgcttgagc ttgaac    46

<210> SEQ ID NO 98
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 98
cgaccagcac tttttgcagt actaaccgca ggccgatttc gactctaaag aatac    55

<210> SEQ ID NO 99
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 99
caagaccggc aacgtggggt tatttcaatg gggaccaagt ccaatc    46

<210> SEQ ID NO 100
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 100

```
ccggagcttg caggatcgcc agagaccggg ttggcggcgc                            40

<210> SEQ ID NO 101
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 101
gagcgagtgt tacacatgga attggacacg ggcatctcac ttg                       43

<210> SEQ ID NO 102
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 102
aattccatgt gtaacactcg ctc                                             23

<210> SEQ ID NO 103
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 103
ggcgatcctg caagctccgg                                                 20

<210> SEQ ID NO 104
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 104
cgaccagcac tttttgcagt actaaccgca ggcccgcaac acaacgga                  48

<210> SEQ ID NO 105
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 105
caagaccggc aacgtggggt taaatgttgg tgaaccgctt ctgt                      44

<210> SEQ ID NO 106
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 106
cgaccagcac tttttgcagt actaaccgca gcgactactc atccgccgaa c              51

<210> SEQ ID NO 107
<211> LENGTH: 39
<212> TYPE: DNA
```

```
<213> ORGANISM: Artificial Sequence
<220> FEATURE:
<223> OTHER INFORMATION: Synthetic Polynucleotide

<400> SEQUENCE: 107
caagaccggc aacgtggggc taagcaacat cgcctgacg                    39

<210> SEQ ID NO 108
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 108
cgaccagcac tttttgcagt actaaccgca gagcactccg gtcagcgagt c       51

<210> SEQ ID NO 109
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 109
caagaccggc aacgtggggt tacttcgtgt cctcctgctc g                  41

<210> SEQ ID NO 110
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 110
cattcttgaa ttaaacacac atcaacaatg gcaaagatag ctattaatgg ttttgg   56

<210> SEQ ID NO 111
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 111
tgcatagcac gcgtgtagat acctattttg ctattttgc aaagtaagct           50

<210> SEQ ID NO 112
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 112
gccgcatagg ccaatagtgg atctgctg                                 28

<210> SEQ ID NO 113
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 113
cagcagatcc actattggcc tatgcggc                                 28
```

<210> SEQ ID NO 114
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 114
cgaccagcac tttttgcagt actaaccgca gaattttcat catctggctt actggc    56

<210> SEQ ID NO 115
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 115
ggccatggaa ctagtcggta cctcaggcct ccaggcttat cc    42

<210> SEQ ID NO 116
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 116
ccagacgcgt ttcatgttgc t    21

<210> SEQ ID NO 117
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 117
ccgaccagca cttttgcag tactaaccgc agtccgccga gaaaaccaat accg    54

<210> SEQ ID NO 118
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 118
ggacaggcca tggaactagt cggtacctta gggcttttг aggagggtct c    51

<210> SEQ ID NO 119
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 119
gggccttgag gaggtctacc agaagt    26

<210> SEQ ID NO 120
<211> LENGTH: 26
<212> TYPE: DNA
<213> ORGANISM: Artificial Sequence
<220> FEATURE:

<223> OTHER INFORMATION: Synthetic Polynucleotide

<400> SEQUENCE: 120
acttctggta gacctcctca aggccc                                          26

<210> SEQ ID NO 121
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 121
ccgaccagca cttttttgcag tactaaccgc aggcttctat cccccattat gactatc       57

<210> SEQ ID NO 122
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 122
ggacaggcca tggaactagt cggtaccctta tctcatggtc accagctcc                49

<210> SEQ ID NO 123
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 123
agctcgccat tgtccttctt gac                                             23

<210> SEQ ID NO 124
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 124
aggaggctac attggcgtgg ag                                              22

<210> SEQ ID NO 125
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 125
cgaccagcac ttttttgcagt actaaccgca ggtcaaggct gtcgctgttc ttcgaggaga    60

<210> SEQ ID NO 126
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 126
ggacaggcca tggaactagt cggtaccctta ggcggtaaga ccaatgaca                49

```
<210> SEQ ID NO 127
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 127
caacaccctc agagtcagtc ttgacg                                    26

<210> SEQ ID NO 128
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 128
ccgaccagca cttttgcag tactaaccgc agacccacag cccagttgtt atcat      55

<210> SEQ ID NO 129
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 129
ggacaggcca tggaactagt cggtaccta ttcctcctca gcaagcagct tc         52

<210> SEQ ID NO 130
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 130
ccgaccagca cttttgcag tactaaccgc agagtgaagg ccccgtcaaa ttcgaa     56

<210> SEQ ID NO 131
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 131
ggacaggcca tggaactagt cggtaccta attatccttc gtatcttctg gcttag     56

<210> SEQ ID NO 132
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 132
ccattacttg ggtaaagagt tggtc                                     25

<210> SEQ ID NO 133
<211> LENGTH: 56
<212> TYPE: DNA
<213> ORGANISM: Artificial Sequence
<220> FEATURE:
<223> OTHER INFORMATION: Synthetic Polynucleotide
```

<400> SEQUENCE: 133
cgaccagcac tttttgcagt actaaccgca gccctcctac gaagctcgag ctaacg            56

<210> SEQ ID NO 134
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 134
gacaggccat ggaactagtc ggtaccctaa cagttaatct tctggtaagc ctcccag           57

<210> SEQ ID NO 135
<211> LENGTH: 1402
<212> TYPE: DNA
<213> ORGANISM: Artificial Sequence
<220> FEATURE:
<223> OTHER INFORMATION: Synthetic Polynucleotide

<400> SEQUENCE: 135
atcgatgctt ttcgtagata tggaataca  aatggatatc cagagtatac acatggatag         60
tatacactga cacgacaatt ctgtatctct ttatgttaac tactgtgagg cgttaaatag        120
agcttgatat ataaaatgtt acatttcaca gtctgaactt ttgcagatta cctaatttgg       180
taagatatta attatgaact gaaagttgat ggcatcccta aatttgatga aagcctaggg       240
acgacagaga ccgggttggc ggcgcatttg tgtcccaaaa aacagcccca attgccccaa       300
ttgaccccaa attgacccag tagcgggccc aaccccggcg agagccccct tctccccaca       360
tatcaaacct cccccggttc ccacacttgc cgttaagggc gtagggtact gcagtctgga       420
atctacgctt gttcagactt tgtacttgtt tctttgtctg gccatccggg taacccatgc       480
cggacgcaaa atagactact gaaaattttt ttgctttgtg gttgggactt tagccaaggg       540
tataaaagac caccgtcccc gaattacctt tcctcttctt ttctctctct ccttgtcaac       600
tcacacccga aatcgttaag catttccttc tgagtataag aatcattcaa atctagaatg       660
gtgagtttca gaggcagcag caattgccac gggctttgag cacacggccg ggtgtggtcc       720
cattcccatc gacacaagac gccacgtcat ccgaccagca cttttttgcag tacgtatcta       780 cacgcgtgct atgcatctga gtgaggtacc gactagttcc atggcctgtc cccacgttgc       840
cggtcttgcc tcctactacc tgtccatcaa tgacgaggtt ctcacccctg cccaggtcga       900
ggctcttatt actgagtcca acaccggtgt tcttcccacc accaacctca agggctctcc       960
caacgctgtt gcctacaacg tgttggcat  ttaggcaatt aacagatagt ttgccggtga      1020
taattctctt aacctcccac actcctttga cataacgatt tatgtaacga aactgaaatt      1080
tgaccagata ttgttgtaaa tagaaaatct ggcttgtagg tggcaaaatg cggcgtcttt      1140
gttcatcaat tccctctgtg actactcgtc atcctttat gttcgactgt cgtatttctt      1200
attttccata catatgcaag tgagatgccc gtgtccgtta tcaaatctag ttagctagcg      1260
agacaataac ggaggagtcg actatgtctg ataaaggat  gtaacatagg caagctgctc      1320
gtgagtgttg agtacgaacc ttagatccaa atcacccgca cccacggata tacttgcttg      1380
aatatacagt agtatgctcg ag                                               1402